US006225066B1

(12) United States Patent
Jacobs, Jr. et al.

(10) Patent No.: US 6,225,066 B1
(45) Date of Patent: May 1, 2001

(54) MYCOBACTERIAL SPECIES-SPECIFIC REPORTER MYCOBACTERIOPHAGES

(75) Inventors: William R. Jacobs, Jr., City Island; Barry R. Bloom, Hastings-on-Hudson, both of NY (US); Graham F. Hatfull, Pittsburgh, PA (US)

(73) Assignees: Albert Einstein College of Medicine of Yeshiva University, Bronx, NY (US); University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/426,436

(22) Filed: Oct. 25, 1999

Related U.S. Application Data

(63) Continuation of application No. 08/705,557, filed on Aug. 29, 1996, which is a continuation of application No. 08/430,314, filed on Apr. 28, 1995, now abandoned, which is a continuation of application No. 08/057,531, filed on Apr. 29, 1993, now abandoned, which is a continuation-in-part of application No. 07/833,431, filed on Feb. 7, 1992, now abandoned.

(51) Int. Cl.[7] ........................................ C12Q 1/68
(52) U.S. Cl. ........................ 435/6; 435/32; 435/253.1
(58) Field of Search ............................ 435/6, 32, 253.1

*Primary Examiner*—James Ketter
(74) *Attorney, Agent, or Firm*—Amster, Rothstein & Ebenstein

(57) ABSTRACT

This invention relates to mycobacterial species-specific reporter mycobacteriophages (reporter mycobacteriophages), methods of producing said reporter mycobacteriophages and the use of said reporter mycobacteriophages for the rapid diagnosis of mycobacterial infection and the assessment of drug susceptibilities of mycobacterial strains in clinical samples. In particular, this invention is directed to the production and use of luciferase reporter mycobacteriophages to diagnose tuberculosis. The mycobacterial species-specific reporter mycobacteriophages comprise mycobacterial species-specific mycobacteriophages which contain reporter genes and transcriptional promoters therein. When the reporter mycobacteriophages are incubated with clinical samples which may contain the mycobacteria of interest, the gene product of the reporter genes will be expressed if the sample contains the mycobacteria of interest, thereby diagnosing mycobacterial infection.

16 Claims, 33 Drawing Sheets

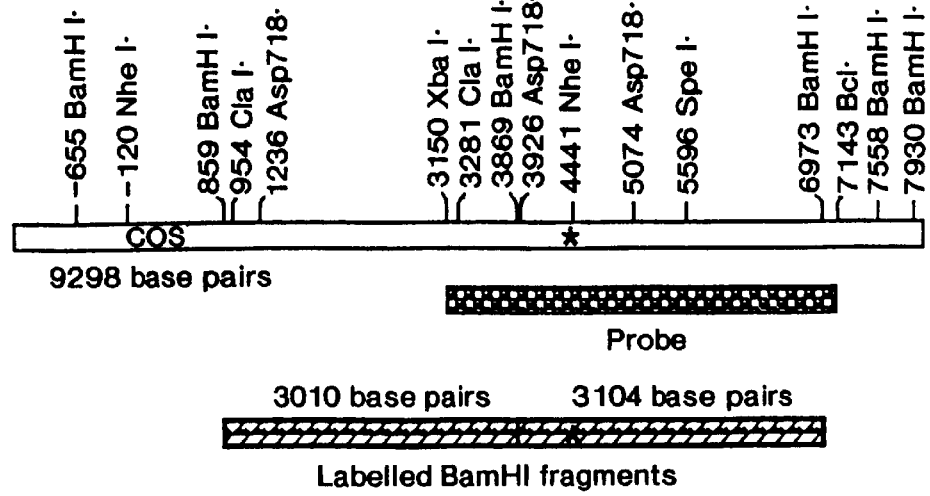
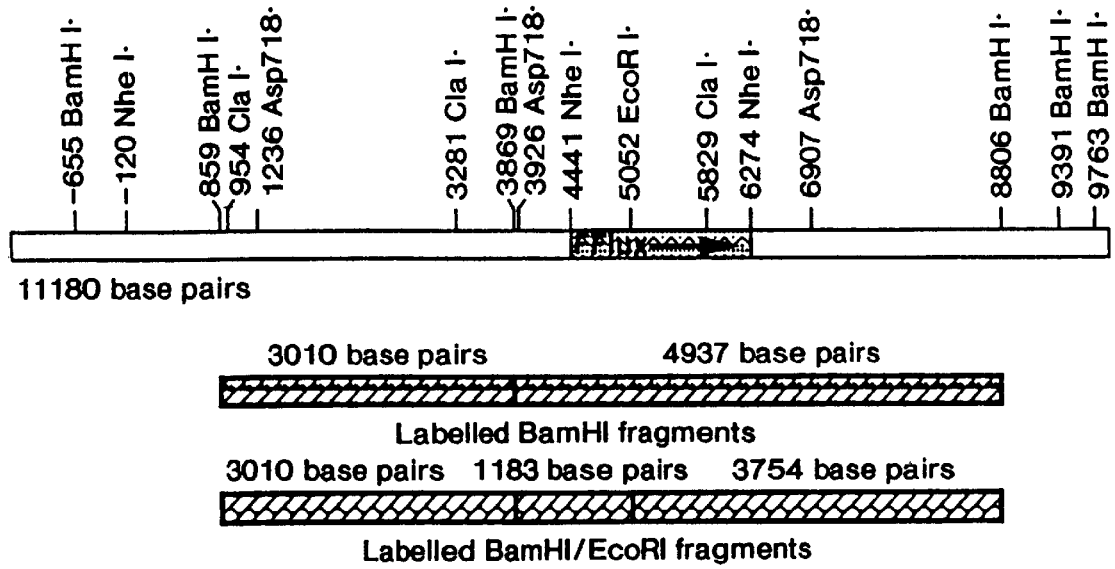
FIG. 21A

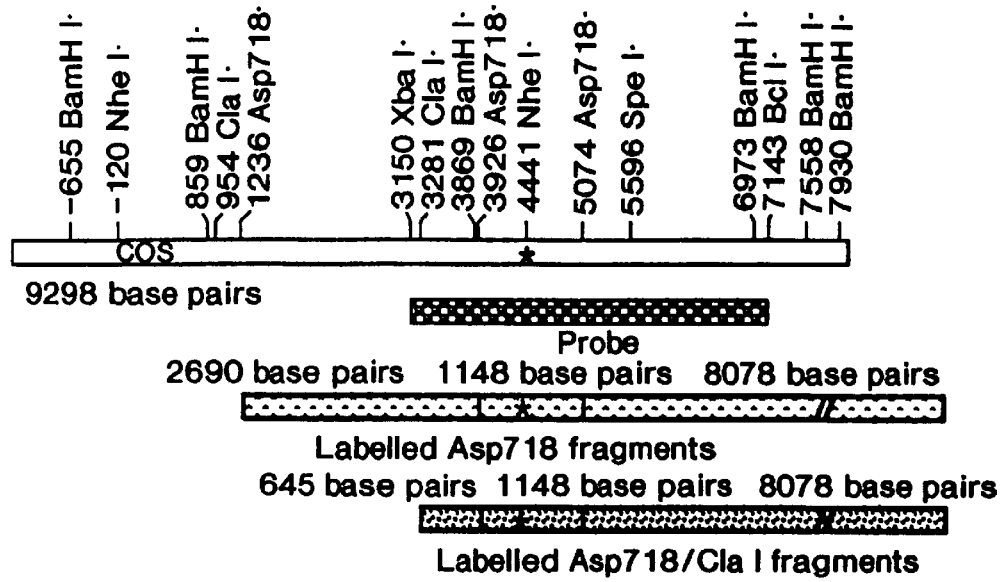
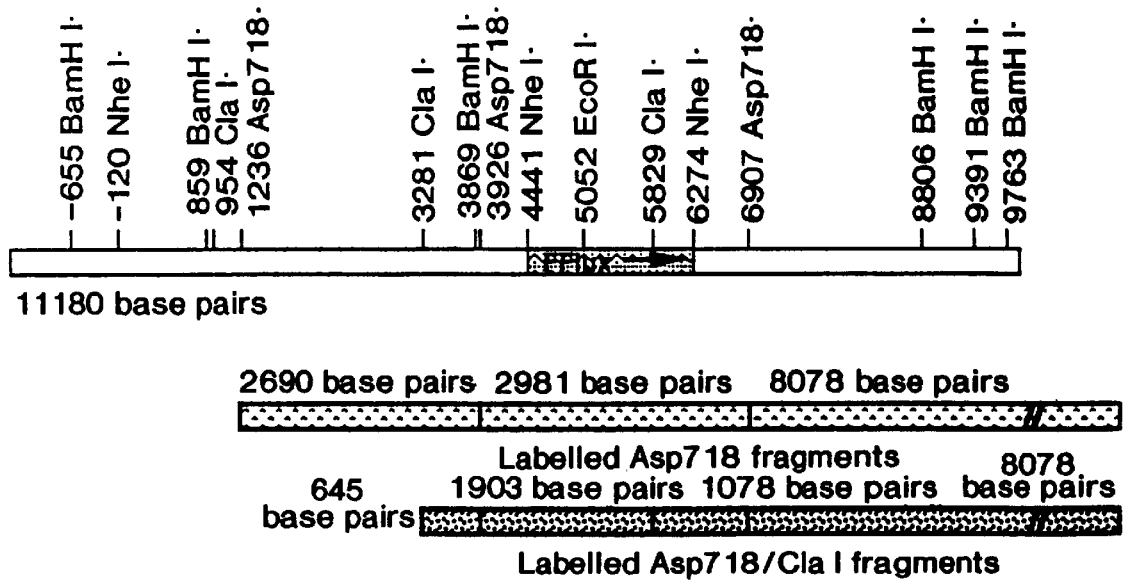
FIG. 21B

| Titer | Cells T=0 | Cells T=20 | RLU | RLU Cell | Cells T=40 | RLU | RLU Cell |
|---|---|---|---|---|---|---|---|
| $5 \times 10^7$ | 6850 | 2125 | 6981 | 3.4 | ND | 49680 | - |
| $5 \times 10^7$ | 685 | 210 | 466 | 2.2 | 2598 | 1943 | 0.8 |
| $5 \times 10^7$ | 69 | 25 | 55 | 2.2 | 305 | 107 | 0.4 |
| $5 \times 10^7$ | 7 | ND | 0 | - | ND | 4 | - |
| $5 \times 10^5$ | 685 | 1300 | 1840 | 1.4 | ND | 21188 | - |
| $5 \times 10^5$ | 69 | 110 | 201.5 | 1.8 | 3175 | 2229 | 0.7 |
| $5 \times 10^5$ | 7 | 22.5 | 37 | 1.7 | 225 | 150 | 0.7 |

FIG. 28B

| Phage | Other name | Characterized | Description | Date isolated |
|---|---|---|---|---|
| phGS1 | ts-phGS-1 | yes | FFlux derivative of L5ts11 | 1/15/93 |
| phGS2 | | no | FFlux derivative of L5ts11 | 1/15/93 |
| phGS3 | | no | FFlux derivative of L5ts11 | 1/15/93 |
| phGS4 | | no | FFlux derivative of L5ts11 | 1/15/93 |
| phGS5 | ts-phGS-5 | yes | FFlux derivative of L5ts11 | 1/15/93 |
| phGS6 | | no | FFlux derivative of L5ts11 | 1/15/93 |
| phGS7 | | no | FFlux derivative of L5ts11 | 1/15/93 |
| phGS8 | | no | FFlux derivative of L5ts11 | 1/15/93 |
| phGS9 | | no | FFlux derivative of L5ts11 | 1/15/93 |
| phGS10 | | no | FFlux derivative of L5ts11 | 1/15/93 |
| phGS11 | | no | FFlux derivative of L5ts11 | 1/15/93 |
| phGS12 | | no | FFlux derivative of L5ts11 | 1/15/93 |
| phGS13 | | no | FFlux derivative of L5ts11 | 1/15/93 |
| phGS14 | | no | FFlux derivative of L5ts11 | 1/15/93 |
| phGS15 | ts+phGS1 | yes | ts+ derivative of phGS1 | 2/10/93 |
| phGS16 | ts+phGS1 | yes | ts+ derivative of phGS1 | 2/10/93 |
| phGS17 | ts+phGS1 | yes | ts+ derivative of phGS1 | 2/10/93 |
| phGS18 | ts+phGS5 | yes | ts+ derivative of phGS5 | 2/10/93 |
| phGS19 | ts+phGS5 | yes | ts+ derivative of phGS5 | 2/10/93 |
| phGS20 | ts+phGS5 | yes | ts+ derivative of phGS5 | 2/10/93 |
| phGS21 | cpm5-1-1 | yes | clear plaque mutant of phGS18 | 3/1/93 |
| phGS22 | cpm5-1-3 | yes | clear plaque mutant of phGS18 | 3/1/93 |
| phGS23 | cpm5-1-4 | yes | clear plaque mutant of phGS18 | 3/1/93 |
| phGS24 | cpm5-2-1 | yes | clear plaque mutant of phGS19 | 3/1/93 |
| phGS25 | cpm5-2-3 | yes | clear plaque mutant of phGS19 | 3/1/93 |
| phGS26 | cpm5-2-4 | yes | clear plaque mutant of phGS19 | 3/1/93 |

FIG. 30

```
                              SEQUENCE LISTING (1) GENERAL INFORMATION:

(iii) NUMBER OF SEQUENCES:   1

(2) INFORMATION FOR SEQ ID NO: 1:

(i) SEQUENCE CHARACTERISTICS:
          (A) LENGTH:         52297
          (B) TYPE:           nucleotide
          (C) STRANDEDNESS:   single
          (D) TOPOLOGY:       linear (ii) MOLECULE TYPE:
          (A) DESCRIPTION:    phage genome sequence (iii) HYPOTHETICAL:     no (iv) ANTI-SENSE:       no (v) FRAGMENT TYPE:    not applicable.

(vi) ORIGINAL SOURCE:
          (A) ORGANISM:    mycobacteriophage L5
          (B) STRAIN:      not applicable
          (C) INDIVIDUAL ISOLATE:  L5
          (D) DEVELOPMENTAL STAGE: not applicable
          (E) HAPLOTYPE:      not applicable
          (F) TISSUE TYPE:    not applicable
          (G) CELL TYPE:      not applicable
          (H) CELL LINE:      not applicable
          (I) ORGANELLE:      not applicable (vii) IMMEDIATE SOURCE:    mycobacteriophage L5 particles (viii) POSITION IN GENOME: entire genome (ix) FEATURE:
          (A) NAME/KEY:
          (B) LOCATION:
          (C) IDENTIFICATION METHOD:
          (D) OTHER INFORMATION:
```

(x) PUBLICATION INFORMATION:
    (A) AUTHORS: Hatfull and Sarkis
    (B) TITLE: DNA Sequence, Structure and Gene
        Expression of Mycobacteriophage L5:
        A Phage System for Mycobacterial
        Genetics
    (C) JOURNAL: Molecular Microbiology
    (D) VOLUME: 7
    (F) PAGES: 395-405
    (G) DATE: 1993

(xi) SEQUENCE DESCRIPTION: SEQ ID NO: 1:

| | | | | | |
|---|---|---|---|---|---|
| GGTCGGTTAT | GCGGCCGAGC | CATCCTGTAC | GGGTTTCCAA | GTCGATCAGA | GGTAGGGGCC | 60 |
| GGCACAGAAA | CCACTCACAT | CAGGGCTGTG | CGCCTCCAGG | GCGCGTGAAC | TCCCACACCC | 120 |
| CGGTGTAGTT | ACATCCCGGA | ATTGTCTCAG | CGCCTCTCAG | GGCGCTTCTC | ATAAACAGTG | 180 |
| ATCTACGCCA | CTCCTGACGG | GTGGCTGTCA | AGGATACTCA | CCTTCCCTAC | TAATGAGGGG | 240 |
| CTAAGAGCCC | CTCTCTATAG | AGCGCCGCAC | AGGCGGCGCG | ATAAGAGCGC | CACCAGGCGC | 300 |
| TCATCTAAAG | ACCGGCCTTG | AAGGGCCGGT | CATAGAGATC | TATTCGATCC | GGCAACCGCC | 360 |
| GGATCTCAAG | GCCGCGCCAG | TGCGCGGCCC | TATAGAGGGG | TGACTCAACT | GTGCATGGCA | 420 |
| CTCGCTCGAG | TGCCCACTGG | AGCACTCAAC | CGGGGAAGTT | CGACGTTCTC | AACCTGCGAA | 480 |
| TGACGTTTGA | ATCGTCATCC | GCGTACGAAA | TCCCCGATCT | GCGGCCGACC | GACTTCGTGC | 540 |
| CGGCCTATCT | CGCGGCCTGG | AATATGCCGC | GTCACCGCGA | TTACGCCGCC | AAGAACGGCG | 600 |
| GCGCGCTGCA | CTTCTTCCTT | GACGATTACC | GGTTTGAGAC | CGCGTGGTCG | TCCCCCGAGC | 660 |
| GCCTTCTCGA | CCGCGTAAAG | CAGGTCGGCG | CTGCACTCAC | GCCGGATTTC | AGCCTCTGGA | 720 |
| CGAACATGCC | GAAGGCGGCG | CAGCTATGGA | ACGTCTACCG | CTCCCGCTGG | TGTGGCGCGT | 780 |
| ATTGGCAGTC | GGAAGGAATC | GAGGTGATTC | CGACGGCGTG | TTGGGCGACT | CCCGACACGT | 840 |
| TCGATTTCTG | TTTCGACGGG | ATCCCGATGG | GATCGACCGT | CGCAATTTCT | TCGATGGGCA | 900 |
| TTCGCTCTTC | AAAAGTCGAC | CAGGAGCTTT | TCCGGTACGG | ACTACGCGAA | CTCATCGATC | 960 |
| GCACTCAACC | GCAACTGCTT | TTGGCATATG | GCCAGCTTCG | GCATTGCGAC | GACATGGATT | 1020 |
| TACCAGAGGT | CCGCGAATAC | CCGACCTACT | GGGACAGACG | ACGAAAGTGG | GTAACTGCCG | 1080 |
| ATGGGAGGCC | GGGGAAGTAA | AGGCGGCCCC | GGTCCCGGAA | CCGGAGCACG | CAACCGCAGA | 1140 |
| GGCGCTGGAG | CCCCCGGATC | GGGCGGCGTA | GGCGGCGTCG | GAGGCGGGGG | TGGAGCTGCA | 1200 |
| GGGAGCAGCG | GAGGCGGCAA | GGGAACGGCA | GCGCCGGTAC | CGGAGGCGTC | ACCGGTGGCG | 1260 |
| GCGGAAGTGG | AGCCGGCGGC | GGTGGCAGCA | GCCCCAACAC | CCCGGTGCCC | CCCACCGAGC | 1320 |
| TGGAGAAGAA | GCGCGGCGAA | TACAACCAGA | TCGCCATCGA | CGCCCAGAAA | CAGCACGCGC | 1380 |
| CCACCGATGA | GAAGCGCGAG | GCCAAGCGCA | AGCAACTGAT | GGATCGAGTC | GGAGGAGACT | 1440 |
| GGCAGGCTTT | GGACCCGGAT | CACCACGACG | CCATCAAGGT | GGCGATGGAT | GACGCCATGC | 1500 |
| GGAAGATCCT | CTCCGAGGAG | GAGATCGTCC | ACCGCACCAA | GCACTTCGGC | GACCTACTCG | 1560 |
| ACTCCGGTCG | ACTCAAGTCG | CTGTTCGAGG | TCGGCTTCTC | AGCCGGTGGC | GACACCCCGA | 1620 |
| CCGAACGCGC | CCTCCTCGAG | GACGCCTGGT | TCGGCGCAGG | CAAGGTTCCC | CCGATCTACT | 1680 |
| CGGCAATCGA | GTTCAACGGC | GCTCCGACAG | CCGGCCTCGG | CATGTACGGC | GGCACCAAGC | 1740 |
| TCTACATGAA | GGACTCGGTC | AAGGACCGCG | TCACCGTGAC | CATCGGCGAC | TCGCTGATGT | 1800 |
| CGAGCTGGGA | CGTATTCCCC | GGCCGTCCTG | GCGACGGCGT | GGGGCTGTGG | GCCAGCCTGT | 1860 |
| CGAAGATCGA | GGGGCTGGTC | GATCCGAGCA | AGACCCGCGA | AGAGAACATG | CAGGCGGTGT | 1920 |
| ACGACTCGTT | CAAGAAGTAC | GGCACCCTGG | ACGGCTTCAT | CGAGGCGCAG | ATCCACGGCG | 1980 |

-continued

```
GCGTCCTGGT CGAGGACATC AAGAAGGTCG TGTTCACGCA GCCGCCGAGC CCGATCTTCA    2040
CCGATAAACT GGACGAACTT GGAATCCCGT GGGAGGTGCA GTAATGGCGC AGATGCAGGC    2100
GACACACACA ATCGAGGGGT TCCTGGCTGT CGAGGTGGCC CCTCGGGCGT TCGTCGCAGA    2160
GAACGGCCAC GTACTGACCC GGCTGTCGGC CACGAAGTGG GGCGGTGGCG AGGGTCTCGA    2220
GATCCTCAAC TACGAGGGTC CAGGGACCGT CGAGGTCTCC GACGAGAAGC TCGCCGAAGC    2280
CCAGCGGGCC AGCGAGGTCG AGGCTGAACT TCGCCGCGAG GTCGGCAAGG AGTGAGCTGG    2340
GCCGGCTCAG GCCGGCGACA GGAACTACCA GAGGACTGGG AGCTGAATTA CCGGCTCCCG    2400
GTCCTTTCTG CTGCCAACTG GCTTTGCCAG ATCAACGGTC CCGGATGCGT AAGGGCCGCA    2460
ACCGATGTCG ACCACATCAA GCGCGGGAAC GACCACAGCC GGTCCAATCT GCAGGCAGCC    2520
TGCCATGTCT GTCACGGCAA GAAATCAGCC GCCGAGGGCG TAGCCCGACG GCGGGAACTT    2580
AGAGCCCGGA GGAAGCGACC ACCCGAACGC CATCCTGGGC GTCGATAAGC GGGCCAGGTG    2640
CCCGCTCCAC CCAGGAGGTG AACAGTGGGC ACGCGAGGCC CAATCGGAAA ACGAGATGAA    2700
GAGCGGGTTC GTCGGAACAC CCCGGACAGT CCAACCGACA CGATCCAGAT GCCCGGTCTG    2760
GTGACGATCC CCGAGATGGG CGATCTAAGC CACGACGGCC GCACGCACCA GCTCGTCAAG    2820
GACATGTACG AGTCGATCAA GCAGTCGGCA GCCGTGAAGT ACTACGAGCC GACCGACTGG    2880
CAGATGGCCC GACTCGCCCT CTACACACTT AACCAGGAAC TCATCGCAGC CGAGAACAAC    2940
GGCAAGCCCG TGGGCGCGAT GAAGCTCACT GCCATCAACC AGATGCTCTC CGCGCTGCTG    3000
CTGACCGAAG GTGACCGACG CCGCGTCCGA CTCGAAGTCG AACGAGCACC CGCTGACCCG    3060
ACAGGCGGGA AGGTCGTTGA CGTGACCGAC GTGCTCAAGC AGCGCCTCGC CAAGGCGAGC    3120
GGCGGGAGCT GATGGTCCCC CGAGGGGTTT CTAGAGCCGC TGCCGCTACC AGCCGCTCCC    3180
CCTCGGGGTA GACATCGAAA GGAACCACAT GGCCGACCTC GGCAACCCAC TCGACCTCGA    3240
GATGCTCTGC CTGGTCACAG GCCGGGACTT CCGCTGGACC ATCGATTACC CGTGGGGTCC    3300
GGGAGAGCTG TTCCTCGAAC TCGAGACCGG CGGCGAACAC AACGCGCTGC ATCAGGTCTA    3360
TGTCACCGGG GCGACCGGAG GCACGTACAC GCTGAACGTC AACGGCACCA ACACCCCGGC    3420
CATCGACTAC AACGACGTGT CGGAGAATCC GCAGGGGCTG GCAGGCGACA TCCAAGACGC    3480
TCTGGACGCA GCCGTCGGAG CCGGAAACGC TGTCGTGCAT CCGGTCTCGC TGTTCCCTGC    3540
GTGGACACTG AACTTCAACC TCAACGCCAG CAAGCCGCTC ACCGAGCAGT TGGTCAACAC    3600
GATCAACAAG GCCGCGAACG ACTTCTTCGA CACGTTCGAC CAACTACTTG GGGTCGACGT    3660
GGAGATGACG GTCACCGACA CCCTGAACTT CAAGCTCAAG GTGACCTCGC GGCGCTCGTT    3720
CGATGAGGTC GGTGTCGTCA CGTTCGCGGT CGACGTGACC AGCCAGGCAG TCATCAACTT    3780
CTTCAACTCC GTCGCCGAAC TCACCGGAGC GGTGAACACC GTCAACGTCG ACTTCTACTG    3840
GAACCGGACG TATGACATCG AGTTCACCGG ATCCCTTGGG CTGCAGCCGA TTCCGGCTAC    3900
TACAGCCGAC ATCACCAACC TGGCGGGTAC CAGCAAGGCC GTCTCAGTCA CGGTGGTCGA    3960
GCCAGGAAAG AAGAGGCTGA CCATCTGGCC GTTCACGGTC AACGGTGAAA CCGCAACCAT    4020
CAAGGTCGAG TCCAAGAGG CCGACAAGAT CCCCAACCGC TGCCGCTGGC AGTTGGTTCA    4080
CATGCCGACC GGCGAGGCAG CCGGCGGCGA TGCAAAGCAG CTCGGCCGCG TTTACCGACA    4140
GCCGAGGTAA CACCGCACCC ATCAGAGATG GTGGGCCAGA CGGCCTTCGG GCCGTCCCCT    4200
GACGTGTAGC TCAATGGCAG AGCGCCCGAC TGTTAATCGG GTGGTTGAAG GTTCGAGTCC    4260
TTCCATGTCA GCGAGGGCTG AACCGGACCC GTGTCCGGTG TAGGCACTTT CCGCAGGCGG    4320
TTCCCCAGAG CGTGGGGAGC CCCTGCCCTG TACACGTAGC TCAATTGGTA GAGCAGCGGT    4380
```

```
CTCCAAAGCC GCCGGTTCCA GGTTCGACTC CTGGCGTGTA TGCACACACC CCTGACTCCT    4440

GCTAGCGGAG TGTTCGCCTT TCGGGCCTGG GGTCTTTTTC CCCGTTCGTC TAATCGGTAA    4500

GACACCCGGC TCTGGACCGG GCAATTGAGG TTCGAGTCCT TGGCGGGGAG CCAACTTGAC    4560

ATCCACCCGA AAGGAACAAC ATGACCTTCA CAGTCACCCG CGAGAGAGCG CAGTGGGTCC    4620

ACGACATGGC CCGCGCTCGC GACGGTCTCC CCTACGCGTA CGGCGGGGCG TTCACCAACA    4680

ACCCGAGGGT GTCGACTGAC TGCTCTGGCC TGGTGCTGCA GACCGGGGCT TGGTATGGAG    4740

GTCGCACCGA CTGGGTCGGA AACCGTTACG GCTCAACCGA ATCGTTCCGG CTCGACCACA    4800

AGATCGTCTA CGACCTAGGG TTCAAGCGGA TGCCCCGAGG CGGGCCAGCG GCCTTGCCGA    4860

TCAAGCCGGT GATGCTCGTC GGGCTCCAGC ACGGAGGCGG CGGGGTCTAC TCGCACACCG    4920

CTTGCACGTT GATGACGATG GACCACCCCG GTGGCCCGGT CAAGATGTCC GACCGAGGCG    4980

TCGACTGGGA GTCCCACGGC AACCGCAACG GCGTAGGCGT CGAACTTTAC GAGGGCGCAC    5040

GGGCATGGAA CGACCCTCTG TTCCATGACT TTTGGTACCT GGACGCAGTC CTCGAAGACG    5100

AAGGAGACGA TGACGAATTG GCTGACCCAG TTCTAGGGAA GATGATCCGC GAGATCCACG    5160

CGTGCCTGTT CAATCAGACC GCGTCGACCA GCGATCTGGC GACCCCTGGT GAAGGCGCTA    5220

TCTGGCAGCT ACACCAGAAG ATCCACTCGA TTGACGGCAT GCTCCACCCG ATCCACGCTG    5280

AGCGGCGCGC TCGCGCAGGC GATCTCGGTG AGCTGCACCG AATCGTGTTG GCCGCGAAGG    5340

GCTTGGGCGT GAAGCGCGAC GAGGTGACCA AGCGGGTCTA CCAGAGCATC CTCGCCGACA    5400

TCGAGCGGGA CAACCCCGAA GTACTTCAGC GATACATCGC AGAAAGAGGT GGCCTATGAG    5460

CCCCAAGATC CGACAGACCA TCTACCTGCT CGGCACCGCC GCCCCGGCAC TGCTGGGCAT    5520

CGTCCTGATC TGGGGCGGGC TCGACGCTGA GTCGGCGGCT GACCTCGGTG ACATCATTGC    5580

GGGCGTCGTG TCGATACTAG TCTCCGGTGC GCCGGCCGTA GCGGCAGGCA CCGTACGCAG    5640

CCAGCGCAAG GACGGCACGT TGTCCACCAG CCCCGGTGGAT CAGGTCACCA AGGGCGTCGA    5700

GCAGGTGCTC GCGGCCAGGC AGAGTGCCGA GGCTGAAGTC GCGAAGGTCA AGCAGGCGCT    5760

GGAGACCGCC GTCAGCGGTT CTCTCCCCCA GCTCGGCCCG CTGGCCACGC AGATCCTCAA    5820

CGTGGCTGAC GACACCGTCT GGCGTCCATG AGCAAGCCCT GGCTGTTCAC CGTCCACGGC    5880

ACAGGCCAGC CCGACCCGCT CGGGCCTGGT CTGCCTGCCG ATACCGCACG GGACGTACTT    5940

GACATCTACC GGTGGCAGCC CATCGGCAAC TACCCGGCAG CGGCGTTCCC GATGTGGCCG    6000

TCGGTCGAAA AGGGTGTCGC TGAGCTGATC CTGCAGATCG AGCTGAAGCT GGACGCAGAT    6060

CCGTACGCGG ACTTCGCGCT GGCCGGCTAC TCGCAGGGAG CCATCGTGGT GGGCCAGGTG    6120

CTCAAGCACC ACATCATCAA CCCGAGAGGT CGACTGCACC GGTTCCTGCA CCGGCTCAGG    6180

AAGGTCATCT TCTGGGGTAA TCCGATGCGG CAGAAGGGCT TTGCCCACAC CGACGAGTGG    6240

ATTCACCAGG TCGCTGCCTC GGACACGATG GGCATCCTCG AGGACCGACT GGAGAACCTC    6300

GAGCAGTACG GCTTTGAGGT CCGCGACTAC GCGCACGACG GCGACATGTA CGCCTCCATC    6360

AAGGAGGACA ACATGCACGA GTACGAGGTG GCCATTGGCC GAATCGTGAT GAGCGCTAGG    6420

CGATTCATCG GAGGTAAGGA CTCCGTCATC GCCCAGCTCA TCGAGCTTGG ACAGCGTCCG    6480

ATCTGGGAGG GAATCGCGAT GGCCAGAGCC ATCATCGACG CCCTCACGTT CTTCGCCAAG    6540

TCGACCCAAG GCCCGAGCTG GCCGCATTTG TACAACCGCT TCCCGGCGGT CGAGTTCCTA    6600

CGACGAATCT GAGAAAGGAG GCGGGGTGAG CCTCAACAAC CACCACCCGG AGCTTGCCCC    6660

GTCTCCCCCT CACATCATCG GCCCGTCCTG GCAGAAGACG GTCGATGGTG AGTGGTATCT    6720

GCCTGAGAAG ACCCTCGGCT GGGGAGTCCT GAAGTGGCTC TCCGAGTACG TGAATACCCC    6780
```

```
TGGCGGGCAT GACGATCCGA ACCGTCTGGC GACGTTGATC GCGCTCTCCG AGGCAGGTCT      6840

TCTCGACAAC GAGAACATGT TCATCCCCAC CGACGAGCAG GTACGCCTGG TCCTCTGGTG      6900

GTACGCAGTA GATGACCAGG GCCAGTACAT CTACCGCGAG GGCGTGATCC GCCGGCTCAA      6960

GGGCTGGGGC AAGGATCCGT TCACCGCCGC GCTCTGCTTG GCGGAACTCT GTGGCCCCGT      7020

AGCCTTTTCA CACTTCGACG CCGACGGTAA CCCGGTCGGC AAGCCGCGTT CAGCCGCGTG      7080

GATCACCGTC GCGGCCGTCA GCCAGGACCA GACGAAGAAC ACGTTCTCGC TGTTCCCGGT      7140

GATGATCAGC AAGAAGCTGA AGGCCGAGTA CGGCCTGGAC GTGAACCGCT TCATCATCTA      7200

CTCCGCAGCC GGTGGCCGTA TTGAGGCAGC GACCTCGAGC CCCGCGTCGA TGGAGGGTAA      7260

CCGCCCGACG TTCGTCGTCC AGAACGAGAC GCAGTGGTGG GGCCAAGGCC CCGACGGCAA      7320

GGTCAATGAA GGCCACGCGA TGGCAGAGGT CATCGAAGGC AACATGACCA AGGTCGAGGG      7380

CTCCCGCACC CTGTCGATCT GCAACGCCCA CATCCCCGGC ACCGAGACGG TCGCCGAGAA      7440

GGCATGGGAC GAGTACCAGA AGGTCCAGGC AGGCGACTCT GTCGACACCG GATGATGTA      7500

CGACGCGCTG GAAGCGCCGG CCGACACCCC GGTCTCCGAG ATCCCCCGC AGAAGGAGGA      7560

TCCCGAGGGA TTCGAGAAGG GCATCGAGAA GCTCCGCGAG GGCCTGCTCA TCGCCCGAGG      7620

CGACTCCACC TGGCTGCCGA TAGACGACAT CATCAAGTCG ATTCTGTCGA CCAAGAACCC      7680

GATCACCGAG TCGCGGCGCA AGTTCCTGAA TCAGGTAAAC GCCGCTGAGG ACTCGTGGCT      7740

CTCACCGCAG GAATGGAACC GGTGCCAGGT CGACCTGGCC AAGTACCTGG ATAAGCACGG      7800

CAGGGAGTTC GCTCCGCTGC AGCGCGGTGA CCGGATCACC CTCGGGTTCG ACGGGTCGAA      7860

GTCCAACGAC TGGACCGCGC TCGTCGGCTG CCGTGTCAGC GACGGCCTGC TGTTCGTCAT      7920

CGACATCTGG GATCCCAGA AGTACGGCGG GGAGGTTCCC CGCGAAGACG TTGACGCCAA      7980

GGTCCATTCG GCGTTCGCCC ACTACGACGT GGTGGCGTTC CGCGCCGACG TGAAGGAGTT      8040

CGAGGCGTAC GTCGACCAGT GGGGCCGGAC CTACAAGAAG AAGCTCAAGG TCAACGCCAG      8100

CCCGAACAAC CCGGTGGCGT TCGACATGCG CGGACAGCAG AAGAGGTTCG CGTTCGACTG      8160

CGAGCGACTC GAGGACGCGG TCCTTGAGGG CGAGGTCTGG CACGACGGCA ATCCCGTTCT      8220

GCGCCAACAC GTTCTGAACG CCAAACGACA CCCAACGAAC TACGACGCCA TCGCGATTCG      8280

CAAGGTCACG AAGGACTCCA GCAAGAAAAT CGACGCTGCA GTCTGCGCTG TCCTCGCGTT      8340

CGGGGCGAGA CAGGACTACC TCATGAGCAA GAAGGCCCGT AGCGGCCGGG TGGTGATGGT      8400

TCGATGACAG CACCGCTCCC CGGTATGGAG GAGATCGAAG ACCCCGCAGT CGTACGAGAA      8460

GAGATGATCT CGGCCTTCGA GGATGCTTCC AAGGATCTCG CCAGCAACAC CAGCTACTAC      8520

GACGCTGAGC GCCGGCCAGA GGCCATCGGC GTCACCGTCC CGAGAGAGAT GCAGCAACTG      8580

CTGGCTCACG TCGGATACCC CAGGCTCTAC GTCGACTCAG TCGCCGAGCG CCAGGCCGTC      8640

GAGGGTTTCC GCCTCGGCGA TGCCGACGAG GCTGACGAAG AGCTGTGGCA GTGGTGGCAG      8700

GCCAACAACC TCGACATCGA GGCACCACTG GGCTACACCG ACGCTTACGT TCACGGCCGG      8760

TCGTTCATCA CGATCAGCAA GCCAGACCCG CAGCTCGACC TGGGTTGGGA TCAGAACGTC      8820

CCGATCATCC GCGTCGAGCC GCCCACCCGA ATGCACGCCG AGATCGACCC CCGGATCAAC      8880

CGGGTGTCCA AGGCCATCCG AGTCGCATAT GACAAGGAGG GCAACGAGAT TCAGGCTGCC      8940

ACGCTGTACA CGCCGATGGA GACCATCGGC TGGTTCCGCG CTGACGGTGA GTGGGCTGAG      9000

TGGTTCAACG TCCCGCACGG TCTGGGCGTC GTTCCCGTTG TGCCGCTTCC GAACCGGACC      9060

CGGCTCTCGG ACCTGTACGG CACCAGTGAG ATCACGCCCG AGCTTCGGTC GATGACCGAC      9120

GCGGCGGCGC GCATCCTCAT GTTGATGCAG GCGACCGCCG AGCTGATGGG TGTCCCCCAG      9180
```

-continued

```
CGCCTGATCT TCGGCATCAA GCCCGAAGAG ATCGGCGTCG ACTCCGAGAC CGGCCAGACG    9240
CTGTTCGATG CGTACCTGGC CCGGATCCTG GCGTTCGAGG ACGCTGAGGG CAAGATCCAG    9300
CAGTTCTCTG CAGCCGAGCT GGCCAACTTC ACCAACGCGC TCGATCAGAT CGCCAAACAG    9360
GTCGCTGCGT ACACGGGATT GCCTCCCCAG TACCTGAGTA CCGCCGCAGA CAATCCGGCC    9420
TCCGCTGAGG CGATCAGGGC CGCTGAGAGC CGACTCATCA AGAAGGTCGA GCGGAAGAAC    9480
CTGATGTTCG GCGGCGCATG GAAGAGGCC ATGCGGATCG CCTACCGGAT CATGAAGGGC     9540
GGCGACGTTC CCCCGGACAT GCTCCGCATG GAGACCGTCT GGCGAGACCC GAGCACTCCC    9600
ACCTACGCGG CCAAGGCCGA CGCAGCCACG AAGCTGTACG GCAACGGCCA GGGTGTCATC    9660
CCGCGTGAAC GTGCTCGCAT CGACATGGGC TACTCCGTCA AGGAGCGCGA AGAGATGCGC    9720
CGATGGGACG AGGAAGAGGC CGCAATGGGT CTCGGCCTGT TGGGCACGAT GGTCGACGCC    9780
GACCCGACGG TCCAGGCTC CCCGAGCCCC ACGGCACCGC CGAAGCCACA GCCGGCCATC     9840
GAGTCGTCTG GTGGTGATGC GTGACCGCAG AGGAGTACGC GGCGGCTCAA GCCGCGATCA    9900
CTGCGGGTCT TGCCACATAC GTCCAGAGGT TCGCTTCGCT CTTCGTCGGT CCAGCTCTCG    9960
CTGTAGGTGA GTGGCTGCGA CTGCTGCAGG TGCTGTTCCC CGAAATCCAA CGGCGGTATG   10020
CAGATGCTGC CGCCTTGGGC AGGGACTTCT ACGACTCCCA ACGCGCACTA CACCACCCAG   10080
AGCTGCCCCG GAACGAGAGG TTCCGGGGAG AGCTTCGGTG GGAGTGGTTC GTCCAGAACA   10140
TGGAGCCCGC TCGAAAAGAG ATGTCGCAGG CCGACTCTCC GCCGAGTGCG ACCTCTAAGT   10200
TGGCTCTGGC CGCAGTTCGC GAAGTGGAGA TGGCAGCACG CCGACAGATC ATCGGCGCTG   10260
TCAAGAACGA TCCGGCCCCG CAGATCGTGC AGGGCTGGGC GAGGGTCGCC ACCGGGCGCG   10320
AAACATGCGC CTGGTGTCTG ATGCTCATCT CACGGGGTGC CGAGCTGAAT CACAAGGGCA   10380
ACTTCGCCTA CAGCTCAGCG GAAGCCGCAG GGCTCAACCT CGATGACGAG ACCGTGATCG   10440
ACCTCTGGAA CGAGTCCGGT CACGACCTTG AGAAGTTCCG CGAGGAGACC AGAGAGGACT   10500
TCGAGAAGTG GCACGCAGGG TGCGACTGTC TGGTGGTCCC GGTCTTCGAT GTGCAGAACT   10560
GGCCCGGAAG AGACGCTGCC CTACGGGCGC AGCAACTTTG GATCGAAGCC AGCGACGAAG   10620
CTGACGACCT CATTGCGTCA GGCAAGGCCC GCTCCAAGAA CAAGAACACG GAGACGCTCA   10680
ACGCGCTCCG ACGCCGCCTA GCACGCGGCG AAATCACCAT GTCCAACTAC GCCCTCGCTG   10740
CGTAGTCCCT CGAACCCCAG GTGGGTTCTC TCAACATGCC CAGGAGGCGA AAACACATGT   10800
CCGACAACCC CACTCCCGAG AGCACCCCAG AGGCCGAGAC CCCGGAGGTC GAGAAGCCGA   10860
TGGAACCGCA GGGCAAGGTC TTCGATGAAG CGTACGTTCA GTCGCTTCGC CAGGAGGCTG   10920
CAGCCGCTCG GGTGGCGAAG AAGGACGCCG TAGAAGCGGC AGAGGCTCGA GTGAAGGCCG   10980
AGTACGAGGC CAAGCTCGCT GAGCGCGACA CCGCTTACAC CGAACTGCAG AACCAGTTGG   11040
GACAGGCGTG GATTGAGCTG GAGAAGGTCT ACCTCTCTCT CGACGCCAAG GTGCCCAACG   11100
ACAAGGTTCG GGCGTTTGTC GAGATCCTCG AAGGCAACGA CAGGGACAGC ATCGCTGAGT   11160
CAGTGAAGTC CCGTCTGGAG CTGGTCGGCG GATTCGGCAA CAAGACCCCG AGTCCTGCGT   11220
TCGACCCGTC TCAGGGTCGC GGCGGTAAGC CGCCGATCCC GCTGAACGGT GACCCGATCC   11280
TCGAGGCCAT CAAGGCCGCT GTCGGGATCA AGAAGTAACC CACCCAACAG ATCTCAAGGA   11340
GAGATAAACA ATGGCAGTCA ACCCTGACCG CACCACGCCG TTCCTCGGCG TGAACGACCC   11400
CAAGGTCGCG CAGACCGGCG ACTCGATGTT CGAGGGCTAC CTCGAGCCCG AGCAGGCCCA   11460
GGACTACTTC GCCGAAGCGG AGAAGATCTC CATCGTCCAG CAGTTCGCCC AGAAGATCCC   11520
GATGGGCACG ACCGGCCAGA AGATCCCGCA CTGGACCGGC GACGTGAGTG CGTCGTGGAT   11580
```

-continued

```
CGGTGAAGGC GACATGAAGC CCATCACCAA GGGCAACATG ACCTCGCAGA CCATCGCCCC      11640

CCACAAGATC GCGACGATCT TCGTGGCCTC GGCGGAAACC GTCCGTGCGA ACCCGGCCAA      11700

CTACCTGGGC ACCATGCGGA CCAAGGTCGC GACCGCCTTC GCGATGGCGT TCGACAACGC      11760

CGCGATCAAC GGCACCGACA GCCCGTTCCC GACCTTCCTA GCGCAGACCA CCAAGGAGGT      11820

CTCGCTGGTG GACCCGGACG GCACCGGCTC CAACGCCGAC CTCACCGTCT ACGACGCGGT      11880

CGCCGTCAAC GCCCTGTCGC TGTTGGTCAA TGCCGGCAAG AAGTGGACCC ACACTCTGCT      11940

GGACGACATC ACCGAGCCGA TCCTCAACGG CGCGAAGGAC AAGAGCGGTC GCCCGCTGTT      12000

CATCGAGTCG ACCTACACCG AGGAGAACAG CCCGTTCCGC CTCGGTCGGA TTGTGGCCCG      12060

TCCGACCATC CTGAGCGACC ACGTCGCCTC GGGCACGGTC GTCGGCTACC AGGGTGACTT      12120

CCGCCAGCTC GTCTGGGGCC AGGTCGGCGG CCTGTCCTTC GACGTGACGG ATCAGGCGAC      12180

TCTGAACCTG GCACCCCCC AGGCTCCGAA CTTCGTCTCG CTGTGGCAGC ACAACCTCGT      12240

CGCAGTCCGA GTCGAGGCCG AGTACGCCTT CCACTGCAAC GACAAGGACG CGTTCGTCAA      12300

GCTCACGAAC GTGGACGCCA CCGAAGCCTG ATCCAGGCTT GACATCCACC GGGAGGGGGC      12360

TCCTTCGGGA GCCCTCTCCT GATGTGGAGC AGGAAGGACC ACATGCGAAT CCAGTCCACC      12420

CTCAACGGCG GTTTCGCCGA GGTTTCCGAG GAGTTCGCCA AGCAGTTGAT CGCCACTGGC      12480

GGCTGGAAGG TGCCCCGGAA ACCGCGCAAC ACCAAGACCA AGACCGCTCC TGAGGAGCCC      12540

AAGAACGAGG AGTAACCCGT GGCCTACGCG ACCGCCAAG ACGTTGTGAC GTTGTGGGCC       12600

AAGGAGCCTG AGCCCGAAGT GATGGCGCTG ATCGAGCGCC GGCTCCAGCA GATCGAGCGC      12660

ATGATCAAGC GCCGGATCCC CGACCTGGAC GTGAAAGCCG CTGCGTCGGC GACGTTCCGG      12720

GCCGATCTGA TCGACATCGA AGCTGATGCT GTTCTGCGCC TCGTGCGTAA CCCGGAGGGC      12780

TACCTCTCGG AGACCGACGG TGCGTACACC TATCAGCTCC AGGCCGACCT GTCGCAAGGC      12840

AAGCTCACCA TCCTCGATGA GGAGTGGGAG ATCCTCGGGG TCAACTCCCA GAAGCGCATG      12900

GCGGTCATCG TCCCGAACGT GGTGATGCCG ACGTGAGCGC GAGCGACCGA CACCGCGCCC      12960

CGATTGTCTA TCCGCCTGGC ACTCAGGCGG TTACGCCGGA TCGGGTCAAC GCGTTTGACT      13020

GCGATCACGA AGCTGATCCT CCGGTGTGCC GGTGCGTCCA CGACTGGCGC ATCGAGTGGG      13080

GAAACGTCAA GAAGGCCACC GCCAGATCAC GGTCGGCGGT GCTCTGATGA GCCTCCTCGA      13140

CACCGGTGCC CGGTACCAGA CCTGCATCGT CTACCCCGAA GAGATGGTCA TCGACTCCGA      13200

TGGCAACAAG CGGACCAGGC CGTCGAATAC CGGCATCCCG GCCATCGCAC GGTTCCAGGT      13260

AGCCAACCAG TCTGGTACGT CGGCACGACG TGCTGAGCAG GACAACGAGG GGTTCGAGAC      13320

CGAGAAGGTC TACCGGATGC GGTTTCCCCG CTCGTTCACC AAGGAGCACG GCATCCTCGG      13380

GGCCCAGTCC CAGATCGAGT GGCGAGACCA GCGGTGGGCG CTCTTCGGAG ACGCCACCGT      13440

CTACGACTCA TCCCCTGCGT TGGCGCGGGT CGACTACACG ATCAAGAGGT ACTGATGGCC      13500

AAGGTCTACG CGAACGCGAA CAAGGTCGCG GCCCGGTACG TCGAGACGAG GGACGCCGTC      13560

CGAGACGAGC GGAACAAGGT CACCCGTCGA GCCAAAGCCA ATCTGGCGCG GCAGAACTCG      13620

ACCACCCGCA TCACCGACGA GGGCTACTTC CCGGCCACCA TCACCGAGCA AGACGGCGAT      13680

GTCGACTTCC ACACGATCCT CAACGCGCCC AACGCGTTGG CGCTTGAGTT CGGCCACGCG      13740

CCGTCTGGCT TCTTCGCTGG CACCGACACG AAACCACCGG AGGCCACTTA CATCCTCACC      13800

CGAGCCGCCA TCGGCGGCAC CGTCTCATAA GGAGGTCACA TGGCGCGAAT GCCTCGCGTC      13860

CAGGCAGTAG CGGCCCCGAT CCTCCGGTCA GACCCCCGAC TGGAGGGAGT GACGGTCACG      13920

ACATGGGTTC CAGACGTGGA CTTCCGAGAG TTCCCGATGA TCAACCTCCG CCGCATAGGC      13980
```

-continued

```
GGGACGAGGA ACCCCAACGC ACCGACGCTG CACACGCTGC CGGTGGTCGA AATGACCGCC    14040

TACACCAGAG ACGGTCTCAT CGAGACTGAG GAGCTGTACG AGACCGCGCT AGAGGTTCTC    14100

TACGACGCGG TGGAGAACGG AACACAAACT CCCGCAGGGT ATTTGACCTC CATCTTCGAG    14160

ACGATGGGCG CCACTCAGTT CAGCTCCCTC TACCAGGACT CCTGGCGCAT CCAGGGTCTG    14220

ATCAGGCTCG GCGTCCGCAG ACCGAGAACC ACCCTCTAAC CGAAAGGTAA AGCCACATGG    14280

CTGAAAACGA CGACGCAGTG TTGACTGCGG CGGTCGGCTA CGTGTACGTC GGTGCTGCAG    14340

GCACCGCTGC TCCTACGCCG GCCTTGCTCA AGACCATCGA CCTCAGCAAG CCCGAGACCT    14400

GGACCGGTGC TACCGGTTGG ACGAGCGTCG GCCACACCAG CCGAGGCACG CTCCCTGAGT    14460

TCGGCTTCGA AGGCGGCGAG TCCGAGGTCA AGGGCTCCTG GCAGAAGAAG AAGCTCCGCG    14520

AGATCACCAC CGAGGATCCC ATCGACTACG TCACGGTCCT ACTGCACCAG TTCGATGAGC    14580

AGTCGCTGGG TCTGTACTAC GGCCCCAACG CCTCTGAGAC TCCTGGTGTG TTCGGTGTGA    14640

AGACCGGCCA GACCAACGAG AAGGCCGTGC TGGTCGTGAT CGAAGACGGC GACATGCGCC    14700

TGGGCATCA CGCCCACAAG GCTGGAGTTC GCCGCGACGA CGCGATTGAG CTGCCCATCG    14760

ATGACCTGGC TGCGCTGCCC GTCCGGTTCA CCTACCTGGA CCACGAAGAC GAGCTGCCGT    14820

TCTCCTGGAT CAACGAAGAC CTCTTCAACG TGCCCGAGGT TCCCGAGGGC TGATCCCAAC    14880

TTGACAGCCA CCCGGCTGTC TACCCCGGAG GGGGAGGTTT CCTTGGCGGG CCTGGCCTCC    14940

CCCTCCTCCC GCCACTCACA GACCCGCCGA CACTGAAAGG TTCGCCATGA CAAACGTATT    15000

CACCATCGAC GCATTCCGCG AAGAGGTCAA GAAGAAGTAC GCTCCGGTCC TCATCGGCCT    15060

GTCCGACGAT GTGACCGTCG AGCTGAAGCC GCTGCTGAAG CTGGGCCAGA AGGCCCGCGA    15120

AGCGGTGGTC GAGGTGTTCA AGGAGTTCGC GGACATCCCC GACCTCGAAG AGGACGACGA    15180

CGACGAGTTG GTCGATGAGT ACTCGCTCCA GGTCTGCGAC ATCATCGCCA AGGCGTTCCG    15240

GCTGATCGCC ACGAAGCCCA AGAAGCTGAT CGCCGCCTTG GACGAGGAGC CGGATCCCCG    15300

TATCCGCGCA GAGCTGTATG CAGCGGTACT CAACACCTGG AAGCGAGAGA CGCAACTGGG    15360

GGAAGCCGCG CCCTCGCCGA GCTGATCGAC AAGTTCGGCG GGCGATCCT CGCAGACCTG    15420

CTCCAGTACT ACCGGGTAGA CCTGCGCGAC CTGTTCCGCG ACGAGGATCC GCTTTCGCCG    15480

AGATTCGTTC TGTCCCTGGT GCTCTGCCTT CCCAAAGACG GCGCGTTCTA CGCAGAACGT    15540

CGTGGTGGGC AGCAGTACCG GGCTGGACC GAGGACCGCT ACGCGCTCGC GGACATCTAC    15600

GACGCCATCC AGGCGGGCAA CCACATCCTG CTGCTGGCGA ATCGTGATCC GAAGAAGCCA    15660

AAGCCCAAGG CACCCAAGTC ATACCCGCGT CCCGACGACC TAGAGAAGAC CACACCGAAG    15720

CCGGGTTCGT TCGCCGCAAT GGTCGTGCGA GCGAAGAAGG CGGCTCGAGA GAGAAGGGAA    15780

AGGGAGGAGG AGAGTGCCGA ATAGTGCTGG CGTAGAAGTC GCCCGGATCT CGGTCAAGGT    15840

CAGCCCGAAC ACCAAGGAGT TCCGCCGGGA ACTCAAGACC GAACTCGAGA AGATCGAGCG    15900

GGAGCTTAAG GGCGATGTCG AGATCAACGG TCATCTCGAT GCGGCCCAGG CCAAGGCCGA    15960

CTTCAAGCGC ATGATGATGC AGCTCAAGAC CGAAGCTGCC AAGGGCGTTC ACGTCCCGGT    16020

CGACGTAACC GTCGACAAGA AGAGCAAGAA GGGAGGTCTC CTCGGAGGTC TCCTCGGCGG    16080

CAGCCGGGGG CTCGGAGATC TAGGCGATGA CGCCGAGAAG GCGTCGTCTC AAGTACAACA    16140

CCTTGGCAAG TCGTTCCTGG GCCTCACACG AGCCGCCTGG ATAGGCGTAG GCATCGTCGC    16200

CGTAGCAGCT CCGCTGGTCG GCATCGTGGC CGGTCTGCTG GCCGGTCTGC CGTCGCTGCT    16260

GTCTGCGTTC GGAGCCGGCG CTGGCGTAGT CGCGCTCGGC ATGGACGGCA TCAAGGCAGC    16320

CGCCTCGACG CTGGCCCCGA CGCTGGAGAC GGTCAAGGCC GCTGTCTCCT CGACGTTCCA    16380
```

```
GCAGGGACTC ACCCCGGTGT TCCAGCAGCT CGGCCCGATG CTGACCGCGA TCACCCCCAA    16440

CCTGCAGAAC GTGGCCTCGG GCCTCGTGAA CATGGCCGGG TCGATCACCG ACGTGATCAC    16500

CCAGGCTCCT GGTCTGCAGC AGATCCAGAA CATCCTCACC AAGACCGGAG AGTTCTTCAC    16560

GGGCCTCGGC CCTGTGCTCG CTACCGGCAC GCAGGCGTTC CTGACGCTGT CCAACGCCGG    16620

CGCGAACTCG TTCGGCACGC TCCTGGCTCC CCTGCAGGAG TTCACCAACG GCTTCAACGA    16680

CATGGTCAAC CGAGTCACGT CCAACGGCGT GTTCGAGGGT GCCATGCAAG GGCTTTCGCA    16740

GACGCTGGGC AGCGTCCTCA ACCTGTTCAA CCGGCTCATG GAGTCCGGTC TGCAGGCGAT    16800

GGGACAGCTC GGCGGTCCGC TGTCGACGTT CATCAACGGG TTCGGAGATC TCTTCGTCTC    16860

GCTGATGCCG GCGCTGACTT CGGTCTCTGG TCTGATCGGC AACGTCCTCG GGACGCTGGG    16920

CACACAGCTC GCTCCCATCG TCACGGCGCT CACGCCGGCC TTCCAGACGC TGGCGAGCAC    16980

GCTCGGCACG ATGCTCACCG GAGCCCTCCA AGCTCTGGGT CCGATCCTGA CTCAGGTCGC    17040

TACGTTGATC GGCACGACGC TGAACACGGC GCTGCAGGCT CTCCAGCCGA TGCTGCCGTC    17100

GCTCATGCAG AGCTTCCAGC AGATCTCCGA CGTACTGGTG ACCAGTCTGG CCCCGCACAT    17160

CCCGGCGCTG GCGACGGCCC TCGGCCAGGT CGCAGGCGCG GTGCTGCAGC TCGCTCCGAC    17220

GATCATCTCG ACGTTGGTTC CGGCGTTCGT TCAGTTGGTC CCAAAGGTCG CTGAGCTAGT    17280

TCCGACCATC GTCAACCTGG TCCAGTCGTT CGCCAACCTG ATGCCGGTGG TTCTGCCCCT    17340

GGCGCAGGCT CTGGTCAGCG TTGCTGGCGC GGTGATTCAG GTGGGTGTCT CCATCGGCGG    17400

CGCGCTCATC GGCGCGCTGG CGAACCTCAC GGAGATCATC TCCAACGTCA TCAAGAAGGT    17460

GTCCGAGTGG GTCAGCAGCT TCTCCAGCGG AGCCCAGCAG ATCGCTGCGA AGGCAGCGGA    17520

ACTGCCGGGG ATGATCCAGT CGGCTCTCGC CAACCTGATG GCCATCGGCC TGCAGGCCGG    17580

TAAGGATCTC GTCCAGGGCC TGATCAACGG CATCGGCGGG ATGGTCAGCG CAGCGGTCAA    17640

CAAGGCCAAG GAGCTGGCGT CCAGCGTGGC TGGTGCAGTG AAGGGCTTCC TGGGCATCGA    17700

GTCCCCGTCG AAGTTGTTCA CCGAGTACGG CCAGTTCACC GCCGAGGGAT TCGGCAACGG    17760

CATGGAGGCA GGGTTCAAGC CCGTCATCGA ACGGGCCAAG GATCTCGCGG CTGAGCTGTC    17820

CAGGGCGATG GAGTCGGGCA CCGACCCCTC CGGGATTCTC GCTGGGCTGG ATCAGAATGA    17880

GCTGAAGCAG ATGCTGGCGG CTCTCGAAGA GGAGCGCAAG CGACTCAAGG TCGAGAAGAA    17940

CGGTATCCCC AAGGGAGACA AGGCAGGCCG AGAGGCGCTG CAGAACCAGC TCGACCAGAT    18000

CCAGGCGCAG AAGGACATCC TGTCCTACCA GCGTGACCGC ATCAAGAACG AGTCTGAGTA    18060

CGGCGACATG GCCGGCGAAG ACCCGTTGGT GAAGGCAGCC TCCGGGCTGA TGAGCGCACC    18120

GGTCGACTTC GCGAAAGCGA CTGGCAAGCA GTTCCTTTCG GACATCGGCA TCAGCGGAGA    18180

TGGGTTCATC TCGAAGGCCA TCACCGAGGG CATCCAGTAC ATCTTCCAGA TCGGCTCTGT    18240

CGATGAGGCG CTGTCGATCA AGGACCGCGA GGAGTCGAAG AACGCGCTGT CCGTCGTTGG    18300

CCGCTGACTT GACATCCACC AGGAGGTAAG CATTGATCAC CGACACCATC GTTGAACTCG    18360

AGGGTGTCAA TGGTGAGCGT TTCAACTTGA CGACCGGTGA CCAGGGTGTG TACCTGGCCA    18420

CAGACGTGGA GGGTTGTTTC TACGACCCTC CCGTCAAGGT CGTTGTTGAA GAGCCGGGGA    18480

ACTACCCCGG CGCTCGCTAC TTGTCCCACC GAGCCCTGAA GCGAGACATC GTCTTTGGGG    18540

TCGTCATCCT CAACGACGCG AAGCAGGGGC CGCGCTCCTG GCTGTCGCGA GACTCCGAGT    18600

GGCGCAAGGC GTGGGCGTTC AACCGCACCT GCAAGCTCTA CGTCACCACC CCGGACTCCG    18660

GTACCCGCTA CCTGAAGCTG GCGCTGTTCG AGTCCCCCAC CGTCAAGATG GACACCGACC    18720

CAAGAGGTAA ACCCCTTGAG GTCACGGTGA TGTCGTGCAT CGCGTACGAC CCGTTCTGGT    18780
```

-continued

```
ACGAGGACGA CAAGGTCTTC TCGGCCAAGA CCAAGACCGA CACCCGGTTC GACCCGTCGT  18840

TCTGGACGCC GCCGTGGCCG TGGGAGGAAC TGCCCAAGGA GACGCTGCGG ATCAAGGTCG  18900

GCCGCGAGCA GGGTGGGCTA AACCCCACCG ACCAGTACAT CTTCCCGAAG TGGACCGTTC  18960

CCGGCTCCAC CGAGAAGGTG CCGAACTTCC CCTGGCCGTT CCCCCCGAAC GTCCCGATCC  19020

CGTGGGAGAC AGCACCGTTC ACTCAGTTCG TCATCCCGGA CTACTCGTTC GAGGATGAGG  19080

AGTTCCGCAA CCGCCGGCTC AAGACGCCGG GGTTGATCTA CGGCGAGAAC TGCGTCATCG  19140

ACACCGACCG GCGCGAGGAG CAGATCGCTT CCGAGTCGGG CTCCCCGGTG TGGGCTCGGA  19200

TGAACGGTGT CCGGTTCCGC AACTCGATCC CGCCCTACAC CGAAGAGGCT GAGTTCGTCA  19260

TAGACGCATC GGGATGCGCT CCGGGACAGG TAGTTACCCT CCGGCTCACG AGGCCGTGGT  19320

CGCGCTGCTG GGGGCTAGAG TGAGTGGTCT GACGAGCGTT CGTGAGGCCG AAGATCTCTG  19380

GCAGAAGATC CAATTGCGGC GCTGCAAGCG CGAGCAGGAA CGGCTCAAGC ATCCCGACGT  19440

AGAGCTGCGC GATGGCGACT TCCGCCTGCG CGGCCTGGTC GCTGGCGAGC GGGTGCTCGA  19500

GTGGGAGTTC ATCGAGAACG AGACTGGCAC CTGCACCTTG CAGCTCTCAC TGAGCCATTA  19560

CCTGGCGAAG TGGGTGATGG ACCACCGGGG TCGAGCAAAG CGCAACGTCA TCATCAACAT  19620

CGAGAAGCAA GGCGCTCGAT GGACCGGGAT GATGGACCAC TACCGGGTCA TCAAGACCGA  19680

CGCAGGGGAC GCCTACATCG AGATCGTGTT TTTGCACGAC TTCGAGCAGA CCAAGCATAT  19740

CCGGGTATGG TGCAACCCGT TCCTACGCCC CGAGCTGCAG TTCCCCAAGG TGTGGATCAT  19800

CTTCGGGCCG GCCAAGTGGT GTTTGCTGGT GACACTGTTC GTCAACCTGC TCAGGCTCGA  19860

GACGAGCTTG TGGACGCTGC CTGATGACCC CACGGACATC AACGAGTGGA TGGGTCCGAG  19920

CTTCAACCCA GCAAATTGGC GGAACATCGT CAAGCCGTTC CCGTTCCTGG CCGACAACTC  19980

ACCGGTCACG ATGGTGTTCA GCCGGTTCGG GACGTTCTAC GACACCGCCA AGAAGATCCT  20040

CGAAGACCAT CAGCTCACGC TGACGTGTCG TCGGTACATC AAGGACCGCG ACCCGCATCC  20100

GTTCGAAGAT CTCAAGGGGC TCTGGGGAAT TGATCCTGTC GAAGACCTGC TGCAGAAGAT  20160

CCCGCTCCGG GACGGCTGCG TGGTCTGGGA CATCGAGGAC AACTCAGGTT GGGGCACTCA  20220

GACCGCGTTC GGCGGTTCGT GGCTGACCGG GTTCGTCCGA GGGATGGTCC AACTGGCCGG  20280

CGACGGCCAG GTCGAGGGCG TCGATGTGTT CACCGGGGAC TACACGTTCC CAGGCGAGTA  20340

CTACTCCCCC TGGTTCATGG GCACCAGCCC GATAGCACCC CACGTCGTGT TCGAAGAAGG  20400

ACCGCTGACC GGGATCAAGT CGTCGGAGTT CTCGTACTAC GAGGCCACCG ACACCAGCTT  20460

CCTGGCTGGT GGACAGAGCG CACCTGGCAT CAACGAGGGC ATCTCGGCCC TGGTGAACAT  20520

CGGTGGCGAC CTGCTGACCT CGTTCATCAA CAGCCAGCTC GCCGCGCTCG GCGCGGTCGG  20580

TGGAGCGATT GACCTCCCGC CTCTGGGCGG TCTGCTCGAT GCGGTGTTGC AGCCTCTGTA  20640

CTCCGATGTG TTCGGCGCGT TCATGGAAGT TCCGACTCTG CGTGCGATGG CATCTCGCT  20700

CCCGATCTCC GGGCTCGAGG ACATCGTCAC CGGACTGGGC GACTTCCACT ACTTCGAGAA  20760

CATGGCCGAC GGGGCGATGA AGGCGTTCAC GCTGTCAGCG TTCGCAGCCA TCGCATCGCA  20820

GATCCACAAG ACGAGGGCTC GAACGACCCA CACCCTCAAG GTGTCTGACG CCGCTCCGTA  20880

CATCTTCGCG CCAAAGCCCT ACGGGCACTG CTGGATCGGA GATCGCGTCG GCACGTCGGT  20940

CCTCGGCTAC CCGGTCGAGC ACCAGTTGTT CGTGGAGCGC ATCCGCAAGG TGAAGTACCG  21000

CATCGACAAA GACGGCATGA AGCCGTTGGA GATCGAGATC GGTTACCGCG AACCGAAGAA  21060

CCCAGCACTA CACATCCTCG AAGAGATCAA GCGCGTCAAC GGCGCTCTTG GCACTGCGGG  21120

GATTCTCTAA ACCGAAAGGC ACGCCGCATG ATTCCCTCAC AAGAGTCTCA CAATCCGAAC  21180
```

```
                                                           -continued

GACCCGCGAC AGCACGTCAT GTGGGCGCTA CGCAATCTCC CGATGATTGC TGGCGTCGGG    21240

GCGATCACGC ATCCGGGTTA CCTGGCGGAT TGGTCAGAGC ACTTGTGGAA GTGCGGCTTT    21300

CGGCACGTCG ACTGGCTCCG GGAGCTGGCT GATGAGGACG GCAACATCCA CGTCAGTCAG    21360

CTTCCTGACC AGGAGATCAA GTTTCAGCAG CCCTTCCGGG GCCAGCGAAG CGACTACAAC    21420

AACGCAGCTC GATGGGTCGG CAAAGACGAT CCTGACCCAG AGCCCGTGCG TATTCCAGAC    21480

ATTCGCAAGC TCACAGACCA GGAGAACAGA GCGATGATCG CGCAGTACGA ACGAGACGGT    21540

TGGATCAAGG ATGGATCCCC CGGCCCAGCG ATAGCCGAGG TCGTGGAGTG ACCCCGTTCA    21600

ACCCAGACTC CATAGGCGAC TACGTGACAC TGCTCGGCGT TGCGTTCCTG ACCTTCTCGG    21660

TTCCCGCATG GTTCACCGGA CGAGCACGCA AGCACAGCAG TGACATCGGC GAAATCAAGG    21720

AACAGGTATG TAACACCCAC GACACGAACC TGCGCGATGA CCTCGACAGC GTCAAGGCAG    21780

ACATCAGCGA CTTGAAAGAG ATTGTGTTGC AAGGGTTCCA CCAGGTGAAC GAGTCGATCA    21840

ACCTCGAGCG CCGTGAGCGG ATCGAAGGAG ACCGCCGAAA GGAGGTTGCG TGACCTACCC    21900

CACCAACCCA CTAGAGGCCA TCGGCGCTGA CGGCGCATTC GAGATCGGTG GGGCGACTG     21960

GAGCTTCGGC CAGGACTACA CCGAACAGGC CATCCGGGCT CTGTTCACGA TGCCAGCGGT    22020

CACGATGGAG AACGCTCTCG GCCTGCTCGA AGAGCACCTG CTGAAGCTGC CTCTGGAGGC    22080

GCTGCAGGGC TTCAAAGACA TGATCCCGGA CTGGGTCGAA GGAGCATTCG ACACGGTCAC    22140

CGGCGCTGTG CAGGCGATCA TGAACGCGCT CCAAGACGGC CCGCTGTTCC TGAAGTTCGC    22200

CGAGTTCCAG CTCTTCCTGC AGCGTCTGCT GAACAACCCG GCCGAGGTCA TCGGCGAGAT    22260

CCCCCAGACG TTGATCGACG GCCTACAGGA CGCGCTCAAC ACCGTCAACA ACACCATCCA    22320

GACCATCGTG GACATGCTCC TGCAGGCGCT GGGCATCACC CCGGAGGGGG AGCTGATCGA    22380

CCGGATCTTC GACCTGAGCG ATGAGATGGA GTGGCTGCAG ACCGCAGCCT CGAATGCAGC    22440

TACCGGCATC CAGGACACCT GGAACAAGTT CTGGGGAGCC CTCACCGGGC GCGTCCCAGA    22500

CCAGGACCAG ACCGTCGCTG AGCCCGCCGA GCGTATCGGC GAGCTGGCCG GCACCACGTC    22560

TGCTAACTCG TCTGCCATCG CGGAGCTGCA GCGTCGACTG GACAACCAGC AGAACGCTGG    22620

CGGCGTGGCC GGCGGTGACG ACTTCGAGCG ACTGAACATA TCCGGTTGGG ACATCAGGTA    22680

TTCCAACGGA TCCAGCGGCC GAGGGTACTA CCGTGCCGAC GGCCACCAAC TGGTCTGGAT    22740

GGACGAAGGC AACCAGCAGA ACACCGCGAC GTTCGTCCGC ACCAACCCCG CAGACGAGAA    22800

GACAGCCACC GACTACCAGA AGATGACGTT GGTCGTCGGG ACTATCTCCG GTGAGGTACA    22860

GACCGTGTTC CCGCCGCAGG GAGGTTCGCA CACCCGGCTA TGGGTCCGCG TCAACGACAA    22920

CGCTCCGACC GTCGGCATCA CCGACGGCGT GTTCGTAGAG ATCGGCGGCG TATCGAAGGC    22980

CCAGATCGGC TACCGCCGCA ACGGCAATGA CACGTTCGTC GGATCTATGG TCGACTGCAC    23040

CTGGGGTGCT GGATCGATCT TCGCTCTGAC CGCCGGCACG GCCAACGGTG CTGAGAAGTT    23100

CGAGGTCTCG AAGAACGGCC CCGTGCTGGC CACATGGTCG GACGACGGCG TCGTCTCCGC    23160

GATGGGTGCG AACTACCGCC GCTGGGGCTG GGAAGGCCAG GCTCGTAACC GCAACCTCGG    23220

CCAGGGCACT CCGAACTCGG TCACCCGAGT GACGATCACC GACAACGATC CTACCGGCGC    23280

AGGCGGTGGA GCTGTCAACG TCGGAGGAGA TGTCGTAGGT GTACTCCCCA TAGAGAACGG    23340

AGGCACCGGA GCTTCGACAG CTTCGGCAGC CCGTACCGCT CTCGGAATCG ATGACCTGGT    23400

CGAAGATATG TCCGACGTAG TTCGTGGATC CGTCGAAGGA CTCCCGTTGA TACCGAAGAT    23460

CTGGGTAGGA ACAGAAGCTC AGTACACGGC TCTCGCCACC AAGGATCAGT CCACGCTATA    23520

CTTCAGGACC GCTTAATGAC TGGTATCTCG TTGGGTGTCA ACGACATCCG CAACCTCTCG    23580
```

-continued

```
ATATTCTTAG GCGTCAGCAA CAAGATATTG AAGGTCAGTC TAGGCACAGA AAAGGTCTGG    23640
CCTGCGTTCA CCCCGGTGCT GACCACGTTC GCCACGGTCG GCACGTACAC CTACAACATC    23700
CCCGACGGGG CCAAGTTCAT CGACGTCATC CTCCTCGGAG GAGGCGGCGG GGGTAAAGGC    23760
ATGGCCCTGG CTGACGGCTG GGGCAGAGGT GGAGACGCCG GAAGCTGGGC TATCGTCACT    23820
CTCGAACGCG GGGTACACAT CCCGTTGTCG ACCAAGACGA TCACCGGGCT CGTCGGAGCT    23880
GGAGGCGCAG CGGGAGCTGG CTCTGTATTC TCAGGCAAGG CCGGAGGCCC TGGAGGAAAC    23940
ACCACGGCGT CCGCTGTCGG ATGGTCAGGT TTGACCGCAA CCGGCGGTCC CGGAGGCTCT    24000
GTGATCGACA TCCTCAGCGT CGCCGGAAAG TCGCCTGGAG ATCGGACCTA CAACGACCAG    24060
CTCTACATAG GCGGCGCACA ACAGAACTCA GCTGGCGGGA ACGGCAATGC TCCTGGCGGC    24120
GGCGGGGCTG GTGCCCAGGT CTCCGCACAG AGCGGCGGTG CTGGCGCTCG CGGCCAGGCG    24180
TGGTTCTTCG CGTACTGACA AGAAACCCCC CTCTTTAGGA CTCAGTGTCC TTGGGAGGGG    24240
GGCTTTTTGC GTTTCAGGAG GTCTTGGCCA GCTTGGACAT CGCCTCAGCG ATAGCCTCGT    24300
CGCGGGCCTC AGACGCCATC TGGTACTTCA TCGCCATCCT AGGAGTCGTG TGACCGAGAC    24360
GGGCCATCAG CTCCTTGGTC GTCGCACCTG CCTGAGCGGC GAACGTAGCG CCGACAGCGC    24420
GGAGGTCGTG GATGCGGAGT TCCGGCCGAC CGATCTTGGC GTAGCCACGC TTCAGCGACT    24480
TGGTGAACGC GGACTTCGAC AGCCGGTTGC CCTGCGTCGT GGTCACCAGG AATGCCTCGG    24540
GGCCCTTGTT CATCTTCGTA CGGTCCTTCA TGTGCGCTCG GATCATCTCC GCGACGTGAG    24600
GCGGAACCGT CACAGGACGC TTCGACCGGA CGGTCTTGGC GTTGCCAACG ACGATCTTGT    24660
TCCCCACGCG GGAAGCGCCA CGGCGCACCC GGAGCTTCAT CGTCATGCCG TCGTCCACGA    24720
TGTCCTTGCG GCGAAGCTCG ATCAGCTCTC CGAACCGGAG GCTCGTCCAC GCCAGGATGT    24780
ATGCCGCGAT CCGGTAGTGC TCGAAGATCT CAGCGGCGAC GATGTCCAGC TCCTCAGGCG    24840
TCAGCGCCTC TACGTCGCGC TCATCGGCTG CCTTCTGCTC GATCCGGCAC GGGTTCTCTG    24900
CGATCAGCTT GTCCTCGACC GCTGTGTTCA TCACCGCCCG GAGGACGTTG TAGGCATGCC    24960
GGCGGGCAGT CGGGTGCTTC CTACCCATCC CGGCCCACCA CGCACGCACC AGAGCTGGCG    25020
TCATCTCTGT GACCGCCACT TCACCTAGCA CCGGGTAGAT GCGGCGCTCC GCGTGCCCGC    25080
TGTACAGATC CCTGGTGCCG TCTGCGAGGT CGCGCTCCAC GAGCCACTTC CGGGTGTACT    25140
CCTCCAGCGT GATGGCGCTG GCGGCTGCCT TCTTCGCCCG GTCCTGTGGA GGGGTCCAGG    25200
TCTCCATCTC GATGAGCCGC TTCTCGCCCG CGAGCCAGGC TTCGGCGTCC ATCTTGTTGT    25260
CGTAGGTCTG CAGCGCGTAG TACCTCACAC CGTCCTGCGG GTTGACGTAT GAGGCTTGGA    25320
TCCTCCCGCT GCGCTGAGTC TTCAGCGATC CCCATCCGCG ACGTGCCAAC TAGGTCTCCT    25380
CTCGTCGTGA ACAAGGCTAC CGGGTTGCAA CTCCTGTGCA ACTCTCAGGC TTCAACGCGC    25440
TTCTACGACC TGCAATTTCT TTCCACTTAG AGGATGCAGC CGAGAGGGGG TAAAAACCTA    25500
TCTTGACCGG CCCATATGTG GTCGGCAGAC ACCCATTCTT CCAAACTAGC TACGCGGGTT    25560
CGATTCCCGT CGCCCGCTCC GCTGGTCAGA GGGTGTTTTC GCCCTCTGGC CATTTTTCTT    25620
TCCAGGGGTC TGCAACTCTT GTGCGACTCT TCTGACCTGG GCATACGCGG TTGCAACGCA    25680
TCCCTGATCT GGCTACTTTC GATGCTGACA AACGAATAGA GCCCCCGCC TGCGCGAACA     25740
GACGAGGGGC ATTCACACCA GATTGGAGCT GGTGCAGTGA AGAGAATAGA CCGGGACAAG    25800
GTTGCACCGG GAGTTGCAGC GGTCGGAACC CTCGCCGTCG GCGGGCTGGC GTTCGCCCTG    25860
TCGTTCACGG CTCTCAGCGA GCTGGCTGCG GCCAACGGGG TGGCCCAAGC AGAGATGGTG    25920
CCCTTGGTGG TCGACGGCCT GACGCTCGTC GCCACGGTCG CCACAGTGGC CCTCAAGCAG    25980
```

```
AACAGTTGGT ACGCGTGGTC GCTGCTGATC CTGTCCACCG TCGTATCGGT GGCCGGCAAC    26040

GTGGCACACG CCTACCCCCA CGGCATCATC GCGATGGTGA TCGCTGCGAT CCCTCCGCTC    26100

TGGCTACTGG CGTCGACCCA CCTAACCGTG ATGCTGGCGA AGCAGCACTC GGAGCACGCC    26160

GAAGTACCTG TCTCGCGGCC AGAACCCGCG CCTCGGGGCC TGGAGCCCGC TGCCGCTTGA    26220

CTGCGCCCGA CCGGGACAGA AATACATAGA GAACCTATGG ATGTAGGAGG CACAAAAAAA    26280

TACCCCCCGA GCCAGCCCGA AGGCCAGCCC AGGGGGCATG GTTCTGCTTC AGTAGACCTT    26340

GCGAGTCCGA CCCGAGTTGA TCATCGCCAT GATGACCCAG ACGGGCAACC ACATTCCGCA    26400

GGTGATGAGC GAAAGCAACA GGTGCATCGC GTGGTTCGTC CTGACAGGCA TGACAGTGGG    26460

CTGCGGCATC GGAGGAGGCG CGACCGGGTA CGGCGAGCCC GCGTACCACT GAGGTCGATC    26520

TTGTTGGGGC GGATACTGAT TGGTCATCCC GACAGCCTAC TTGCCGATGG GTCGCATCAG    26580

CTCCTCGACC GACTCGCGCT CCACGCGGAT CAGCCGGGGA CCGAGCCGAA CGGCCTTGAG    26640

CCGGCCGTCG GCGATGTAGT TGCGGACGGT CTTGGTGCTG ACACCGAGGT AGTCAGCGGT    26700

CTCCTGGATG GATGCTCTCG GGGGCATCAG CGCGGTCCTC CGTGCTTCAT CGGTTGTCTC    26760

CCGAACCCTG GATCACGCCA CGATCCTTGC GGCTCTGGAG CTTGTTGAGG TTCCTCTGGG    26820

TGACGGTGCT CAACCAGACA TCGAGCTGGT TGGCTAGCTG GGCGACGTAC CACATCACGT    26880

CTCCGAGTTC CGCCTGGAGG TCGTCTCGGT TCTCCTGGGT GATGACACCG TCTTTATCCC    26940

GGAGGATTTT CTTGACCTTG TTGGCGATCT CGCCGGCTTC GCCTACGAGA CCCATCGTCA    27000

CGTAGGAGAG ACCCTCGATG CTGTCGCAGT CGCCTGCACC GGGGTAGATC GCTGTGTCGC    27060

TCGCGGCGAT CTGGTAGATG TCGACGTGCA TCAGATCATC ACCGGGAACA ACTGGCCACC    27120

GGGCATCTGG ATGAACACCG GGACGCTGGG GGTGTAGTCC GACGAACCCG TGCCGCCCTC    27180

ACAGGCGGAC AGGCTCAGGG TGGCGGCAAG GCCGATGATG GCTGCTGCGA TGGTCTTCTT    27240

CATCTGTTGC TCCAGTAGCT AAGTTCGGAC TCCAGTTCGC GGATACGCTC CTGTAGCCCT    27300

TGGTTTTCCA GGTACGCCTC GGCGAGGTTG GCCTCGGCGC GGTCACGGGC CTCGTCCTTC    27360

GACGTGGCCT CATCGATTGC CTCGTGTAGC CGGCGGATCA GATCTGGGAT GGCACCGTGC    27420

AGACCGCATA TGAAGTCGGC GTCTGCCTCG GAGAGGTGGG ACGCCACCAG ATCCTTGTCC    27480

TGGGTCTCCT GGTTGACCGC CCAGATGACG TGATCCTCTA GCCCGTGGTC GGTCTCGCAG    27540

ATAGAAGGCG GTTCTACCTC CTCTGGCATC CAGTAAGTCT TCTCAGCCCC GGTGGACTTC    27600

GCCCACTGCT GGTAGAGGAT GTCGAAGAAC TCGTGGTCCT GTTCGTCGGC GGTAATCACA    27660

GATCGTCCTC TTCATCCCAT TCGTCGTAGT AACACGTACA GCCGCAGCAG GTGCAGCAGC    27720

CGCACTCGTA GGTGCCGTAG TCGTAGTCAT CCCAGTCGTC TTCGTCCATC TAGCTGTACT    27780

CCTTCATGAT TCGGTCGAAC GCACGCGTCT GCACGCGCAT CTCCAGGTCG ACCGTTCGCT    27840

TCAACCACGC CCATTCGCCG TCGTGGTTGA TCTCCCACTG GCTCTTGAAT GTCGCTGTCT    27900

CAACGAGGAA CTCGACAGTC AACGTGTGCA GTCCGTTGTT GCTGGGCTGG AATCCGATAC    27960

CGTCCTCAGC GATGTACCAG GGCAACTCCT GGCCGTCGAA GTAGACGGCC TTGTCGGTCA    28020

CCAGTACTTC AGGGAAGGTG TGCTCGGTCA ACGGCGTCCC AGGTATGGGA TGACGCTGGC    28080

CCGGAACTCA AGGAACACCA TGTTGTCCGG GCAGTCCTCG GGGACGTTGT CGGGGCGTTC    28140

GGCGGTGTAG ACGCCGATCT CGTTGCCCTC CAGGGTTCCA AGCTCGTTGA GCTTGTAGAT    28200

CGCCAGACCC ATCAGCTCTT CATCGAGACC GTTCGGTGCT GGCAGTACAA CTTTGGCTTG    28260

TGGCATTAGC CCTCCCTCGG AATTACGTAT GCGCTGAACT CGACGGCCGT AATGCCGTCT    28320

GGCAGTTGGA ATCCGAACCG CTCTTCGAAC TCCTCGTTGG TGATGGGGCC GTACTCGAAG    28380
```

```
GTTCCGGGCA CTACCTCGCC CTCCCCCTCG ATCAGGAGGT ACGCACCGGC GGCGTACACC    28440

TCCTCGTCGT TCGGCCATCC GACTACGGTC CCGAGGACCG TGAACTTCCT CGGCTCCATC    28500

AGGGCACGTC CACTTCGTTG ATGAGGAACC GCATCGGAGG TGGAGTGAGC ATTGCCTCGG    28560

CTATGGCGAT GAGGGCGTTC AACTGACCCT TCAGCAGCTT CTCCTCGTCG CCTGCGGGAA    28620

GGTGGCGCAC TCGGCGCTCC ATCTCCTTGG CGCGTTCCAG ATATTCGGTG CTGTCAAGT    28680

TGTCCTCCTT AGTAATCAGC GCCGTAGAGC GAACCCCACG AACGCTTTCC GACCTCGGGG    28740

TCGGTGCCAA CCAGCACCGG ACCCATCTGT TCTTGCATCA GGTGGCCAAT GTGTGCAGCG    28800

GCTCTCTCAG CCTCTGAGGC GGGCAGAGAC GCGACGATCT CGTCGTGGAT AGGCAACCGT    28860

AGGTACGGGG TGTATCCGGC CTCGTGGAGG CGAATCAGAG CCCGACAGGT CACGTCCCGC    28920

GACGACGACT GGATCATGTA GTTCAGCGCG GAGTATGTCC GCGAGCTGTC CACCGGCAGC    28980

CGCCGGCCCA TCGCGTTGAC GATGTAGCCG TTGCGGCCAG CTTCCATCGC CAGCTTCTTG    29040

CTCAGCCGCT CCACACCGGG GTATGTCGCA GAGAACGCCT CATGAACTCG CTTGGCCACA    29100

GGGATCGAGA TCCCCACTGC CTCAGCGAGA GCCTTCGCCC CACCGCCGTA GACCTTCTGA    29160

AAGTTGGCGG TCTTCCCAAC CTTTCGCGGC ACCTGGGCTG CGTCAGCGGT CATCTGGTGG    29220

AGGTCCGCAC CGTTCTCGAA TGCCTCGATC ATGTTGCGGT CGCCCGACAG CGCCGCCAGG    29280

ACGCGAAGCT CCTGCGCCTG GTAGTCGACT GAGGCCATCA CATCGCCTGG CTCAGCGATG    29340

AAGCATCGCC GCACGATCCA GTCCGACGAC GGCAGCGTCT GCGCCGGGAT GCCGGTGATC    29400

GACATGCGCG AGGTCCGCGC CTGCAGTGGG TTGATGAACG TGTGGCAGCG GTCCTCAGAG    29460

TCCCTGGTGT CGATGAACTT CTGGACCCAG GTCTTCCGCC ACTTCCCCAG CTTCTTAGCC    29520

TCCTGAGCGA TGGCGGCAAG CTCGTTGCCA TCTTCGACCA GCTTGTCGAG CAGAGCCGCG    29580

TTGACCTGGC GCTTGCCAGT CTCGGTGCGA CCGGTGATCT TGACGCCCAT CTCCTCAAGC    29640

CCCTCGGCCA GATCCTCGGT CGAGTTGACC TTCTCCACGC CGTACTCGGT GAAAGCGATT    29700

GCCTCCCAGA CCTCCTGATC GGCCAACCAC TTCTCGGCGA GCGACCGCGA GTACTCCACA    29760

TCGAGCAGGA AGCCCTGCCT GTCGATGTAG CTGCAGATCT CACTGATCTT GTGCTCGTAC    29820

GGCACCAGCG ACCGACTCAC GTCGGGCACC AACGGTGTCA GGCTCTTGCA GACCCTCGCG    29880

GTGAAGATCG TGTCCATCCC GGCGTACAGC AGGTACTCCG GGTGGAACAG GTCGATGGTC    29940

GACCAGATCT TGGCCTTGGT CGTCTTGTGC TCGGCGGCTA GCTTGGCCAT GAGCTTCTTG    30000

ACGTTCTCGG CCTGGTCCTC GGAGATGAAC TTCGCGATCA GCTCTTCGAG CGAGTGCCCG    30060

AACCCGCCGG CCTCGAAGGG CCGGGGGTCC ACCAGCTTCG CCAGGATCTG CGTGTCAAGC    30120

ACGCGGGGCC ACAGACCCTC CATCTCGATC CCGAAGCACT GGTCGAGCAC CTGGAGGTCG    30180

AAGGAGGCGT TCTGGAGCAC CATGCGCTTG AGAGCGCCGA TGGCGATCCG CACGTCCTCG    30240

ATGAACACGT CTCCCAGCTC CACCGGCACC ACCCAGGCTT CGTCCTGAGT ACCGAACTGG    30300

ACGAGGCGGC ACTCGAAGGT GTCGCTGTAG ATGTCCAGCC CGGTGGTCTC AGTGTCGACG    30360

GCGAGGCAGT TCAGGTGAGC CCGGATGAAG TTGCGGAAGC CTTCCAGATC CTCTGGGGTT    30420

TCAACGACGT TGACGGTGAC GAGGTCTCCC TGAACCTCAT GCCGCAGCTC GATCAAAATG    30480

CTCTCCTACT GGAAGTACTG AGGCGGAATC CAGGTGGCTG AGGCCATCTC CTTGATGGCC    30540

TGCTGCATGG CCGCTTCGAA CGGACAGTCC GGGTCGATGT CCGGCTTGTA ATGGGTGACG    30600

ATGATCCGGC TGTTGCCGCC GAAGTCGTGG CTGACCAAGC CCTTTGGGGG CAGCTTCTTC    30660

AGCGCCTTGA TCAGTTCCTC AACCGTGGTC CCGGTAGGGG CCTTGCCGTC AGGCAATGCC    30720

TCCCCTCCGT ACGGCACGTC CAATGGGATC GTGTACCGCT CAACGTCTTT GATCTTCATC    30780
```

```
GAGCCTCTTC CTCTTCGACT ACCTCGTCTA CCCGGCGGAA TAACTCCGCT AGTTCTGCGG    30840

GTAGCAATAC TGGGTACTTC TCTCGGGCTT CCTGCATCGC TACCGCGATC CCAATCAGGG    30900

CAGCGAGCAG TTCATTGACG GAGTACGCCA ACAGCTCTTC GCGGATCTCT TCTCGGGTCA    30960

TTAGTGGTAG ATCCCCCGGA CGGTGCGCGA GATCGTGGCA GGGTTCACGC CGTAGTTCTC    31020

GGCGAGATCC TTCTGCTTCA TACCGCCCAG GTACGCCTGG CGGATGTCCT TGACCTCGCG    31080

CTCGGTGAGC TTCTTGCGGT TCGGCCGGCT CGGGCCGGTC TCAGGCTTGA CCTGAGCCAG    31140

CGCCTTGCCG AACAGCTCGT TCTGCGTCCG CTGCTTGATC GCGTACCGAC GGTTCGCTGC    31200

AAGCACCTCG TTGAGCCGCT GGGACAACTT GACATTGGCC TCACGCACTA CCTCGACCTC    31260

TCCGAGCAAG TTCGTGATCC GGTAGTCCTT GTCCTGGTTC TCGATGGCCA ACCGGTTGTT    31320

CTCCTCGGAA AGCATCGAGA CCTTGTATTG CGCCTCTCCC AGCGCAGCTT TCAGGTGCTT    31380

CTTCCTCATT CAGCGCCCCT CTCTCGGCGG AACTGTTCGT ACTCGTCTTC GGTCATGTAG    31440

TAGTAGTAGT CAACGACCTT GTCCCAGTTG AAGGTTCGGG ACGTGCCGTC ATCGAACGCG    31500

ATGATCAGGA CACCCTCTTG GGTGTCTAGG ATCGGCTCGC CAGCCACGAC GTGGAAGCGG    31560

TCCTCGAGGG TCACCGCAGT CGCTCTGCGT GCCATGTCAG TTCCTCTCAG TAGCTGTAGG    31620

GGACATCCGG GATGTCCTGG TAGGTGTTGG GTGCGATCTG TCGGAGCTGC CGAAGCAATT    31680

CCCCTGCCAG CTCACGGATC TCGGCATCCG CGGCCTCGTG CCAGCGGGCC TTGATGACGT    31740

ACCGCCACGC CCGATGGTTG CCCGTGACGA CCATCGGTGA GTTCGTCATG TTCGGCAGGA    31800

CAGCTCGCGC TGCCTCGCGG GCCTGCTTGC GCGGCAAGCC CCGGTCAGCC AGCCGGTTGA    31860

CGATGTGTTC GTAGACAGCG TCAATCTCAG AGCTGACGGA CTCCATGATG TGGACGAGGT    31920

CGTCTCGGTC GTCGGGGTGG AGCTTGAACA GAGCCGGGGG CAGATGGATG CCAAGGTCGG    31980

TCGGATCCAC ATATCGCTGA GACACCACCG AGAAGCTCAA GTGACGGTGA CGCTCCAGCT    32040

CGGTCAGCAC CGACCTGCTG GCCTCGATGT AGAACGTCGC CGAGGCGTGC TCGAACACGC    32100

TCTCGTGGCC CAGATCGATG ATGTGGTTGA GGTAGTCCTC GTTCTCGGCA GTTGCCGGGT    32160

TCGGTCGGTG GAACGACCGG TAGCAGTTCC GGCCCGCGAA CTCGGCCAGC TCGTCGGCAT    32220

CGAAGTCGCC GAAGTAGGGA TCTTCGTCCT TGGATTCTTC GAAGTCATCG ACCTCGAATC    32280

CGATGTCCCG CAACGCACCC GGATCGATCT CGGTGGCAGC GATCAGTTTG GCTTTCATAC    32340

TCTCCGCTCA GAGTTGGTGG AACGAGGTCA GCCAGGGGGC AGCGAAGCCC TTCTACAGCT    32400

CCCCTTGGCT CGTTACCGGC TTCTCGACCT CGGTGGATGT CAAGTAGTCG AGATGACTAC    32460

TTCTTGTCGG GCCATTGCGC GTCACACTGC TGATCGCGAG GTGCGGTGCA GGAGAACAGC    32520

GCGTACGGCT TGCCCGTCTT CTTCGAGACG CCCGACTTGT AGACCATCTC GCCGTGCTGG    32580

CAGTACCGCT TCTCGCCACC AGGCGCTTCC TGAGCTGCCT GCGGGCGCG AGACTGCTGC     32640

TGGCCACCGC CGCCGCCGTT GGCCGGCGCG GATCCACCGG AGCCTGCGTA GTGGCCTGCG    32700

ATCTGCTGGA CCTTGTCCAT CAGCGCCTTG AACTCGGCGG TGTTGACCTT GGCCAGCACG    32760

TCGGCCGGGT CCGCACCCTT CACGACCACC CACGGGTCGC TGTACTGACC GGCGAACTTG    32820

AACGTGGCCG ACACCCCATC GGTGGAGTGC TGGACCGCCA TCGAGTCGCG CACAGCAGCC    32880

GAGGCCGTCG TCACCGTCGC CGACGGCGCG GTCTCAGGCT CAGGAGCCGG GGCCGGCTCG    32940

GGCTGGGCAG GGGCGGTGCT CCACGGATCG TCGTAGGACA ACTGGTTACC TTTCACTTAA    33000

TGGGCATGC GCCGTTGGCG CACTCTTCAT CGACACCGTC TTCGACGGCT TTGGCCGCAG     33060

CAGATTCGTA CTGCTGCTTG GTGATTCGCT CGTACGGAGC CTGCGGGAAG CTGGACTCCG    33120

GGAAGATCGT GGAGCCCTTG ATGAGCCCCG CGAACCTCTT GAGATCGGCT GCGACATCCT    33180
```

```
CGGCCTCGTA GGCGTCTGGA TGGACGTTGG CGGTGAACGA CACCGCGTTG TCAGCCCAGC   33240

ACATCTGGTA GAGCGCCTGG AACGCCAGGA GCTGGTGGAG GGTCAACTCG TCGGCTGACT   33300

CAACGATCTC CTCGTCCCAA CCGAGTTCCT CGACAGCCTG GACCAACGTG TCCTTGGTCG   33360

GGATCGAAAC CACCTCGGTG TTCGGAGCGA AGAGATCCTT CTCGATCTCG TAACCCTCGG   33420

CTGCCAACCT CCGCAGCTCG GCCATGTCGC TGTTGAGGTT GAACCGCACA CGCCGGATGA   33480

AGTACCGCGA GAAGATCGGG TGGATCCCCT CGGAGACTCC TGGCATCTTC GCCACCGTGC   33540

CTGTGGGAGC GATGGTTCGC TTCTTCACCG GGACAGGGAT CCTCAGATCA TGGGCGAACC   33600

GTTCGGCCTC TGAGTCGACC TCAGCGGCCA TCTCCCGCAA GAACTGGGTG AACCGCTTAT   33660

CTCCGGGTGC CTCGGAGTAC CTGCTACCTG TGAGGGCCAA ATAGGAGGCA ACTCCGAGAT   33720

GACCCACGCC GATGCGACGG TTTCGGTCCA GAACCTCCCG GCTCTTCGGG TCGGCCACTT   33780

CCGAGAACGT CGCCCGGATC AGGAATCTCG TCATCAGACG ATGCGCCCGG ATCAGGTCGA   33840

GGTAGTCGGT CTTGCCGGCC GGCGTCACGA ACGCCGCCAG GTTGATGTGG CCGAGGTTGC   33900

ACGGCTCCCA CGGTTCGAGA GTGATCTCGC CGCATGGGTT GGTGCAGACC ACCCGGTTGG   33960

GCTCACCGAC GTTGGACAGT GACGAGTCCC ACATCCCCGG CTCTCCGTTG CGTACGGCTC   34020

CCTCGGAGAG TGCCTTGAGC ACTCGGTGGG CTCGCTTCTG CTTGGGCATG TCCTCGCGGG   34080

CGACCGCGAA GCTGCCGTAG CCCTCCTTGG CCAGACGCCA GAACTCGTCG TCAACCTCGA   34140

CCGAGATGTT CGTCGTCCAG TGCTCGCCCG TGCTCGCCTT GATGTTGATG AACTTGTCGA   34200

TCTGGTAGTC GTCCCAGTGC ATCATCGACA TCCGCGCCGA CCGGCGCACA CCGCCGGCCA   34260

CAACACACTG AGCGATGGCG TGGTCGACCT CCATCGCGGC GATGCCGTCG AGCGTGATCC   34320

CTGCGTACTC CGAGAAGATG TTGGCGACCT TCTGCAGCAT CACAGCGAAC GGCAGCGGGC   34380

CGCTGGCCAC TCCACCGAAC GTCTTGAGCT TGGCCCCTTG CGGCCGGATG CGGCTCACGT   34440

CGTACACCCG CTGGTAGTGG ACCGTGCCGG GTCGGTAGTG CGTGTCGATC AGATCGACCA   34500

GCGCAGCAGC CCAGCCCTCT CGTGAGTCCT CGATGGCGTA GGCACCGGCC CAGTCGTGGC   34560

TGTAGTGCTC CGACAGAATG CCTACATCCT TCATCGCCTG GTAGTCGACA TGCTCTGGAT   34620

CACAGACGAT CTCGACCCGC AGGGGGTTTA CGACCTCGGG GTAGCCTTCG AGGTAGTGGT   34680

TCGAGTAGTT CGCCCCGACT CCCCCGCCCT CCATCAGGCG CATGAACGTG AACTGGAAGT   34740

GGTCCGAGAT CTTCTCGGGC CAGCCAGCTA CCCAGCAGTT GAAGAGGTGC TGCGCGTTCT   34800

TGACCCCCGA GGCCCACAGA TGCCGACCTG CCGGCAGCAC CTTGAACTTG GTCATCAGAC   34860

GAACGAGATC TTCTCGCTCT CCTTCCAACA TATGTCGCCG GTCGACAAGA GCAAGATTGC   34920

CGTCCACGAC CCTCTCGACC GTTTCCGGCC AGGTTTCCTT CGAGCCGTCA GGCTTGGTCC   34980

TGGCGTAGGT TCGGTTGTAA ACGAGTTCAC CGGTTGGTCC CCAAGGGATT TCGTCAGTCA   35040

ACTACTTCCT CTCAGTCAGT TCGTATCGCT TGAAATAGGC GTCGGCAGAG TCGCCGCCAG   35100

AGAACGAGAC CCCGTACTCG ACCGGGCCTG CACCACGCAC CTCGCAGGTA ACGACGCCCT   35160

TCCTTCCCCG GAACATCGGC CAGGTTCCCT TGGAGGGGTG CTTGGTCTCG TCCCGCTGGA   35220

CGATGACCTT GGTGCCCTTC TTCATGCCGA CTTCCGTTCT CCGTAGCCGG GAGTGAAGCA   35280

ACCCCCGACG TACAGCTCGA GATCTTCTTG CGACCAGTTC TCCAGTCGCA TCGGCGGCTG   35340

GTGCGGGAAC AGCTCCGGGA ACACCTCGGC CCGGTACAGC TCCGAACCGG GCATCCCGTT   35400

GAACGTCGGA TCAAGAATGT TGTGCATGGC ACCTCCCTCC CAAGAACTCG GAGATCGGCG   35460

GCTCGTAGAG GTAGCCATCG CGCAGCTCGG GGTTCTCGAT GAGCATGATC GCGATGTTCG   35520

CTGTGGGGTC AGAGTGCCCA TCCCCCTGCG ACTTTCGGAT GTCTGGGAAG ATAGCGTGCT   35580
```

```
                                            -continued

TGCTGCCCGG ACCATCCTTG ACGATGACCT TGCCCTTGTC GTCCTTCTCC ACGCCAGCCG    35640

TGATCGCGAT GATGTTGACG TGCTCGGTCA GCGACTTGTG AGCGCGGAAC AACCGGTTCT    35700

GCCCGCTCTT ATCCTTCGGG GAGATCCCGT CGGTGTAGCG GCTCCTGATC GCCTCTGCAT    35760

AGCCCCCGTT CTGAGCGTCC AGAGCCTTCA TCGCCAGCGG GAGGATGTCG ACCAGGTACC    35820

GATTGGTCGA CTCCCCCTGC AGAGCCTCTT TGACGTTCTC GGACGAGTAG TGGCTGCGCT    35880

CCTGGAACAA GTCGCGGGCC TTGGCCGCTC CCGACAGGAT GTTGCGAACC TGATTGCGTA    35940

CGTAGTGAAC TGCCTCACCA CGGTGCAAGC TCTCCAGCGT CTTCTGGATG TACGGGCTCT    36000

CGAGGTACCA GACCCACAGC TCTTGGATGA TCTCCTCGGC TGTCAGGTTG GTCTCCCAAC    36060

CGATCAGCGC CTTCCGGGTG GCCCTGCTGA ACAGCTTGCT GATGTCGTCG GTCAAGGCAT    36120

CACCTTTCGT AGGTACTCCT CCCGGTCCAA TCGGCGGTCG AGGTGTCGAG TGACCTCCTC    36180

CGCGAAGACC TCGCGGACTT CGCTGGAGGT GATCTGGCGC GAACGTGCGT TCTTGTGCAG    36240

GTACGGCAGC TTGGTGGCTG TCAAGTTCTA GACCTCCCAG ACTCGGCCGT CGACCGAGAA    36300

CCGGCCTCCG ACAATCGGAA CAAGCTCAGG CTTGACGTGC TGGCCGTCGA CCGTCAGCAG    36360

AGCAAAACCA CTCTGCCAGT TGGCTGTTGC ACCCTTGAGG TACTGAGCTA GCTTCATGTT    36420

CATCAGGTTG CCGACCTCCA TCGACCACAG CACCTTCTGG TTGCCGCCGT AGCCCAGCGT    36480

GTGTGGCTTG ATGCCCTGGC GGTGGGTGTG TCCGATGATC ACCGACGTGC CGAACCGCAT    36540

CATCGCGTTG TACGCGGTGT CAGCGGACTT CTGCGTCACC CGGACCCCAC CACGGTGGCC    36600

GTGGGTGGAG ATCCAGCCTG GAGCGATCTT GTAGAACTCA GGCAGCACGT CAACACCGAA    36660

CCCGTCGAAG TCCAGCAGGT TCTGGAACTG GAACGAGCTG ACGTACTCGA CCAGCGCCGG    36720

GGCGAACTGG TGCAGGTAGT CGACTGGCCG GCGGTCGTGG TTGCCCTCGT GGACACCAAC    36780

CGGGCCGTCG TAGACCTGGC GCAGCGGCTC CAGGAACCGC CGCTTGCACT GCTCGGAGTC    36840

GGGCTTGATC CGCTGAGCGA ACTCTTCCTT GGTGCCCTTG GTCACCGAG ACGGGCTCGG     36900

GTAGTCCATC AGGTCACCGA TGTGGACGAC CTCGTCAGGC TGGGTGTCCC CGATGTAGCC    36960

GATGACCGCC TTCAACTGCT TGCGATCATC GAACGGAATC TGGGTGTCCG AGATGACGAC    37020

GATGCGCTTG CTCACTCAGC GACCTCGGTG AAGGGGCCCC GCATACGTTC CTCGTGGGAG    37080

CTGGCGTTGC CTCCTGACCA GCGTCGCTTG CCCACCTTGG TGTGGTGCAA CCCGTTGGGG    37140

TAGTAGATCC ACTTCACTCC TGTGGCGTTG GTGACGGTCT TCACATCGGC AGGAACGTCC    37200

AGCAAGGTGT CCCACTGGCG AGGCCCCTTG GGATACCGCT CGTCCTCGGG GAGCTGCATC    37260

TTCTCCAGAA CGCCTGCGTA ACCGGCGATG TCGACCACCG TGTCCTGGTG GTAGCCGTTC    37320

TCCATGAACC GGGCGATCTT CAGCAGGATC ATCATGACGG CCACGTCCTC CGGGGTGAAC    37380

TCGACGCCGC GCTTGTACGC GCCCCACAGG GTCGCGATGC GTTCGTGGTT CTCCTTGGCG    37440

TCCCCGTAGT CCTGGGCTCG CTGTCCGTTG ATGATCTCTT CGGCGGTGGT CAGAATGCTC    37500

ACAGTCCAGT CTCCGATGCG GTGTAGTAGT CGATCAGCTC ATCGAGCTGG TCCGGTTGAT    37560

AGCCGAGGAT CGGCTTGTGG GTGTCAGTGA CGACACGGG AACCGACATC GCGTTGAGCA     37620

CCTTGGTGAC GTAGTCGTAC GCCTCCGAGT TGGCCGTGAC ATCGACTGCG TCGAAGTCGA    37680

TCCCGGCAGC CGTCAGCTTG TCTTTGACTC GCTCGCATGG CTTGCAGCCG GGACGGGTGT    37740

ACACCGTGAC CGGCGCGAAC AGCGTTCTCA CGTGAGCACC ATCCCAGTCG ATGTATCGGT    37800

CTCCATACAT CAGATCCTTT CCAGCAGAGC AGCTTTGCCC TGCGATGTGA CTAGTGAGTT    37860

GACATCCTCG CCTTCTGGCA TCGGGATGAT TCGGGCGTTC GGCAGCGTCT TCGCCACCGA    37920

CCGGGCGAAC TCCATACCGG CGTCGTCGCC GTCGGCCAGG ATGTTCACGT TGCGGTAGCC    37980
```

```
                                                    -continued
CAGGAACAGC TCTCGGAAGT ACGGCTTCCA CTTCTGGGCT CCGCTGAGCC CCACCGTCGG   38040

CAGCCCACAC AGCTCGGCGG TGATCGTGTC GAGTTCTCCC TCGCAGATCG CCATGTCCTT   38100

GCTGTATTTG GTCAGCGCGT AGGTGTTGTA GAGCCGGTTC TTCTCCCCTG GCATCGACAG   38160

GTACTTCGGT GTGCCACCGT CGATTCGGCG ATACCGGATC GCAGCTACCG TCCAGTGACG   38220

CCAGGGCGAC CACCGCATAT ACGGAATCGC CAGGCAGCCC CGGTACATCT CATGTCCAGG   38280

GAGTGGGTCG TCCACGAATC CCAGACCGAA CCGGCTTAGT TCCGCTCGGC CGGCCAGCCC   38340

GCGACTCGCC AAATACTCGT CGGCTGGGCT TCCGGGCAGG CTTTCTCTGT ACCGGGACGT   38400

TGCCTCCCAC AGATAGGTTC TCTGCGATTC GCTTAGCCTC TGCAAATGTC ACCTCCTCTT   38460

CGTGACGAAT GATCGAGATC ACGTCTCCAC GGACCCCGCA GGCCATGCAG TTGTAGCCCT   38520

GTAGGTCGTA ACTGACTGCG GCAGACGGCG TTTCGTCGCC GTGGAAGGGG CACAGGCACT   38580

TGTTCCACTC GTGGTGGTCA GGTGGTGGTT CCCAATCCGG GTGGTAGCGA AGAATCGCCC   38640

TCGCGATGGG CGAGTCGTTC ATTCGTCCTC GTCAAGCTCC TCGGGAGAGA GCCCTTCGAA   38700

GATCCCGTTC AGGACGGCGG CGAAGCCCTC GCCGGTCTCC GCTGCGTCGA GCATCTCTGC   38760

AATCGTCTTT GCCATGTTTC CTCCTGGTGG ATGTCAAGTT CGAGACAGCT TGTCAGCCTC   38820

GACTGGAGCG ATGCGCTCCC CGATGACTTG GACGGCCGGC GGGTTCAGCA GGTACTCGAT   38880

GGCCCGTTTG AAGAACTCGA TGCAGTCCCT CGCCCAGCCC AGCGTGTACT TGTTGCACAT   38940

CGTGCAGAGC AACCCTCGGA CGATGCCTGT CTTGTGATCG TGGTCGACCG ACAGGCGCTT   39000

CTTCTTACCG TTGGCTCGCT GGCAGATGTA GCACCGACCA CCTTGGAACT CGTAGATCTG   39060

CCAATACTCA TCGCCGGTGA TGCCGTAGGT GGCCAGGATC CGGGTCTCCC AGCTCGTAGA   39120

GCTGCGAGCC GTCCTGAACT CTCGGTGATG AGTAGCGCAT CGTGGCCCTG GATACTTGGC   39180

GTCTCGCGTG AGCGGGAGCC CCTGTGCGAC ACAGTCTTTG CAAGGCTTCC GCTTGTGCTT   39240

ACGGTTCTGC ACCCGGTACC CCGGAGACCT CTTCGCCGCC CTCGGCACGC GCGTCCTCCT   39300

CCCGGTTCTC CATCACCATG CAGAACCACG ACAGCAGCCC TGCCAGGGAG ATGTAGAAGG   39360

CCACCAGAAC TTGGCCGCTC ACTTCACCAT TCCTCGAACC CACCAGCGAG ACAGCGCCTT   39420

ACGCCCTTTG TCGAGCGGGG TCAGCTCGCG CTCATCGTCC TCACCGAAGT CGAACTCGAT   39480

GCTGGCGATC TCGTAGCCGA GGATCTTGAA CGACACGTTC ATAGGCGGTC TCCGAAGTTG   39540

ATGACGGGAA TGCCGGCCCT TTCGGCCTCT CGCATGCAGT GCCGGGTGCC GACTGAGTTG   39600

CCGAGGGGGA ACGCCAGACA GATGTCCGCA CCGGCCCTGA CCATCTCGAT GTTGCGGAGG   39660

ATGCCAGCCC GCTTGCCGTA GCGTTCCCAG TCGGCTCGGT GCAGCTCGGG GAGCACGTCC   39720

CATCCCTCCT GCTTCATCCC CCAGGCCCAG CGGTCTGCGA TGTCGTCAGC GCCGCGAGCG   39780

CCGCCGTGGA CGACCGTGAG ACCGGAGAAG GACCGGTGGT ACTCAGTGGC CAACGCTTCC   39840

CAGACCGTGG TGCGGTCCTT CCAGATCCGA GATCCGGTGA TCAGTACTCG CCGCATCAGA   39900

TCGCCTCCCA CTGCAGGCCG TCGTGCGACG TGACCAGCTC CGCTTCGTAG ACGCCGTAGC   39960

GGGTGGCCAG GAACTGGATC ATCTGCGCCT GCTTGTACCC GAAGGGACAT TCGTGGACGC   40020

CGCTGATCGG GTATCTGACT CCGTATTTCA CTTGATCCAC CGCTTCGCGA TTCGGTCGAC   40080

GTTCTCCTCG GAGACGTTGC GGGCGAGGCC GGTGAACTCC TGGCCGTGGA CCTTGGTCTC   40140

GATCACGCGA GGCTTGCGGG GATCCGGGCT CTCCGGGTCG ATCCGCTTGT GGGTCCAGAC   40200

GGTCGGCTTC GTCTTGATCA GAGCGCCCAG CACCTGCTGG CGCAGTGGGT TGGTCTTGCG   40260

GGGCATAGCG TTTGGAGTGG TCATCTGGAT CCTTTCCTCG GTGGCTGTCA AGTCGGTGTG   40320

CGTAGTGAAG CCCCCCCAGG CATGCGCGCC CCGCCTGGGG AGAGTTGATC AGCGCAGTTC   40380
```

```
GATGTCGGGC AGGATCGCCT GCGGCTTGAA GTTGACCTGG TAGAAGTCGG TCGAGACGTT   40440
TGCGCCATCG ACCTGCTCCA TGAAGTAGGA GACGTTGTCC GACAGGCCCA GGAAGTGCTT   40500
CTTGATCCCG TCCTTGGTCT TGCAGGTCAC GTCGAGCTTC TTCGACGCGG TGTCCGCGTT   40560
GATTGAGCAC CGGCCCTGGA TCTCGAGCAG GTACTTGTCC GTGATCCCGT TGAAGAACAC   40620
GATCCGGCGA TTGATCTCGA AGTTGTCAGC GGCCTTGCTG ACGTTCTCCG ATGCGACGTC   40680
GGCGTCGGAG GTACACGCGG AGAGGCCCAG GATCGCCGAT CCGGCGATGA GTGCGGTGGC   40740
GATGATCTTC TTCATGTTCG CTACTTTCTG TTTGGTGGAT GTCAAGTTAG TGACCGAAGT   40800
CGTTGATCTG CATAGTGTCT CCGACGAACT CCAAGGAAGC GAAGTCTTGT CCCGACGGGT   40860
CCGACTTCCC CCCTCGGTTC TTGACCGTGG AGACGTTGAG CATGTCCGGG CCGAACCCGT   40920
CCGATACTCG GTGGAGAGTG AGGATCATCT CAGGAACACG CCCGATCTGA CCTTTGATGC   40980
CCGACAACGG GATCGGCTTG TCGCCGTCGT TGTGCGGGCC GGTGACGTGG TGGAGCCCGA   41040
CGACGCATGA GCCTGTCTCA CGGCCCATCT CGTGTAGGTA GTCCATCAGC GACTCCAGAC   41100
CCGAGAACGG GTCGTCTCCC TCGCTTGAAT CGGTGCGGAC GTTGGTGATG TTGTCCACGA   41160
CGATCAACGC TGGGAAGTCC TCGTACAGCG CGTCATACGC GGCCAGAGCG TTCTCGATCT   41220
CGTCCAACGA CGGTGATGCC TTGTAGTTGA ACCGGATCGG GATCTCGTCT AGTGAGTCAG   41280
CTACCGCGTC CTCGATGTTC TGCTCGCGAA CAGCCCGCGT AGCTCGTTCG AGCGACCATC   41340
CGCTGAGGAT GGACACCGAA CGGGAGAGCT GGGTGAACGC ATCAGAGTCG CCGAGAAGT    41400
ACAACGTCGG CACCTTCGAC TTGAGCGCGT AGGCGAGGAC GAACGCCGAC TTCCCGGTGC   41460
CGGGGCCGGC GCAGACCAGG ACTAGCTGGC CTCGTCGGAG ATGTGTACCT TTCTGGTCAA   41520
GCGCGGCCCA GACCGGGGGT AGCGGATCCC CCGCCGACCC TCGGATGTAG AGCGATTGTC   41580
TAGGTGTGTA CACCTTCCTC CTCGTGGATG TGATTGACCA GGTCATAGAT CTCGTCGCGA   41640
GAGACCAGCC GGCCCCAGGC GTCGATCCCC ACGTGGATCT GTCTCCGGTG GATGTGTCGG   41700
GACAGGATCA TCGGCGAATG CGTGTGCCCG TGGATCAGGA TCTTGCCATC GTCACGGAGC   41760
CTCCACTGGG TGTGTCGGTC CTCGCTGGTG TGGTCCCCGA CGTATGGGAA GTGGCTCAGC   41820
AGAACATCTG TGTGCCCGCC AGCGTCCCCG TACAGCGGCA CCCGGATACG AGCTGCCGTC   41880
GACACATGCT CGAACACCAT CCAGTACGCA CCAACCAGCT TGTGAGCATC GCGGTTCATC   41940
GGGTGGGGCC CATCGTGGTT GCCCAGGATC AGCCGTTTGC GGCCTGGCCG ATCCGAGATC   42000
CACCCGAGGG CATGTATCTG CCCCTTGGTG GAGCCAGAGG AGATGTCACC TAGGATCCAG   42060
ACCGTGTCGT CCTTGCCGAC GACCGAGTCC CACGCCTTCG CCAGGGTGGC GTCGTGCTCT   42120
TCGACATCAT CCGCCAGGTT GCGGATCTCC ATCAGCCGCT TGTGTCCGAT GTGTAGATCG   42180
GACGTGAACC AGGTGTTGCT CATGGCTTCC TTTCAGAACG GCGGGCCGTA CAGCTCGATC   42240
ACCAGCGCGT GCAGCTCCTC TGCCGCGTCG TCACGCTCGA ATCCGCAGCA GGAATCGTGC   42300
CGGTCGAGGA TTGCGACGAT CTGGTCGTAG AGGCTGGGCC TCACTTCACC TTCTTCGGAT   42360
CGATCAAGGC GTCGTGAATC GGCCGACCGG CGCGAGCCGC GTGCGTCTCG GCGTCCAAGG   42420
CTCGCTGCAT CTGGTTCATC AGCCGGGTGC CGCGCAGCTT GAGGATCTTC ATGGTCGCCC   42480
GACCCTTGTA TCCAGCGCGG TGCATCCGTA GGACGCAGGC TGTCTCGTGC GGGGCTATAG   42540
GTGACCTCAG CGACGGGTGG TTTGGATCCC AGTTCGTCAT GTCTTCCTCT CGGTGGCTGT   42600
CAAGTTGGTC ACAGACCGAA CTCTTCCTGG TACTGCGGGA TGAAGTGGCC GGCCGTTCAT   42660
GTTCGGCTCG ATACCTCTCG CGTCACGAAC TCCTGCCCGT TCCATCTCCG ACCGTCCTCG   42720
AACTCGATCA CGATCTCTCG TCCGGGATGA CGCACGGCCT CCGCTTGGGC AAACCTGCGT   42780
```

-continued

```
GCAGCCTCTG GGGTCGGGAA CGGAAACTTC TGCGAGGCGT ACAGCTCCTG GTGCCACTTC    42840

GGCTTGTCAG GAATCGGCCC CATTTCCACG TACGTGTAAC CCGCGTCGGG GTCGAGTTCG    42900

AGCGTTTTCT TGTATTCCTT CGTGCCTGCC TTAGAGGGAA GGTGAGTATC GGTGGCTGTC    42960

AAGGTGACCT CACTTAAAAA CAGGGCAGCT GTAATTCACA TCACAGAAGC CGCATTTGTC    43020

AGGTTCAGGC AGAGGCTCGA AGTCACCAGC CTGGATCCGA GCCTCGACCT CATGGAACCT    43080

CTCGGTGATC CGCTCCCGCG TCCAATCGGT CAGGTCGTAG GGCGCAGTGG GCTTCGCCTT    43140

GATGCCCTTC TTCCCCGCCA TGAAGTAGTC GCCCGTCTTC GGAGCCTCCA CGTCATAGGT    43200

CATCGCGACC GCGAGCGCGT ACACGCCGAG CTGGAAGTCG TCACCCGGCG AGTTGCCGGT    43260

CTTGTAGTCC CGGACTCGAA GCTCACCGTT GACCACGACG ACCGCGTCGA TGAACCCTCG    43320

GACGCGGATG CCGTCCAGCT CGATGTTGAA CGGAAGCTCG ATGGCCGGCT TGGGCTGTTC    43380

ACACTCCTTG CAGTTGGTGT CTTTCCACGC CTCCGTAGAG CAGATCCCTC GCCCAGGGGT    43440

AGTCCAGATC TGCTGGCCCT TGTCCTTCCG CCACGCGATG AACTTCTCTA CCTGCTCCAG    43500

TCCAAGGTGG AACCGGCGCT CGATGTCACG CTCACCGTTG TACGGCCCGG ACCAAAACCA    43560

CCACTCGAAG TTCGGGGTTT CGTCGCACAG TGCTCCGATG TCCTTGGCGT ACTCCTCGCG    43620

GAAGATCTCT TGTGCCCGTT CGAGGCTCAT CTCGCGGCCC TCGGCCAGAG CCTTCTCGTA    43680

GACCTCAGCG ACGGTGTGAA ACGCGGTGCC CTGCGGCAAC CACGCCGCAG GACGAGCCCA    43740

TACCTTGTCG ATGCGAGCCA GCTTGTACGC CTGCGGGCAA CGTGTGTATT GGTTCAACTG    43800

GCTGACGCTT CGCAGCGGCA GCAATGTCTT GGTGTCTGTC ACGCAGCGGC CATCCTTCCC    43860

TTGCCTATCG TCTCGTTCAG CGCCCCGTCG ACAGCGACAC TGAGCAGTTT TGCGACCTCC    43920

GACATGTCAA TCGGATCCTT GGGGAATTGG TCAGCCTGAG TCATCCTGAG CACCATCCAC    43980

TCGGTGCCCT TGTCGCAGTG GATCATGGTC GGATCAAAGC GAGTTCCCCG TGCTACGTAC    44040

TCGACTTTGT TCGCGGAAAG AATCAAATTC GACACAGGCC GATAAAGTCG TGAGGTGTCT    44100

TTTACACGAG GACTGCGGTA GACGAGCAGA ACTGAGACTG GGTCTTCGTC CAGTTGGCCC    44160

TTCCACCACG CCTCACACCT CTGCGCGAAC AGCCACCCTG GATGATCGGC GATGACTTGC    44220

GGTGAGGTGT GGACGAGGTT GTCTGCGAAC AGCTTTGCGA GCCGAGTGAG GGGCACGGGG    44280

TTTCCTTTCG TTGCGCGGCC TGGGTTGGCT CACACAACCG GTCGTGACTT TTAGGGCTCC    44340

GAGAGAAGCT CCTCGATGTC GTCTGGCCAC GACCAGAGGA GTTCACCCTC GGCGGTGAGG    44400

TTGGTGTGCT CGTTCACCCG GATCAGGAGA TCGTCATCCT CGATGCCTCG GGGACGTAC    44460

CTGAACCCGC CGCCGGCCAT ACCTTCGTAG GGCTCGATGG ATGGGTCGAA CTCGAGCACT    44520

AAGTCGTCGT CGCGGAGCAT CTTCCACCAC GACAATAGGC GCTTCTTCTT GTCTTCGGAC    44580

ATCGTGCGGA AGCTACCCAC TCGCATGTAC TCGCCGTGAT CCCGGAGCCT CTGAAAAGCC    44640

TTCGACTTAT CGTGAGGTTT CCGCGTGTCC CACGGCCAGT TCTGCTGGAC GATCTGCCTG    44700

GTGGTCAACC GTCCTCCGTA GGTCTTCTTG TGCCACGACA CCGCTTGTCG AGTCACGCCA    44760

TACAGCTCTG CGATTTCGGT CTGATTAAAC CCCTTCCTGC GAAGATCTTC GATCTCGCTG    44820

AGAGTGAGTG GTATTCGGCT AGGGGCCGGA ACCACTGCTT TGTGTTGGAT TTTGCCGCTC    44880

ATGTTTCCCT CCATGAGAAA GGTGCGTGCG CTCCGCCGA TTACGAGAC ATGTTGGTGC     44940

CTGTCAAGGA TACCCCTAAT TTAGTTGCGT CTGCGGAACC ATATTCAGTT GTGTTCCCCG    45000

ACGCCGTGGC CGTCTCCCAC TGGGCGTGGG ATCGACTGGC GTTACGCGGT CGTAAATGTA    45060

GCGGCCTGCC CCACTCGGTA GCAAACCTTG TGACAGGTAT CACTTAGGTC GCCTTCTGTT    45120

ACACGTTGAC CTCGGGTTTC ATCGTCACGA CTCTCCTTTC TTAGACAGCC TCAAGATCGT    45180
```

```
TACACCGGCT TGCGAAGATG TACCTTCGCC TTGAATCCGG CCCTTGCCAG CTCGAACTCG    45240

ACCACCTGGC GGGCGGTCTC CTTCAGGTCG GACTTCGCCG ACAGCGGCCC GACGAACCCG    45300

TAGCTCTTGA TGTACTCCTC GAGGTCGATG TCGACGTACA GCGTGACAGG GACCACCGAC    45360

AAGTCACACC TCCAATTCGT GGGGCTTGAT CTCGTTGGTC ACGTCGTAGT CGTTCAGCAG    45420

CGACTGGAAG TCGGAGTCTG TCAAGTCGTC CAACTCATCC TGCTCGAACG GCGCGGGCTC    45480

GTCATGCCAC GTCTTCCACT GGTCGTGGTC GGCGCGGAAC CACTTCCGCA GATCCTTGAT    45540

GGCCTCGTCC TCGGTGGCGA AGACGTAGGT CTCGAGCACG TCCTCGTACT CGACGGTCAG    45600

CGACCAGACG GTGATCTTCA CTCCCCGTTC ACCTCCGCTT TGTAGTTCAT CTCGGCGGTC    45660

TCCTCCTAGT TGGGTAGCAG TCGGTTGTAC TCGTCGTGGC TGATCTCGCC AACGATGAAC    45720

TGGCGCATCA GATTTGCGAC CGAAGCCGCG TCCATCCCTT CGGGAATGGG CTTGGCGTGG    45780

CCGAACTGCC AGTCTCGTGA GCGCCAGCGG AACCAGAGTT GGACCTTGTC CAGTGAGGTC    45840

AGGTGCAGGC ACTGAAACGT CATGCCTCCG AACGGGAACT CCATCACACC TCCTGTTTGA    45900

CCTTGACGGT GTGGCCTGTC ATTACTTCGT GGATTCGGAT GCTGGTGCCG AACGTCTTTC    45960

GCGTCTCGGC CTTGAACTCG GTGGAGCACC CCGAGCACTT CGCTTTGAAT CGCACTAGCA    46020

GTACCAACGC TTTCTGCAGA ATCGGGACTT GCCGCCGTCC CGGTTGTCGT TGTCCCGGCG    46080

GGCTTCGCCC TTCGGTGATT CGTCACATGA CGGAAGCTCG CCATGCTTGA TGTGCCATGC    46140

GTCGTCGGCG ACTTTTCCGC CGTGCTCGGC GATGTGCGCT GCGCTCCGGT ACTCACAGAG    46200

CGGGGAAGCC GATGCCTCGG CGATGATCCC AGGCAGGTTG CCTAGAACCA CCGCCAAGCA    46260

CATCAGCAGA ACGACGTGCC ACGCCTTCAT CAGCCCGCCA GCGCGTGGTT CATCGCCGCG    46320

TTGCGGCCGT CGCGCTGACC GTGGGCATAG CCGCTGAGGT CGTACCGGGT CCGAGGCTTG    46380

ACGTTCTTGG TGCGAGGATG CGCCTGGCGC AGAGCCAGCG CAGCTCGTTC CTTGTCGCCT    46440

CGGTAGAGCA CCAACGCTCC CCCGCCGGCC GATTCCACGG CCTTGTTCTC CTCGGCGGTC    46500

AGGCGTTCCT TGACGGCCTG GGCGAAGCCT GCGATCCACG ACCGGCGGTA GCTCTTGAGC    46560

TGGCCAGCGG TGCTCTTCGG CTTGTACTCC CCGGTGTTGT AGTCGTACTT GTACCGAGGC    46620

TCGAAAGCCT GCTCCGGGCG GACATTCTCA ACCAGGCGCA TCATCTGCGG CTGCATGATC    46680

GACCAGAGGA ATTGGAGCCT CTCGATGTGG CGGGGCACGC CGTAGACGTA GATCCGCTGA    46740

CCGCCCGTGA GGCTGGCGTA CACCGTCTTG CAGTGCAGGG CCTGAGCCAT GCCGTGCAGC    46800

AACAACGCTT GTGCGGCAAC GTACTTGCCG GTGACGTAGG TGACCCACTG GATGGCGTCG    46860

GGCAGGTCGG TGGTGTCCAA CCCTTGCTTG CTCGCCTCGA CCTGGGCCAT CTCCAGCCCG    46920

TACTTGGCCA TCAGCTCGAA CGCTTTCGCC TGGAACACAG CCTCTTCCGG CGTACCGGCC    46980

ACGTCTTCGG CCTGGCGCAG CAGCTTGGCG ACCTTGTCCT GCATCTTCTT CGTCTTGCCG    47040

TCGATCATGG TCAGTACTCC TTCTTCCAGT TGTTCCGGTT GCCCTTGCCG GGGCGCTTCA    47100

TCTCTCGCTT GCGGTTACGG TGCGGCTGCG CCGCGTTGGA GAGACGCAAC TCGAGCCGTG    47160

CCTTGAGCTG GTCGCTCATC TTCTTCACCT CTTCTGGTTC AGCGGATCTG GTCGACGTGG    47220

ATGCAGCCGA CGCGGTCTGG CCCGAACTCG GGAGCGAAGC CAAGACTTC GTCCTCCTCG     47280

CATGGGAACG CTCGCTGGTC GAACGTGATT GGGTCGGCCG AAGCCTCGTA TGGATCGGCC    47340

AAGGCCATCG CTCCGACCGC TGTAGCGAAT GCAACGACGA CGGTGATCAG GTGCTTCTTC    47400

ACTCTTCTTC CCTCCACTTT TGGTCTGCGA GAAGCCTTCT GGCGATCTCG ATAGGTTCGA    47460

TCTCAGGAGT CACTCATCGC CCTCCAAGAT CTTCAGGTTG CCAGCAGTG CATTGGCCAC     47520

AGCTCCGATG TGGCCACCGC CCTTACCTCC ACGGCGGGAG TACTCGCGGT TCGCGGCCTG    47580
```

-continued

```
CATGAAGTGG AACCTCGGTG AGCCGTCCTC GTGAACCCAC GAGGCTTTCT CGGCGGGCAG    47640

AGCCCGGTTC ATCTCCACCG ACATCGTGAC GATGATGTGG TCCCTCTGGA GCCGAGCCTC    47700

GGTCTCGGCG TAGTGGGCAG CTTGGATTAC TGCGCCTCGT GTGGTCATGT CTTCTCCTTC    47760

GGTAGATGTC AAGCTGTCGT CACCACTCTT CGACCGGTAT CGGTTTGTCA CAGCCAGCAA    47820

GGATCGCGGC GTTGCTGCGG TGATGCCCGT CCCACAGCGT CTTTCGGTCC CTCGAAACCT    47880

CGAGGGGTTC GAACGGCCAC TCGTTCGATG AGTTGAGGAT GTCCACGACT TCGTGGACCT    47940

TGGCCCAGAA CTTGCCGGTC ACGCCTCCCT GGTAGTTGTA GCGGGCGTG GTCTGGTAGA    48000

ACTCTTCGAG CACTGGTCCG CTGTCGGCGA CGGTGCAGTC GACACCAGCG CAGGACATGC    48060

AGTCGCTGGC GCGGAGCTGG GCAACTTCAT CGGTGGTCAT GAACGCCGTG GTCACATCGA    48120

GCCTTTCAGG TGTATGTCAA GCGGCGCGGA CGCCGGAATC GGAGAGGTAG ACGCGGTCAG    48180

CTCCCAGGAA CGGAGCCTGT GTGTTGGCGT GGACGAACGT GTCGTTCTCG TAGGGGTTGT    48240

AGGCGATCTT CGATCCCACG AAGTCTTGCG GGAGAAGCGA GATCAGCTCG CCTACGATGC    48300

CAGCGTGGAC CACCTTGCGG CGCTCGCGCC GTACCTTGTC GCGGCCGGCC GGCCGAACCA    48360

CACCCTTGGC GTGGGCCAGC AGGACGTGGC CGCTGCGGTG GATGACTCGA CCCTTGAAGT    48420

CTCCCTCCAA GGCTTGCACC GAGTACCACG GCTTGCCCTC GCGGTGCGTG CGGTGCAGGT    48480

TCTTGTAGAC GAAGACTCGG ATCGGCTTGG GAGTCATGAG ACCTCCAGTG TGCGAACGGC    48540

CTTGTAGGCA CTGATGAGTG ACGCCCCGA CAGCTCGTTA CCGTGCAGGT GATACCTGTA    48600

TTTCAGATAC ACGGCTTGGT CGACCGGCTT GTACTCGACC GAAGTGACCT CGACAACCAT    48660

CCCGTCGATG ATCGCGAAGT CTCCAGCGCG GAGATGGGTG GGGAATTTGA TCTCGGTGTT    48720

GACTACGGTC ACAGCTTCGA AACCTCCCAG GTACCAACGA ACTTGCCGTT GCGCTTGATG    48780

TATCCGCTCT CACCGGGCTC GTACCAATCG ACCTCGAACC CGTAGCGGGC GGCGCAAGCC    48840

TCGAGGTGGT CGAGCAGGAC GCGGCGACCG GACGCGGTAG CTTCTCCGGT CAGCCCGCTG    48900

TCGTTCTTGC GGACGATGAG CTTGAACACT TGGTGCCTAC CCTTCTGCGA TGTCTCGGGA    48960

GATCTCGGCG AAGACTTTCT TTGCCCACGC CACGCCGTCC CAGGTGATGT CGAACAGTGC    49020

CTCGTAGAAC TGGTCTCGCA AGGCTTCGTT GCCGTCGGCC AGCGTTGTGA CGAGCCGGTC    49080

GATGCGGTCC TCGTGGAACT TGTAGACCGA GTGGTTGTAC GGCTCAGCCA TATTGGCGTT    49140

GGCTCGTTTC ACGTTCTCAA CCACGATGGC TTCGAATAGG TGGTTAACCA GCTCCTCGGT    49200

CATGTTCTAT CTCTCCTCAG TAGTCGCTGT GCTGGGTCTC GAAGCCTTCG AGGTCACCGA    49260

CCTCGTCGTC GTACGCGCTC GGGTTGCCGC GCCAGTCGTC GCGGAGCCTT TGACCGCTGG    49320

CGTTGTAGCA GGCACCACAG TTCGGGCAGT CCACATCGCT CTGGCCGTAG TAGCGGCAAA    49380

CCTCGCCGCC GCAGCGTTGG CAGTCCCACG CGCTGTAACC AGGGATCAGG AAACCTTGGT    49440

CGTCGGTCTG ATCAGGGATG CGTCGGAAGT TCTTGGCAGG CATAGCTACT CCTCATAGAA    49500

ACTCGTGGTT GATGGCTCGG TGGGCAGCCT CGCGGAAGGT CAGCCCGTCG TCGTACGCGT    49560

CCCGGTACGT CCAGTCCGCG ATGTCTTGGT AACCAAGACC AAAGGTCTCG GTCATGTAGC    49620

CGTCCAGCGC GGCCATCCAG GTCTCGAAGC TCATGTCTTC CCTCACTTCT TTGTGGTCGA    49680

GAACAGCACG TTCCTGCGGC CGTTGACGCA CAGACCGCAA CGGGCACAAG CCGATCCCTT    49740

GTCGTTGATC AGGTCGATGG CTTTGTTGTT CTCCGGGCAG CGCACCGCCG TCGGAAACTC    49800

GGCCTTGCCT TTGGCGAACG TGGTGTCGAC GTAGGCGATG TTGATGCCCT TGTCTTCCAA    49860

GAAGCGCGCC ACGTCGATGT TGTCCGGGTC TGCGCTGAAG TACAGCGCCA GGTTGTCGAG    49920

CCTCTGCGAG TGCAGGTAGA CAGCCGCCGT CTGAACCCTT GTGTAGGCCC AGAACTGGAC    49980
```

-continued

```
ATCCGGGTTG TCGCGGATGA CTCGACCCCA AGCGGCCACA TAGGTGGGGC TGAAGAAGTC     50040
TCCATCCCAG TGGATGCGGA ACAGCTTCGG AGCCTTGCGA CGGTCGCAAT CCTTGACGAA     50100
CTCGGCGACC ATCTCGGACA GCAGCGTCAC GGTGTCTGTC AAGTCAGCGT CACGCAACAG     50160
TTCCCAGTTG TGCAGCAGGA CCGAGCTGAC AGCCTTGCGA ACTTTCTCCA GCTTGCCGGC     50220
GTAGCACACC TTGGCACAGA AGGCCGTCGC GTCCGGGCAG GAGAAGCCTT GACCGGAGGG     50280
CAGGCCGATG CTGTTGGCGA TACCTACGGT GGCGTTGCCG CCCTTGGTGA CGTGGACGTA     50340
GTTGGTGACC TTGCGGTCGT TCGAACGCTT CAGCTTGGCC ATACCTAGCC TTCCTTCGGT     50400
GGCTGTCAAG TTGTTGGATA CAAAGCGCCC CGAGAGGGAG TCGAACCCTC ACACCGCGAA     50460
CCGTCGCGGG GCCACCGTGC CTAGTCGATA GAGGTCACTC GACTCTCGTG GACGTAGACC     50520
ACGGTGTTGC CTACGTTCAC CGCGTAGTAC AGGCCATCGG CACCTCGTAG CTTGTGCCGA     50580
ACCGTGCCCG ACGTGGCCGT CATGTCTTCG CCCCAGTCGG CGTTAGGTGC CCAGGTGACT     50640
CGCATGGTGA TCCCTTCAGT AGTCGGTGGC TGTCAAGTCA GCGGATACGG ACGTACCCGT     50700
TGCCTCGAGC GACGTAGATC TTGCCGTCGA TGTAAACGCG CTGCTGCTGG TTCATAATCC     50760
TATTCCTTTC GGTGGCTGTC AAGTCTCAGG CCCAGCGACG AGTCGTCGGC CGGGGCGGC     50820
GCACCTTGGG CGCGTTGGCT CGCGGTGCCT TACGGATGGC GGTGCCTACC GTGATCTCTT     50880
CCAACTGGCG TTCAGCCAGG CCGACAGGCC GGGCGTCACC GGGCAGTTCG ATCTTGTAAT     50940
CGAAGTCAGT CCACCCCTTC AGACCCTTCT CCAGCTCGCG ATCCAACAGA CGCGGAGCCG     51000
ACAGCTCAGG CGCAACAAAC GGTGTCTTGA CGCTCTCGCG GGCAGTAACC CGAACCTCAC     51060
GGTGCTCAGC GAAGACTGGC ATAGTTCACC CCTTTGGTGG ATGTCAAGCC TGAGCACCAA     51120
AGCTCAGGCG TAGTGGGTAG TCGGGAATCG AACCCGATAG CTTCATAGCC ACGTTCTACG     51180
GCTCAGCCAT AGCTCAGCGA TCATTCCATC GCGCCAAGAG CTACCCTCCC GAATGCCGAA     51240
CCAAAGCTCA GCATTCGTAA GTGTGTATTC TCCCCGTGGC TCAGACAGTA TCTATCGAAA     51300
CCTAACCACA GGTCTACATT TAGTTATCCG CAGTGCTCGC ACTTTAACGG CATCGAGCTT     51360
CCGCCGACCC TCAGTCCTCT GGCAGCGAAC TAAAGGTTTG AGTCGGGCTG CGGCCCTTCT     51420
CGGTCTTGCG TGATTCTCAC TCTACCGGAT GTTTCGGTGG CTGTCAAGCG GGCCGTTTTG     51480
GTGTTGCAAC GATGCCCTCG TTTAGCGCCG CTGGCGTAAT GCGCTACCCG CCTGATCTCA     51540
CCGGTCCAAG TTGGTGATGC TTGCAGCTTA CCCGATAACC GGGTGGCTGT CAAACCGGAG     51600
AATCTTGCCG CCGGATTTTC ACCGGCACCG GCACGATCCT CTCGGATCCG CCTACCGCCT     51660
TGCTGCTGCG GTGACACAAG AATGCACTAC TGGCCGGGTG GCTGTCAAGC CCTAATCGCA     51720
AATTGGTGCC CTAGCTGCAG ATATGGCGCG TTCTCGGTGG CTGTAAAGGG CACTACGTGC     51780
CGCTATCCGC TGGTCACGCT GGACAGTCCC GGCAGCCCGT GCCGCGCATA GGCTGCTCAC     51840
TACGTGCCCG GTATCGGCGT TGTCGTGCCG CTGTCGTGGT CGTCGCCCCG TCGCTGTCGC     51900
TGGTCTCGGT GGCATCGCTT GACAGTCGCC CCGCTATCCC CCGTTGCCGC TGGTCAGACG     51960
CTAATCCGCT TATTTCGCAT AGGCTGCTCA CTATCGCATC GGTATGCGTA TGCGCTGGTC     52020
ACATATGCGT GTGGTGGTGG TGTGGTGTGC GTGTGTTTGC GCTGGTCAGC CGTGTGCGTA     52080
CCGTATCCGC ACACTGTGCT TGTGCGTTTG CTGTGTGTCG AGGCCGGCTC TCGCATCGTC     52140
GCATGTCAGC GCGGGTATGG GCGTGTATCG CACGCTTTGC TAGCCGCGTG CCGCGGCGCT     52200
CTCGCATCGC ATCGAGTGTT TGCTGTGTCT CTCATCGTCG CAGGTCAGAA GGGGTAGGGG     52260
GGTTCCCCCT AGGGGTCGGT CCTTGACCGG TCGGTTA                              52297
```

MYCOBACTERIAL SPECIES-SPECIFIC REPORTER MYCOBACTERIOPHAGES

CROSS-REFERENCE TO RELATED APPLICATIONS

This Application is a continuation of application Ser. No. 08/705,557, filed Aug. 29, 1996 and entitled MYCOBACTERIAL SPECIES-SPECIFIC REPORTER MYCOBACTERIOPHAGES, which is in turn a file wrapper continuation of application Ser. No. 08/430,314, filed Apr. 28, 1995, now abandoned, which is in turn a file wrapper continuation of application Ser. No. 08/057,531, filed Apr. 29, 1993, now abandoned, which is in turn a continuation-in-part of application Ser. No. 07/833,431, filed Feb. 7, 1992 and entitled MYCOBACTERIAL SPECIES-SPECIFIC REPORTER MYCOBACTERIOPHAGES, now abandoned.

STATEMENT OF GOVERNMENT INTEREST

This invention was made with government support under NIH Grant Number AI26170.

FIELD OF THE INVENTION

This invention relates to mycobacterial species-specific reporter mycobacteriophages (reporter mycobacteriophages), methods of making such reporter mycobacteriophages, and the use of such reporter mycobacteriophages, for example, to rapidly diagnose mycobacterial infection and to assess drug susceptibilities of mycobacterial strains in clinical samples. Specifically, this invention relates to the use of mycobacterial species-specific luciferase reporter mycobacteriophages to diagnose tuberculosis and to assess the drug susceptibilities of the various strains of Mycobacterium tuberculosis (M. tuberculosis).

To produce the mycobacterial species-specific reporter mycobacteriophages of the invention, transcriptional promoters and reporter genes are introduced into the genomes of mycobacterial species-specific mycobacteriophages. These reporter genes may be the genes for luciferase or the β-galactosidase gene, and provide the DNA which encodes the production of a gene product.

The reporter mycobacteriophages may be used for diagnosing mycobacterial infections by incubating same with samples which may contain the specific mycobacteria of interest. If the mycobacteria of interest is present, then the reporter mycobacteriophages introduce the recombinant nucleic acids which encode expression of the gene product into the mycobacteria of interest, and the mycobacteria then express the gene product. The expressed reporter gene product may be detected by a suitable assay, for example, through the detection of photons or the conversion of an easily assayable chemical reaction. The presence of such gene product indicates that the sample contains the mycobacteria of interest, and hence the mycobacterial species-specific reporter mycobacteriophages may be used to detect and thereby diagnose the specific mycobacterial infection.

Since signals may not be generated by cells which are not metabolically active in the presence of antibiotics, the mycobacteria species-specific reporter mycobacteriophages of this invention may be used to assess the drug susceptibilities of various strains of mycobacteria. If antibiotic drugs are added to the sample containing the reporter mycobacteriophages and the gene product is detected, the mycobacteria is metabolically active and hence resistant to the antibiotic drug.

BACKGROUND OF THE INVENTION

In 1990, there was a 10% increase in the incidence of tuberculosis in the United States. In addition, there has been an increase in the appearance of clinical isolates of tuberculosis that are resistant to antibiotics used to treat the disease. This problem is exacerbated by the length of time that is currently needed both to diagnose tuberculosis, and to determine the drug susceptibilities of various strains of M. tuberculosis. As a result, patients with M. tuberculosis may remain infectious for long periods of time without being treated, or may be treated with a drug to which the bacterial strain is resistant. Therefore, a need has arisen in the field for a method of diagnosis of M. tuberculosis (and other mycobacterial infections) which is rapid, sensitive and specific, which method is also capable of assessing the drug susceptibilities of the various strains of M. tuberculosis and other mycobacterial strains. It is critical that a mycobacterial strain be assessed for drug resistance rapidly because a patient infected with a strain of M. tuberculosis or another mycobacteria must be treated immediately with the particular antibiotic drug(s) to which the strain is not resistant, and not with antibiotic drug(s) to which the strain is resistant, or the patient may die.

Currently, the most rapid test available for the diagnosis of M. tuberculosis is the staining of sputum samples for acid-fast bacilli, which is a tedious procedure, and which procedure has low sensitivity. Alternative methods for diagnosis require cultivation of the bacilli for approximately two to six weeks followed by classification of the cultured organism. Typical diagnostic tools include biochemical tests, analysis of mycolic acids and serotyping. All of these tests are time-consuming. More recently, the use of oligonucleotide probes and Polymerase Chain Reaction have been suggested for the identification of M. tuberculosis species. Although these methods may be useful approaches, their uses in a clinical setting have not yet been determined. Further, these methods do not distinguish between live and dead organisms, and are therefore of limited use in the determination of drug sensitivities of clinical isolates.

In addition, *Mycobacterium avium* (*M. avium*) is a mycobacteria which is often found in immunosuppressed patients. This mycobacteria is typically disseminated throughout the bodies of immunosuppressed patients, such as AIDS patients, and causes *M. avium* infection. Because this mycobacteria often causes death in immunosuppressed patients, it is necessary to be able to diagnose and assess the drug susceptibilities of the various strains of *M. avium*.

It is therefore an object of this invention to construct broad mycobacterial host range and mycobacterial species-specific reporter mycobacteriophages.

It is another object of this invention to provide mycobacterial species-specific reporter mycobacteriophages which may be used to rapidly diagnose mycobacterial infections.

It is still another object of this invention to provide mycobacterial species-specific reporter mycobacteriophages which may be used to rapidly assess the drug susceptibilities of different strains of mycobacteria in clinical samples.

It is yet another object of this invention to provide mycobacterial species-specific reporter mycobacteriophages wherein the reporter genes are luciferase genes, which mycobacterial species-specific reporter mycobacteriophages may be used to rapidly diagnose mycobacterial infections and to rapidly assess the drug susceptibilities of various strains of mycobacteria.

It is a further object of this invention to provide mycobacterial species-specific luciferase gene reporter mycobacteriophages which may be used to rapidly diagnose tuberculosis and assess the drug susceptibilities of the various strains of M. tuberculosis.

SUMMARY OF THE INVENTION

This invention relates to broad host range and mycobacterial species-specific reporter mycobacteriophages, (reporter mycobacteriophages), methods of producing such reporter mycobacteriophages, and the use of such reporter mycobacteriophages to rapidly diagnose mycobacterial infection, such as M. tuberculosis, and to distinguish which strains of the mycobacteria are drug-resistant.

To produce these reporter mycobacteriophages, reporter genes and transcriptional promoters are introduced into the genomes of mycobacterial species-specific mycobacteriophages. The promoter and reporter gene-containing mycobacteriophages (reporter mycobacteriophages) are then incubated with a clinical sample which may contain the mycobacteria of interest, such as M. tuberculosis. The reporter mycobacteriophages are specific for the mycobacteria which is sought to be detected. The reporter mycobacteriophages efficiently introduce the recombinant nucleic acids which encode the expression of the reporter gene's gene product into the mycobacteria of interest, and the mycobacteria then express the gene product. A substrate or other means capable of allowing for the detection of the gene product is then added to the sample. If the gene product or the signal generated by the gene product is detected, the presence of the infectious mycobacteria is known, thereby diagnosing the disease.

To assess drug susceptibility of mycobacteria, drugs such as antibiotics may be added to a sample containing the reporter mycobacteriophages of this invention. If the mycobacteria are susceptible to a drug after exposure to the drug, the mycobacteria will be killed. However, drug-resistant mycobacteria will continue to be metabolically active in the presence of the drug, and will continue to express the detectable gene product of the reporter genes. Preferably, the reporter mycobacteriophages of the invention are temperate, and have increased sensitivity for use in drug screening.

The preferred reporter genes of the present invention are the *Firefly luciferase* lux gene (FFlux), the luciferase lux genes of *Vibrio fischeri,* the luciferase lux genes of *Xenorhabdus luminescens* and the *E. coli* β-galactosidase gene (lacZ). Some preferred promoters of the present invention are hsp60 and gene 71-70-69 promoters, and the preferred mycobacteriophages are L5, TM4 and DS6A. These reporter mycobacteriophages are preferably used for the rapid diagnosis of tuberculosis and *M. avium* infection, and the accurate assessment of drug susceptibilities of the various strains of M. tuberculosis and *M. avium.*

BRIEF DESCRIPTION OF THE DRAWING

The above brief description, as well as further objects and features of the present invention, will be more fully understood by reference to the following detailed description of the presently preferred, albeit illustrative, embodiment of the present invention when taken in conjunction with the accompanying drawing wherein:

FIGS. 21A and 21B represent a map of expected DNA fragments resulting from a pair of homologous recombination events in common flanking sequences when FFlux is inserted into the L5 genome in a corresponding location to that in pGS24;

FIG. 28B represents the light produced (RLU);

FIG. 30 represents a list of L5 reporter mycobacteriophages of the invention which have been developed.

DETAILED DESCRIPTION OF THE INVENTION

Figure 1:
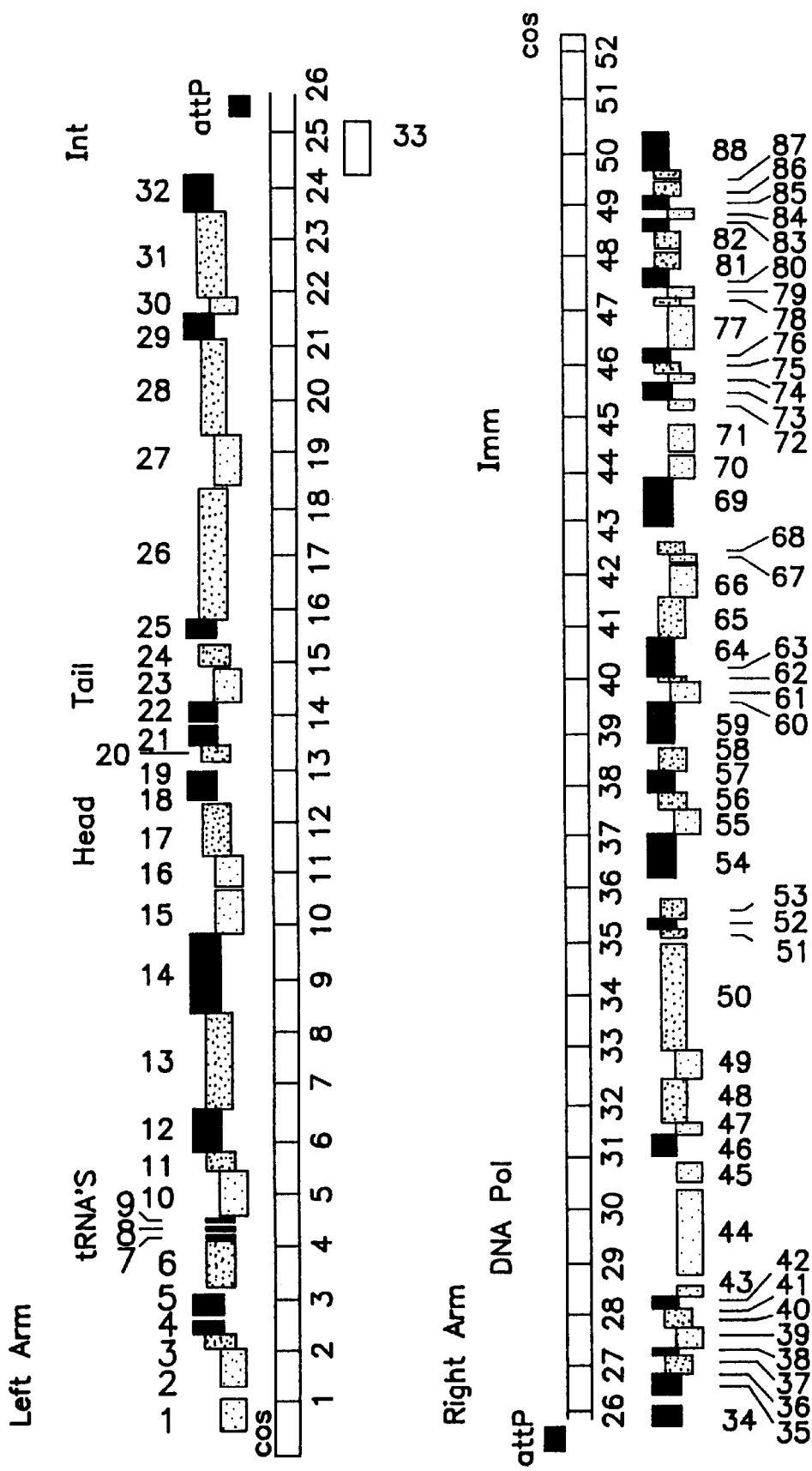
FIG. 1 represents the genome organization of mycobacteriophage L5.

This invention is directed to mycobacterial species-specific reporter mycobacteriophages, (reporter mycobacteriophages), methods of producing such reporter mycobacteriophages and the use of such reporter mycobacteriophages for the rapid diagnosis of mycobacterial infections and the accurate assessment of mycobacterial drug susceptibilities.

In order to produce such reporter mycobacteriophages, mycobacterial species-specific mycobacteriophage genomes are modified by introducing therein transcriptional promoters and reporter genes whose gene product can be sensitively detected. The reporter mycobacteriophages may then be incubated with clinical samples suspected of containing the mycobacteria of interest, either directly of after culture, and the samples tested for the presence of the reporter gene product, thereby diagnosing mycobacterial infection.

The method of this invention allows for rapid diagnosis because only the amount of time necessary for the reporter mycobacteriophages to infect their host cells and the amount of time necessary for the host cells to synthesize the reporter gene product are required to allow for diagnosis. Typically, the amount of time required for the reporter mycobacteriophages to infect their host cells and for the host cells to synthesize the reporter gene product is between ten minutes and sixteen hours.

The assessment of drug susceptibilities with the reporter mycobacteriophages of this invention is accurate because the reporter mycobacteriophages only allow for the detection of metabolically active mycobacterial organisms, the presence of which metabolic activity indicates that a drug has not killed the mycobacteria and that the mycobacteria is resistant to the drug.

The L5 reporter mycobacteriophages of this invention are temperate, i.e., they are able to exist in bacterial cells as prophages integrated into mycobacterial genomes without causing cell lysis. Because the L5 reporter mycobacteriophages do not cause cell lysis, they replicate as part of the bacterial genomes in bacterial cells. The integrated reporter phages express high levels of luciferase activity, since the luciferase reporter phages can be stably maintained. This growth causes amplification of photon signal. Because temperate phages possess the ability to site specifically integrate into mycobacterial genomes, they are replicated as part of the mycobacterial chromosome. In addition, the integrated luciferase reporter phages confer to the infected cell the ability to produce amounts of luciferase activity comparable to plasmid transformed cells and 100 to 1000 times more luciferase activity than phage-infected cells. The luciferase lysogens can be readily used to screen for drug activity by simply observing the inhibition of growth measured by proportional luciferase activity. Hence, the use of temperate L5 reporter mycobacteriophages results in a more sensitive assay for drug screening, as compared to the use of lytic reporter mycobacteriophages.

Mycobacteriophage L5, a temperate virus with a broad host-range among mycobacteria, is the most thoroughly characterized of the mycobacteriophages. L5 particles are morphologically similar to the family of phages that includes phage λ and contain a linear dsDNA genome with cohesive ends. The inventors have determined the DNA sequence of the entire genome of L5, as well as several gene functions. The DNA sequence of the L5 mycobacteriophage is as follows:

```
SEQ ID NO: 1:
GGTCGGTTAT GCGGCCGAGC CATCCTGTAC GGGTTTCCAA GTCGATCAGA GGTAGGGGCC      60

GGCACAGAAA CCACTCACAT CAGGGCTGTG CGCCTCCAGG GCGCGTGAAC TCCCACACCC     120

CGGTGTAGTT ACATCCCGGA ATTGTCTCAG CGCCTCTCAG GGCGCTTCTC ATAAACAGTG     180

ATCTACGCCA CTCCTGACGG GTGGCTGTCA AGGATACTCA CCTTCCCTAC TAATGAGGGG     240

CTAAGAGCCC CTCTCTATAG AGCGCCGCAC AGGCGGCGCG ATAAGAGCGC CACCAGGCGC     300

TCATCTAAAG ACCGGCCTTG AAGGGCCGGT CATAGAGATC TATTCGATCC GGCAACCGCC     360

GGATCTCAAG GCCGCGCCAG TGCGCGGCCC TATAGAGGGG TGACTCAACT GTGCATGGCA     420

CTCGCTCGAG TGCCCACTGG AGCACTCAAC CGGGGAAGTT CGACGTTCTC AACCTGCGAA     480

TGACGTTTGA ATCGTCATCC GCGTACGAAA TCCCCGATCT GCGGCCGACC GACTTCGTGC     540

CGGCCTATCT CGCGGCCTGG AATATGCCGC GTCACCGCGA TTACGCCGCC AAGAACGGCG     600

GCGCGCTGCA CTTCTTCCTT GACGATTACC GGTTTGAGAC CGCGTGGTCG TCCCCCGAGC     660

GCCTTCTCGA CCGCGTAAAG CAGGTCGGCG CTGCACTCAC GCCGGATTTC AGCCTCTGGA     720

CGAACATGCC GAAGGCGGCG CAGCTATGGA ACGTCTACCG CTCCCGCTGG TGTGGCGCGT     780
```

-continued

```
ATTGGCAGTC GGAAGGAATC GAGGTGATTC CGACGGCGTG TTGGGCGACT CCCGACACGT    840

TCGATTTCTG TTTCGACGGG ATCCCGATGG GATCGACCGT CGCAATTTCT TCGATGGGCA    900

TTCGCTCTTC AAAAGTCGAC CAGGAGCTTT TCCGGTACGG ACTACGCGAA CTCATCGATC    960

GCACTCAACC GCAACTGCTT TTGGCATATG GCCAGCTTCG GCATTGCGAC GACATGGATT   1020

TACCAGAGGT CCGCGAATAC CCGACCTACT GGGACAGACG ACGAAAGTGG GTAACTGCCG   1080

ATGGGAGGCC GGGGAAGTAA AGGCGGCCCC GGTCCCGGAA CCGGAGCACG CAACCGCAGA   1140

GGCGCTGGAG CCCCCGGATC GGGCGGCGTA GGCGGCGTCG GAGGCGGGGG TGGAGCTGCA   1200

GGGAGCAGCG GAGGCGGCAA GGGAACGGCA GCGCCGGTAC CGGAGGCGTC ACCGGTGGCG   1260

GCGGAAGTGG AGCCGGCGGC GGTGGCAGCA GCCCCAACAC CCCGGTGCCC CCACCGAGC    1320

TGGAGAAGAA GCGCGGCGAA TACAACCAGA TCGCCATCGA CGCCCAGAAA CAGCACGCGC   1380

CCACCGATGA GAAGCGCGAG GCCAAGCGCA AGCAACTGAT GGATCGAGTC GGAGGAGACT   1440

GGCAGGCTTT GGACCCGGAT CACCACGACG CCATCAAGGT GGCGATGGAT GACGCCATGC   1500

GGAAGATCCT CTCCGAGGAG GAGATCGTCC ACCGCACCAA GCACTTCGGC GACCTACTCG   1560

ACTCCGGTCG ACTCAAGTCG CTGTTCGAGG TCGGCTTCTC AGCCGGTGGC GACACCCCGA   1620

CCGAACGCGC CCTCCTCGAG GACGCCTGGT TCGGCGCAGG CAAGGTTCCC CCGATCTACT   1680

CGGCAATCGA GTTCAACGGC GCTCCGACAG CCGGCCTCGG CATGTACGGC GGCACCAAGC   1740

TCTACATGAA GGACTCGGTC AAGGACCGCG TCACCGTGAC CATCGGCGAC TCGCTGATGT   1800

CGAGCTGGGA CGTATTCCCC GGCCGTCCTG GCGACGGCGT GGGGCTGTGG GCCAGCCTGT   1860

CGAAGATCGA GGGGCTGGTC GATCCGAGCA AGACCCGCGA AGAGAACATG CAGGCGGTGT   1920

ACGACTCGTT CAAGAAGTAC GGCACCCTGG ACGGCTTCAT CGAGGCGCAG ATCCACGGCG   1980

GCGTCCTGGT CGAGGACATC AAGAAGGTCG TGTTCACGCA GCCGCCGAGC CCGATCTTCA   2040

CCGATAAACT GGACGAACTT GGAATCCCGT GGGAGGTGCA GTAATGGCGC AGATGCAGGC   2100

GACACACACA ATCGAGGGGT TCCTGGCTGT CGAGGTGGCC CCTCGGGCGT TCGTCGCAGA   2160

GAACGGCCAC GTACTGACCC GGCTGTCGGC ACGAAGTGG GGCGGTGGCG AGGGTCTCGA   2220

GATCCTCAAC TACGAGGGTC CAGGGACCGT CGAGGTCTCC GACGAGAAGC TCGCCGAAGC   2280

CCAGCGGGCC AGCGAGGTCG AGGCTGAACT TCGCCGCGAG GTCGGCAAGG AGTGAGCTGG   2340

GCCGGCTCAG GCCGGCGACA GGAACTACCA GAGGACTGGG AGCTGAATTA CCGGCTCCCG   2400

GTCCTTTCTG CTGCCAACTG GCTTTGCCAG ATCAACGGTC CCGGATGCGT AAGGGCCGCA   2460

ACCGATGTCG ACCACATCAA GCGCGGGAAC GACCACAGCC GGTCCAATCT GCAGGCAGCC   2520

TGCCATGTCT GTCACGGCAA GAAATCAGCC GCCGAGGGCG TAGCCCGACG GCGGGAACTT   2580

AGAGCCCGGA GGAAGCGACC ACCCGAACGC CATCCTGGGC GTCGATAAGC GGGCCAGGTG   2640

CCCGCTCCAC CCAGGAGGTG AACAGTGGGC ACGCGAGGCC CAATCGGAAA ACGAGATGAA   2700

GAGCGGGTTC GTCGGAACAC CCCGGACAGT CCAACCGACA CGATCCAGAT GCCCGGTCTG   2760

GTGACGATCC CCGAGATGGG CGATCTAAGC CACGACGGCC GCACGCACCA GCTCGTCAAG   2820

GACATGTACG AGTCGATCAA GCAGTCGGCA GCCGTGAAGT ACTACGAGCC GACCGACTGG   2880

CAGATGGCCC GACTCGCCCT CTACACACTT AACCAGGAAC TCATCGCAGC CGAGAACAAC   2940

GGCAAGCCCG TGGGCGCGAT GAAGCTCACT GCCATCAACC AGATGCTCTC CGCGCTGCTG   3000

CTGACCGAAG GTGACCGACG CCGCGTCCGA CTCGAAGTCG AACGAGCACC CGCTGACCCG   3060

ACAGGCGGGA AGGTCGTTGA CGTGACCGAC GTGCTCAAGC AGCGCCTCGC CAAGGCGAGC   3120

GGCGGGAGCT GATGGTCCCC CGAGGGGTTT CTAGAGCCGC TGCCGCTACC AGCCGCTCCC   3180
```

-continued

```
CCTCGGGGTA GACATCGAAA GGAACCACAT GGCCGACCTC GGCAACCCAC TCGACCTCGA    3240

GATGCTCTGC CTGGTCACAG GCCGGGACTT CCGCTGGACC ATCGATTACC CGTGGGGTCC    3300

GGGAGAGCTG TTCCTCGAAC TCGAGACCGG CGGCGAACAC AACGCGCTGC ATCAGGTCTA    3360

TGTCACCGGG GCGACCGGAG GCACGTACAC GCTGAACGTC AACGGCACCA ACACCCCGGC    3420

CATCGACTAC AACGACGTGT CGGAGAATCC GCAGGGGCTG GCAGGCGACA TCCAAGACGC    3480

TCTGGACGCA GCCGTCGGAG CCGGAAACGC TGTCGTGCAT CCGGTCTCGC TGTTCCCTGC    3540

GTGGACACTG AACTTCAACC TCAACGCCAG CAAGCCGCTC ACCGAGCAGT TGGTCAACAC    3600

GATCAACAAG GCCGCGAACG ACTTCTTCGA CACGTTCGAC CAACTACTTG GGGTCGACGT    3660

GGAGATGACG GTCACCGACA CCCTGAACTT CAAGCTCAAG GTGACCTCGC GGCGCTCGTT    3720

CGATGAGGTC GGTGTCGTCA CGTTCGCGGT CGACGTGACC AGCCAGGCAG TCATCAACTT    3780

CTTCAACTCC GTCGCCGAAC TCACCGGAGC GGTGAACACC GTCAACGTCG ACTTCTACTG    3840

GAACCGGACG TATGACATCG AGTTCACCGG ATCCCTTGGG CTGCAGCCGA TTCCGGCTAC    3900

TACAGCCGAC ATCACCAACC TGGCGGGTAC CAGCAAGGCC GTCTCAGTCA CGGTGGTCGA    3960

GCCAGGAAAG AAGAGGCTGA CCATCTGGCC GTTCACGGTC AACGGTGAAA CCGCAACCAT    4020

CAAGGTCGAG TCCGAAGAGG CCGACAAGAT CCCCAACCGC TGCCGCTGGC AGTTGGTTCA    4080

CATGCCGACC GGCGAGGCAG CCGGCGGCGA TGCAAAGCAG CTCGGCCGCG TTTACCGACA    4140

GCCGAGGTAA CACCGCACCC ATCAGAGATG GTGGGCCAGA CGGCCTTCGG GCCGTCCCCT    4200

GACGTGTAGC TCAATGGCAG AGCGCCCGAC TGTTAATCGG GTGGTTGAAG GTTCGAGTCC    4260

TTCCATGTCA GCGAGGGCTG AACCGGACCC GTGTCCGGTG TAGGCACTTT CCGCAGGCGG    4320

TTCCCCAGAG CGTGGGGAGC CCCTGCCCTG TACACGTAGC TCAATTGGTA GAGCAGCGGT    4380

CTCCAAAGCC GCCGGTTCCA GGTTCGACTC CTGGCGTGTA TGCACACACC CCTGACTCCT    4440

GCTAGCGGAG TGTTCGCCTT TCGGGCCTGG GGTCTTTTTC CCCGTTCGTC TAATCGGTAA    4500

GACACCCGGC TCTGGACCGG GCAATTGAGG TTCGAGTCCT TGGCGGGGAG CCAACTTGAC    4560

ATCCACCCGA AAGGAACAAC ATGACCTTCA CAGTCACCCG CGAGAGAGCG CAGTGGGTCC    4620

ACGACATGGC CCGCGCTCGC GACGGTCTCC CCTACGCGTA CGGCGGGGCG TTCACCAACA    4680

ACCCGAGGGT GTCGACTGAC TGCTCTGGCC TGGTGCTGCA GACCGGGGCT TGGTATGGAG    4740

GTCGCACCGA CTGGGTCGGA AACCGTTACG GCTCAACCGA ATCGTTCCGG CTCGACCACA    4800

AGATCGTCTA CGACCTAGGG TTCAAGCGGA TGCCCCGAGG CGGGCCAGCG GCCTTGCCGA    4860

TCAAGCCGGT GATGCTCGTC GGGCTCCAGC ACGGAGGCGG CGGGGTCTAC TCGCACACCG    4920

CTTGCACGTT GATGACGATG GACCACCCCG GTGGCCCGGT CAAGATGTCC GACCGAGGCG    4980

TCGACTGGGA GTCCCACGGC AACCGCAACG GCGTAGGCGT CGAACTTTAC GAGGGCGCAC    5040

GGGCATGGAA CGACCCTCTG TTCCATGACT TTTGGTACCT GGACGCAGTC CTCGAAGACG    5100

AAGGAGACGA TGACGAATTG GCTGACCCAG TTCTAGGGAA GATGATCCGC GAGATCCACG    5160

CGTGCCTGTT CAATCAGACC GCGTCGACCA GCGATCTGGC GACCCCTGGT GAAGGCGCTA    5220

TCTGGCAGCT ACACCAGAAG ATCCACTCGA TTGACGGCAT GCTCCACCCG ATCCACGCTG    5280

AGCGGCGCGC TCGCGCAGGC GATCTCGGTG AGCTGCACCG AATCGTGTTG GCCGCGAAGG    5340

GCTTGGGCGT GAAGCGCGAC GAGGTGACCA AGCGGGTCTA CCAGAGCATC CTCGCCGACA    5400

TCGAGCGGGA CAACCCCGAA GTACTTCAGC GATACATCGC AGAAAGAGGT GGCCTATGAG    5460

CCCCAAGATC CGACAGACCA TCTACCTGCT CGGCACCGCC GCCCCGGCAC TGCTGGGCAT    5520

CGTCCTGATC TGGGGCGGGC TCGACGCTGA GTCGGCGGCT GACCTCGGTG ACATCATTGC    5580
```

-continued

```
GGGCGTCGTG TCGATACTAG TCTCCGGTGC GCCGGCCGTA GCGGCAGGCA CCGTACGCAG      5640

CCAGCGCAAG GACGGCACGT TGTCCACCAG CCCGGTGGAT CAGGTCACCA AGGGCGTCGA      5700

GCAGGTGCTC GCGGCCAGGC AGAGTGCCGA GGCTGAAGTC GCGAAGGTCA AGCAGGCGCT      5760

GGAGACCGCC GTCAGCGGTT CTCTCCCCCA GCTCGGCCCG CTGGCCACGC AGATCCTCAA      5820

CGTGGCTGAC GACACCGTCT GGCGTCCATG AGCAAGCCCT GGCTGTTCAC CGTCCACGGC      5880

ACAGGCCAGC CCGACCCGCT CGGGCCTGGT CTGCCTGCCG ATACCGCACG GGACGTACTT      5940

GACATCTACC GGTGGCAGCC CATCGGCAAC TACCCGGCAG CGGCGTTCCC GATGTGGCCG      6000

TCGGTCGAAA AGGGTGTCGC TGAGCTGATC CTGCAGATCG AGCTGAAGCT GGACGCAGAT      6060

CCGTACGCGG ACTTCGCGCT GGCCGGCTAC TCGCAGGGAG CCATCGTGGT GGGCCAGGTG      6120

CTCAAGCACC ACATCATCAA CCCGAGAGGT CGACTGCACC GGTTCCTGCA CCGGCTCAGG      6180

AAGGTCATCT TCTGGGGTAA TCCGATGCGG CAGAAGGGCT TGCCCACAC CGACGAGTGG       6240

ATTCACCAGG TCGCTGCCTC GGACACGATG GCATCCTCG AGGACCGACT GGAGAACCTC       6300

GAGCAGTACG GCTTTGAGGT CCGCGACTAC GCGCACGACG GCGACATGTA CGCCTCCATC      6360

AAGGAGGACG ACATGCACGA GTACGAGGTG GCCATTGGCC GAATCGTGAT GAGCGCTAGG      6420

CGATTCATCG GAGGTAAGGA CTCCGTCATC GCCCAGCTCA TCGAGCTTGG ACAGCGTCCG      6480

ATCTGGGAGG GAATCGCGAT GGCCAGAGCC ATCATCGACG CCCTCACGTT CTTCGCCAAG      6540

TCGACCCAAG GCCCGAGCTG GCCGCATTTG TACAACCGCT TCCCGGCGGT CGAGTTCCTA      6600

CGACGAATCT GAGAAAGGAG GCGGGGTGAG CCTCAACAAC CACCACCCGG AGCTTGCCCC      6660

GTCTCCCCCT CACATCATCG GCCCGTCCTG GCAGAAGACG GTCGATGGTG AGTGGTATCT      6720

GCCTGAGAAG ACCCTCGGCT GGGGAGTCCT GAAGTGGCTC TCCGAGTACG TGAATACCCC      6780

TGGCGGGCAT GACGATCCGA ACCGTCTGGC GACGTTGATC GCGCTCTCCG AGGCAGGTCT      6840

TCTCGACAAC GAGAACATGT TCATCCCCAC CGACGAGCAG GTACGCCTGG TCCTCTGGTG      6900

GTACGCAGTA GATGACCAGG GCCAGTACAT CTACCGCGAG GGCGTGATCC GCCGGCTCAA      6960

GGGCTGGGGC AAGGATCCGT TCACCGCCGC GCTCTGCTTG GCGGAACTCT GTGGCCCCGT      7020

AGCCTTTTCA CACTTCGACG CCGACGGTAA CCCGGTCGGC AAGCCGCGTT CAGCCGCGTG      7080

GATCACCGTC GCGGCCGTCA GCCAGGACCA GACGAAGAAC ACGTTCTCGC TGTTCCCGGT      7140

GATGATCAGC AAGAAGCTGA AGGCCGAGTA CGGCCTGGAC GTGAACCGCT TCATCATCTA      7200

CTCCGCAGCC GGTGGCCGTA TTGAGGCAGC GACCTCGAGC CCCGCGTCGA TGGAGGGTAA      7260

CCGCCCGACG TTCGTCGTCC AGAACGAGAC GCAGTGGTGG GGCCAAGGCC CCGACGGCAA      7320

GGTCAATGAA GGCCACGCGA TGGCAGAGGT CATCGAAGGC AACATGACCA AGGTCGAGGG      7380

CTCCCGCACC CTGTCGATCT GCAACGCCCA CATCCCCGGC ACCGAGACGG TCGCCGAGAA      7440

GGCATGGGAC GAGTACCAGA AGGTCCAGGC AGGCGACTCT GTCGACACCG GGATGATGTA      7500

CGACGCGCTG GAAGCGCCGG CCGACACCCC GGTCTCCGAG ATCCCCCCGC AGAAGGAGGA      7560

TCCCGAGGGA TTCGAGAAGG GCATCGAGAA GCTCCGCGAG GGCCTGCTCA TCGCCCGAGG      7620

CGACTCCACC TGGCTGCCGA TAGACGACAT CATCAAGTCG ATTCTGTCGA CCAAGAACCC      7680

GATCACCGAG TCGCGGCGCA AGTTCCTGAA TCAGGTAAAC GCCGCTGAGG ACTCGTGGCT      7740

CTCACCGCAG GAATGGAACC GGTGCCAGGT CGACCTGGCC AAGTACCTGG ATAAGCACGG      7800

CAGGGAGTTC GCTCCGCTGC AGCGCGGTGA CCGGATCACC CTCGGGTTCG ACGGGTCGAA      7860

GTCCAACGAC TGGACCGCGC TCGTCGGCTG CCGTGTCAGC GACGGCCTGC TGTTCGTCAT      7920

CGACATCTGG GATCCCCAGA AGTACGGCGG GGAGGTTCCC CGCGAAGACG TTGACGCCAA      7980
```

-continued

```
GGTCCATTCG GCGTTCGCCC ACTACGACGT GGTGGCGTTC CGCGCCGACG TGAAGGAGTT      8040

CGAGGCGTAC GTCGACCAGT GGGGCCGGAC CTACAAGAAG AAGCTCAAGG TCAACGCCAG      8100

CCCGAACAAC CCGGTGGCGT TCGACATGCG CGGACAGCAG AAGAGGTTCG CGTTCGACTG      8160

CGAGCGACTC GAGGACGCGG TCCTTGAGGG CGAGGTCTGG CACGACGGCA ATCCCGTTCT      8220

GCGCCAACAC GTTCTGAACG CCAAACGACA CCCAACGAAC TACGACGCCA TCGCGATTCG      8280

CAAGGTCACG AAGGACTCCA GCAAGAAAAT CGACGCTGCA GTCTGCGCTG TCCTCGCGTT      8340

CGGGGCGAGA CAGGACTACC TCATGAGCAA GAAGGCCCGT AGCGGCCGGG TGGTGATGGT      8400

TCGATGACAG CACCGCTCCC CGGTATGGAG GAGATCGAAG ACCCCGCAGT CGTACGAGAA      8460

GAGATGATCT CGGCCTTCGA GGATGCTTCC AAGGATCTCG CCAGCAACAC CAGCTACTAC      8520

GACGCTGAGC GCCGGCCAGA GGCCATCGGC GTCACCGTCC GAGAGAGAT GCAGCAACTG       8580

CTGGCTCACG TCGGATACCC CAGGCTCTAC GTCGACTCAG TCGCCGAGCG CCAGGCCGTC      8640

GAGGGTTTCC GCCTCGGCGA TGCCGACGAG GCTGACGAAG AGCTGTGGCA GTGGTGGCAG      8700

GCCAACAACC TCGACATCGA GGCACCACTG GGCTACACCG ACGCTTACGT TCACGGCCGG      8760

TCGTTCATCA CGATCAGCAA GCCAGACCCG CAGCTCGACC TGGGTTGGGA TCAGAACGTC      8820

CCGATCATCC GCGTCGAGCC GCCCACCCGA ATGCACGCCG AGATCGACCC CCGGATCAAC      8880

CGGGTGTCCA AGGCCATCCG AGTCGCATAT GACAAGGAGG GCAACGAGAT TCAGGCTGCC      8940

ACGCTGTACA CGCCGATGGA GACCATCGGC TGGTTCCGCG CTGACGGTGA GTGGGCTGAG      9000

TGGTTCAACG TCCCGCACGG TCTGGGCGTC GTTCCCGTTG TGCCGCTTCC GAACCGGACC      9060

CGGCTCTCGG ACCTGTACGG CACCAGTGAG ATCACGCCCG AGCTTCGGTC GATGACCGAC      9120

GCGGCGGCGC GCATCCTCAT GTTGATGCAG GCGACCGCCG AGCTGATGGG TGTCCCCCAG      9180

CGCCTGATCT TCGGCATCAA GCCCGAAGAG ATCGGCGTCG ACTCCGAGAC CGGCCAGACG      9240

CTGTTCGATG CGTACCTGGC CCGGATCCTG GCGTTCGAGG ACGCTGAGGG CAAGATCCAG      9300

CAGTTCTCTG CAGCCGAGCT GGCCAACTTC ACCAACGCGC TCGATCAGAT CGCCAAACAG      9360

GTCGCTGCGT ACACGGGATT GCCTCCCCAG TACCTGAGTA CCGCCGCAGA CAATCCGGCC      9420

TCCGCTGAGG CGATCAGGGC CGCTGAGAGC CGACTCATCA AGAAGGTCGA GCGGAAGAAC      9480

CTGATGTTCG GCGGCGCATG GGAAGAGGCC ATGCGGATCG CCTACCGGAT CATGAAGGGC      9540

GGCGACGTTC CCCCGGACAT GCTCCGCATG GAGACCGTCT GGCGAGACCC GAGCACTCCC      9600

ACCTACGCGG CCAAGGCCGA CGCAGCCACG AAGCTGTACG GCAACGGCCA GGGTGTCATC      9660

CCGCGTGAAC GTGCTCGCAT CGACATGGGC TACTCCGTCA AGGAGCGCGA AGAGATGCGC      9720

CGATGGGACG AGGAAGAGGC CGCAATGGGT CTCGGCCTGT TGGGCACGAT GGTCGACGCC      9780

GACCCGACGG TCCCAGGCTC CCCGAGCCCC ACGGCACCGC CGAAGCCACA GCCGGCCATC      9840

GAGTCGTCTG GTGGTGATGC GTGACCGCAG AGGAGTACGC GGCGGCTCAA GCCGCGATCA      9900

CTGCGGGTCT TGCCACATAC GTCCAGAGGT TCGCTTCGCT CTTCGTCGGT CCAGCTCTCG      9960

CTGTAGGTGA GTGGCTGCGA CTGCTGCAGG TGCTGTTCCC CGAAATCCAA CGGCGGTATG     10020

CAGATGCTGC CGCCTTGGGC AGGGACTTCT ACGACTCCCA ACGCGCACTA CACCACCCAG     10080

AGCTGCCCCG GAACGAGAGG TTCCGGGGAG AGCTTCGGTG GGAGTGGTTC GTCCAGAACA     10140

TGGAGCCCGC TCGAAAAGAG ATGTCGCAGG CCGACTCTCC GCCGAGTGCG ACCTCTAAGT     10200

TGGCTCTGGC CGCAGTTCGC GAAGTGGAGA TGGCAGCACG CCGACAGATC ATCGGCGCTG     10260

TCAAGAACGA TCCGGCCCCG CAGATCGTGC AGGGCTGGGC GAGGGTCGCC ACCGGGCGCG     10320

AAACATGCGC CTGGTGTCTG ATGCTCATCT CACGGGGTGC CGAGCTGAAT CACAAGGGCA     10380
```

-continued

```
ACTTCGCCTA CAGCTCAGCG GAAGCCGCAG GGCTCAACCT CGATGACGAG ACCGTGATCG    10440

ACCTCTGGAA CGAGTCCGGT CACGACCTTG AGAAGTTCCG CGAGGAGACC AGAGAGGACT    10500

TCGAGAAGTG GCACGCAGGG TGCGACTGTC TGGTGGTCCC GGTCTTCGAT GTGCAGAACT    10560

GGCCCGGAAG AGACGCTGCC CTACGGGCGC AGCAACTTTG GATCGAAGCC AGCGACGAAG    10620

CTGACGACCT CATTGCGTCA GGCAAGGCCC GCTCCAAGAA CAAGAACACG GAGACGCTCA    10680

ACGCGCTCCG ACGCCGCCTA GCACGCGGCG AAATCACCAT GTCCAACTAC GCCCTCGCTG    10740

CGTAGTCCCT CGAACCCCAG GTGGGTTCTC TCAACATGCC CAGGAGGCGA AAACACATGT    10800

CCGACAACCC CACTCCCGAG AGCACCCCAG AGGCCGAGAC CCCGGAGGTC GAGAAGCCGA    10860

TGGAACCGCA GGGCAAGGTC TTCGATGAAG CGTACGTTCA GTCGCTTCGC CAGGAGGCTG    10920

CAGCCGCTCG GGTGGCGAAG AAGGACGCCG TAGAAGCGGC AGAGGCTCGA GTGAAGGCCG    10980

AGTACGAGGC CAAGCTCGCT GAGCGCGACA CCGCTTACAC CGAACTGCAG AACCAGTTGG    11040

GACAGGCGTG GATTGAGCTG GAGAAGGTCT ACCTCTCTCT CGACGCCAAG GTGCCCAACG    11100

ACAAGGTTCG GGCGTTTGTC GAGATCCTCG AAGGCAACGA CAGGGACAGC ATCGCTGAGT    11160

CAGTGAAGTC CCGTCTGGAG CTGGTCGGCG GATTCGGCAA CAAGACCCCG AGTCCTGCGT    11220

TCGACCCGTC TCAGGGTCGC GGCGGTAAGC CGCCGATCCC GCTGAACGGT GACCCGATCC    11280

TCGAGGCCAT CAAGGCCGCT GTCGGGATCA AGAAGTAACC CACCCAACAG ATCTCAAGGA    11340

GAGATAAACA ATGGCAGTCA ACCCTGACCG CACCACGCCG TTCCTCGGCG TGAACGACCC    11400

CAAGGTCGCG CAGACCGGCG ACTCGATGTT CGAGGGCTAC CTCGAGCCCG AGCAGGCCCA    11460

GGACTACTTC GCCGAAGCGG AGAAGATCTC CATCGTCCAG CAGTTCGCCC AGAAGATCCC    11520

GATGGGCACG ACCGGCCAGA AGATCCCGCA CTGGACCGGC GACGTGAGTG CGTCGTGGAT    11580

CGGTGAAGGC GACATGAAGC CCATCACCAA GGGCAACATG ACCTCGCAGA CCATCGCCCC    11640

CCACAAGATC GCGACGATCT TCGTGGCCTC GGCGGAAACC GTCCGTGCGA ACCCGGCCAA    11700

CTACCTGGGC ACCATGCGGA CCAAGGTCGC GACCGCCTTC GCGATGGCGT TCGACAACGC    11760

CGCGATCAAC GGCACCGACA GCCCGTTCCC GACCTTCCTA GCGCAGACCA CCAAGGAGGT    11820

CTCGCTGGTG GACCCGGACG GCACCGGCTC CAACGCCGAC CTCACCGTCT ACGACGCGGT    11880

CGCCGTCAAC GCCCTGTCGC TGTTGGTCAA TGCCGGCAAG AAGTGGACCC ACACTCTGCT    11940

GGACGACATC ACCGAGCCGA TCCTCAACGG CGCGAAGGAC AAGAGCGGTC GCCCGCTGTT    12000

CATCGAGTCG ACCTACACCG AGGAGAACAG CCCGTTCCGC CTCGGTCGGA TTGTGGCCCG    12060

TCCGACCATC CTGAGCGACC ACGTCGCCTC GGGCACGGTC GTCGGCTACC AGGGTGACTT    12120

CCGCCAGCTC GTCTGGGGCC AGGTCGGCGG CCTGTCCTTC GACGTGACGG ATCAGGCGAC    12180

TCTGAACCTG GCACCCCCC AGGCTCCGAA CTTCGTCTCG CTGTGGCAGC ACAACCTCGT    12240

CGCAGTCCGA GTCGAGGCCG AGTACGCCTT CCACTGCAAC GACAAGGACG CGTTCGTCAA    12300

GCTCACGAAC GTGGACGCCA CCGAAGCCTG ATCCAGGCTT GACATCCACC GGGAGGGGGC    12360

TCCTTCGGGA GCCCTCTCCT GATGTGGAGC AGGAAGGACC ACATGCGAAT CCAGTCCACC    12420

CTCAACGGCG GTTTCGCCGA GGTTTCCGAG GAGTTCGCCA AGCAGTTGAT CGCCACTGGC    12480

GGCTGGAAGG TGCCCCGGAA ACCGCGCAAC ACCAAGACCA AGACCGCTCC TGAGGAGCCC    12540

AAGAACGAGG AGTAACCCGT GGCCTACGCG ACCGCCGAAG ACGTTGTGAC GTTGTGGGCC    12600

AAGGAGCCTG AGCCCGAAGT GATGGCGCTG ATCGAGCGCC GGCTCCAGCA GATCGAGCGC    12660

ATGATCAAGC GCCGGATCCC CGACCTGGAC GTGAAAGCCG CTGCGTCGGC GACGTTCCGG    12720

GCCGATCTGA TCGACATCGA AGCTGATGCT GTTCTGCGCC TCGTGCGTAA CCCGGAGGGC    12780
```

```
                                                          -continued
TACCTCTCGG AGACCGACGG TGCGTACACC TATCAGCTCC AGGCCGACCT GTCGCAAGGC    12840

AAGCTCACCA TCCTCGATGA GGAGTGGGAG ATCCTCGGGG TCAACTCCCA GAAGCGCATG    12900

GCGGTCATCG TCCCGAACGT GGTGATGCCG ACGTGAGCGC GAGCGACCGA CACCGCGCCC    12960

CGATTGTCTA TCCGCCTGGC ACTCAGGCGG TTACGCCGGA TCGGGTCAAC GCGTTTGACT    13020

GCGATCACGA AGCTGATCCT CCGGTGTGCC GGTGCGTCCA CGACTGGCGC ATCGAGTGGG    13080

GAAACGTCAA GAAGGCCACC GCCAGATCAC GGTCGGCGGT GCTCTGATGA GCCTCCTCGA    13140

CACCGGTGCC CGGTACCAGA CCTGCATCGT CTACCCCGAA GAGATGGTCA TCGACTCCGA    13200

TGGCAACAAG CGGACCAGGC CGTCGAATAC CGGCATCCCG GCCATCGCAC GGTTCCAGGT    13260

AGCCAACCAG TCTGGTACGT CGGCACGACG TGCTGAGCAG GACAACGAGG GGTTCGAGAC    13320

CGAGAAGGTC TACCGGATGC GGTTTCCCCG CTCGTTCACC AAGGAGCACG GCATCCTCGG    13380

GGCCCAGTCC CAGATCGAGT GGCGAGACCA GCGGTGGGCG CTCTTCGGAG ACGCCACCGT    13440

CTACGACTCA TCCCCTGCGT TGGCGCGGGT CGACTACACG ATCAAGAGGT ACTGATGGCC    13500

AAGGTCTACG CGAACGCGAA CAAGGTCGCG GCCCGGTACG TCGAGACGAG GGACGCCGTC    13560

CGAGACGAGC GGAACAAGGT CACCCGTCGA GCCAAAGCCA ATCTGGCGCG GCAGAACTCG    13620

ACCACCCGCA TCACCGACGA GGGCTACTTC CCGGCCACCA TCACCGAGCA AGACGGCGAT    13680

GTCGACTTCC ACACGATCCT CAACGCGCCC AACGCGTTGG CGCTTGAGTT CGGCCACGCG    13740

CCGTCTGGCT TCTTCGCTGG CACCGACACG AAACCACCGG AGGCCACTTA CATCCTCACC    13800

CGAGCCGCCA TCGGCGGCAC CGTCTCATAA GGAGGTCACA TGGCGCGAAT GCCTCGCGTC    13860

CAGGCAGTAG CGGCCCCGAT CCTCCGGTCA GACCCCCGAC TGGAGGGAGT GACGGTCACG    13920

ACATGGGTTC CAGACGTGGA CTTCCGAGAG TTCCCGATGA TCAACCTCCG CCGCATAGGC    13980

GGGACGAGGA ACCCCAACGC ACCGACGCTG CACACGCTGC CGGTGGTCGA AATGACCGCC    14040

TACACCGAGA CGGTCTCAT CGAGACTGAG GAGCTGTACG AGACCGCGCT AGAGGTTCTC    14100

TACGACGCGG TGGAGAACGG AACACAAACT CCCGCAGGGT ATTTGACCTC CATCTTCGAG    14160

ACGATGGGCG CCACTCAGTT CAGCTCCCTC TACCAGGACT CCTGGCGCAT CCAGGGTCTG    14220

ATCAGGCTCG GCGTCCGCAG ACCGAGAACC ACCCTCTAAC CGAAAGGTAA AGCCACATGG    14280

CTGAAAACGA CGACGCAGTG TTGACTGCGG CGGTCGGCTA CGTGTACGTC GGTGCTGCAG    14340

GCACCGCTGC TCCTACGCCG GCCTTGCTCA AGACCATCGA CCTCAGCAAG CCCGAGACCT    14400

GGACCGGTGC TACCGGTTGG ACGAGCGTCG GCCACACCAG CCGAGGCACG CTCCCTGAGT    14460

TCGGCTTCGA AGGCGGCGAG TCCGAGGTCA AGGGCTCCTG GCAGAAGAAG AAGCTCCGCG    14520

AGATCACCAC CGAGGATCCC ATCGACTACG TCACGGTCCT ACTGCACCAG TTCGATGAGC    14580

AGTCGCTGGG TCTGTACTAC GGCCCCAACG CCTCTGAGAC TCCTGGTGTG TTCGGTGTGA    14640

AGACCGGCCA GACCAACGAG AAGGCCGTGC TGGTCGTGAT CGAAGACGGC GACATGCGCC    14700

TGGGGCATCA CGCCCACAAG GCTGGAGTTC GCCGCGACGA CGCGATTGAG CTGCCCATCG    14760

ATGACCTGGC TGCGCTGCCC GTCCGGTTCA CCTACCTGGA CCACGAAGAC GAGCTGCCGT    14820

TCTCCTGGAT CAACGAAGAC CTCTTCAACG TGCCCGAGGT TCCCGAGGGC TGATCCCAAC    14880

TTGACAGCCA CCCGGCTGTC TACCCCGGAG GGGGAGGTTT CCTTGGCGGG CCTGGCCTCC    14940

CCCTCCTCCC GCCACTCACA GACCCGCCGA CACTGAAAGG TTCGCCATGA CAAACGTATT    15000

CACCATCGAC GCATTCCGCG AAGAGGTCAA GAAGAAGTAC GCTCCGGTCC TCATCGGCCT    15060

GTCCGACGAT GTGACCGTCG AGCTGAAGCC GCTGCTGAAG CTGGGCCAGA AGGCCCGCGA    15120

AGCGGTGGTC GAGGTGTTCA AGGAGTTCGC GGACATCCCC GACCTCGAAG AGGACGACGA    15180
```

-continued

| | | | | | |
|---|---|---|---|---|---|
| CGACGAGTTG | GTCGATGAGT | ACTCGCTCCA | GGTCTGCGAC | ATCATCGCCA | AGGCGTTCCG | 15240 |
| GCTGATCGCC | ACGAAGCCCA | AGAAGCTGAT | CGCCGCCTTG | GACGAGGAGC | CGGATCCCCG | 15300 |
| TATCCGCGCA | GAGCTGTATG | CAGCGGTACT | CAACACCTGG | AAGCGAGAGA | CGCAACTGGG | 15360 |
| GGAAGCCGCG | CCCTCGCCGA | GCTGATCGAC | AAGTTCGGCG | GGGCGATCCT | CGCAGACCTG | 15420 |
| CTCCAGTACT | ACCGGGTAGA | CCTGCGCGAC | CTGTTCCGCG | ACGAGGATCC | GCTTTCGCCG | 15480 |
| AGATTCGTTC | TGTCCCTGGT | GCTCTGCCTT | CCCAAAGACG | GCGCGTTCTA | CGCAGAACGT | 15540 |
| CGTGGTGGGC | AGCAGTACCG | GGGCTGGACC | GAGGACCGCT | ACGCGCTCGC | GGACATCTAC | 15600 |
| GACGCCATCC | AGGCGGGCAA | CCACATCCTG | CTGCTGGCGA | ATCGTGATCC | GAAGAAGCCA | 15660 |
| AAGCCCAAGG | CACCCAAGTC | ATACCCGCGT | CCCGACGACC | TAGAGAAGAC | CACACCGAAG | 15720 |
| CCGGGTTCGT | TCGCCGCAAT | GGTCGTGCGA | GCGAAGAAGG | CGGCTCGAGA | GAGAAGGGAA | 15780 |
| AGGGAGGAGG | AGAGTGCCGA | ATAGTGCTGG | CGTAGAAGTC | GCCCGGATCT | CGGTCAAGGT | 15840 |
| CAGCCCGAAC | ACCAAGGAGT | TCCGCCGGGA | ACTCAAGACC | GAACTCGAGA | AGATCGAGCG | 15900 |
| GGAGCTTAAG | GGCGATGTCG | AGATCAACGG | TCATCTCGAT | GCGGCCCAGG | CCAAGGCCGA | 15960 |
| CTTCAAGCGC | ATGATGATGC | AGCTCAAGAC | CGAAGCTGCC | AAGGGCGTTC | ACGTCCCGGT | 16020 |
| CGACGTAACC | GTCGACAAGA | AGAGCAAGAA | GGGAGGTCTC | CTCGGAGGTC | TCCTCGGCGG | 16080 |
| CAGCCGGGGG | CTCGGAGATC | TAGGCGATGA | CGCCGAGAAG | GCGTCGTCTC | AAGTACAACA | 16140 |
| CCTTGGCAAG | TCGTTCCTGG | GCCTCACACG | AGCCGCCTGG | ATAGGCGTAG | GCATCGTCGC | 16200 |
| CGTAGCAGCT | CCGCTGGTCG | GCATCGTGGC | CGGTCTGCTG | GCCGGTCTGC | CGTCGCTGCT | 16260 |
| GTCTGCGTTC | GGAGCCGGCG | CTGGCGTAGT | CGCGCTCGGC | ATGGACGGCA | TCAAGGCAGC | 16320 |
| CGCCTCGACG | CTGGCCCCGA | CGCTGGAGAC | GGTCAAGGCC | GCTGTCTCCT | CGACGTTCCA | 16380 |
| GCAGGGACTC | ACCCCGGTGT | TCCAGCAGCT | CGGCCCGATG | CTGACCGCGA | TCACCCCCAA | 16440 |
| CCTGCAGAAC | GTGGCCTCGG | GCCTCGTGAA | CATGGCCGGG | TCGATCACCG | ACGTGATCAC | 16500 |
| CCAGGCTCCT | GGTCTGCAGC | AGATCCAGAA | CATCCTCACC | AAGACCGGAG | AGTTCTTCAC | 16560 |
| GGGCCTCGGC | CCTGTGCTCG | CTACCGGCAC | GCAGGCGTTC | CTGACGCTGT | CCAACGCCGG | 16620 |
| CGCGAACTCG | TTCGGCACGC | TCCTGGCTCC | CCTGCAGGAG | TTCACCAACG | GCTTCAACGA | 16680 |
| CATGGTCAAC | CGAGTCACGT | CCAACGGCGT | GTTCGAGGGT | GCCATGCAAG | GGCTTTCGCA | 16740 |
| GACGCTGGGC | AGCGTCCTCA | ACCTGTTCAA | CCGGCTCATG | GAGTCCGGTC | TGCAGGCGAT | 16800 |
| GGGACAGCTC | GGCGGTCCGC | TGTCGACGTT | CATCAACGGG | TTCGGAGATC | TCTTCGTCTC | 16860 |
| GCTGATGCCG | GCGCTGACTT | CGGTCTCTGG | TCTGATCGGC | AACGTCCTCG | GGACGCTGGG | 16920 |
| CACACAGCTC | GCTCCCATCG | TCACGGCGCT | CACGCCGGCC | TTCCAGACGC | TGGCGAGCAC | 16980 |
| GCTCGGCACG | ATGCTCACCG | GAGCCCTCCA | AGCTCTGGGT | CCGATCCTGA | CTCAGGTCGC | 17040 |
| TACGTTGATC | GGCACGACGC | TGAACACGGC | GCTGCAGGCT | CTCCAGCCGA | TGCTGCCGTC | 17100 |
| GCTCATGCAG | AGCTTCCAGC | AGATCTCCGA | CGTACTGGTG | ACCAGTCTGG | CCCCGCACAT | 17160 |
| CCCGGCGCTG | GCGACGGCCC | TCGGCCAGGT | CGCAGGCGCG | GTGCTGCAGC | TCGCTCCGAC | 17220 |
| GATCATCTCG | ACGTTGGTTC | GGCGTTCGT | TCAGTTGGTC | CCAAAGGTCG | CTGAGCTAGT | 17280 |
| TCCGACCATC | GTCAACCTGG | TCCAGTCGTT | CGCCAACCTG | ATGCCGGTGG | TTCTGCCCCT | 17340 |
| GGCGCAGGCT | CTGGTCAGCG | TTGCTGGCGC | GGTGATTCAG | GTGGGTGTCT | CCATCGGCGG | 17400 |
| CGCGCTCATC | GGCGCGCTGG | CGAACCTCAC | GGAGATCATC | TCCAACGTCA | TCAAGAAGGT | 17460 |
| GTCCGAGTGG | GTCAGCAGCT | TCTCCAGCGG | AGCCCAGCAG | ATCGCTGCGA | AGGCAGCGGA | 17520 |
| ACTGCCGGGG | ATGATCCAGT | CGGCTCTCGC | CAACCTGATG | GCCATCGGCC | TGCAGGCCGG | 17580 |

-continued

```
TAAGGATCTC GTCCAGGGCC TGATCAACGG CATCGGCGGG ATGGTCAGCG CAGCGGTCAA    17640

CAAGGCCAAG GAGCTGGCGT CCAGCGTGGC TGGTGCAGTG AAGGGCTTCC TGGGCATCGA    17700

GTCCCCGTCG AAGTTGTTCA CCGAGTACGG CCAGTTCACC GCCGAGGGAT TCGGCAACGG    17760

CATGGAGGCA GGGTTCAAGC CCGTCATCGA ACGGGCCAAG GATCTCGCGG CTGAGCTGTC    17820

CAGGGCGATG GAGTCGGGCA CCGACCCCTC CGGGATTCTC GCTGGGCTGG ATCAGAATGA    17880

GCTGAAGCAG ATGCTGGCGG CTCTCGAAGA GGAGCGCAAG CGACTCAAGG TCGAGAAGAA    17940

CGGTATCCCC AAGGGAGACA AGGCAGGCCG AGAGGCGCTG CAGAACCAGC TCGACCAGAT    18000

CCAGGCGCAG AAGGACATCC TGTCCTACCA GCGTGACCGC ATCAAGAACG AGTCTGAGTA    18060

CGGCGACATG GCCGGCGAAG ACCCGTTGGT GAAGGCAGCC TCCGGGCTGA TGAGCGCACC    18120

GGTCGACTTC GCGAAAGCGA CTGGCAAGCA GTTCCTTTCG GACATCGGCA TCAGCGGAGA    18180

TGGGTTCATC TCGAAGGCCA TCACCGAGGG CATCCAGTAC ATCTTCCAGA TCGGCTCTGT    18240

CGATGAGGCG CTGTCGATCA AGGACCGCGA GGAGTCGAAG AACGCGCTGT CCGTCGTTGG    18300

CCGCTGACTT GACATCCACC AGGAGGTAAG CATTGATCAC CGACACCATC GTTGAACTCG    18360

AGGGTGTCAA TGGTGAGCGT TTCAACTTGA CGACCGGTGA CCAGGGTGTG TACCTGGCCA    18420

CAGACGTGGA GGGTTGTTTC TACGACCCTC CCGTCAAGGT CGTTGTTGAA GAGCCGGGGA    18480

ACTACCCCGG CGCTCGCTAC TTGTCCCACC GAGCCCTGAA GCGAGACATC GTCTTTGGGG    18540

TCGTCATCCT CAACGACGCG AAGCAGGGGC CGCGCTCCTG GCTGTCGCGA GACTCCGAGT    18600

GGCGCAAGGC GTGGGCGTTC AACCGCACCT GCAAGCTCTA CGTCACCACC CCGGACTCCG    18660

GTACCCGCTA CCTGAAGCTG GCGCTGTTCG AGTCCCCCAC CGTCAAGATG GACACCGACC    18720

CAAGAGGTAA ACCCCTTGAG GTCACGGTGA TGTCGTGCAT CGCGTACGAC CCGTTCTGGT    18780

ACGAGGACGA CAAGGTCTTC TCGGCCAAGA CCAAGACCGA CACCCGGTTC GACCCGTCGT    18840

TCTGGACGCC GCCGTGGCCG TGGGAGGAAC TGCCCAAGGA GACGCTGCGG ATCAAGGTCG    18900

GCCGCGAGCA GGGTGGGCTA AACCCCACCG ACCAGTACAT CTTCCCGAAG TGGACCGTTC    18960

CCGGCTCCAC CGAGAAGGTG CCGAACTTCC CCTGGCCGTT CCCCCCGAAC GTCCCGATCC    19020

CGTGGGAGAC AGCACCGTTC ACTCAGTTCG TCATCCCGGA CTACTCGTTC GAGGATGAGG    19080

AGTTCCGCAA CCGCCGGCTC AAGACGCCGG GGTTGATCTA CGGCGAGAAC TGCGTCATCG    19140

ACACCGACCG GCGCGAGGAG CAGATCGCTT CCGAGTCGGG CTCCCCGGTG TGGGCTCGGA    19200

TGAACGGTGT CCGGTTCCGC AACTCGATCC CGCCCTACAC CGAAGAGGCT GAGTTCGTCA    19260

TAGACGCATC GGGATGCGCT CCGGGACAGG TAGTTACCCT CCGGCTCACG AGGCCGTGGT    19320

CGCGCTGCTG GGGGCTAGAG TGAGTGGTCT GACGAGCGTT CGTGAGGCCG AAGATCTCTG    19380

GCAGAAGATC CAATTGCGGC GCTGCAAGCG CGAGCAGGAA CGGCTCAAGC ATCCCGACGT    19440

AGAGCTGCGC GATGGCGACT TCCGCCTGCG CGGCCTGGTC GCTGGCGAGC GGGTGCTCGA    19500

GTGGGAGTTC ATCGAGAACG AGACTGGCAC CTGCACCTTG CAGCTCTCAC TGAGCCATTA    19560

CCTGGCGAAG TGGGTGATGG ACCACCGGGG TCGAGCAAAG CGCAACGTCA TCATCAACAT    19620

CGAGAAGCAA GGCGCTCGAT GGACCGGGAT GATGGACCAC TACCGGGTCA TCAAGACCGA    19680

CGCAGGGGAC GCCTACATCG AGATCGTGTT TTTGCACGAC TTCGAGCAGA CCAAGCATAT    19740

CCGGGTATGG TGCAACCCGT TCCTACGCCC CGAGCTGCAG TTCCCCAAGG TGTGGATCAT    19800

CTTCGGGCCG GCCAAGTGGT GTTTGCTGGT GACACTGTTC GTCAACCTGC TCAGGCTCGA    19860

GACGAGCTTG TGGACGCTGC CTGATGACCC CACGGACATC AACGAGTGGA TGGGTCCGAG    19920

CTTCAACCCA GCAAATTGGC GGAACATCGT CAAGCCGTTC CCGTTCCTGG CCGACAACTC    19980
```

-continued

```
ACCGGTCACG ATGGTGTTCA GCCGGTTCGG GACGTTCTAC GACACCGCCA AGAAGATCCT    20040
CGAAGACCAT CAGCTCACGC TGACGTGTCG TCGGTACATC AAGGACCGCG ACCCGCATCC    20100
GTTCGAAGAT CTCAAGGGGC TCTGGGGAAT TGATCCTGTC GAAGACCTGC TGCAGAAGAT    20160
CCCGCTCCGG GACGGCTGCG TGGTCTGGGA CATCGAGGAC AACTCAGGTT GGGGCACTCA    20220
GACCGCGTTC GGCGGTTCGT GGCTGACCGG GTTCGTCCGA GGGATGGTCC AACTGGCCGG    20280
CGACGGCCAG GTCGAGGGCG TCGATGTGTT CACCGGGGAC TACACGTTCC CAGGCGAGTA    20340
CTACTCCCCC TGGTTCATGG GCACCAGCCC GATAGCACCC CACGTCGTGT TCGAAGAAGG    20400
ACCGCTGACC GGGATCAAGT CGTCGGAGTT CTCGTACTAC GAGGCCACCG ACACCAGCTT    20460
CCTGGCTGGT GGACAGAGCG CACCTGGCAT CAACGAGGGC ATCTCGGCCC TGGTGAACAT    20520
CGGTGGCGAC CTGCTGACCT CGTTCATCAA CAGCCAGCTC GCCGCGCTCG GCGCGGTCGG    20580
TGGAGCGATT GACCTCCCGC TCTGGGCGG TCTGCTCGAT GCGGTGTTGC AGCCTCTGTA    20640
CTCCGATGTG TTCGGCGCGT TCATGGAAGT TCCGACTCTG CGTGCGATGG GCATCTCGCT    20700
CCCGATCTCC GGGCTCGAGG ACATCGTCAC CGGACTGGGC GACTTCCACT ACTTCGAGAA    20760
CATGGCCGAC GGGGCGATGA AGGCGTTCAC GCTGTCAGCG TTCGCAGCCA TCGCATCGCA    20820
GATCCACAAG ACGAGGGCTC GAACGACCCA CACCCTCAAG GTGTCTGACG CCGCTCCGTA    20880
CATCTTCGCG CCAAAGCCCT ACGGGCACTG CTGGATCGGA GATCGCGTCG GCACGTCGGT    20940
CCTCGGCTAC CCGGTCGAGC ACCAGTTGTT CGTGGAGCGC ATCCGCAAGG TGAAGTACCG    21000
CATCGACAAA GACGGCATGA AGCCGTTGGA GATCGAGATC GGTTACCGCG AACCGAAGAA    21060
CCCAGCACTA CACATCCTCG AAGAGATCAA GCGCGTCAAC GGCGCTCTTG GCACTGCGGG    21120
GATTCTCTAA ACCGAAAGGC ACGCCGCATG ATTCCCTCAC AAGAGTCTCA CAATCCGAAC    21180
GACCCGCGAC AGCACGTCAT GTGGGCGCTA CGCAATCTCC CGATGATTGC TGGCGTCGGG    21240
GCGATCACGC ATCGGGTTA CCTGGCGGAT TGGTCAGAGC ACTTGTGGAA GTGCGGCTTT    21300
CGGCACGTCG ACTGGCTCCG GGAGCTGGCT GATGAGGACG GCAACATCCA CGTCAGTCAG    21360
CTTCCTGACC AGGAGATCAA GTTTCAGCAG CCCTTCCGGG GCCAGCGAAG CGACTACAAC    21420
AACGCAGCTC GATGGGTCGG CAAAGACGAT CCTGACCCAG AGCCCGTGCG TATTCCAGAC    21480
ATTCGCAAGC TCACAGACCA GGAGAACAGA GCGATGATCG CGCAGTACGA ACGAGACGGT    21540
TGGATCAAGG ATGGATCCCC CGGCCCAGCG ATAGCCGAGG TCGTGGAGTG ACCCCGTTCA    21600
ACCCAGACTC CATAGGCGAC TACGTGACAC TGCTCGGCGT TGCGTTCCTG ACCTTCTCGG    21660
TTCCCGCATG GTTCACCGGA CGAGCACGCA AGCACAGCAG TGACATCGGC GAAATCAAGG    21720
AACAGGTATG TAACACCCAC GACACGAACC TGCGCGATGA CCTCGACAGC GTCAAGGCAG    21780
ACATCAGCGA CTTGAAAGAG ATTGTGTTGC AAGGGTTCCA CCAGGTGAAC GAGTCGATCA    21840
ACCTCGAGCG CCGTGAGCGG ATCGAAGGAG ACCGCCGAAA GGAGGTTGCG TGACCTACCC    21900
CACCAACCCA CTAGAGGCCA TCGGCGCTGA CGGCGCATTC GAGATCGGTG GGGCGACTG    21960
GAGCTTCGGC CAGGACTACA CCGAACAGGC CATCCGGGCT CTGTTCACGA TGCCAGCGGT    22020
CACGATGGAG AACGCTCTCG GCCTGCTCGA AGAGCACCTG CTGAAGCTGC TCTCTGGAGGC    22080
GCTGCAGGGC TTCAAAGACA TGATCCCGGA CTGGGTCGAA GGAGCATTCG ACACGGTCAC    22140
CGGCGCTGTG CAGGCGATCA TGAACGCGCT CCAAGACGGC CCGCTGTTCC TGAAGTTCGC    22200
CGAGTTCCAG CTCTTCCTGC AGCGTCTGCT GAACAACCCG GCCGAGGTCA TCGGCGAGAT    22260
CCCCCAGACG TTGATCGACG GCCTACAGGA CGCGCTCAAC ACCGTCAACA ACACCATCCA    22320
GACCATCGTG GACATGCTCC TGCAGGCGCT GGGCATCACC CCGGAGGGGG AGCTGATCGA    22380
```

-continued

```
CCGGATCTTC GACCTGAGCG ATGAGATGGA GTGGCTGCAG ACCGCAGCCT CGAATGCAGC      22440
TACCGGCATC CAGGACACCT GGAACAAGTT CTGGGGAGCC CTCACCGGGC GCGTCCCAGA      22500
CCAGGACCAG ACCGTCGCTG AGCCCGCCGA GCGTATCGGC GAGCTGGCCG GCACCACGTC      22560
TGCTAACTCG TCTGCCATCG CGGAGCTGCA GCGTCGACTG GACAACCAGC AGAACGCTGG      22620
CGGCGTGGCC GGCGGTGACG ACTTCGAGCG ACTGAACATA TCCGGTTGGG ACATCAGGTA      22680
TTCCAACGGA TCCAGCGGCC GAGGGTACTA CCGTGCCGAC GGCCACCAAC TGGTCTGGAT      22740
GGACGAAGGC AACCAGCAGA ACACCGCGAC GTTCGTCCGC ACCAACCCCG CAGACGAGAA      22800
GACAGCCACC GACTACCAGA AGATGACGTT GGTCGTCGGG ACTATCTCCG GTGAGGTACA      22860
GACCGTGTTC CCGCCGCAGG GAGGTTCGCA CACCCGGCTA TGGGTCCGCG TCAACGACAA      22920
CGCTCCGACC GTCGGCATCA CCGACGGCGT GTTCGTAGAG ATCGGCGGCG TATCGAAGGC      22980
CCAGATCGGC TACCGCCGCA ACGGCAATGA CACGTTCGTC GGATCTATGG TCGACTGCAC      23040
CTGGGGTGCT GGATCGATCT TCGCTCTGAC CGCCGGCACG GCCAACGGTG CTGAGAAGTT      23100
CGAGGTCTCG AAGAACGGCC CCGTGCTGGC ACATGGTCG GACGACGGCG TCGTCTCCGC       23160
GATGGGTGCG AACTACCGCC GCTGGGGCTG GGAAGGCCAG GCTCGTAACC GCAACCTCGG      23220
CCAGGGCACT CCGAACTCGG TCACCCGAGT GACGATCACC GACAACGATC CTACCGGCGC      23280
AGGCGGTGGA GCTGTCAACG TCGGAGGAGA TGTCGTAGGT GTACTCCCCA TAGAGAACGG      23340
AGGCACCGGA GCTTCGACAG CTTCGGCAGC CCGTACCGCT CTCGGAATCG ATGACCTGGT      23400
CGAAGATATG TCCGACGTAG TTCGTGGATC CGTCGAAGGA CTCCCGTTGA TACCGAAGAT      23460
CTGGGTAGGA ACAGAAGCTC AGTACACGGC TCTCGCCACC AAGGATCAGT CCACGCTATA      23520
CTTCAGGACC GCTTAATGAC TGGTATCTCG TTGGGTGTCA ACGACATCCG CAACCTCTCG      23580
ATATTCTTAG GCGTCAGCAA CAAGATATTG AAGGTCAGTC TAGGCACAGA AAAGGTCTGG      23640
CCTGCGTTCA CCCCGGTGCT GACCACGTTC GCCACGGTCG GCACGTACAC CTACAACATC      23700
CCCGACGGGG CCAAGTTCAT CGACGTCATC CTCCTCGGAG GAGGCGGCGG GGGTAAAGGC      23760
ATGGCCCTGG CTGACGGCTG GGGCAGAGGT GGAGACGCCG GAAGCTGGGC TATCGTCACT      23820
CTCGAACGCG GGGTACACAT CCCGTTGTCG ACCAAGACGA TCACCGGGCT CGTCGGAGCT      23880
GGAGGCGCAG CGGGAGCTGG CTCTGTATTC TCAGGCAAGG CCGGAGGCCC TGGAGGAAAC      23940
ACCACGGCGT CCGCTGTCGG ATGGTCAGGT TTGACCGCAA CCGGCGGTCC CGGAGGCTCT      24000
GTGATCGACA TCCTCAGCGT CGCCGGAAAG TCGCCTGGAG ATCGGACCTA CAACGACCAG      24060
CTCTACATAG GCGGCGCACA ACAGAACTCA GCTGGCGGGA ACGGCAATGC TCCTGGCGGC      24120
GGCGGGGCTG GTGCCCAGGT CTCCGCACAG AGCGGCGGTG CTGGCGCTCG CGGCCAGGCG      24180
TGGTTCTTCG CGTACTGACA AGAAACCCCC CTCTTTAGGA CTCAGTGTCC TTGGGAGGGG      24240
GGCTTTTTGC GTTTCAGGAG GTCTTGGCCA GCTTGGACAT CGCCTCAGCG ATAGCCTCGT      24300
CGCGGGCCTC AGACGCCATC TGGTACTTCA TCGCCATCCT AGGAGTCGTG TGACCGAGAC      24360
GGCCATCAG CTCCTTGGTC GTCGCACCTG CCTGAGCGGC GAACGTAGCG CCGACAGCGC       24420
GGAGGTCGTG GATGCGGAGT TCCGGCCGAC CGATCTTGGC GTAGCCACGC TTCAGCGACT      24480
TGGTGAACGC GGACTTCGAC AGCCGGTTGC CCTGCGTCGT GGTCACCAGG AATGCCTCGG      24540
GGCCCTTGTT CATCTTCGTA CGGTCCTTCA TGTGCGCTCG GATCATCTCC GCGACGTGAG      24600
GCGGAACCGT CACAGGACGC TTCGACCGGA CGGTCTTGGC GTTGCCAACG ACGATCTTGT      24660
TCCCCACGCG GGAAGCGCCA CGGCGCACCC GGAGCTTCAT CGTCATGCCG TCGTCCACGA      24720
TGTCCTTGCG GCGAAGCTCG ATCAGCTCTC CGAACCGGAG GCTCGTCCAC GCCAGGATGT      24780
```

-continued

```
ATGCCGCGAT CCGGTAGTGC TCGAAGATCT CAGCGGCGAC GATGTCCAGC TCCTCAGGCG    24840

TCAGCGCCTC TACGTCGCGC TCATCGGCTG CCTTCTGCTC GATCCGGCAC GGGTTCTCTG    24900

CGATCAGCTT GTCCTCGACC GCTGTGTTCA TCACCGCCCG GAGGACGTTG TAGGCATGCC    24960

GGCGGGCAGT CGGGTGCTTC CTACCCATCC CGGCCCACCA CGCACGCACC AGAGCTGGCG    25020

TCATCTCTGT GACCGCCACT TCACCTAGCA CCGGGTAGAT GCGGCGCTCC GCGTGCCCGC    25080

TGTACAGATC CCTGGTGCCG TCTGCGAGGT CGCGCTCCAC GAGCCACTTC CGGGTGTACT    25140

CCTCCAGCGT GATGGCGCTG GCGGCTGCCT TCTTCGCCCG GTCCTGTGGA GGGGTCCAGG    25200

TCTCCATCTC GATGAGCCGC TTCTCGCCCG CGAGCCAGGC TTCGGCGTCC ATCTTGTTGT    25260

CGTAGGTCTG CAGCGCGTAG TACCTCACAC CGTCCTGCGG GTTGACGTAT GAGGCTTGGA    25320

TCCTCCCGCT GCGCTGAGTC TTCAGCGATC CCCATCCGCG ACGTGCCAAC TAGGTCTCCT    25380

CTCGTCGTGA ACAAGGCTAC CGGGTTGCAA CTCCTGTGCA ACTCTCAGGC TTCAACGCGC    25440

TTCTACGACC TGCAATTTCT TTCCACTTAG AGGATGCAGC CGAGAGGGGG TAAAAACCTA    25500

TCTTGACCGG CCCATATGTG GTCGGCAGAC ACCCATTCTT CCAAACTAGC TACGCGGGTT    25560

CGATTCCCGT CGCCCGCTCC GCTGGTCAGA GGGTGTTTTC GCCCTCTGGC CATTTTTCTT    25620

TCCAGGGGTC TGCAACTCTT GTGCGACTCT TCTGACCTGG GCATACGCGG TTGCAACGCA    25680

TCCCTGATCT GGCTACTTTC GATGCTGACA AACGAATAGA GCCCCCCGCC TGCGCGAACA    25740

GACGAGGGGC ATTCACACCA GATTGGAGCT GGTGCAGTGA AGAGAATAGA CCGGGACAAG    25800

GTTGCACCGG GAGTTGCAGC GGTCGGAACC CTCGCCGTCG GCGGGCTGGC GTTCGCCCTG    25860

TCGTTCACGG CTCTCAGCGA GCTGGCTGCG GCCAACGGGG TGGCCCAAGC AGAGATGGTG    25920

CCCTTGGTGG TCGACGGCCT GACGCTCGTC GCCACGGTCG CCACAGTGGC CCTCAAGCAG    25980

AACAGTTGGT ACGCGTGGTC GCTGCTGATC CTGTCCACCG TCGTATCGGT GGCCGGCAAC    26040

GTGGCACACG CCTACCCCCA CGGCATCATC GCGATGGTGA TCGCTGCGAT CCCTCCGCTC    26100

TGGCTACTGG CGTCGACCCA CCTAACCGTG ATGCTGGCGA AGCAGCACTC GGAGCACGCC    26160

GAAGTACCTG TCTCGCGGCC AGAACCCGCG CCTCGGGGCC TGGAGCCCGC TGCCGCTTGA    26220

CTGCGCCCGA CCGGGACAGA AATACATAGA GAACCTATGG ATGTAGGAGG CACAAAAAAA    26280

TACCCCCCGA GCCAGCCCGA AGGCCAGCCC AGGGGGCATG GTTCTGCTTC AGTAGACCTT    26340

GCGAGTCCGA CCCGAGTTGA TCATCGCCAT GATGACCCAG ACGGGCAACC ACATTCCGCA    26400

GGTGATGAGC GAAAGCAACA GGTGCATCGC GTGGTTCGTC CTGACAGGCA TGACAGTGGG    26460

CTGCGGCATC GGAGGAGGCG CGACCGGGTA CGGCGAGCCC GCGTACCACT GAGGTCGATC    26520

TTGTTGGGGC GGATACTGAT TGGTCATCCC GACAGCCTAC TTGCCGATGG GTCGCATCAG    26580

CTCCTCGACC GACTCGCGCT CCACGCGGAT CAGCCGGGGA CCGAGCCGAA CGGCCTTGAG    26640

CCGGCCGTCG GCGATGTAGT TGCGGACGGT CTTGGTGCTG ACACCGAGGT AGTCAGCGGT    26700

CTCCTGGATG GATGCTCTCG GGGGCATCAG CGCGGTCCTC CGTGCTTCAT CGGTTGTCTC    26760

CCGAACCCTG GATCACGCCA CGATCCTTGC GGCTCTGGAG CTTGTTGAGG TTCCTCTGGG    26820

TGACGGTGCT CAACCAGACA TCGAGCTGGT TGGCTAGCTG GGCGACGTAC CACATCACGT    26880

CTCCGAGTTC CGCCTGGAGG TCGTCTCGGT TCTCCTGGGT GATGACACCG TCTTTATCCC    26940

GGAGGATTTT CTTGACCTTG TTGGCGATCT CGCCGGCTTC GCCTACGAGA CCCATCGTCA    27000

CGTAGGAGAG ACCCTCGATG CTGTCGCAGT CGCCTGCACC GGGGTAGATC GCTGTGTCGC    27060

TCGCGGCGAT CTGGTAGATG TCGACGTGCA TCAGATCATC ACCGGGAACA ACTGGCCACC    27120

GGGCATCTGG ATGAACACCG GGACGCTGGG GGTGTAGTCC GACGAACCCG TGCCGCCCTC    27180
```

-continued

```
ACAGGCGGAC AGGCTCAGGG TGGCGGCAAG GCCGATGATG GCTGCTGCGA TGGTCTTCTT    27240

CATCTGTTGC TCCAGTAGCT AAGTTCGGAC TCCAGTTCGC GGATACGCTC CTGTAGCCCT    27300

TGGTTTTCCA GGTACGCCTC GGCGAGGTTG GCCTCGGCGC GGTCACGGGC CTCGTCCTTC    27360

GACGTGGCCT CATCGATTGC CTCGTGTAGC CGGCGGATCA GATCTGGGAT GGCACCGTGC    27420

AGACCGCATA TGAAGTCGGC GTCTGCCTCG GAGAGGTGGG ACGCCACCAG ATCCTTGTCC    27480

TGGGTCTCCT GGTTGACCGC CCAGATGACG TGATCCTCTA GCCCGTGGTC GGTCTCGCAG    27540

ATAGAAGGCG GTTCTACCTC CTCTGGCATC CAGTAAGTCT TCTCAGCCCC GGTGGACTTC    27600

GCCCACTGCT GGTAGAGGAT GTCGAAGAAC TCGTGGTCCT GTTCGTCGGC GGTAATCACA    27660

GATCGTCCTC TTCATCCCAT TCGTCGTAGT AACACGTACA GCCGCAGCAG GTGCAGCAGC    27720

CGCACTCGTA GGTGCCGTAG TCGTAGTCAT CCCAGTCGTC TTCGTCCATC TAGCTGTACT    27780

CCTTCATGAT TCGGTCGAAC GCACGCGTCT GCACGCGCAT CTCCAGGTCG ACCGTTCGCT    27840

TCAACCACGC CCATTCGCCG TCGTGGTTGA TCTCCCACTG GCTCTTGAAT GTCGCTGTCT    27900

CAACGAGGAA CTCGACAGTC AACGTGTGCA GTCCGTTGTT GCTGGGCTGG AATCCGATAC    27960

CGTCCTCAGC GATGTACCAG GGCAACTCCT GGCCGTCGAA GTAGACGGCC TTGTCGGTCA    28020

CCAGTACTTC AGGGAAGGTG TGCTCGGTCA ACGGCGTCCC AGGTATGGGA TGACGCTGGC    28080

CCGGAACTCA AGGAACACCA TGTTGTCCGG GCAGTCCTCG GGGACGTTGT CGGGGCGTTC    28140

GGCGGTGTAG ACGCCGATCT CGTTGCCCTC CAGGGTTCCA AGCTCGTTGA GCTTGTAGAT    28200

CGCCAGACCC ATCAGCTCTT CATCGAGACC GTTCGGTGCT GGCAGTACAA CTTTGGCTTG    28260

TGGCATTAGC CCTCCCTCGG AATTACGTAT GCGCTGAACT CGACGGCCGT AATGCCGTCT    28320

GGCAGTTGGA ATCCGAACCG CTCTTCGAAC TCCTCGTTGG TGATGGGGCC GTACTCGAAG    28380

GTTCCGGGCA CTACCTCGCC CTCCCCCTCG ATCAGGAGGT ACGCACCGGC GGCGTACACC    28440

TCCTCGTCGT TCGGCCATCC GACTACGGTC CCGAGGACCG TGAACTTCCT CGGCTCCATC    28500

AGGGCACGTC CACTTCGTTG ATGAGGAACC GCATCGGAGG TGGAGTGAGC ATTGCCTCGG    28560

CTATGGCGAT GAGGGCGTTC AACTGACCCT TCAGCAGCTT CTCCTCGTCG CCTGCGGGAA    28620

GGTGGCGCAC TCGGCGCTCC ATCTCCTTGG CGCGTTCCAG ATATTCGGTG GCTGTCAAGT    28680

TGTCCTCCTT AGTAATCAGC GCCGTAGAGC GAACCCACG AACGCTTTCC GACCTCGGGG     28740

TCGGTGCCAA CCAGCACCGG ACCCATCTGT TCTTGCATCA GGTGGCCAAT GTGTGCAGCG    28800

GCTCTCTCAG CCTCTGAGGC GGGCAGAGAC GCGACGATCT CGTCGTGGAT AGGCAACCGT    28860

AGGTACGGGG TGTATCCGGC CTCGTGGAGG CGAATCAGAG CCCGACAGGT CACGTCCCGC    28920

GACGACGACT GGATCATGTA GTTCAGCGCG GAGTATGTCC GCGAGCTGTC CACCGGCAGC    28980

CGCCGGCCCA TCGCGTTGAC GATGTAGCCG TTGCGGCCAG CTTCCATCGC CAGCTTCTTG    29040

CTCAGCCGCT CCACACCGGG GTATGTCGCA GAGAACGCCT CATGAACTCG CTTGGCCACA    29100

GGGATCGAGA TCCCCACTGC CTCAGCGAGA GCCTTCGCCC CACCGCCGTA GACCTTCTGA    29160

AAGTTGGCGG TCTTCCCAAC CTTTCGCGGC ACCTGGGCTG CGTCAGCGGT CATCTGGTGG    29220

AGGTCCGCAC CGTTCTCGAA TGCCTCGATC ATGTTGCGGT CGCCCGACAG CGCCGCCAGG    29280

ACGCGAAGCT CCTGCGCCTG GTAGTCGACT GAGGCCATCA CATCGCCTGG CTCAGCGATG    29340

AAGCATCGCC GCACGATCCA GTCCGACGAC GGCAGCGTCT GCGCCGGGAT GCCGGTGATC    29400

GACATGCGCG AGGTCCGCGC CTGCAGTGGG TTGATGAACG TGTGGCAGCG GTCCTCAGAG    29460

TCCCTGGTGT CGATGAACTT CTGGACCCAG GTCTTCCGCC ACTTCCCCAG CTTCTTAGCC    29520

TCCTGAGCGA TGGCGGCAAG CTCGTTGCCA TCTTCGACCA GCTTGTCGAG CAGAGCCGCG    29580
```

-continued

```
TTGACCTGGC GCTTGCCAGT CTCGGTGCGA CCGGTGATCT TGACGCCCAT CTCCTCAAGC    29640

CCCTCGGCCA GATCCTCGGT CGAGTTGACC TTCTCCACGC CGTACTCGGT GAAAGCGATT    29700

GCCTCCCAGA CCTCCTGATC GGCCAACCAC TTCTCGGCGA GCGACCGCGA GTACTCCACA    29760

TCGAGCAGGA AGCCCTGCCT GTCGATGTAG CTGCAGATCT CACTGATCTT GTGCTCGTAC    29820

GGCACCAGCG ACCGACTCAC GTCGGGCACC AACGGTGTCA GGCTCTTGCA GACCCTCGCG    29880

GTGAAGATCG TGTCCATCCC GGCGTACAGC AGGTACTCCG GGTGGAACAG GTCGATGGTC    29940

GACCAGATCT TGGCCTTGGT CGTCTTGTGC TCGGCGGCTA GCTTGGCCAT GAGCTTCTTG    30000

ACGTTCTCGG CCTGGTCCTC GGAGATGAAC TTCGCGATCA GCTCTTCGAG CGAGTGCCCG    30060

AACCCGCCGG CCTCGAAGGG CCGGGGGTCC ACCAGCTTCG CCAGGATCTG CGTGTCAAGC    30120

ACGCGGGGCC ACAGACCCTC CATCTCGATC CCGAAGCACT GGTCGAGCAC CTGGAGGTCG    30180

AAGGAGGCGT TCTGGAGCAC CATGCGCTTG AGAGCGCCGA TGGCGATCCG CACGTCCTCG    30240

ATGAACACGT CTCCCAGCTC CACCGGCACC ACCCAGGCTT CGTCCTGAGT ACCGAACTGG    30300

ACGAGGCGGC ACTCGAAGGT GTCGCTGTAG ATGTCCAGCC CGGTGGTCTC AGTGTCGACG    30360

GCGAGGCAGT TCAGGTGAGC CCGGATGAAG TTGCGGAAGC CTTCCAGATC CTCTGGGGTT    30420

TCAACGACGT TGACGGTGAC GAGGTCTCCC TGAACCTCAT GCCGCAGCTC GATCAAAATG    30480

CTCTCCTACT GGAAGTACTG AGGCGGAATC CAGGTGGCTG AGGCCATCTC CTTGATGGCC    30540

TGCTGCATGG CCGCTTCGAA CGGACAGTCC GGGTCGATGT CCGGCTTGTA ATGGGTGACG    30600

ATGATCCGGC TGTTGCCGCC GAAGTCGTGG CTGACCAAGC CCTTTGGGGG CAGCTTCTTC    30660

AGCGCCTTGA TCAGTTCCTC AACCGTGGTC CCGGTAGGGG CCTTGCCGTC AGGCAATGCC    30720

TCCCCTCCGT ACGGCACGTC CAATGGGATC GTGTACCGCT CAACGTCTTT GATCTTCATC    30780

GAGCCTCTTC CTCTTCGACT ACCTCGTCTA CCCGGCGGAA TAACTCCGCT AGTTCTGCGG    30840

GTAGCAATAC TGGGTACTTC TCTCGGGCTT CCTGCATCGC TACCGCGATC CCAATCAGGG    30900

CAGCGAGCAG TTCATTGACG GAGTACGCCA ACAGCTCTTC GCGGATCTCT TCTCGGGTCA    30960

TTAGTGGTAG ATCCCCCGGA CGGTGCGCGA GATCGTGGCA GGGTTCACGC CGTAGTTCTC    31020

GGCGAGATCC TTCTGCTTCA TACCGCCCAG GTACGCCTGG CGGATGTCCT TGACCTCGCG    31080

CTCGGTGAGC TTCTTGCGGT TCGGCCGGCT CGGGCCGGTC TCAGGCTTGA CCTGAGCCAG    31140

CGCCTTGCCG AACAGCTCGT TCTGCGTCCG CTGCTTGATC GCGTACCGAC GGTTCGCTGC    31200

AAGCACCTCG TTGAGCCGCT GGGACAACTT GACATTGGCC TCACGCACTA CCTCGACCTC    31260

TCCGAGCAAG TTCGTGATCC GGTAGTCCTT GTCCTGGTTC TCGATGGCCA ACCGGTTGTT    31320

CTCCTCGGAA AGCATCGAGA CCTTGTATTG CGCCTCTCCC AGCGCAGCTT TCAGGTGCTT    31380

CTTCCTCATT CAGCGCCCCT CTCTCGGCGG AACTGTTCGT ACTCGTCTTC GGTCATGTAG    31440

TAGTAGTAGT CAACGACCTT GTCCCAGTTG AAGGTTCGGG ACGTGCCGTC ATCGAACGCG    31500

ATGATCAGGA CACCCTCTTG GGTGTCTAGG ATCGGCTCGC CAGCCACGAC GTGGAAGCGG    31560

TCCTCGAGGG TCACCGCAGT CGCTCTGCGT GCCATGTCAG TTCCTCTCAG TAGCTGTAGG    31620

GGACATCCGG GATGTCCTGG TAGGTGTTGG GTGCGATCTG TCGGAGCTGC CGAAGCAATT    31680

CCCCTGCCAG CTCACGGATC TCGGCATCCG CGGCCTCGTG CCAGCGGGCC TTGATGACGT    31740

ACCGCCACGC CCGATGGTTG CCCGTGACGA CCATCGGTGA GTTCGTCATG TTCGGCAGGA    31800

CAGCTCGCGC TGCCTCGCGG GCCTGCTTGC GCGGCAAGCC CCGGTCAGCC AGCCGGTTGA    31860

CGATGTGTTC GTAGACAGCG TCAATCTCAG AGCTGACGGA CTCCATGATG TGGACGAGGT    31920

CGTCTCGGTC GTCGGGGTGG AGCTTGAACA GAGCCGGGGG CAGATGGATG CCAAGGTCGG    31980
```

-continued

```
TCGGATCCAC ATATCGCTGA GACACCACCG AGAAGCTCAA GTGACGGTGA CGCTCCAGCT    32040
CGGTCAGCAC CGACCTGCTG GCCTCGATGT AGAACGTCGC CGAGGCGTGC TCGAACACGC    32100
TCTCGTGGCC CAGATCGATG ATGTGGTTGA GGTAGTCCTC GTTCTCGGCA GTTGCCGGGT    32160
TCGGTCGGTG GAACGACCGG TAGCAGTTCC GGCCCGCGAA CTCGGCCAGC TCGTCGGCAT    32220
CGAAGTCGCC GAAGTAGGGA TCTTCGTCCT TGGATTCTTC GAAGTCATCG ACCTCGAATC    32280
CGATGTCCCG CAACGCACCC GGATCGATCT CGGTGGCAGC GATCAGTTTG GCTTTCATAC    32340
TCTCCGCTCA GAGTTGGTGG AACGAGGTCA GCCAGGGGGC AGCGAAGCCC TTCTACAGCT    32400
CCCCTTGGCT CGTTACCGGC TTCTCGACCT CGGTGGATGT CAAGTAGTCG AGATGACTAC    32460
TTCTTGTCGG GCCATTGCGC GTCACACTGC TGATCGCGAG GTGCGGTGCA GGAGAACAGC    32520
GCGTACGGCT TGCCCGTCTT CTTCGAGACG CCCGACTTGT AGACCATCTC GCCGTGCTGG    32580
CAGTACCGCT TCTCGCCACC AGGCGCTTCC TGAGCTGCCT GCGGGGCGCG AGACTGCTGC    32640
TGGCCACCGC CGCCGCCGTT GGCCGGCGCG GATCCACCGG AGCCTGCGTA GTGGCCTGCG    32700
ATCTGCTGGA CCTTGTCCAT CAGCGCCTTG AACTCGGCGG TGTTGACCTT GGCCAGCACG    32760
TCGGCCGGGT CCGCACCCTT CACGACCACC CACGGGTCGC TGTACTGACC GGCGAACTTG    32820
AACGTGGCCG ACACCCCATC GGTGGAGTGC TGGACCGCCA TCGAGTCGCG CACAGCAGCC    32880
GAGGCCGTCG TCACCGTCGC CGACGGCGCG GTCTCAGGCT CAGGAGCCGG GGCCGGCTCG    32940
GGCTGGGCAG GGGCGGTGCT CCACGGATCG TCGTAGGACA ACTGGTTACC TTTCACTTAA    33000
TGGGCATGC GCCGTTGGCG CACTCTTCAT CGACACCGTC TTCGACGGCT TTGGCCGCAG    33060
CAGATTCGTA CTGCTGCTTG GTGATTCGCT CGTACGGAGC CTGCGGGAAG CTGGACTCCG    33120
GGAAGATCGT GGAGCCCTTG ATGAGCCCCG CGAACCTCTT GAGATCGGCT GCGACATCCT    33180
CGGCCTCGTA GGCGTCTGGA TGGACGTTGG CGGTGAACGA CACCGCGTTG TCAGCCCAGC    33240
ACATCTGGTA GAGCGCCTGG AACGCCAGGA GCTGGTGGAG GGTCAACTCG TCGGCTGACT    33300
CAACGATCTC CTCGTCCCAA CCGAGTTCCT CGACAGCCTG GACCAACGTG TCCTTGGTCG    33360
GGATCGAAAC CACCTCGGTG TTCGGAGCGA AGAGATCCTT CTCGATCTCG TAACCCTCGG    33420
CTGCCAACCT CCGCAGCTCG GCCATGTCGC TGTTGAGGTT GAACCGCACA CGCCGGATGA    33480
AGTACCGCGA GAAGATCGGG TGGATCCCCT CGGAGACTCC TGGCATCTTC GCCACCGTGC    33540
CTGTGGGAGC GATGGTTCGC TTCTTCACCG GGACAGGGAT CCTCAGATCA TGGGCGAACC    33600
GTTCGGCCTC TGAGTCGACC TCAGCGGCCA TCTCCCGCAA GAACTGGGTG AACCGCTTAT    33660
CTCCGGGTGC CTCGGAGTAC CTGCTACCTG TGAGGGCCAA ATAGGAGGCA ACTCCGAGAT    33720
GACCCACGCC GATGCGACGG TTTCGGTCCA GAACCTCCCG GCTCTTCGGG TCGGCCACTT    33780
CCGAGAACGT CGCCCGGATC AGGAATCTCG TCATCAGACG ATGCGCCCGG ATCAGGTCGA    33840
GGTAGTCGGT CTTGCCGGCC GGCGTCACGA ACGCCGCCAG GTTGATGTGG CCGAGGTTGC    33900
ACGGCTCCCA CGGTTCGAGA GTGATCTCGC CGCATGGGTT GGTGCAGACC ACCCGGTTGG    33960
GCTCACCGAC GTTGGACAGT GACGAGTCCC ACATCCCCGG CTCTCCGTTG CGTACGGCTC    34020
CCTCGGAGAG TGCCTTGAGC ACTCGGTGGG CTCGCTTCTG CTTGGGCATG TCCTCGCGGG    34080
CGACCGCGAA GCTGCCGTAG CCCTCCTTGG CCAGACGCCA GAACTCGTCG TCAACCTCGA    34140
CCGAGATGTT CGTCGTCCAG TGCTCGCCCG TGCTCGCCTT GATGTTGATG AACTTGTCGA    34200
TCTGGTAGTC GTCCCAGTGC ATCATCGACA TCCGCGCCGA CCGGCGCACA CCGCCGGCCA    34260
CAACACACTG AGCGATGGCG TGGTCGACCT CCATCGCGGC GATGCCGTCG AGCGTGATCC    34320
CTGCGTACTC CGAGAAGATG TTGGCGACCT TCTGCAGCAT CACAGCGAAC GGCAGCGGGC    34380
```

-continued

```
CGCTGGCCAC TCCACCGAAC GTCTTGAGCT TGGCCCCTTG CGGCCGGATG CGGCTCACGT     34440

CGTACACCCG CTGGTAGTGG ACCGTGCCGG GTCGGTAGTG CGTGTCGATC AGATCGACCA     34500

GCGCAGCAGC CCAGCCCTCT CGTGAGTCCT CGATGGCGTA GGCACCGGCC CAGTCGTGGC     34560

TGTAGTGCTC CGACAGAATG CCTACATCCT TCATCGCCTG GTAGTCGACA TGCTCTGGAT     34620

CACAGACGAT CTCGACCCGC AGGGGGTTTA CGACCTCGGG GTAGCCTTCG AGGTAGTGGT     34680

TCGAGTAGTT CGCCCCGACT CCCCCGCCCT CCATCAGGCG CATGAACGTG AACTGGAAGT     34740

GGTCCGAGAT CTTCTCGGGC CAGCCAGCTA CCCAGCAGTT GAAGAGGTGC TGCGCGTTCT     34800

TGACCCCCGA GGCCCACAGA TGCCGACCTG CCGGCAGCAC CTTGAACTTG GTCATCAGAC     34860

GAACGAGATC TTCTCGCTCT CCTTCCAACA TATGTCGCCG GTCGACAAGA GCAAGATTGC     34920

CGTCCACGAC CCTCTCGACC GTTTCCGGCC AGGTTTCCTT CGAGCCGTCA GGCTTGGTCC     34980

TGGCGTAGGT TCGGTTGTAA ACGAGTTCAC CGGTTGGTCC CCAAGGGATT TCGTCAGTCA     35040

ACTACTTCCT CTCAGTCAGT TCGTATCGCT TGAAATAGGC GTCGGCAGAG TCGCCGCCAG     35100

AGAACGAGAC CCCGTACTCG ACCGGGCCTG CACCACGCAC CTCGCAGGTA ACGACGCCCT     35160

TCCTTCCCCG GAACATCGGC CAGGTTCCCT TGGAGGGGTG CTTGGTCTCG TCCCGCTGGA     35220

CGATGACCTT GGTGCCCTTC TTCATGCCGA CTTCCGTTCT CCGTAGCCGG GAGTGAAGCA     35280

ACCCCCGACG TACAGCTCGA GATCTTCTTG CGACCAGTTC TCCAGTCGCA TCGGCGGCTG     35340

GTGCGGGAAC AGCTCCGGGA ACACCTCGGC CCGGTACAGC TCCGAACCGG GCATCCCGTT     35400

GAACGTCGGA TCAAGAATGT TGTGCATGGC ACCTCCCTCC CAAGAACTCG GAGATCGGCG     35460

GCTCGTAGAG GTAGCCATCG CGCAGCTCGG GGTTCTCGAT GAGCATGATC GCGATGTTCG     35520

CTGTGGGGTC AGAGTGCCCA TCCCCCTGCG ACTTTCGGAT GTCTGGGAAG ATAGCGTGCT     35580

TGCTGCCCGG ACCATCCTTG ACGATGACCT TGCCCTTGTC GTCCTTCTCC ACGCCAGCCG     35640

TGATCGCGAT GATGTTGACG TGCTCGGTCA GCGACTTGTG AGCGCGGAAC AACCGGTTCT     35700

GCCCGCTCTT ATCCTTCGGG GAGATCCCGT CGGTGTAGCG GCTCCTGATC GCCTCTGCAT     35760

AGCCCCCGTT CTGAGCGTCC AGAGCCTTCA TCGCCAGCGG GAGGATGTCG ACCAGGTACC     35820

GATTGGTCGA CTCCCCCTGC AGAGCCTCTT TGACGTTCTC GGACGAGTAG TGGCTGCGCT     35880

CCTGGAACAA GTCGCGGGCC TTGGCCGCTC CCGACAGGAT GTTGCGAACC TGATTGCGTA     35940

CGTAGTGAAC TGCCTCACCA CGGTGCAAGC TCTCCAGCGT CTTCTGGATG TACGGGCTCT     36000

CGAGGTACCA GACCCACAGC TCTTGGATGA TCTCCTCGGC TGTCAGGTTG GTCTCCCAAC     36060

CGATCAGCGC CTTCCGGGTG GCCCTGCTGA ACAGCTTGCT GATGTCGTCG GTCAAGGCAT     36120

CACCTTTCGT AGGTACTCCT CCCGGTCCAA TCGGCGGTCG AGGTGTCGAG TGACCTCCTC     36180

CGCGAAGACC TCGCGGACTT CGCTGGAGGT GATCTGGCGC GAACGTGCGT TCTTGTGCAG     36240

GTACGGCAGC TTGGTGGCTG TCAAGTTCTA GACCTCCCAG ACTCGGCCGT CGACCGAGAA     36300

CCGGCCTCCG ACAATCGGAA CAAGCTCAGG CTTGACGTGC TGGCCGTCGA CCGTCAGCAG     36360

AGCAAAACCA CTCTGCCAGT TGGCTGTTGC ACCCTTGAGG TACTGAGCTA GCTTCATGTT     36420

CATCAGGTTG CCGACCTCCA TCGACCACAG CACCTTCTGG TTGCCGCCGT AGCCCAGCGT     36480

GTGTGGCTTG ATGCCCTGGC GGTGGGTGTG TCCGATGATC ACCGACGTGC CGAACCGCAT     36540

CATCGCGTTG TACGCGGTGT CAGCGGACTT CTGCGTCACC CGGACCCCAC CACGGTGGCC     36600

GTGGGTGGAG ATCCAGCCTG GAGCGATCTT GTAGAACTCA GGCAGCACGT CAACACCGAA     36660

CCCGTCGAAG TCCAGCAGGT TCTGGAACTG GAACGAGCTG ACGTACTCGA CCAGCGCCGG     36720

GGCGAACTGG TGCAGGTAGT CGACTGGCCG GCGGTCGTGG TTGCCCTCGT GGACACCAAC     36780
```

-continued

```
CGGGCCGTCG TAGACCTGGC GCAGCGGCTC CAGGAACCGC CGCTTGCACT GCTCGGAGTC   36840

GGGCTTGATC CGCTGAGCGA ACTCTTCCTT GGTGCCCTTG GTCCACCGAG ACGGGCTCGG   36900

GTAGTCCATC AGGTCACCGA TGTGGACGAC CTCGTCAGGC TGGGTGTCCC CGATGTAGCC   36960

GATGACCGCC TTCAACTGCT TGCGATCATC GAACGGAATC TGGGTGTCCG AGATGACGAC   37020

GATGCGCTTG CTCACTCAGC GACCTCGGTG AAGGGGCCCC GCATACGTTC CTCGTGGGAG   37080

CTGGCGTTGC CTCCTGACCA GCGTCGCTTG CCCACCTTGG TGTGGTGCAA CCCGTTGGGG   37140

TAGTAGATCC ACTTCACTCC TGTGGCGTTG GTGACGGTCT TCACATCGGC AGGAACGTCC   37200

AGCAAGGTGT CCCACTGGCG AGGCCCCTTG GGATACCGCT CGTCCTCGGG GAGCTGCATC   37260

TTCTCCAGAA CGCCTGCGTA ACCGGCGATG TCGACCACCG TGTCCTGGTG GTAGCCGTTC   37320

TCCATGAACC GGGCGATCTT CAGCAGGATC ATCATGACGG CCACGTCCTC CGGGGTGAAC   37380

TCGACGCCGC GCTTGTACGC GCCCCACAGG GTCGCGATGC GTTCGTGGTT CTCCTTGGCG   37440

TCCCCGTAGT CCTGGGCTCG CTGTCCGTTG ATGATCTCTT CGGCGGTGGT CAGAATGCTC   37500

ACAGTCCAGT CTCCGATGCG GTGTAGTAGT CGATCAGCTC ATCGAGCTGG TCCGTTGAT   37560

AGCCGAGGAT CGGCTTGTGG GTGTCAGTGA CGACGACGGG AACCGACATC GCGTTGAGCA   37620

CCTTGGTGAC GTAGTCGTAC GCCTCCGAGT TGGCCGTGAC ATCGACTGCG TCGAAGTCGA   37680

TCCCGGCAGC CGTCAGCTTG TCTTTGACTC GCTCGCATGG CTTGCAGCCG GGACGGGTGT   37740

ACACCGTGAC CGGCGCGAAC AGCGTTCTCA CGTGAGCACC ATCCCAGTCG ATGTATCGGT   37800

CTCCATACAT CAGATCCTTT CCAGCAGAGC AGCTTTGCCC TGCGATGTGA CTAGTGAGTT   37860

GACATCCTCG CCTTCTGGCA TCGGGATGAT TCGGGCGTTC GGCAGCGTCT TCGCCACCGA   37920

CCGGGCGAAC TCCATACCGG CGTCGTCGCC GTCGGCCAGG ATGTTCACGT TGCGGTAGCC   37980

CAGGAACAGC TCTCGGAAGT ACGGCTTCCA CTTCTGGGCT CCGCTGAGCC CCACCGTCGG   38040

CAGCCCACAC AGCTCGGCGG TGATCGTGTC GAGTTCTCCC TCGCAGATCG CCATGTCCTT   38100

GCTGTATTTG GTCAGCGCGT AGGTGTTGTA GAGCCGGTCC TTCTCCCCTG GCATCGACAG   38160

GTACTTCGGT GTGCCACCGT CGATTCGGCG ATACCGGATC GCAGCTACCG TCCAGTGACG   38220

CCAGGGCGAC CACCGCATAT ACGGAATCGC CAGGCAGCCC CGGTACATCT CATGTCCAGG   38280

GAGTGGGTCG TCCACGAATC CCAGACCGAA CCGGCTTAGT TCCGCTCGGC CGGCCAGCCC   38340

GCGACTCGCC AAATACTCGT CGGCTGGGCT TCCGGGCAGG CTTTCTCTGT ACCGGGACGT   38400

TGCCTCCCAC AGATAGGTTC TCTGCGATTC GCTTAGCCTC TGCAAATGTC ACCTCCTCTT   38460

CGTGACGAAT GATCGAGATC ACGTCTCCAC GGACCCCGCA GGCCATGCAG TTGTAGCCCT   38520

GTAGGTCGTA ACTGACTGCG GCAGACGGCG TTTCGTCGCC GTGGAAGGGG CACAGGCACT   38580

TGTTCCACTC GTGGTGGTCA GGTGGTGGTT CCCAATCCGG GTGGTAGCGA AGAATCGCCC   38640

TCGCGATGGG CGAGTCGTTC ATTCGTCCTC GTCAAGCTCC TCGGGAGAGA GCCCTTCGAA   38700

GATCCCGTTC AGGACGGCGG CGAAGCCCTC GCCGGTCTCC GCTGCGTCGA GCATCTCTGC   38760

AATCGTCTTT GCCATGTTTC CTCCTGGTGG ATGTCAAGTT CGAGACAGCT TGTCAGCCTC   38820

GACTGGAGCG ATGCGCTCCC CGATGACTTG GACGGCCGGC GGGTTCAGCA GGTACTCGAT   38880

GGCCCGTTTG AAGAACTCGA TGCAGTCCCT CGCCCAGCCC AGCGTGTACT TGTTGCACAT   38940

CGTGCAGAGC AACCCTCGGA CGATGCCTGT CTTGTGATCG TGGTCGACCG ACAGGCGCTT   39000

CTTCTTACCG TTGGCTCGCT GGCAGATGTA GCACCGACCA CCTTGGAACT CGTAGATCTG   39060

CCAATACTCA TCGCCGGTGA TGCCGTAGGT GGCCAGGATC CGGGTCTCCC AGCTCGTAGA   39120

GCTGCGAGCC GTCCTGAACT CTCGGTGATG AGTAGCGCAT CGTGGCCCTG GATACTTGGC   39180
```

-continued

```
GTCTCGCGTG AGCGGGAGCC CCTGTGCGAC ACAGTCTTTG CAAGGCTTCC GCTTGTGCTT      39240
ACGGTTCTGC ACCCGGTACC CCGGAGACCT CTTCGCCGCC CTCGGCACGC GCGTCCTCCT      39300
CCCGGTTCTC CATCACCATG CAGAACCACG ACAGCAGCCC TGCCAGGGAG ATGTAGAAGG      39360
CCACCAGAAC TTGGCCGCTC ACTTCACCAT TCCTCGAACC CACCAGCGAG ACAGCGCCTT      39420
ACGCCCTTTG TCGAGCGGGG TCAGCTCGCG CTCATCGTCC TCACCGAAGT CGAACTCGAT      39480
GCTGGCGATC TCGTAGCCGA GGATCTTGAA CGACACGTTC ATAGGCGGTC TCCGAAGTTG      39540
ATGACGGGAA TGCCGGCCCT TTCGGCCTCT CGCATGCAGT GCCGGGTGCC GACTGAGTTG      39600
CCGAGGGGGA ACGCCAGACA GATGTCCGCA CCGGCCCTGA CCATCTCGAT GTTGCGGAGG      39660
ATGCCAGCCC GCTTGCCGTA GCGTTCCCAG TCGGCTCGGT GCAGCTCGGG GAGCACGTCC      39720
CATCCCTCCT GCTTCATCCC CCAGGCCCAG CGGTCTGCGA TGTCGTCAGC GCCGCGAGCG      39780
CCGCCGTGGA CGACCGTGAG ACCGGAGAAG GACCGGTGGT ACTCAGTGGC CAACGCTTCC      39840
CAGACCGTGG TGCGGTCCTT CCAGATCCGA GATCCGGTGA TCAGTACTCG CCGCATCAGA      39900
TCGCCTCCCA CTGCAGGCCG TCGTGCGACG TGACCAGCTC CGCTTCGTAG ACGCCGTAGC      39960
GGGTGGCCAG GAACTGGATC ATCTGCGCCT GCTTGTACCC GAAGGGACAT TCGTGGACGC      40020
CGCTGATCGG GTATCTGACT CCGTATTTCA CTTGATCCAC CGCTTCGCGA TTCGGTCGAC      40080
GTTCTCCTCG GAGACGTTGC GGGCGAGGCC GGTGAACTCC TGGCCGTGGA CCTTGGTCTC      40140
GATCACGCGA GGCTTGCGGG GATCCGGGCT CTCCGGGTCG ATCCGCTTGT GGGTCCAGAC      40200
GGTCGGCTTC GTCTTGATCA GAGCGCCCAG CACCTGCTGG CGCAGTGGGT TGGTCTTGCG      40260
GGGCATAGCG TTTGGAGTGG TCATCTGGAT CCTTTCCTCG GTGGCTGTCA AGTCGGTGTG      40320
CGTAGTGAAG CCCCCCCAGG CATGCGCGCC CCGCCTGGGG AGAGTTGATC AGCGCAGTTC      40380
GATGTCGGGC AGGATCGCCT GCGGCTTGAA GTTGACCTGG TAGAAGTCGG TCGAGACGTT      40440
TGCGCCATCG ACCTGCTCCA TGAAGTAGGA GACGTTGTCC GACAGGCCCA GGAAGTGCTT      40500
CTTGATCCCG TCCTTGGTCT TGCAGGTCAC GTCGAGCTTC TTCGACGCGG TGTCCGCGTT      40560
GATTGAGCAC CGGCCCTGGA TCTCGAGCAG GTACTTGTCC GTGATCCCGT TGAAGAACAC      40620
GATCCGGCGA TTGATCTCGA AGTTGTCAGC GGCCTTGCTG ACGTTCTCCG ATGCGACGTC      40680
GGCGTCGGAG GTACACGCGG AGAGGCCCAG GATCGCCGAT CCGGCGATGA GTGCGGTGGC      40740
GATGATCTTC TTCATGTTCG CTACTTTCTG TTTGGTGGAT GTCAAGTTAG TGACCGAAGT      40800
CGTTGATCTG CATAGTGTCT CCGACGAACT CCAAGGAAGC GAAGTCTTGT CCCGACGGGT      40860
CCGACTTCCC CCCTCGGTTC TTGACCGTGG AGACGTTGAG CATGTCCGGG CCGAACCCGT      40920
CCGATACTCG GTGGAGAGTG AGGATCATCT CAGGAACACG CCCGATCTGA CCTTTGATGC      40980
CCGACAACGG GATCGGCTTG TCGCCGTCGT TGTGCGGGCC GGTGACGTGG TGGAGCCCGA      41040
CGACGCATGA GCCTGTCTCA CGGCCCATCT CGTGTAGGTA GTCCATCAGC GACTCCAGAC      41100
CCGAGAACGG GTCGTCTCCC TCGCTTGAAT CGGTGCGGAC GTTGGTGATG TTGTCCACGA      41160
CGATCAACGC TGGGAAGTCC TCGTACAGCG CGTCATACGC GGCCAGAGCG TTCTCGATCT      41220
CGTCCAACGA CGGTGATGCC TTGTAGTTGA ACCGGATCGG GATCTCGTCT AGTGAGTCAG      41280
CTACCGCGTC CTCGATGTTC TGCTCGCGAA CAGCCCGCGT AGCTCGTTCG AGCGACCATC      41340
CGCTGAGGAT GGACACCGAA CGGGAGAGCT GGGTGAACGC ATCAGAGTCG GCCGAGAAGT      41400
ACAACGTCGG CACCTTCGAC TTGAGCGCGT AGGCGAGGAC GAACGCCGAC TTCCCGGTGC      41460
CGGGGCCGGC GCAGACCAGG ACTAGCTGGC CTCGTCGGAG ATGTGTACCT TTCTGGTCAA      41520
GCGCGGCCCA GACCGGGGGT AGCGGATCCC CCGCCGACCC TCGGATGTAG AGCGATTGTC      41580
```

-continued

```
TAGGTGTGTA CACCTTCCTC CTCGTGGATG TGATTGACCA GGTCATAGAT CTCGTCGCGA    41640

GAGACCAGCC GGCCCCAGGC GTCGATCCCC ACGTGGATCT GTCTCCGGTG GATGTGTCGG    41700

GACAGGATCA TCGGCGAATG CGTGTGCCCG TGGATCAGGA TCTTGCCATC GTCACGGAGC    41760

CTCCACTGGG TGTGTCGGTC CTCGCTGGTG TGGTCCCCGA CGTATGGGAA GTGGCTCAGC    41820

AGAACATCTG TGTGCCCGCC AGCGTCCCCG TACAGCGGCA CCCGGATACG AGCTGCCGTC    41880

GACACATGCT CGAACACCAT CCAGTACGCA CCAACCAGCT TGTGAGCATC GCGGTTCATC    41940

GGGTGGGGCC CATCGTGGTT GCCCAGGATC AGCCGTTTGC GGCCTGGCCG ATCCGAGATC    42000

CACCCGAGGG CATGTATCTG CCCCTTGGTG GAGCCAGAGG AGATGTCACC TAGGATCCAG    42060

ACCGTGTCGT CCTTGCCGAC GACCGAGTCC CACGCCTTCG CCAGGGTGGC GTCGTGCTCT    42120

TCGACATCAT CCGCCAGGTT GCGGATCTCC ATCAGCCGCT TGTGTCCGAT GTGTAGATCG    42180

GACGTGAACC AGGTGTTGCT CATGGCTTCC TTTCAGAACG GCGGGCCGTA CAGCTCGATC    42240

ACCAGCGCGT GCAGCTCCTC TGCCGCGTCG TCACGCTCGA ATCCGCAGCA GGAATCGTGC    42300

CGGTCGAGGA TTGCGACGAT CTGGTCGTAG AGGCTGGGCC TCACTTCACC TTCTTCGGAT    42360

CGATCAAGGC GTCGTGAATC GGCCGACCGG CGCGAGCCGC GTGCGTCTCG GCGTCCAAGG    42420

CTCGCTGCAT CTGGTTCATC AGCCGGGTGC CGCGCAGCTT GAGGATCTTC ATGGTCGCCC    42480

GACCCTTGTA TCCAGCGCGG TGCATCCGTA GGACGCAGGC TGTCTCGTGC GGGGCTATAG    42540

GTGACCTCAG CGACGGGTGG TTTGGATCCC AGTTCGTCAT GTCTTCCTCT CGGTGGCTGT    42600

CAAGTTGGTC ACAGACCGAA CTCTTCCTGG TACTGCGGGA TGAAGTGGCC GGCCGTTCAT    42660

GTTCGGCTCG ATACCTCTCG CGTCACGAAC TCCTGCCCGT TCCATCTCCG ACCGTCCTCG    42720

AACTCGATCA CGATCTCTCG TCCGGGATGA CGCACGGCCT CCGCTTGGGC AAACCTGCGT    42780

GCAGCCTCTG GGGTCGGGAA CGGAAACTTC TGCGAGGCGT ACAGCTCCTG GTGCCACTTC    42840

GGCTTGTCAG GAATCGGCCC CATTTCCACG TACGTGTAAC CCGCGTCGGG GTCGAGTTCG    42900

AGCGTTTTCT TGTATTCCTT CGTGCCTGCC TTAGAGGGAA GGTGAGTATC GGTGGCTGTC    42960

AAGGTGACCT CACTTAAAAA CAGGGCAGCT GTAATTCACA TCACAGAAGC CGCATTTGTC    43020

AGGTTCAGGC AGAGGCTCGA AGTCACCAGC CTGGATCCGA GCCTCGACCT CATGGAACCT    43080

CTCGGTGATC CGCTCCCGCG TCCAATCGGT CAGGTCGTAG GGCGCAGTGG GCTTCGCCTT    43140

GATGCCCTTC TTCCCCGCCA TGAAGTAGTC GCCCGTCTTC GGAGCCTCCA CGTCATAGGT    43200

CATCGCGACC GCGAGCGCGT ACACGCCGAG CTGGAAGTCG TCACCCGGCG AGTTGCCGGT    43260

CTTGTAGTCC CGGACTCGAA GCTCACCGTT GACCACGACG ACCGCGTCGA TGAACCCTCG    43320

GACGCGGATG CCGTCCAGCT CGATGTTGAA CGGAAGCTCG ATGGCCGGCT TGGGCTGTTC    43380

ACACTCCTTG CAGTTGGTGT CTTTCCACGC CTCCGTAGAG CAGATCCCTC GCCCAGGGGT    43440

AGTCCAGATC TGCTGGCCCT TGTCCTTCCG CCACGCGATG AACTTCTCTA CCTGCTCCAG    43500

TCCAAGGTGG AACCGGCGCT CGATGTCACG CTCACCGTTG TACGGCCCGG ACCAAAACCA    43560

CCACTCGAAG TTCGGGGTTT CGTCGCACAG TGCTCCGATG TCCTTGGCGT ACTCCTCGCG    43620

GAAGATCTCT TGTGCCCGTT CGAGGCTCAT CTCGCGGCCC TCGGCCAGAG CCTTCTCGTA    43680

GACCTCAGCG ACGGTGTGAA ACGCGGTGCC CTGCGGCAAC CACGCCGCAG GACGAGCCCA    43740

TACCTTGTCG ATGCGAGCCA GCTTGTACGC CTGCGGGCAA CGTGTGTATT GGTTCAACTG    43800

GCTGACGCTT CGCAGCGGCA GCAATGTCTT GGTGTCTGTC ACGCAGCGGC CATCCTTCCC    43860

TTGCCTATCG TCTCGTTCAG CGCCCCGTCG ACAGCGACAC TGAGCAGTTT TGCGACCTCC    43920

GACATGTCAA TCGGATCCTT GGGGAATTGG TCAGCCTGAG TCATCCTGAG CACCATCCAC    43980
```

-continued

```
TCGGTGCCCT TGTCGCAGTG GATCATGGTC GGATCAAAGC GAGTTCCCCG TGCTACGTAC   44040

TCGACTTTGT TCGCGGAAAG AATCAAATTC GACACAGGCC GATAAAGTCG TGAGGTGTCT   44100

TTTACACGAG GACTGCGGTA GACGAGCAGA ACTGAGACTG GGTCTTCGTC CAGTTGGCCC   44160

TTCCACCACG CCTCACACCT CTGCGCGAAC AGCCACCCTG GATGATCGGC GATGACTTGC   44220

GGTGAGGTGT GGACGAGGTT GTCTGCGAAC AGCTTTGCGA GCCGAGTGAG GGCACGGGG   44280

TTTCCTTTCG TTGCGCGGCC TGGGTTGGCT CACACAACCG GTCGTGACTT TTAGGGCTCC   44340

GAGAGAAGCT CCTCGATGTC GTCTGGCCAC GACCAGAGGA GTTCACCCTC GGCGGTGAGG   44400

TTGGTGTGCT CGTTCACCCG GATCAGGAGA TCGTCATCCT CGATGCCTCG GGGGACGTAC   44460

CTGAACCCGC CGCCGGCCAT ACCTTCGTAG GGCTCGATGG ATGGGTCGAA CTCGAGCACT   44520

AAGTCGTCGT CGCGGAGCAT CTTCCACCAC GACAATAGGC GCTTCTTCTT GTCTTCGGAC   44580

ATCGTGCGGA AGCTACCCAC TCGCATGTAC TCGCCGTGAT CCCGGAGCCT CTGAAAAGCC   44640

TTCGACTTAT CGTGAGGTTT CCGCGTGTCC CACGGCCAGT TCTGCTGGAC GATCTGCCTG   44700

GTGGTCAACC GTCCTCCGTA GGTCTTCTTG TGCCACGACA CCGCTTGTCG AGTCACGCCA   44760

TACAGCTCTG CGATTTCGGT CTGATTAAAC CCCTTCCTGC GAAGATCTTC GATCTCGCTG   44820

AGAGTGAGTG GTATTCGGCT AGGGGCCGGA ACCACTGCTT TGTGTTGGAT TTTGCCGCTC   44880

ATGTTTCCCT CCATGAGAAA GGTGCGTGCG TCTCCGCCGA TTACGGAGAC ATGTTGGTGC   44940

CTGTCAAGGA TACCCCTAAT TTAGTTGCGT CTGCGGAACC ATATTCAGTT GTGTTCCCCG   45000

ACGCCGTGGC CGTCTCCCAC TGGGCGTGGG ATCGACTGGC GTTACGCGGT CGTAAATGTA   45060

GCGGCCTGCC CCACTCGGTA GCAAACCTTG TGACAGGTAT CACTTAGGTC GCCTTCTGTT   45120

ACACGTTGAC CTCGGGTTTC ATCGTCACGA CTCTCCTTTC TTAGACAGCC TCAAGATCGT   45180

TACACCGGCT TGCGAAGATG TACCTTCGCC TTGAATCCGG CCCTTGCCAG CTCGAACTCG   45240

ACCACCTGGC GGGCGGTCTC CTTCAGGTCG GACTTCGCCG ACAGCGGCCC GACGAACCCG   45300

TAGCTCTTGA TGTACTCCTC GAGGTCGATG TCGACGTACA GCGTGACAGG GACCACCGAC   45360

AAGTCACACC TCCAATTCGT GGGGCTTGAT CTCGTTGGTC ACGTCGTAGT CGTTCAGCAG   45420

CGACTGGAAG TCGGAGTCTG TCAAGTCGTC CAACTCATCC TGCTCGAACG GCGCGGGCTC   45480

GTCATGCCAC GTCTTCCACT GGTCGTGGTC GGCGCGGAAC CACTTCCGCA GATCCTTGAT   45540

GGCCTCGTCC TCGGTGGCGA AGACGTAGGT CTCGAGCACG TCCTCGTACT CGACGGTCAG   45600

CGACCAGACG GTGATCTTCA CTCCCCGTTC ACCTCCGCTT TGTAGTTCAT CTCGGCGGTC   45660

TCCTCCTAGT TGGGTAGCAG TCGGTTGTAC TCGTCGTGGC TGATCTCGCC AACGATGAAC   45720

TGGCGCATCA GATTTGCGAC CGAAGCCGCG TCCATCCCTT CGGGAATGGG CTTGGCGTGG   45780

CCGAACTGCC AGTCTCGTGA GCGCCAGCGG AACCAGAGTT GGACCTTGTC CAGTGAGGTC   45840

AGGTGCAGGC ACTGAAACGT CATGCCTCCG AACGGGAACT CCATCACACC TCCTGTTTGA   45900

CCTTGACGGT GTGGCCTGTC ATTACTTCGT GGATTCGGAT GCTGGTGCCG AACGTCTTTC   45960

GCGTCTCGGC CTTGAACTCG GTGGAGCACC CCGAGCACTT CGCTTTGAAT CGCACTAGCA   46020

GTACCAACGC TTTCTGCAGA ATCGGGACTT GCCGCCGTCC CGGTTGTCGT TGTCCCGGCG   46080

GGCTTCGCCC TTCGGTGATT CGTCACATGA CGGAAGCTCG CCATGCTTGA TGTGCCATGC   46140

GTCGTCGGCG ACTTTTCCGC CGTGCTCGGC GATGTGCGCT GCGCTCCGGT ACTCACAGAG   46200

CGGGGAAGCC GATGCCTCGG CGATGATCCC AGGCAGGTTG CCTAGAACCA CCGCCAAGCA   46260

CATCAGCAGA ACGACGTGCC ACGCCTTCAT CAGCCCGCCA GCGCGTGGTT CATCGCCGCG   46320

TTGCGGCCGT CGCGCTGACC GTGGGCATAG CCGCTGAGGT CGTACCGGGT CCGAGGCTTG   46380
```

-continued

```
ACGTTCTTGG TGCGAGGATG CGCCTGGCGC AGAGCCAGCG CAGCTCGTTC CTTGTCGCCT    46440

CGGTAGAGCA CCAACGCTCC CCCGCCGGCC GATTCCACGG CCTTGTTCTC CTCGGCGGTC    46500

AGGCGTTCCT TGACGGCCTG GGCGAAGCCT GCGATCCACG ACCGGCGGTA GCTCTTGAGC    46560

TGGCCAGCGG TGCTCTTCGG CTTGTACTCC CCGGTGTTGT AGTCGTACTT GTACCGAGGC    46620

TCGAAAGCCT GCTCCGGGCG GACATTCTCA ACCAGGCGCA TCATCTGCGG CTGCATGATC    46680

GACCAGAGGA ATTGGAGCCT CTCGATGTGG CGGGCACGC CGTAGACGTA GATCCGCTGA    46740

CCGCCCGTGA GGCTGGCGTA CACCGTCTTG CAGTGCAGGG CCTGAGCCAT GCCGTGCAGC    46800

AACAACGCTT GTGCGGCAAC GTACTTGCCG GTGACGTAGG TGACCCACTG GATGGCGTCG    46860

GGCAGGTCGG TGGTGTCCAA CCCTTGCTTG CTCGCCTCGA CCTGGGCCAT CTCCAGCCCG    46920

TACTTGGCCA TCAGCTCGAA CGCTTTCGCC TGGAACACAG CCTCTTCCGG CGTACCGGCC    46980

ACGTCTTCGG CCTGGCGCAG CAGCTTGGCG ACCTTGTCCT GCATCTTCTT CGTCTTGCCG    47040

TCGATCATGG TCAGTACTCC TTCTTCCAGT TGTTCCGGTT GCCCTTGCCG GGGCGCTTCA    47100

TCTCTCGCTT GCGGTTACGG TGCGGCTGCG CCGCGTTGGA GAGACGCAAC TCGAGCCGTG    47160

CCTTGAGCTG GTCGCTCATC TTCTTCACCT CTTCTGGTTC AGCGGATCTG GTCGACGTGG    47220

ATGCAGCCGA CGCGGTCTGG CCCGAACTCG GGAGCGAAGC CCAAGACTTC GTCCTCCTCG    47280

CATGGGAACG CTCGCTGGTC GAACGTGATT GGGTCGGCCG AAGCCTCGTA TGGATCGGCC    47340

AAGGCCATCG CTCCGACCGC TGTAGCGAAT GCAACGACGA CGGTGATCAG GTGCTTCTTC    47400

ACTCTTCTTC CCTCCACTTT TGGTCTGCGA GAAGCCTTCT GGCGATCTCG ATAGGTTCGA    47460

TCTCAGGAGT CACTCATCGC CCTCCAAGAT CTTCAGGTTG GCCAGCAGTG CATTGGCCAC    47520

AGCTCCGATG TGGCCACCGC CCTTACCTCC ACGGCGGGAG TACTCGCGGT TCGCGGCCTG    47580

CATGAAGTGG AACCTCGGTG AGCCGTCCTC GTGAACCCAC GAGGCTTTCT CGGCGGGCAG    47640

AGCCCGGTTC ATCTCCACCG ACATCGTGAC GATGATGTGG TCCCTCTGGA GCCGAGCCTC    47700

GGTCTCGGCG TAGTGGGCAG CTTGGATTAC TGCGCCTCGT GTGGTCATGT CTTCTCCTTC    47760

GGTAGATGTC AAGCTGTCGT CACCACTCTT CGACCGGTAT CGGTTTGTCA CAGCCAGCAA    47820

GGATCGCGGC GTTGCTGCGG TGATGCCCGT CCCACAGCGT CTTTCGGTCC CTCGAAACCT    47880

CGAGGGGTTC GAACGGCCAC TCGTTCGATG AGTTGAGGAT GTCCACGACT TCGTGGACCT    47940

TGCCCAGAA CTTGCCGGTC ACGCCTCCCT GGTAGTTGTA GCGGGCGTG GTCTGGTAGA    48000

ACTCTTCGAG CACTGGTCCG CTGTCGGCGA CGGTGCAGTC GACACCAGCG CAGGACATGC    48060

AGTCGCTGGC GCGGAGCTGG GCAACTTCAT CGGTGGTCAT GAACGCCGTG GTCACATCGA    48120

GCCTTTCAGG TGTATGTCAA GCGGCGCGGA CGCCGGAATC GGAGAGGTAG ACGCGGTCAG    48180

CTCCCAGGAA CGGAGCCTGT GTGTTGGCGT GGACGAACGT GTCGTTCTCG TAGGGGTTGT    48240

AGGCGATCTT CGATCCCACG AAGTCTTGCG GGAGAAGCGA GATCAGCTCG CCTACGATGC    48300

CAGCGTGGAC CACCTTGCGG CGCTCGCGCC GTACCTTGTC GCGGCCGGCC GGCCGAACCA    48360

CACCCTTGGC GTGGGCCAGC AGGACGTGGC CGCTGCGGTG GATGACTCGA CCCTTGAAGT    48420

CTCCCTCCAA GGCTTGCACC GAGTACCACG GCTTGCCCTC GCGGTGCGTG CGGTGCAGGT    48480

TCTTGTAGAC GAAGACTCGG ATCGGCTTGG GAGTCATGAG ACCTCCAGTG TGCGAACGGC    48540

CTTGTAGGCA CTGATGAGTG ACGCCCCGA CAGCTCGTTA CCGTGCAGGT GATACCTGTA    48600

TTTCAGATAC ACGGCTTGGT CGACCGGCTT GTACTCGACC GAAGTGACCT CGACAACCAT    48660

CCCGTCGATG ATCGCGAAGT CTCCAGCGCG GAGATGGGTG GGGAATTTGA TCTCGGTGTT    48720

GACTACGGTC ACAGCTTCGA AACCTCCCAG GTACCAACGA ACTTGCCGTT GCGCTTGATG    48780
```

-continued

```
TATCCGCTCT CACCGGGCTC GTACCAATCG ACCTCGAACC CGTAGCGGGC GGCGCAAGCC    48840

TCGAGGTGGT CGAGCAGGAC GCGGCGACCG GACGCGGTAG CTTCTCCGGT CAGCCCGCTG    48900

TCGTTCTTGC GGACGATGAG CTTGAACACT TGGTGCCTAC CCTTCTGCGA TGTCTCGGGA    48960

GATCTCGGCG AAGACTTTCT TTGCCCACGC CACGCCGTCC CAGGTGATGT CGAACAGTGC    49020

CTCGTAGAAC TGGTCTCGCA AGGCTTCGTT GCCGTCGGCC AGCGTTGTGA CGAGCCGGTC    49080

GATGCGGTCC TCGTGGAACT TGTAGACCGA GTGGTTGTAC GGCTCAGCCA TATTGGCGTT    49140

GGCTCGTTTC ACGTTCTCAA CCACGATGGC TTCGAATAGG TGGTTAACCA GCTCCTCGGT    49200

CATGTTCTAT CTCTCCTCAG TAGTCGCTGT GCTGGGTCTC GAAGCCTTCG AGGTCACCGA    49260

CCTCGTCGTC GTACGCGCTC GGGTTGCCGC GCCAGTCGTC GCGGAGCCTT TGACCGCTGG    49320

CGTTGTAGCA GGCACCACAG TTCGGGCAGT CCACATCGCT CTGGCCGTAG TAGCGGCAAA    49380

CCTCGCCGCC GCAGCGTTGG CAGTCCCACG CGCTGTAACC AGGGATCAGG AAACCTTGGT    49440

CGTCGGTCTG ATCAGGGATG CGTCGGAAGT TCTTGGCAGG CATAGCTACT CCTCATAGAA    49500

ACTCGTGGTT GATGGCTCGG TGGGCAGCCT CGCGGAAGGT CAGCCCGTCG TCGTACGCGT    49560

CCCGGTACGT CCAGTCCGCG ATGTCTTGGT AACCAAGACC AAAGGTCTCG GTCATGTAGC    49620

CGTCCAGCGC GGCCATCCAG GTCTCGAAGC TCATGTCTTC CCTCACTTCT TTGTGGTCGA    49680

GAACAGCACG TTCCTGCGGC CGTTGACGCA CAGACCGCAA CGGGCACAAG CCGATCCCTT    49740

GTCGTTGATC AGGTCGATGG CTTTGTTGTT CTCCGGGCAG CGCACCGCCG TCGGAAACTC    49800

GGCCTTGCCT TTGGCGAACG TGGTGTCGAC GTAGGCGATG TTGATGCCCT TGTCTTCCAA    49860

GAAGCGCGCC ACGTCGATGT TGTCCGGGTC TGCGCTGAAG TACAGCGCCA GGTTGTCGAG    49920

CCTCTGCGAG TGCAGGTAGA CAGCCGCCGT CTGAACCCTT GTGTAGGCCC AGAACTGGAC    49980

ATCCGGGTTG TCGCGGATGA CTCGACCCCA AGCGGCCACA TAGGTGGGGC TGAAGAAGTC    50040

TCCATCCCAG TGGATGCGGA ACAGCTTCGG AGCCTTGCGA CGGTCGCAAT CCTTGACGAA    50100

CTCGGCGACC ATCTCGGACA GCAGCGTCAC GGTGTCTGTC AAGTCAGCGT CACGCAACAG    50160

TTCCCAGTTG TGCAGCAGGA CCGAGCTGAC AGCCTTGCGA ACTTTCTCCA GCTTGCCGGC    50220

GTAGCACACC TTGGCACAGA AGGCCGTCGC GTCCGGGCAG GAGAAGCCTT GACCGGAGGG    50280

CAGGCCGATG CTGTTGGCGA TACCTACGGT GGCGTTGCCG CCCTTGGTGA CGTGGACGTA    50340

GTTGGTGACC TTGCGGTCGT TCGAACGCTT CAGCTTGGCC ATACCTAGCC TTCCTTCGGT    50400

GGCTGTCAAG TTGTTGGATA CAAAGCGCCC CGAGAGGGAG TCGAACCCTC ACACCGCGAA    50460

CCGTCGCGGG GCCACCGTGC CTAGTCGATA GAGGTCACTC GACTCTCGTG GACGTAGACC    50520

ACGGTGTTGC CTACGTTCAC CGCGTAGTAC AGGCCATCGG CACCTCGTAG CTTGTGCCGA    50580

ACCGTGCCCG ACGTGGCCGT CATGTCTTCG CCCCAGTCGG CGTTAGGTGC CCAGGTGACT    50640

CGCATGGTGA TCCCTTCAGT AGTCGGTGGC TGTCAAGTCA GCGGATACGG ACGTACCCGT    50700

TGCCTCGAGC GACGTAGATC TTGCCGTCGA TGTAAACGCG CTGCTGCTGG TTCATAATCC    50760

TATTCCTTTC GGTGGCTGTC AAGTCTCAGG CCCAGCGACG AGTCGTCGGC CGGGGCGGC    50820

GCACCTTGGG CGCGTTGGCT CGCGGTGCCT TACGGATGGC GGTGCCTACC GTGATCTCTT    50880

CCAACTGGCG TTCAGCCAGG CCGACAGGCC GGGCGTCACC GGGCAGTTCG ATCTTGTAAT    50940

CGAAGTCAGT CCACCCCTTC AGACCCTTCT CCAGCTCGCG ATCCAACAGA CGCGGAGCCG    51000

ACAGCTCAGG CGCAACAAAC GGTGTCTTGA CGCTCTCGCG GGCAGTAACC CGAACCTCAC    51060

GGTGCTCAGC GAAGACTGGC ATAGTTCACC CCTTTGGTGG ATGTCAAGCC TGAGCACCAA    51120

AGCTCAGGCG TAGTGGGTAG TCGGGAATCG AACCCGATAG CTTCATAGCC ACGTTCTACG    51180
```

-continued

```
GCTCAGCCAT AGCTCAGCGA TCATTCCATC GCGCCAAGAG CTACCCTCCC GAATGCCGAA      51240

CCAAAGCTCA GCATTCGTAA GTGTGTATTC TCCCCGTGGC TCAGACAGTA TCTATCAGAA      51300

CCTAACCACA GGTCTACATT TAGTTATCCG CAGTGCTCGC ACTTTAACGG CATCGAGCTT      51360

CCGCCGACCC TCAGTCCTCT GGCAGCGAAC TAAAGGTTTG AGTCGGGCTG CGGCCCTTCT      51420

CGGTCTTGCG TGATTCTCAC TCTACCGGAT GTTTCGGTGG CTGTCAAGCG GGCCGTTTTG      51480

GTGTTGCAAC GATGCCCTCG TTTAGCGCCG CTGGCGTAAT GCGCTACCCG CCTGATCTCA      51540

CCGGTCCAAG TTGGTGATGC TTGCAGCTTA CCCGATAACC GGGTGGCTGT CAAACCGGAG      51600

AATCTTGCCG CCGGATTTTC ACCGGCACCG GCACGATCCT CTCGGATCCG CCTACCGCCT      51660

TGCTGCTGCG GTGACACAAG AATGCACTAC TGGCCGGGTG GCTGTCAAGC CCTAATCGCA      51720

AATTGGTGCC CTAGCTGCAG ATATGGCGCG TTCTCGGTGG CTGTAAAGGG CACTACGTGC      51780

CGCTATCCGC TGGTCACGCT GGACAGTCCC GGCAGCCCGT GCCGCGCATA GGCTGCTCAC      51840

TACGTGCCCG GTATCGGCGT TGTCGTGCCG CTGTCGTGGT CGTCGCCCCG TCGCTGTCGC      51900

TGGTCTCGGT GGCATCGCTT GACAGTCGCC CCGCTATCCC CCGTTGCCGC TGGTCAGACG      51960

CTAATCCGCT TATTTCGCAT AGGCTGCTCA CTATCGCATC GGTATGCGTA TGCGCTGGTC      52020

ACATATGCGT GTGGTGGTGG TGTGGTGTGC GTGTGTTTGC GCTGGTCAGC CGTGTGCGTA      52080

CCGTATCCGC ACACTGTGCT TGTGCGTTTG CTGTGTGTCG AGGCCGGCTC TCGCATCGTC      52140

GCATGTCAGC GCGGGTATGG GCGTGTATCG CACGCTTTGC TAGCCGCGTG CCGCGGCGCT      52200

CTCGCATCGC ATCGAGTGTT TGCTGTGTCT CTCATCGTCG CAGGTCAGAA GGGGTAGGGG      52260

GGTTCCCCCT AGGGGTCGGT CCTTGACCGG TCGGTTA                              52297
```

It is known that during the establishment of lysogeny, the L5 genome becomes integrated into the mycobacterial chromosome via the phage attachment site (attP). Integration-proficient plasmid vectors have been constructed which efficiently transform both fast-growing and slow-growing mycobacteria through stable integration of the plasmid sequences into the bacterial chromosomal attachment site (attB).

Because the L5 sequence is now known, and because L5 has been previously characterized, the use of transcriptional promoters with this mycobacteriophage may be evaluated efficiently, and host synthesis inhibition may also be evaluated efficiently.

FIG. 1 represents the genome organization of the entire L5 genome. DNA analysis has indicated that the L5 genome is organized into a right and left arm with the attachment site at the center of the genome. The integration functions have been successfully employed to construct integration-proficient vectors for mycobacteria.

Part of the L5 genome is not essential for mycobacteriophage growth. By way of example, gene 71-70-69 may be deleted without affecting the lytic cycle of the L5 phage. Therefore, it may be a suitable region in the L5 mycobacteriophage for the insertion of reporter genes. As a general role, it is critical that reporter genes be inserted into non-essential regions of the mycobacteriophage. Otherwise, the mycobacteriophage will be unable to survive and replicate.

For example, the L5 mycobacteriophage may have introduced therein promoter gene 71 fused to reporter gene lacZ, and this reporter mycobacteriophage would be capable of rapid diagnosis of mycobacterial infection and accurate assessment of mycobacterial strain drug susceptibilities.

Another mycobacteriophage which may be successfully used to produce the reporter mycobacteriophages is the mycobacteriophage TM4. TM4 has been used to construct a first generation reporter mycobacteriophage, and has the ability to discriminate between M. tuberculosis and BCG. A shuttle plasmid may be employed with TM4, and may be useful in the construction of recombinant and other mycobacteriophages. Unlike L5, which is a broad host-range mycobacteriophage, TM4 is a species-specific mycobacteriophage. However, TM4 is not as well characterized as the L5 mycobacteriophage, and therefore it is more difficult to analyze its functions.

DS6A is a mycobacteriophage that has been found to be specific for the M. tuberculosis complex of mycobacteria. It has been shown to infect both M. tuberculosis and BCG. It has been demonstrated that DS6A can infect over 3,000 different types of M. tuberculosis strains. Current efforts are under way to develop DS6A shuttle phasmids containing Firefly luciferase genes as the reporter molecule.

Figure 31:
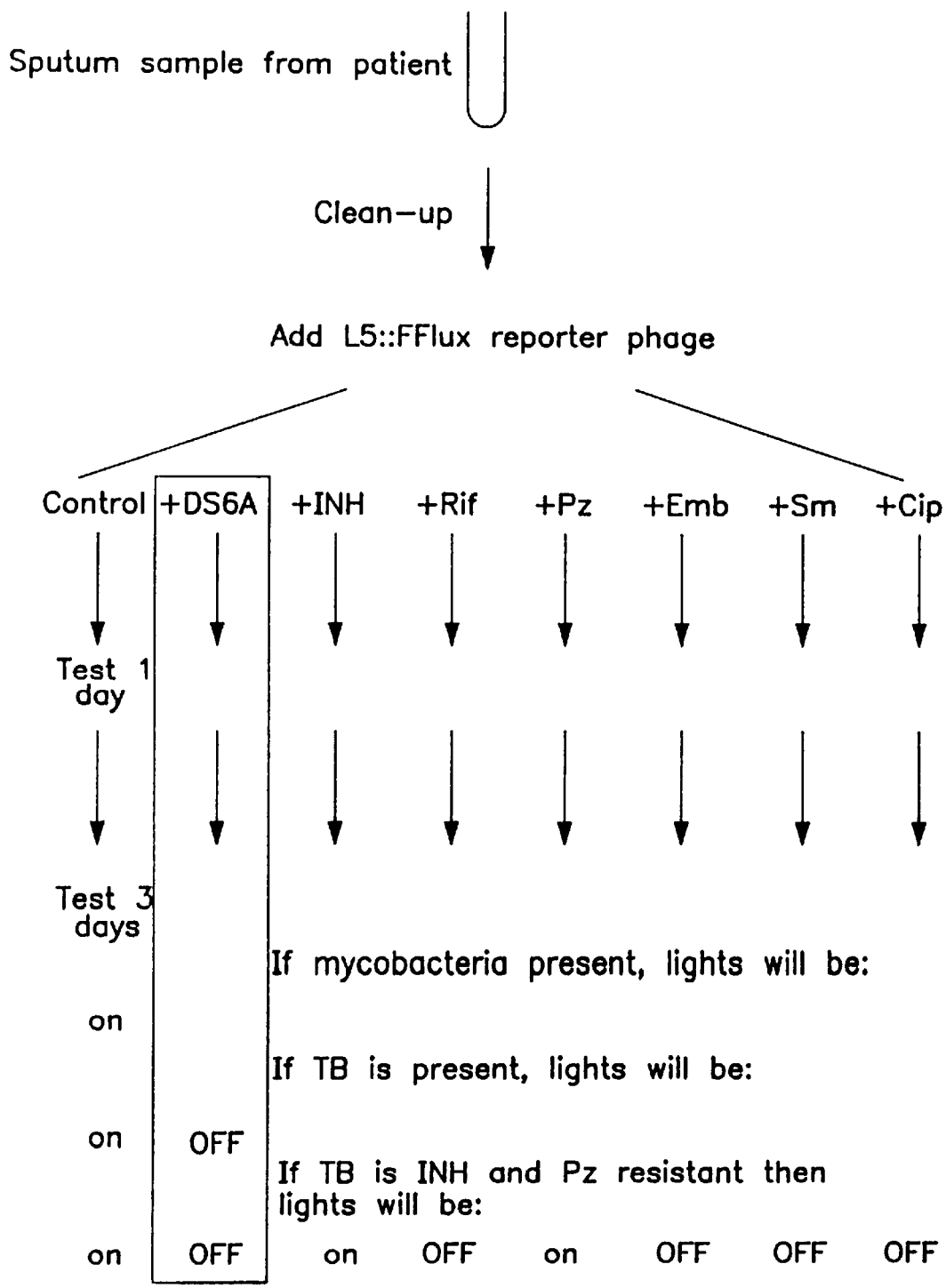
FIG. 31 represents an outline of a method which can be used to diagnose tuberculosis and determine drug susceptibility using reporter mycobacteriophage DS6A.

Different mycobacteriophages have varying host specificities. For example, DS6A mycobacteriophage is specific for only M. tuberculosis strains. In contrast, L5 and TM4 mycobacteriophages are specific for several mycobacteria, including M. tuberculosis and M. smegmatis. In order to diagnose tuberculosis according to the invention, it is necessary to use mycobacteriophages which are specific for M. tuberculosis strains only. Because DS6A mycobacteriophage is specific for M. tuberculosis strains only, it can be used to narrow the host specificity of L5 and TM4 mycobacteriophages so that L5 and TM4 mycobacteriophages can be used to accurately diagnose tuberculosis. For example, a clinical sample (control) can be infected with L5 reporter mycobacteriophages. Another clinical sample from the same source (experimental) can be co-infected with both L5 reporter mycobacteriophages and DS6A reporter mycobacteriophages. If the photon signal generated by the experimental sample is lower than the signal generated by the control sample, a diagnosis of tuberculosis is confirmed. If, however, there is no decrease in photon signal, then the diagnosis for tuberculosis is negative. Hence, DS6A mycobacteriophages can be used to confer specificity for M. tuberculosis onto L5 mycobacteriophages. FIG. 31 represents an outline of a method which can be used to diagnose tuberculosis and determine drug susceptibility using reporter mycobacteriophage DS6A.

In anticipation of the need for a diverse set of mycobacteriophages that can effect a broad or limited range of mycobacterial cells, a total of more than 50 unique mycobacteriophages have been collected and isolated by the inventors. 21 new mycobacteriophages have been isolated from soil samples from India, France, England, Israel, Tunisia, Carville, LA and New York. In addition, another 30 mycobacteriophages from both the Centers for Disease Control in Atlanta and the World Health Organization Phage Reference Laboratory in Amsterdam were collected. The characterization of the nucleic acid content of the phage particles of 30 of these mycobacteriophages have revealed that all of the mycobacteriophages contain double stranded DNA whose genome sizes range from 45 to 100 kb as sized on pulsed field gels. Restriction analysis has shown that all of these mycobacteriophages are different, except that one of the mycobacteriophages from France had a considerable similarity to the L5 mycobacteriophage, which was originally isolated in Japan. The host range of the mycobacteriophages varies greatly, some being able to infect only M. smegmatis and others being able to infect M. smegmatis, BCG and M. tuberculosis, but not M. avium. These mycobacteriophages may be developed into reporter mycobacteriophages and cosmid cloning systems, and may provide a source of useful transcriptional translation initiating sequences, transcriptional terminators, or host-range specificity genes.

In addition, the choice of reporter gene and its method of expression are critical. It is necessary to choose a reporter gene whose product would not normally be found in clinical samples, but whose product is also easily detectable.

Luciferase reporter genes have been used in many diversified biological systems, including E. coli, cyanobacteria, phytopathogenic bacteria and Bacillus. The presence of luciferase reporter genes can be detected by the emission of photons in the presence of a substrate, such as luciferin or decanal. Luciferin and decanal can permeate mycobacteria, and thereby allow for the detection of gene products, such as photons. Since one molecule of the luciferase gene product can yield 0.85 photons of light, it is the most sensitive biological reporter molecule known. The preferred reporter genes of this invention are luciferase reporter genes, such as the Firefly lux gene (FFlux), the *Vibrio fischeri* lux genes and the *Xenorhabdus luminescens* lux genes, as well as the *E. coli* β-galactosidase (lacZ) genes. Luciferase genes, especially the Firefly lux gene, generate a high amount of luminescence activity. They generate photons, the detection of which is simple and sensitive, using commercially available luminometers that can detect 100–1000 molecules of luciferase with a linear relationship to enzyme concentration. In addition, it is unlikely that clinical samples will contain significant levels of endogenous luciferase activity.

In choosing transcriptional promoters to be introduced into the mycobacteriophages, it is desirable to use strong promoters since this will increase the sensitivity of the system. In addition, it is important that the promoter be active following mycobacteriophage infection. Promoter candidates currently available are the BCG hsp60 promoter and the L5 gene 71 promoter, which are of comparable strength. The hsp60 promoter gives good levels of luciferase expression from plasmid recombinants, but lower levels of luciferase expression where the mycobacteriophage is TM4. It is possible that the reason for this is that the hsp60 promoter is shut off by the TM4 enzymes following infection, thus producing only a modest level of luciferase. The gene 71 promoter may behave in a similar manner with the TM4 phage since the gene 71 product is a good candidate for the L5 repressor and is expressed at high levels in the absence of other mycobacteriophage functions. Knowing the sequence of the mycobacteriophage used will help in identifying, characterizing and cloning the appropriate promoter to be used in the reporter mycobacteriophages of this invention.

There are several methods which can be utilized to introduce the reporter genes and transcriptional promoters into mycobacterial species-specific mycobacteriophages. One method is the utilization of shuttle phasmids. When utilizing shuttle phasmid technology, it is necessary to know the sequence of the mycobacteriophage so that the reporter genes are inserted into non-essential regions of the mycobacteriophage. Insertion of reporter genes into non-essential regions permits the mycobacteriophage to survive and replicate. In order to use the shuttle phasmid methodology, it is necessary to first generate a cosmid library of large double-stranded recombinant DNA fragments of mycobacteriophage. This can be done using cosmid cloning in E. coli. Next, the cosmid library is introduced into the mycobacteria of interest to select for cosmids which have been inserted into non-essential regions of the mycobacteriophage. The shuttle phasmids, which consist of the E. coli cosmid, the reporter genes and mycobacteriophage promoters, may then be characterized. Shuttle phasmids can be propagated in E. coli as plasmids, and propagated in mycobacteria as mycobacteriophages.

A second method of introducing the reporter genes and transcriptional promoters into mycobacteriophages is by homologous recombination. First, non-essential regions of a mycobacteriophage must be determined. Again, in order to do this, it is necessary to know the sequence of the mycobacteriophage. Consequently, L5 is an ideal phage to use with this method as its genome has already been sequenced and characterized by the inventors. Next, plasmids are constructed wherein reporter genes hooked to transcriptional promoters are flanked by mycobacteriophage non-essential region sequences in mycobacterial plasmids. Then, homologous recombination systems may be utilized in M. smegmatis or E. coli to perform gene replacement whereby the plasmid constructs containing the reporter genes are put into mycobacteriophages.

A third method of introducing reporter genes and transcriptional promoters into mycobacteriophages is by use of transposons. For example, transposon IS1096 may be utilized. In order to use this methodology, reporter genes and transcriptional promoters are put into transposons, and the transposons containing the reporter genes and transcriptional promoters are delivered on plasmids in mycobacteria. Next, it is necessary to grow up the mycobacteriophages on a strain such as *M. smegmatis,* which strain contains the transposons. At certain frequencies, the transposons will hop into non-essential regions of the mycobacteriophages, thereby introducing themselves therein. The mycobacteriophages are still viable, and contain the reporter genes and transcriptional promoters.

A fourth method of introducing reporter genes and transcriptional promoters into mycobacteriophages is by debilitated phages packaged into phage heads and tails (phage particles). To utilize this methodology, it is necessary to develop helper phage systems which allow for pieces of DNA containing pac sites to be packaged. These helper phages allow for the synthesis of head and tail genes at will in mycobacteria, prevent themselves from being packaged into phage heads and tails, and facilitate packaging of pacmids into phage heads and tails. Helper phage systems may be generated from the L5 mycobacteriophage. The genome of the helper phage is put into the mycobacterial chromosome, at which time the mycobacteria are grown up. Next, pacmids which comprise phages which have pac sites, reporter genes, transcriptional promoters and mycobacterial replicons are transformed onto the mycobacterial strain. The production of head and tail proteins may be induced, for example, through an increase in temperature, and the pacmids are then packaged into phage heads and tails. The L5 genome has cohesive (cos) termini. This suggests the possibility of constructing L5 cosmid vectors, which could be packaged through the cos sites into L5 particles either in vivo or in vitro. Then, a large number of genes could be easily and efficiently delivered to mycobacteria.

Packaging into phage heads and tails may also be utilized in a fifth methodology wherein the pacmid is a plasmid. The methodology is similar to the methodology wherein a debilitated phage is used, however, instead of using phage pacmids, the pacmids comprise plasmids which have pac sites, reporter genes, transcriptional promoters, and plasmid replicons.

Finally, direct cloning using recombinant DNA techniques in vitro may be used to introduce reporter genes and transcriptional promoters into mycobacteriophages. This methodology consists of ligating a mycobacteriophage, identifying or introducing unique restriction enzyme sites in non-essential regions of the mycobacteriophage, cleaving the mycobacteriophage with the restriction enzyme sites, and cleaving DNA which encodes the promoter and the reporter gene so that it has the unique sites flanking it on either side. Next, ligation is set up in vitro between the cleaved mycobacteriophage with the unique restriction enzyme sites and the reporter gene cassette. The result is a circular DNA molecule which consists of the mycobacteriophage, the reporter genes and the transcriptional promoters. The circular DNA may then be electroporated directly into mycobacteria.

EXAMPLES

Expression of Reporter Gene lacZ and FFlux in Mycobacteria

A promoter probe vector was constructed which incorporated a truncated *E. coli* β-galactosidase (lacZ) gene as a reporter probe into a shuttle plasmid vector that replicated in either mycobacteria or *E. coli*. Random DNA fragments from the three mycobacteriophages L1, TM4 and Bxb1 were cloned into a unique BamH1 site immediately upstream of the lacZ gene and screened for their ability to produce β-galactosidase. This established that lacZ could be used as a reporter gene in the mycobacteria, and identified the DNA sequences which could effectively express foreign genes in both *M. smegmatis* and M. tuberculosis. β-galactosidase activity could be detected from lysed cells using OMpg, or from unlysed cells using either X-gal or a fluorescent methylumbelliferyl β-galactosidase derivative. The promoter hsp60 gene highly expressed the lacZ gene in both *M. smegmatis* and BCG.

Figure 2:
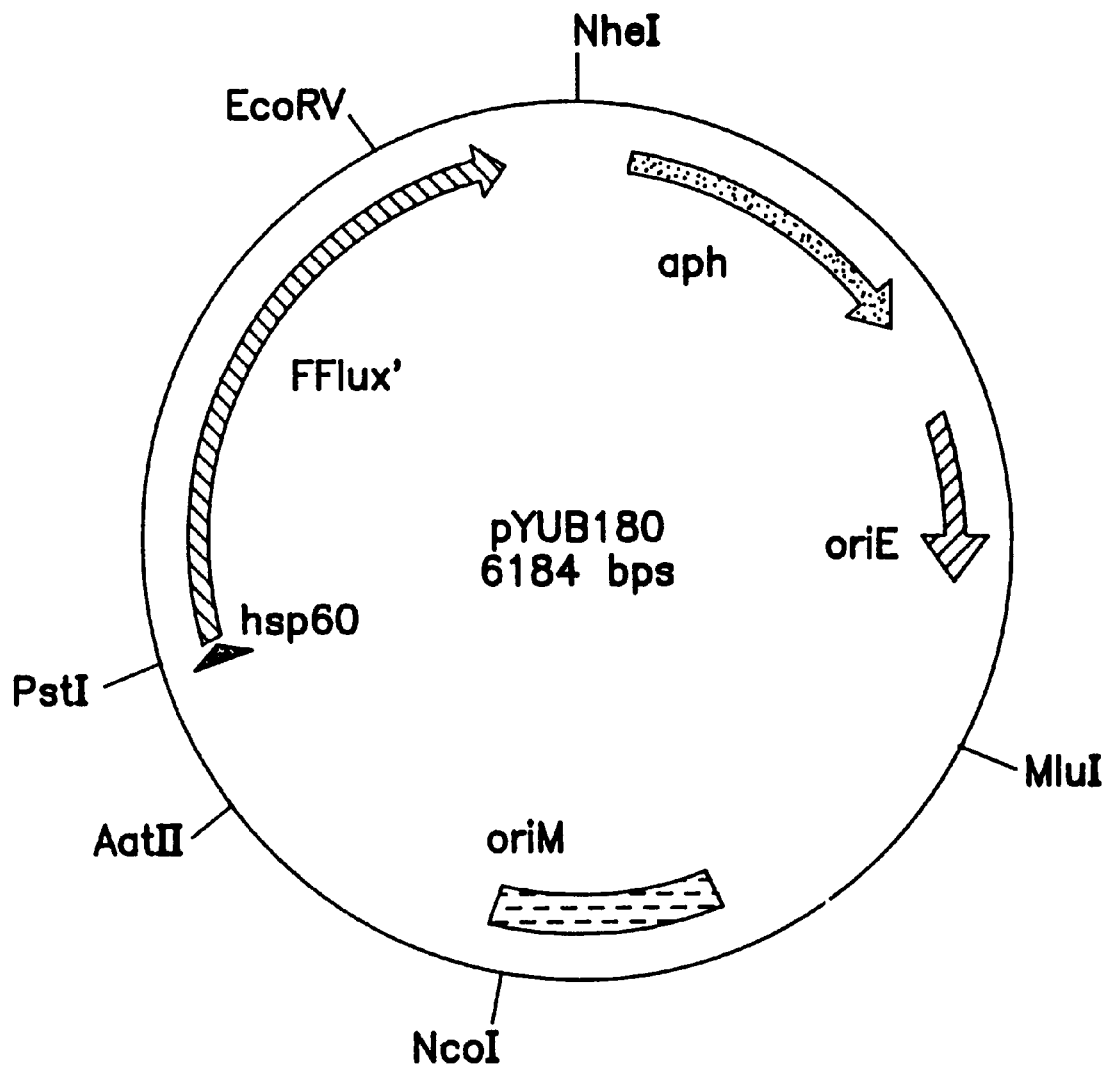
FIG. 2 represents a luciferase shuttle plasmid pYUB180 wherein reporter gene FFlux is fused to the BCG hsp60 promoter.

The FFlux gene was cloned into pMV261 downstream from the hsp60 promoter in plasmid pYUB180 (see FIG. 2), which plasmid was shown to express the FFlux gene in *M. smegmatis,* BCG and M. tuberculosis H37Ra. The expression of the FFlux gene was detected by observing luminescence of mycobacterial clones containing the cloned gene in the dark room, and verified use in photographic film. This demonstrated that the luciferase was expressed in the mycobacteria, and that luciferin, the substrate used, was able to penetrate mycobacterial cell walls and yield photons expressed by the mycobacteria.

Detection of Photons in Mycobacterial Cells Expressing FFlux

Figure 3:
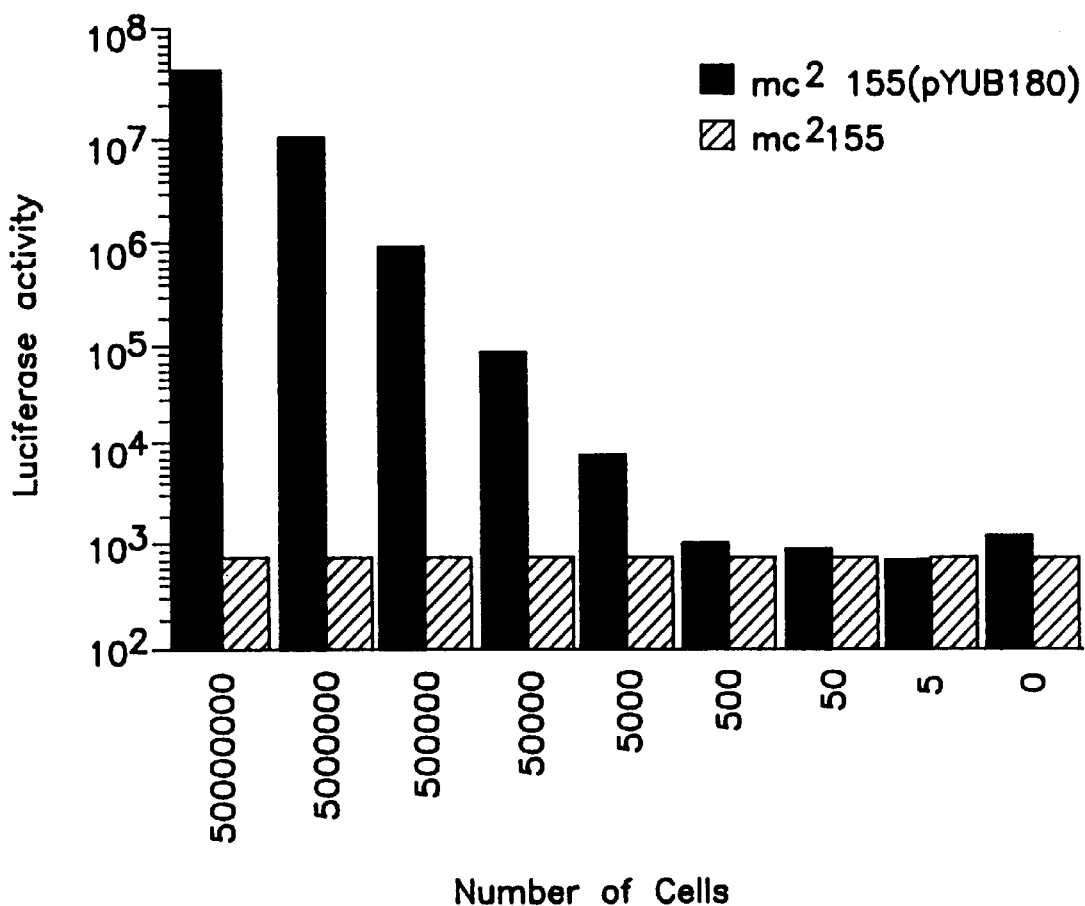
FIG. 3 represents the amount of luciferase activity of *M. smegmatis* which contains the pYUB180 shuttle plasmid and the FFlux gene.

The expression of FFlux from the plasmid pYUB180 in *M. smegmatis* provided a model with which to determine a minimal number of individual cells detectable with the luciferase assay. *M. smegmatis* containing pYUB180 were grown in the presence of kanamycin to ensure that every cell contained the plasmid. The cells were diluted 10-fold serially and the amount of luciferase activity was determined using a luminometer. FIG. 3 shows that the amount of luciferase activity from $5 \times 10^7$ cells approached $10^8$ luciferase units, though at this level of activity the luminometer was unable to yield an accurate measurement. However, the activity decreased in a linear manner down to 1200 units for 500 cells. Hence, 5000 cells expressing the FF lux gene can be clearly discerned above the background measurement, which approaches the number of cells that one would expect to observe in clinical samples.

Demonstration of Luciferin Uptake by Mycobacteria

Figure 12:
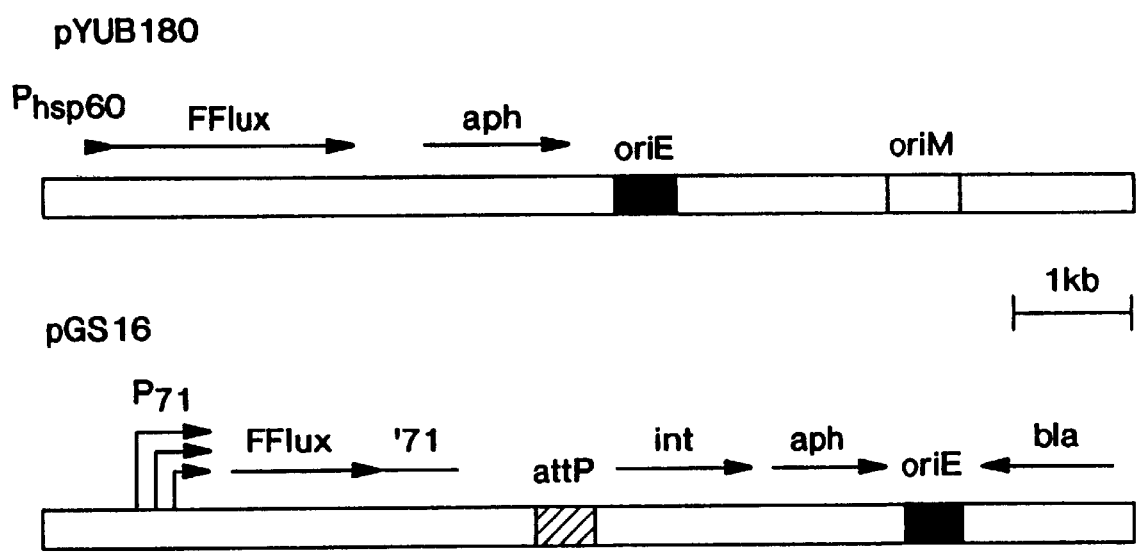
FIG. 12 represents a schematic diagram of the extrachromosomal plasmid pYUB180 and the integration plasmid pGS16.

In order to ascertain whether the substrate luciferin could be transported across the intact mycobacterial cell wall, the firefly luciferase (FFlux) gene was cloned downstream of the hsp60 promoter in a mycobacterial extrachromosomal plasmid, and was also cloned downstream of the gene 71 promoter of the mycobacteriophage L5 in a mycobacterial integrating vector. FIG. 12 shows a schematic diagram of the extrachromosomal plasmid pYUB180 and the integration plasmid pGS16.

Figure 13:
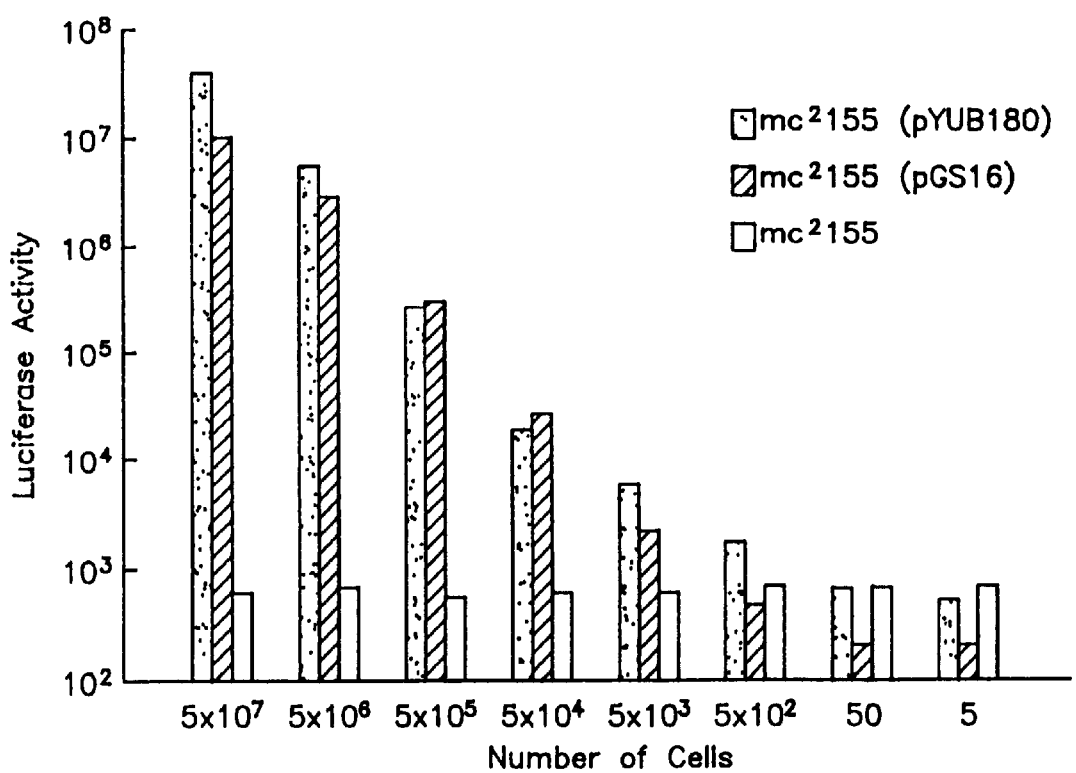
FIG. 13 represents the expression of luciferase by *M. smegmatis* after plasmids pYUB180 and pGS16 were electroporated therein.

Both of the luciferase constructs were electroporated into the *M. smegmatis* strain mc²155. Kan$^r$ transformants were grown to a density of approximately $5 \times 10^8$ cells/ml and 10-fold serial dilutions were prepared. 100 μl samples were mixed with 250 μl of 0.1 M Na citrate, pH5 in a 13×75 mM polystyrene tube. This mixture was placed in the monolight 2010 luminometer (Analytical Luminescence Laboratory, San Diego, Calif.) and 100 μl of 1 mM luciferin (Sigma, St. Louis, Mo.) was injected into the tube and the luciferase activity was measured as relative light units. As shown in FIG. 13, upon the addition of luciferin, luciferase activity was readily measured from intact mycobacterial cells infected with both the extrachromosomal and the integrating vectors. Serial dilutions indicated that it was possible to detect as few as 500 to 5,000 *M. smegmatis* cells expressing firefly luciferase, thereby establishing that the luciferase-luciferin system could be developed as a sensitive reporter system for ATP in mycobacteria.

Distinguishing Drug-Resistant Mycobacteria From Drug-Sensitive Mycobacteria Using Luciferase Activity Since Firefly luciferase activity requires ATP, and ATP is produced only by living cells which are metabolically active, luciferase is a powerful indicator of the metabolic abilities of a bacterial cell. Since anti-tuberculosis drugs are likely to significantly decrease the metabolic activity of a cell, the measurement of luciferase activity should provide a sensitive means of distinguishing drug-resistant mycobacteria from drug-sensitive mycobacteria.

First, the kinetics of the production of luciferase activity of *M. smegmatis* containing pYUB180 following the addition of streptomycin, isoniazid, ethambutol, rifampicin, ciprofloxacin, novobiocin or cyanide, added at levels that inhibit the growth of *M. smegmatis* in plate assays, was measured.

Figure 4C:
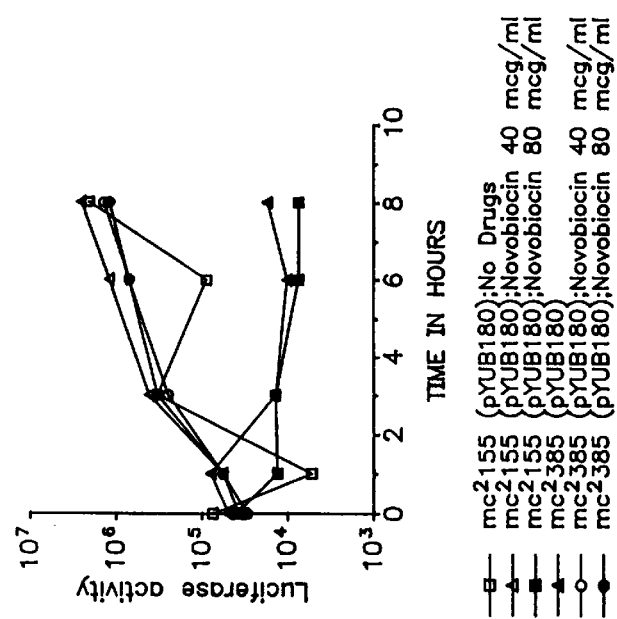
FIGS. 4A–4C represent the effect of various antibiotic drugs on the metabolic activity of control mycobacteria and drug resistant mycobacteria in the presence of reporter mycobacteriophages which contain luciferase reporter genes.
Figure 4B:
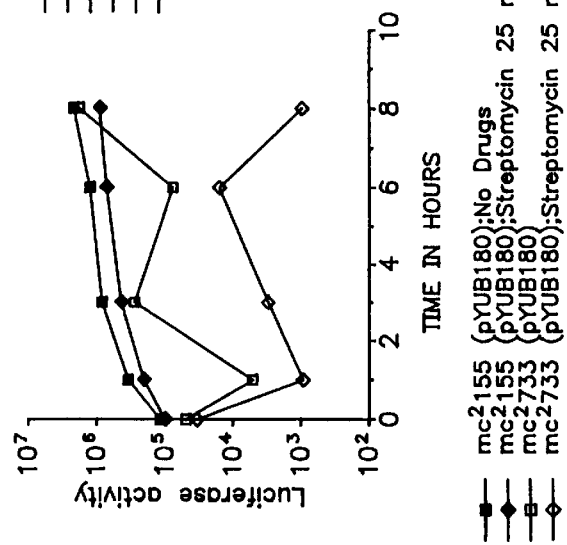
Figure 4A:
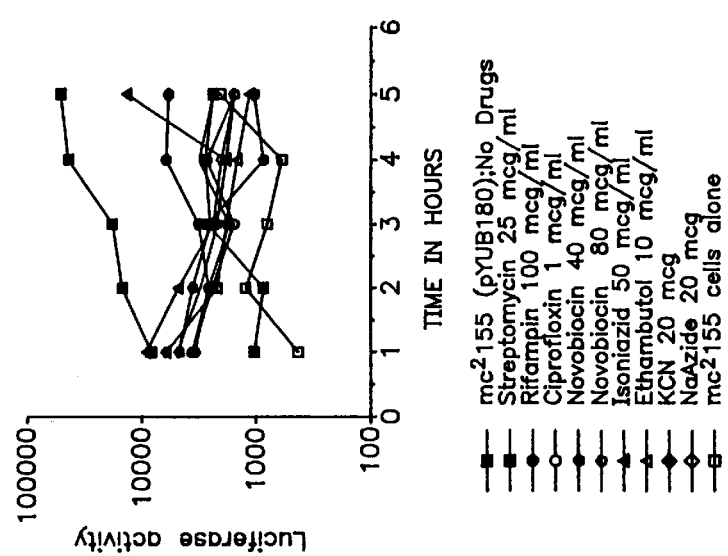

As shown in FIG. 4, Panel A, the levels of luciferase production were 100 to 1000 times less at eight hours after the addition of the drugs compared to the untreated control.

Next, this approach was used to distinguish drug-resistant from drug-sensitive mycobacteria. The pYUB180 deposit was transformed into streptomycin-resistant or novobiocin-resistant *M. smegmatis* mutants. Photon production by the drug-sensitive parent was compared to the streptomycin-resistant or novobiocin-resistant mutants. The drug-resistant mutants continued to produce luciferase activity levels comparable to the untreated patent in the presence of the appropriate antibiotic. In addition, the drug-resistant mutants produced 100 to 1000 times more luciferase activity than the drug-sensitive parent (see FIG. 4, Panels B and C). Hence, a luciferase-based assay may be used to determine mycobacterial drug susceptibility.

Figure 5A:
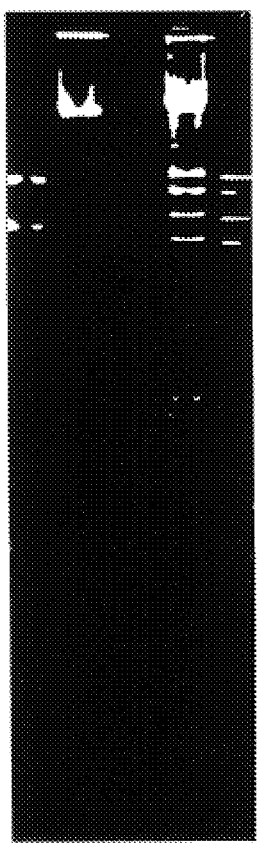
FIGS. 5A and 5B represents shuttle plasmid phAE39 wherein the reported gene is FFlux, the promoter is hsp60, the phage is TM4 and the cosmid is pYUB216.
Figure 5B:
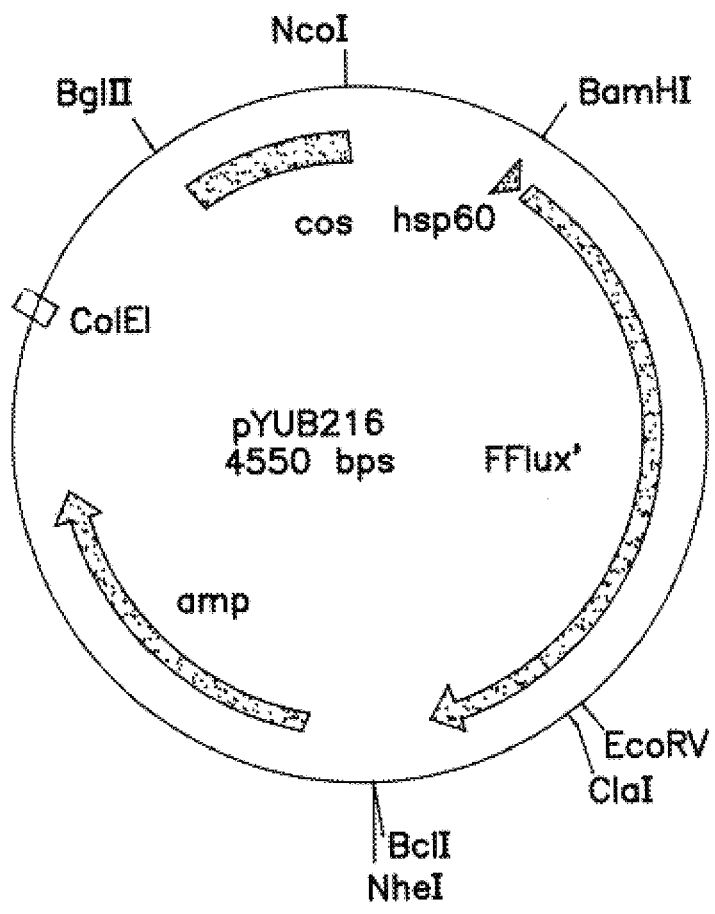

Construction of TM4 Reporter Mycobacteriophages (phAE39, phAE37 and phAE40) and Detection of Photons Following TM4::lux Infection The first vectors developed to introduce recombinant DNA into mycobacteria were shuttle phasmid phage vectors. Shuttle phasmids have the ability to replicate in *E. coli* as cosmids and then replicate in mycobacteria as phages. Shuttle phasmids of TM4 which contained the FFlux and lacZ genes transcribed from hsp60 and L1 promoters, respectively, were constructed (see FIG. 5).

Figure 6:
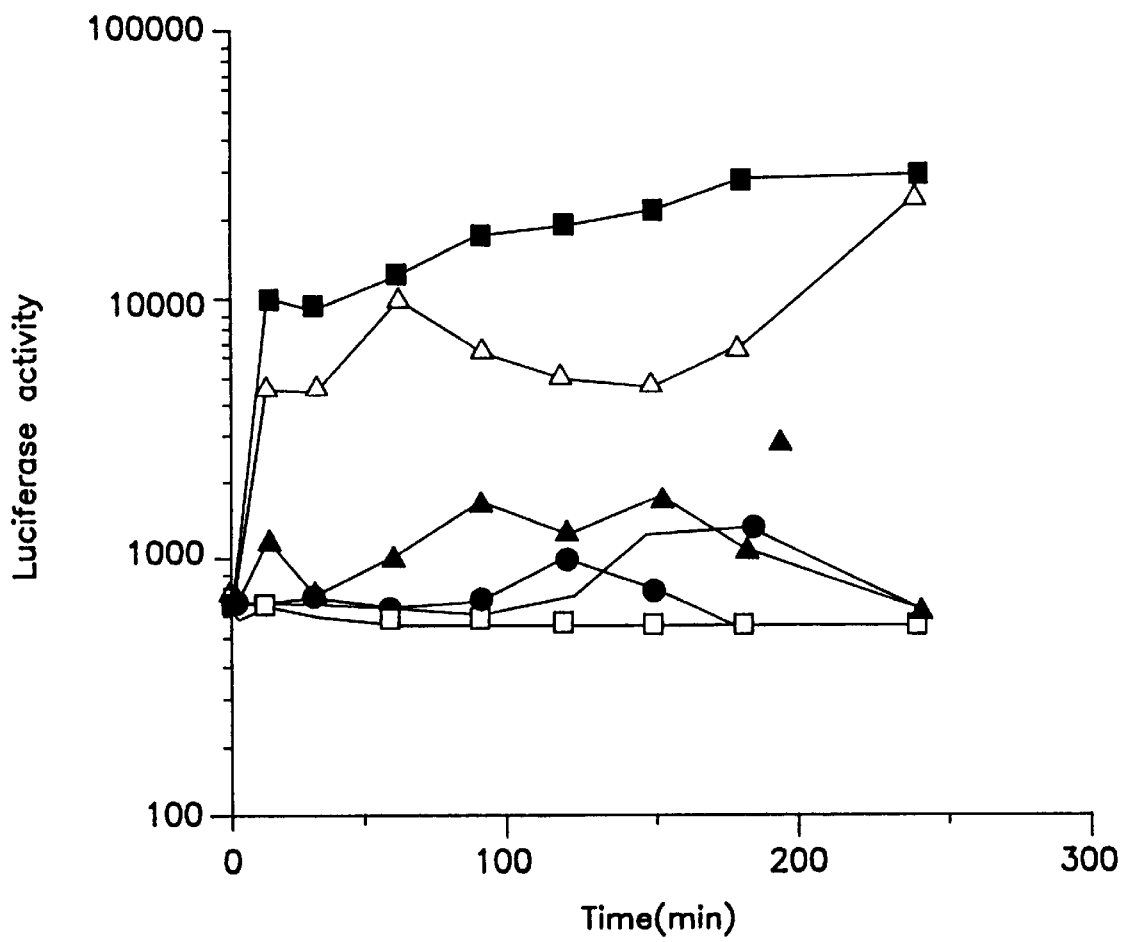
FIG. 6 represents luciferase activity of *M. smegmatis* cells infected with shuttle phasmids phAE39.
Figure 7:
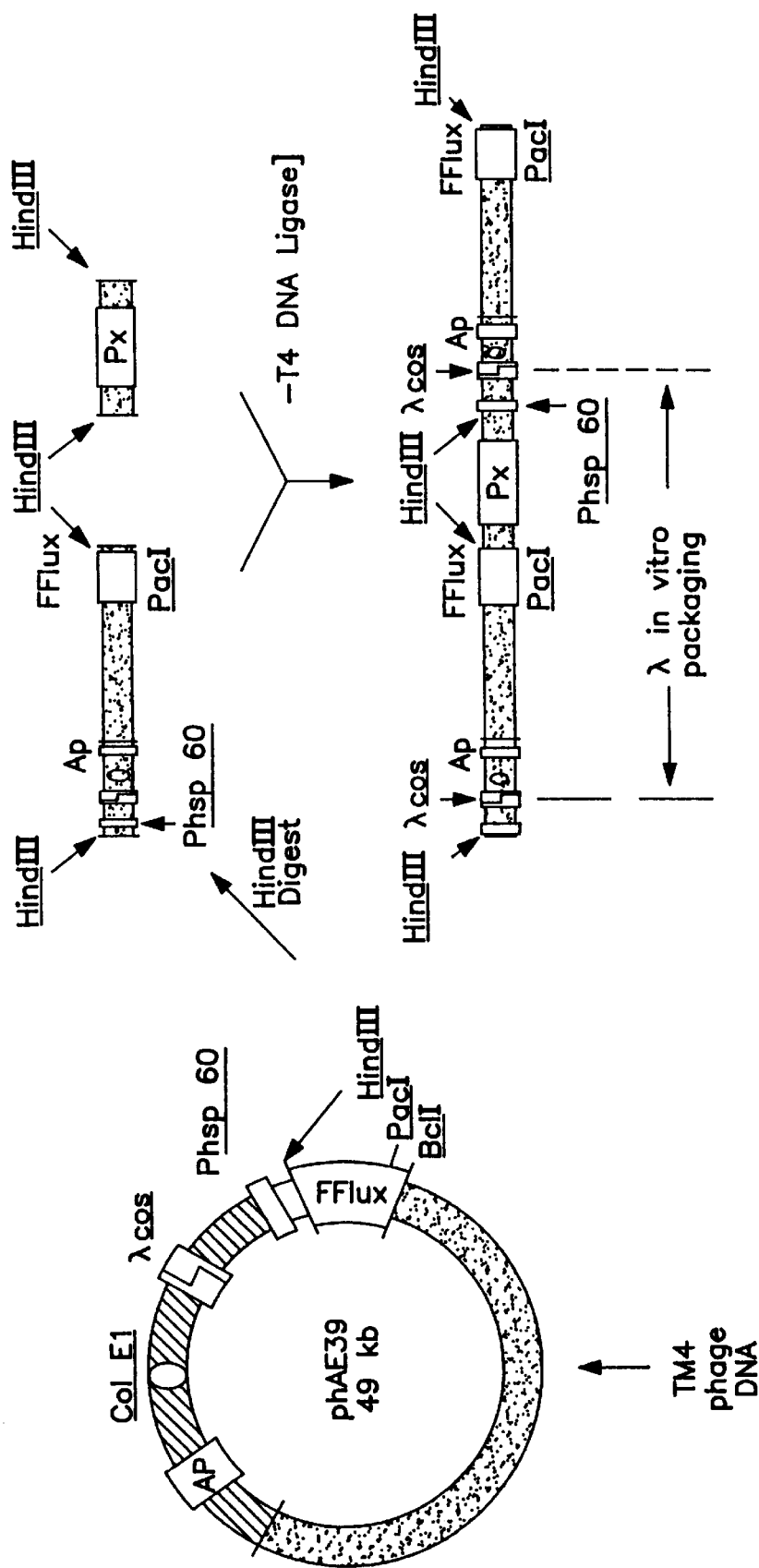
FIG. 7 represents a flow chart for cloning different promoters into TM4::lux shuttle phasmid phAE39.

A deposit of the shuttle phasmid (reporter mycobacteriophage) phAE39 which contains mycobacteriophage TM4, cosmid pYUB216, reporter gene FFlux and promoter hsp60, was made with the American Type Culture Collection on Jan. 15, 1992 and catalogued as ATCC No. 75183. When the TM4::lux shuttle phasmid phAE39 was mixed with *M. smegmatis* cells, luciferase activity could be detected within 15 minutes of incubation, and continued to increase slightly over the next 4 hours (see FIG. 6). These results show that the TM4::lux mycobacteriophage is capable of introducing the FFlux gene into mycobacterial cells, and that the FFlux gene can be expressed in mycobacteriophage-infected cells. FIG. 7 represents a flow chart for cloning different promoters into the TM4::lux shuttle phasmid phAE39.

A deposit of the shuttle phasmid (reporter mycobacteriophage) phAE37 which contains mycobacteriophage TM4, cosmid pYUB216, reporter gene lacZ and promoter L1, was made with the American Type Culture Collection on Feb. 10, 1992 and catalogued as ATCC No. 75204. The TM4::lacZ mycobacteriophage formed bright blue plaques when plated on media containing X-gal.

Figure 8:
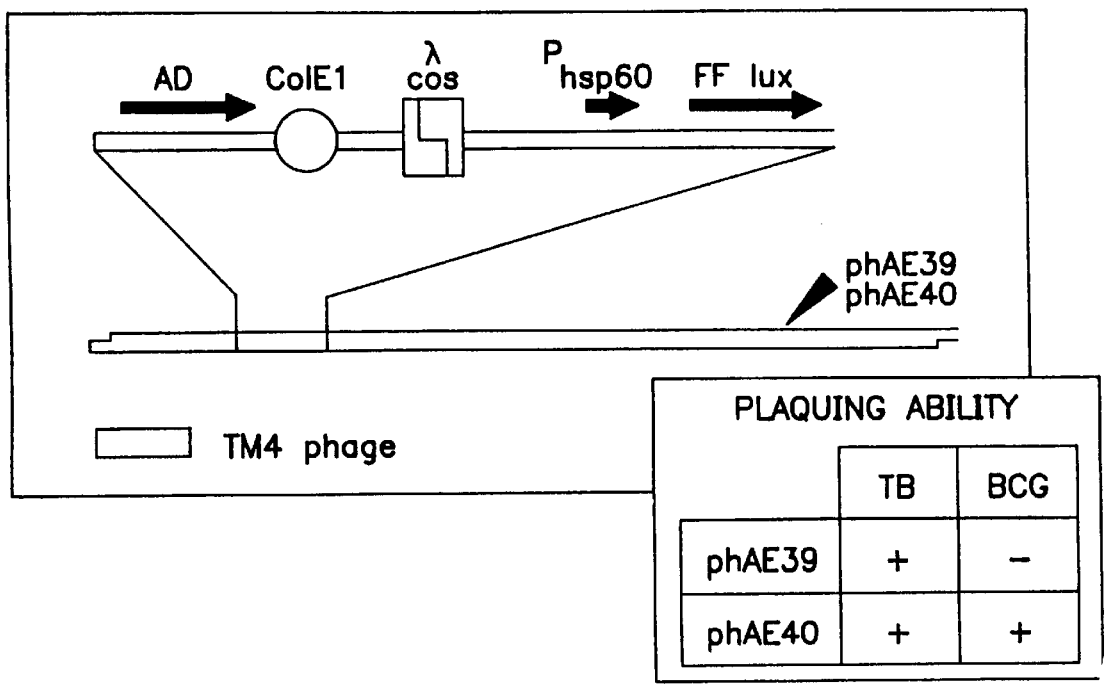
FIG. 8 represents a schematic diagram of the luciferase reporter mycobacteriophages phAE39 and phAE40.
Figure 9:
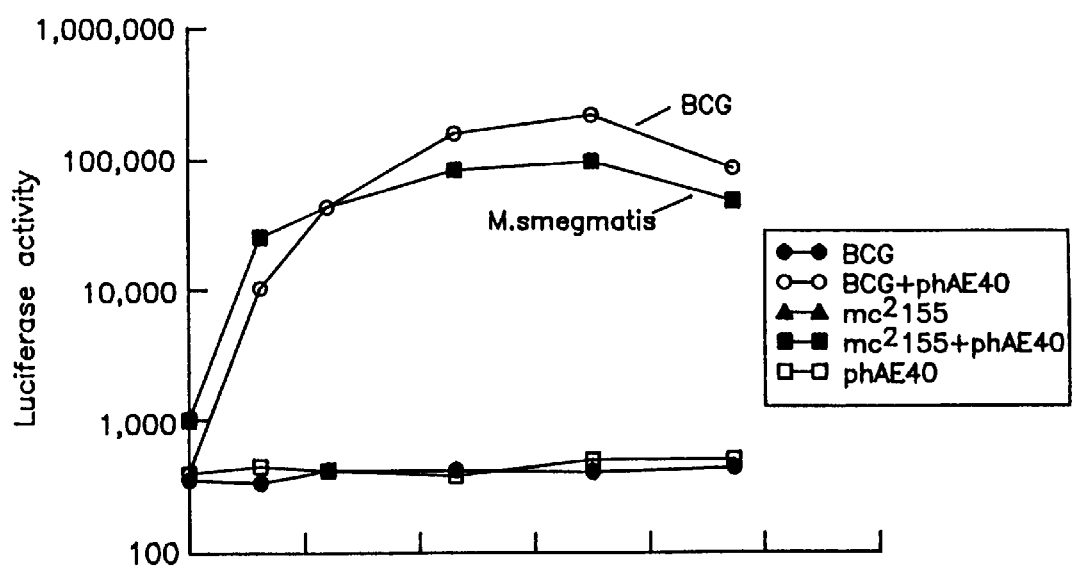
FIG. 9 represents the production of light (photons) by mycobacteria following infection with the luciferase reporter phage phAE40.

A mutant of the shuttle phasmid phAE39, designated phAE40, was isolated. As discussed hereinabove, in order to produce shuttle phasmid phAE39, *E. coli* cosmid pYUB216 was inserted into a non-essential region of the mycobacteriophage TM4. The pYUB216 cosmid contained FFlux in a transcriptional fusion with the hsp60 promoter of BCG, a ColE1 origin and an ampicillin-resistant gene (AP) for replication and selection in *E. coli*, and a bacteriophage lambda cos sequence as well as unique Bc/1 site. The phAE39 shuttle phasmid was constructed with Bc/1-digested pYUB216 being ligated to Sau3A-partially digested TM4 DNA. As shown in FIG. 8, the shuttle phasmid phAE39 readily forms plaques of M. tuberculosis, but does not efficiently plaque on BCG. A spontaneous host range mutant of phAE39 was isolated at a frequency of $10^{-6}$ to $10^{-7}$, and designated phAE40. Mutant shuttle phasmid phAE40 was found to be capable of infecting BCG vaccine strains, in addition to being capable of infecting *M. smegmatis* and M. tuberculosis strains.

In order to test whether the phAE39 and phAE40 reporter mycobacteriophages were capable of eliciting the production of light following infection of mycobacteria, the reporter mycobacteriophages were mixed with *M. smegmatis* cells and then exposed at different times to luciferin. In order to perform this, high titers of phAE40 were prepared as described above for TM4 phages. Both *M. smegmatis,* $mc^2155$ cells and BCG-Pasteur cells were grown in roller bottles to approximately $5 \times 10^7$ cells per ml in M-ADC-TW broth at 37° C. Either the *M. smegmatis* or the BCG cells were harvested by centrifugation and washed two times in M-ADC broth, containing no tween. The resulting pellet was resuspended in the original volume of M-ADC broth. The cells were then diluted into fresh M-ADC broth and allowed to incubate overnight standing at 37° C. Tween-80 appeared to remove the receptors, and it was determined that the optimal activities were achieved if the cells were given a chance to grow in the absence of tween. This may have allowed the regeneration of phage receptors. Next, 1 ml of washed cells (approximately $5 \times 10^7$ cells) was mixed with 0.1 ml phAE40 particles ($5 \times 10^8$ pfu/ml) that had been concentrated on CsCl gradients to achieve a multiplicity of infection of 10. The cells phage mixture was incubated at 37° C. Beginning at the time of the addition of the phAE40, 0.1 ml samples were removed. Luciferase activity was measured as described in FIG. 13. Light signals were detected within minutes following infection using a luminometer and increased 1,000 fold within 2 hours. The rapid kinetics of light production allowed for the testing of the simple hypothesis that one reason slow-growing mycobacteria, such as BCG and M. tuberculosis, have generation times 10-fold longer than other mycobacteria is the consequence of a generalized slow rate of transcription or translation. The observation that the kinetics of light production following infection of BCG with the reporter mycobacteriophages is almost identical to that of *M. smegmatis,* thereby suggesting that the slow growth of slow growing mycobacteria is unlikely to be attributable to slower rates of metabolic processes, but rather is the result of a highly regulated event, such as the initiation of chromosome replication or cell division.

Figure 10A:
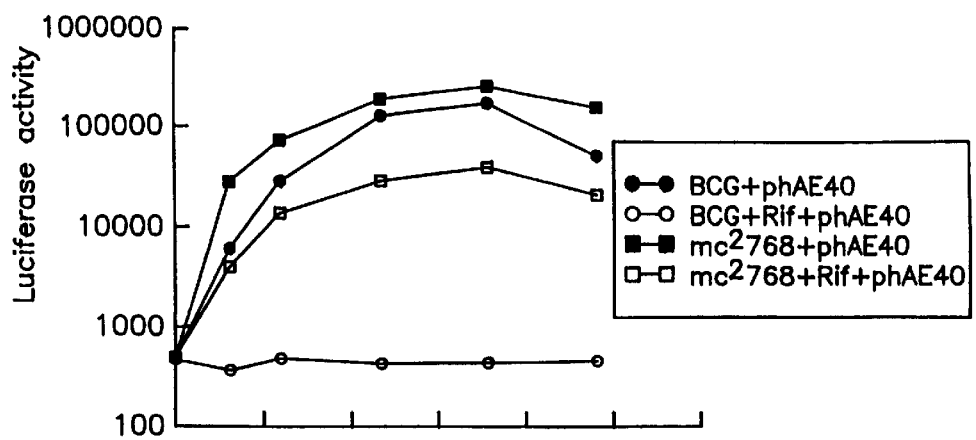
FIGS. 10A–10C represent a comparison of the kinetics of light production following phage infection of drug-sensitive BCG cells to drug-resistant BCG mutant cells.
Figure 10B:
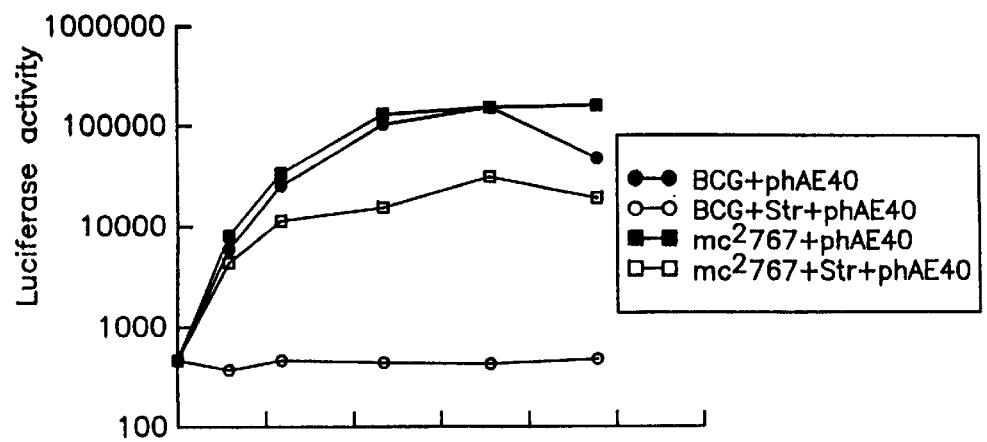
Figure 10C:
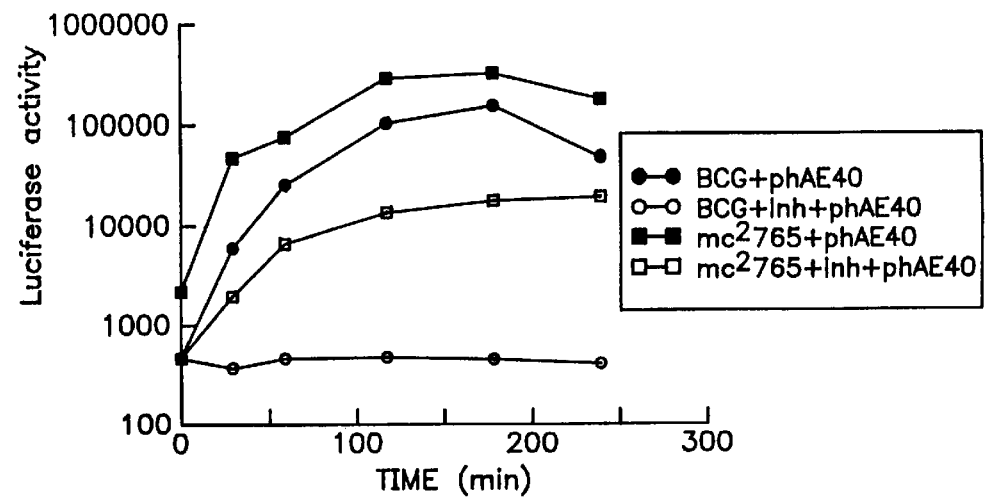

Since it was determined that the phAE39 and phAE40 reporter mycobacteriophages were able to elicit the production of light following infection of mycobacteria, they were used to distinguish between drug-resistant and drug-sensitive organisms. In order to perform this, mutants of BCG were selected that were resistant to streptomycin, isoniazid and rifampicin. Spontaneous mutants of BCG-Pasteur were isolated on Middlebrook 7H10 agar containing either 50 µg/ml rifampicin, 250 µg/ml streptomycin or 50 µg/ml isoniazid. The rifampicin-, streptomycin-, or isoniazid-resistant mutants were purified and designated $mc^2768$, $mc^2767$ and $mc^2765$, respectively. All three mutants and the BCG parent were grown to midlog phase, harvested and washed. As shown in the top panel of FIG. 10, the mc²768 cells and the BCG cells were incubated standing at 37° C. in the presence or absence of rifampicin (50 μg/ml) for 24 hours. A 0.5 ml sample (approximately 5×10⁷ viable cells) was mixed with 0.1 ml (5×10⁸ pfu) of phAE40 particles and luciferase activity was determined. The samples were removed and luciferase activity was measured. As shown in the middle panel of FIG. 10, the mc²767 cells and the BCG cells were incubated standing at 37° C. in the presence or absence of streptomycin (250 μg/ml) for 24 hours. A reporter assay was performed as described above. As shown in the bottom panel of FIG. 10, the mc²765 cells and the BCG cells were incubated standing at 37° C. in the presence or absence of isoniazid (50 μg/ml) for 24 hours. The reporter assay was performed as described above. As shown in FIG. 10, when wild-type BCG and the mutants were cultured for 24 hours with the antibiotics, the parental strain (wild-type BCG) failed to produce any signal, whereas light was produced by the drug-resistant mutants.

Next, the luciferase reporter phage assay was tested on clinically-derived M. tuberculosis strains, which were both singly and multiply drug-resistant. In order to perform this, the following M. tuberculosis strains were grown in a biological safety level 3 containment facility: (i) the virulent drug-sensitive M. tuberculosis Erdman strain; (ii) strain 92-2025, a singly isoniazid-resistant strain; and (iii) an MDR strain of tuberculosis that has been shown to be resistant to rifampicin, streptomycin, isoniazid, ethambutol and ethionamide and the cause of several nosocomial outbreaks in New York City. The Erdman strain was subcultured from the starter culture by inoculation of 0.4 ml into 20 ml of Middlebrook 7H9 broth containing OADC enrichment (Difco Laboratories, Detroit, Mich.) plus 0.5 Tween-80 (M-OADC-TW broth). The 92-2025 and the MDR strains, which grow more slowly than the Erdman strain, were subcultured by inoculation of 2 ml into 20 ml M-OADC-TW broth.

All three cultures were grown standing at 37° C. for 7 to 8 days. The cells were washed and resuspended in 0.5× the original volume. Washed cells (0.2 ml) were inoculated into 0.7 ml of M-OADC broth and incubated in 13×100 mm polypropylene tubes in a heating block in a Biohazard hood for 48 hours. Rifampicin, streptomycin, or isoniazid were added to final concentrations of 2 μg/ml, 0 μg/ml, and 1 μg/ml, respectively. After 48 hours of incubation, 0.1 ml of phAE40 particles (1×10¹¹ particles) were added to attain a multiplicity of infection of 1000. Samples of 100 μl were removed at 1, 3 and 5 hours after addition of the phage and were mixed with 250 μl of 0.1 M sodium citrate (pH 5) in a Lumacuvette (Lumac, BV, Netherlands). One hundred microliters of 1 mM luciferin were added, and the Lumacuvette was plugged with cotton. The tube was placed in a Lumac Biocounter (M1500P), and readings were recorded as described above. (The Lumac Biocounter had dimensions that permit it to fit in a standard biohazard hood.) The light production followed kinetics similar to the BCG experiments, and the readings at 3 and 5 hours differed by no more than twofold. The results at 3 hours are shown for the Erdman (A), 92-2025 (B), and the MDR (C) M. tuberculosis strains.

Figure 11A:
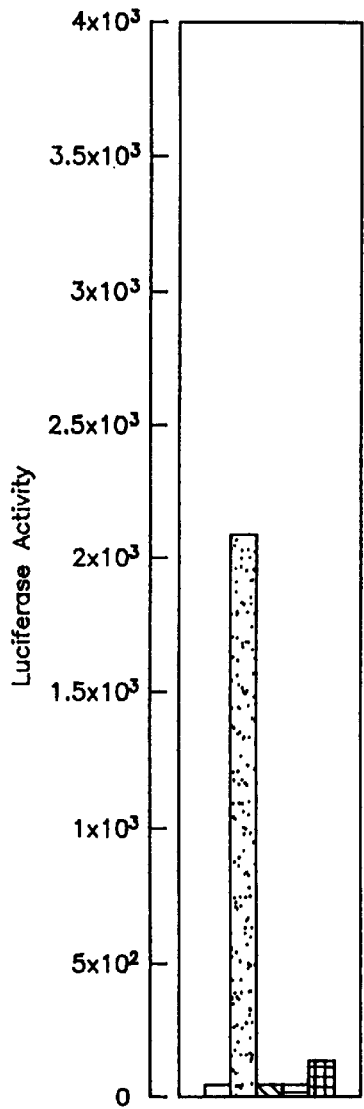
FIGS. 11A–11C represent a comparison of drug-sensitive M. tuberculosis and drug-resistant M. tuberculosis using the luciferase reporter phage assay.
Figure 11B:
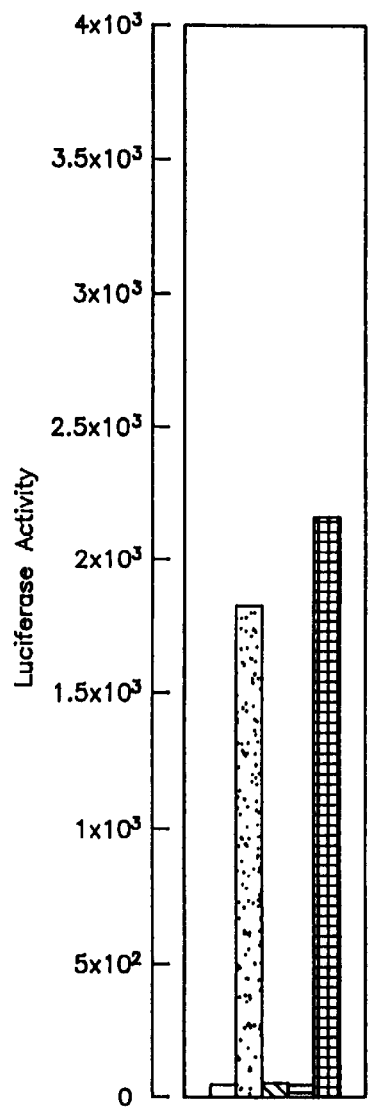
Figure 11C:
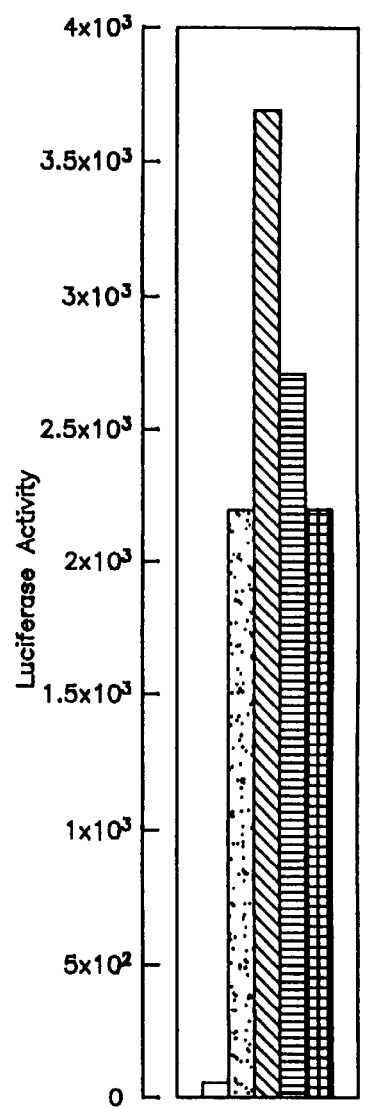

A repeated experiment gave similar results, with the samples cultured in the absence of drug exhibiting an 80-fold greater luminescence than the cells cultured with rifampicin or streptomycin and greater than 10-fold luminescence relative to those cultured with isoniazid at 3 and 5 hours. Open bars represent cells alone; filled bars represent cells plus LRP; diagonal lines represent cells plus rifampicin plus LRP; cross-hatching represents cells plus streptomycin plus LRP; squares represents cells plus isoniazid. As shown in FIG. 11, the luciferase reporter phages were capable of rapidly revealing the patterns of drug-susceptibility or resistance of M. tuberculosis strains.

Construction of L5 Reporter Mycobacteriophages
(phGS1 and phGS5)

In order to construct L5::FF*lux* phages, a plasmid (PGS12) was constructed in which a DNA segment of the L5 genome was inserted into the *E. coli*-mycobacterial shuttle plasmid pMD31. pMD31 is described by Donnelly-Wu et al. in "Superinfection Immunity of Mycobacteriophage L5: Applications for Genetic Transformation of Mycobacteria", *Molecular Microbiology*, Vol. 7, No. 3, pages 407–417 (1993). This DNA segment contained the tRNA gene cluster from L5 as described by Hatfull et al. in "DNA Sequence, Structure and Gene Expression of Mycobacteriophage L5: A Phage System for Mycobacterial Genetics", *Molecular Microbiology*, Vol. 7, No. 3, pages 395–405 (1993). Next, this plasmid was further manipulated by insertion of a segment of DNA containing the FF*lux* gene between the second and third tRNA, to produce pGS24. The resulting plasmid DNA was introduced into *M. smegmatis* by electroporation, and an L5 lysate was prepared by growth of L5 phage on this plasmid-containing strain.

Individual phages were screened by hybridization using an FF*lux* probe and filters containing 10⁶–10⁷ plaques. Several positive plaques were identified and two were purified and characterized. These two phages were named phGS1 and phGS5.

Construction of plasmids pGS11, pGS12, pGS22 and pGS24

Plasmids pGS11, pGS12 and pGS22 were constructed as described below and then used to construct plasmid pGS24.

Figure 14:
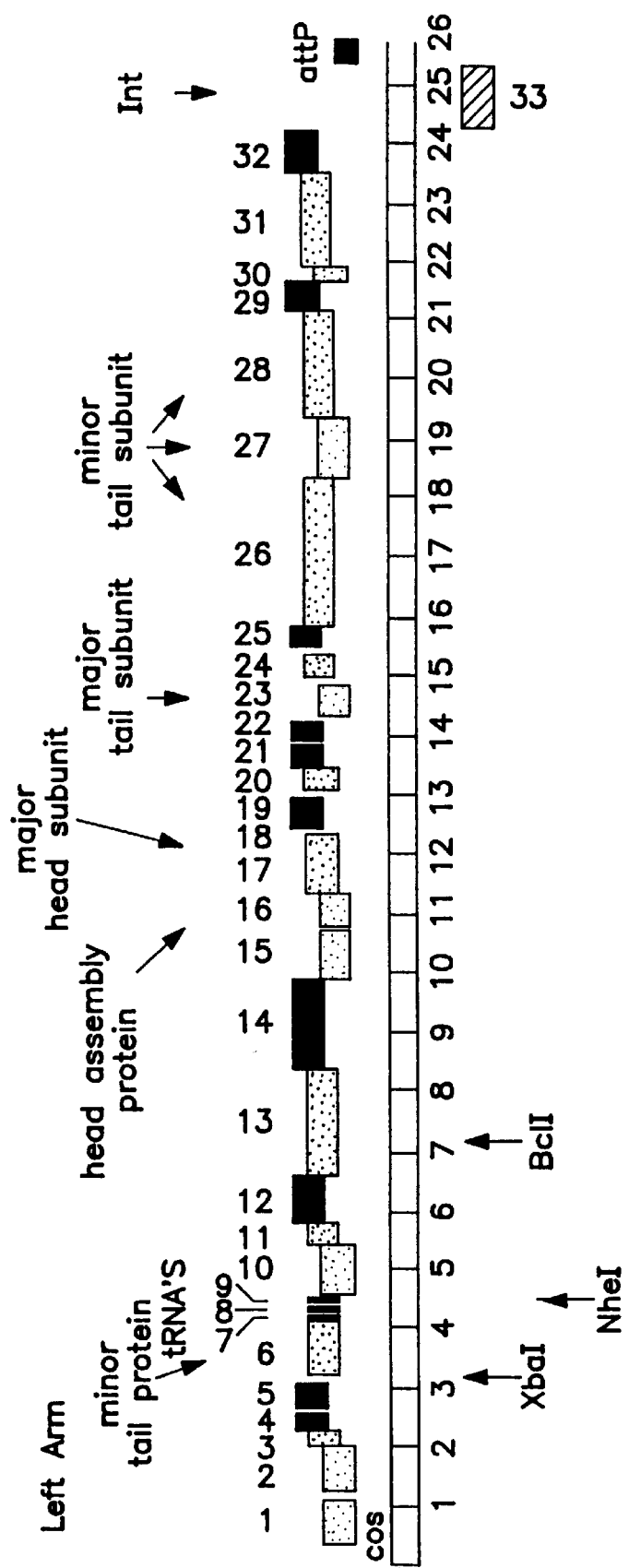
FIG. 14 represents a DNA fragment of the L5 segment defined by the coordinates 3,150–7,143 after cleaving with Xba I and Bcl I.
Figure 15:
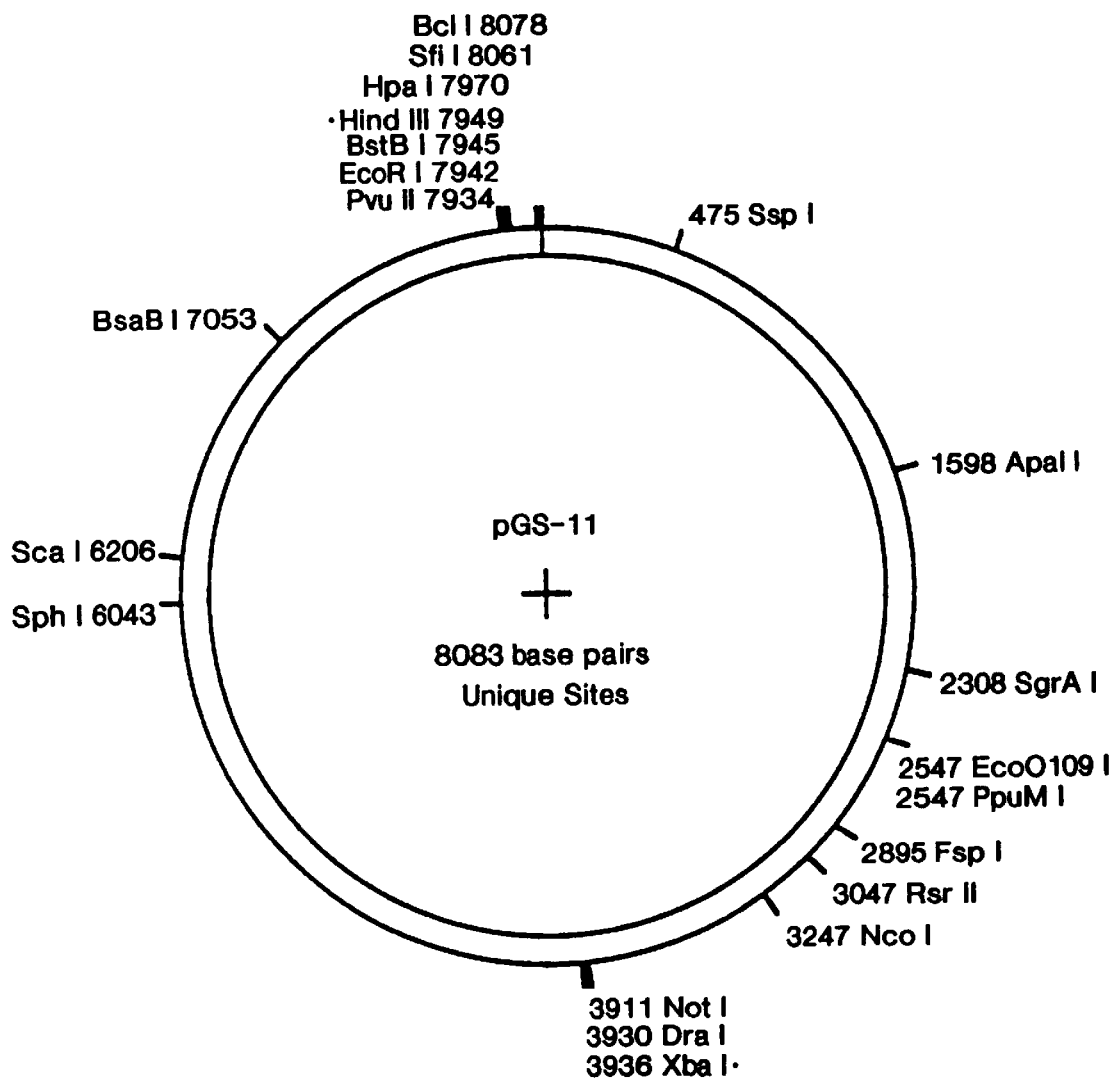
FIG. 15 represents the DNA fragment of L5 after insertion into plasmid pMV261lacZ and cleaving with Xba I and BAMHI to produce plasmid pGS11.

L5 DNA was cleaved with Xba I and Bcl I and the 3,993 bp fragment was purified. This DNA fragment represents the L5 segment defined by the coordinates 3,150–7,143. FIG. 14 is a segment of L5 DNA used for FF*lux* insertion which shows the left arm of the L5 genome with genes 1–33 indicated. The segment of L5 taken to make FF*lux* inserts is between the Xba I and Bcl I sites indicated. The Nhe I site that defines the position of insertion of FF*lux* is shown. This DNA fragment was inserted into plasmid pMV261*lacZ* (see Stover et al., *Nature*, Vol. 351, pp. 456–460, 1991) cleaved with Xba I and Bam HI to produce plasmid pGS11 (see FIG. 15). FIG. 15 is a map of plasmid pGS11 which contains the Xba I-Bcl I segment of L5 inserted into pMV261*lacZ*. The Bcl I end was inserted into the Bam HI site of the vector and both the Bcl I and Bam HI sites were destroyed. The Hind III and Xba I sites that were used to construct pGS12 are indicated.

Figure 16:
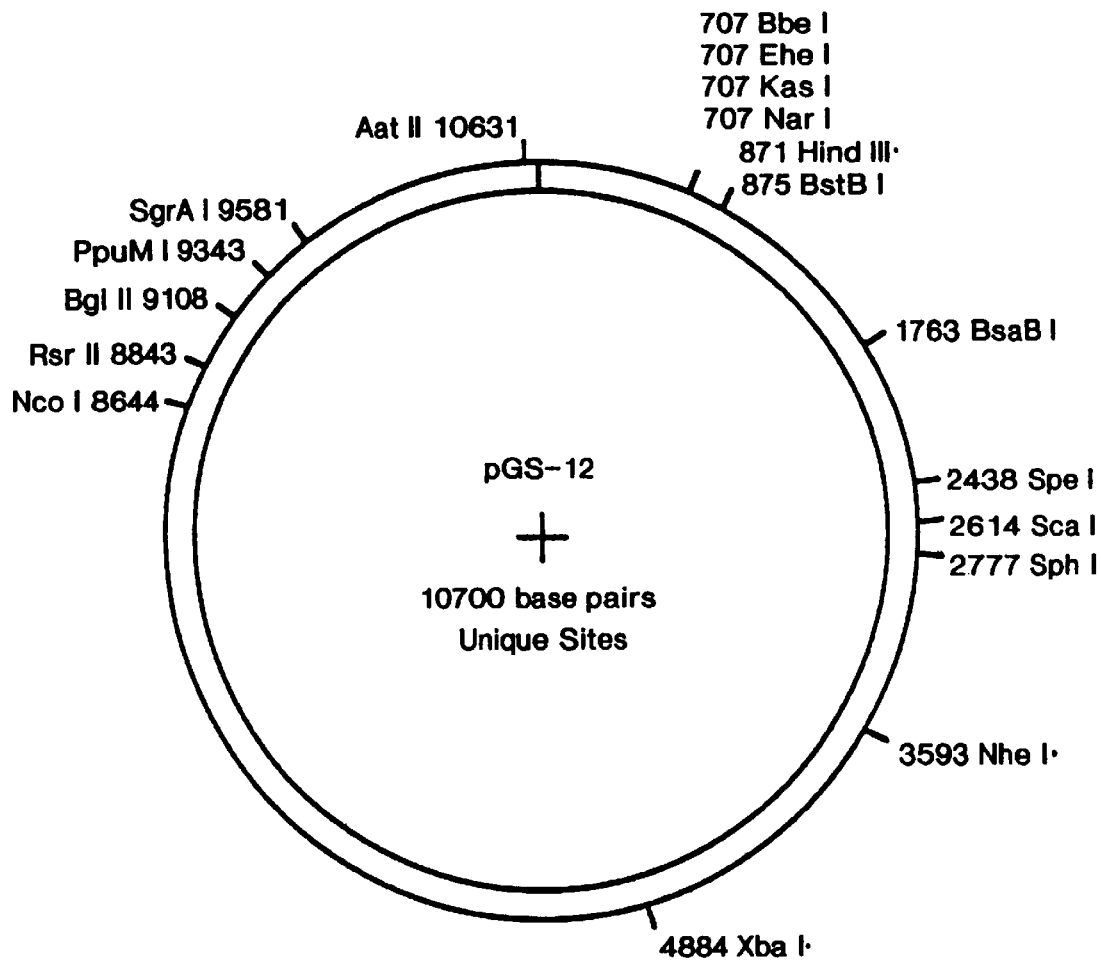
FIG. 16 represents plasmid pGS12 which was produced by cleaving pGS11 DNA with Xba I and Hind III, and inserting fragment 4,013 bp into plasmid pMD31.

Plasmid pGS11 DNA was cleaved with Xba I and Hind III and the 4,013 bp fragment was purified and inserted into plasmid pMD31 (Donnelly-Wu et al., 1993) cleaved with Xba I and Hind III. This plasmid was named pGS12. FIG. 16 is a map of plasmid pGS12 showing the location of the Xba I and Hind III sites used to insert the Xba I-Hind III piece from pGS11 into pMD31. The unique Nhe I site used for the insertion of FF*lux* is also shown. Plasmid pGS12 contains a unique Nhe I restriction site which corresponds to the Nhe I site at position 4,441 in the L5 genome which is located between the tRNA-trp and tRNA-gln genes (genes 8 and 9).

Figure 17:
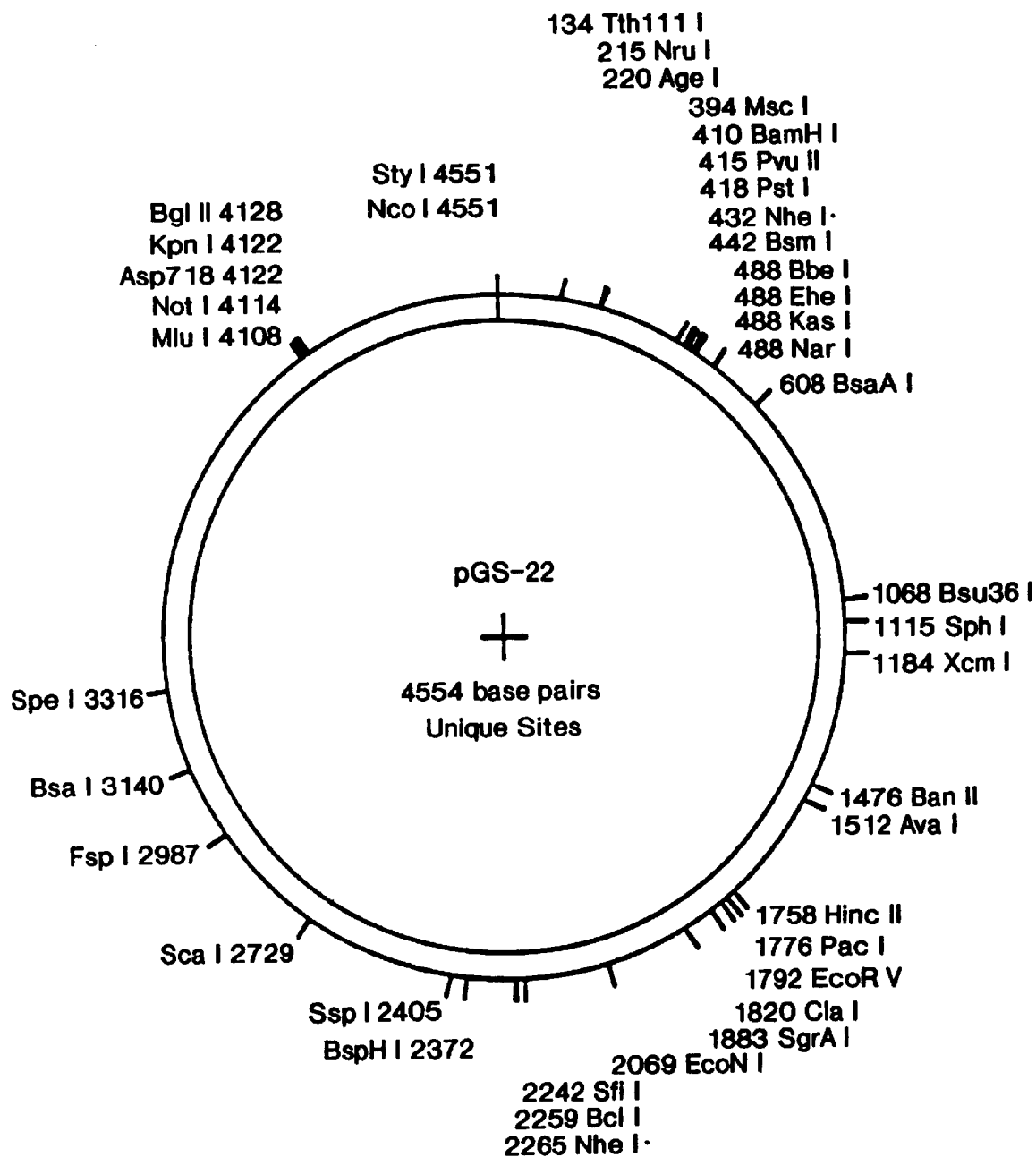
FIG. 17 represents plasmid pGS22, which was produced by cutting plasmid pYUB216 with Hind III and converting the sticky ends to blunt ends by Klenow enzyme and dNTP's.
Figure 18:
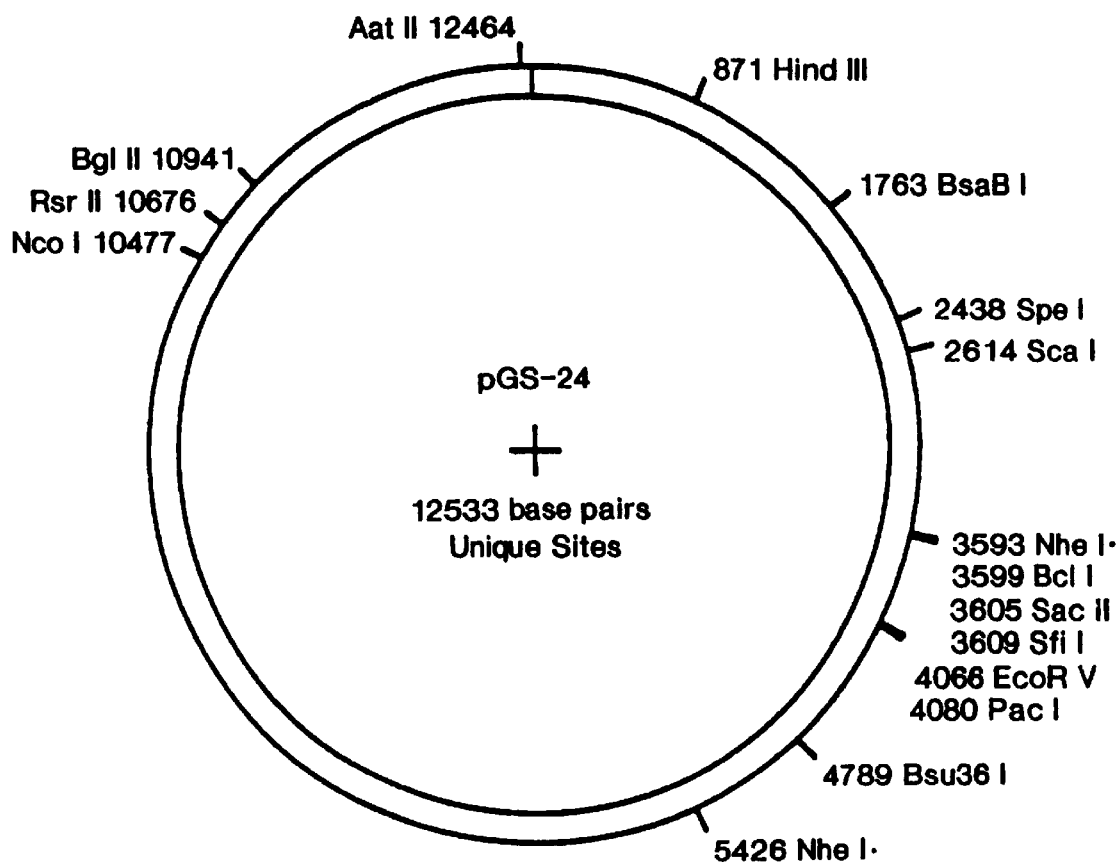
FIG. 18 represents plasmid pGS24, which was produced by inserting plasmid pGS22 into the NHE I site of pGS12 plasmid.

Plasmid pYUB216 was cut with Hind III, the sticky ends converted to blunt ends by Klenow enzyme and dNTP's and the DNA religated. The resulting plasmid was named pGS22. FIG. 17 is a map of plasmid pGS22 which shows the two Nhe I sites that flank the FF*lux* gene. This procedure was followed to generate an additional Nhe I site upstream of the FFlux gene in pYUB216.

pGS12 was digested with Nhe I. pGS22 was also digested with Nhe I which produces a fragment of approximately 2.4 kb. The DNA's were mixed, ligated and a recombinant recovered in which the Nhe I fragment derived from pGS22 was inserted into the Nhe I site of pGS12. This plasmid was named pGS24. FIG. 18 is a map of plasmid pGS24 which contains the Nhe I FFlux DNA fragment inserted into the unique Nhe I site of pGS12. The two Nhe I sites are indicated. The orientation of the inserted DNA was determined by restriction enzyme digestion and found to be in the appropriate orientation for FFlux to be expressed from the same DNA strand as the L5 tRNA's. pGS24 is thus a *E. coli*-mycobacterial shuttle plasmid that contains the FFlux gene flanked upstream by approximately 1,291 bp of L5 DNA and downstream by approximately 2,702 bp L5 DNA.
Construction of phGS1 and phGS5

Figure 19:
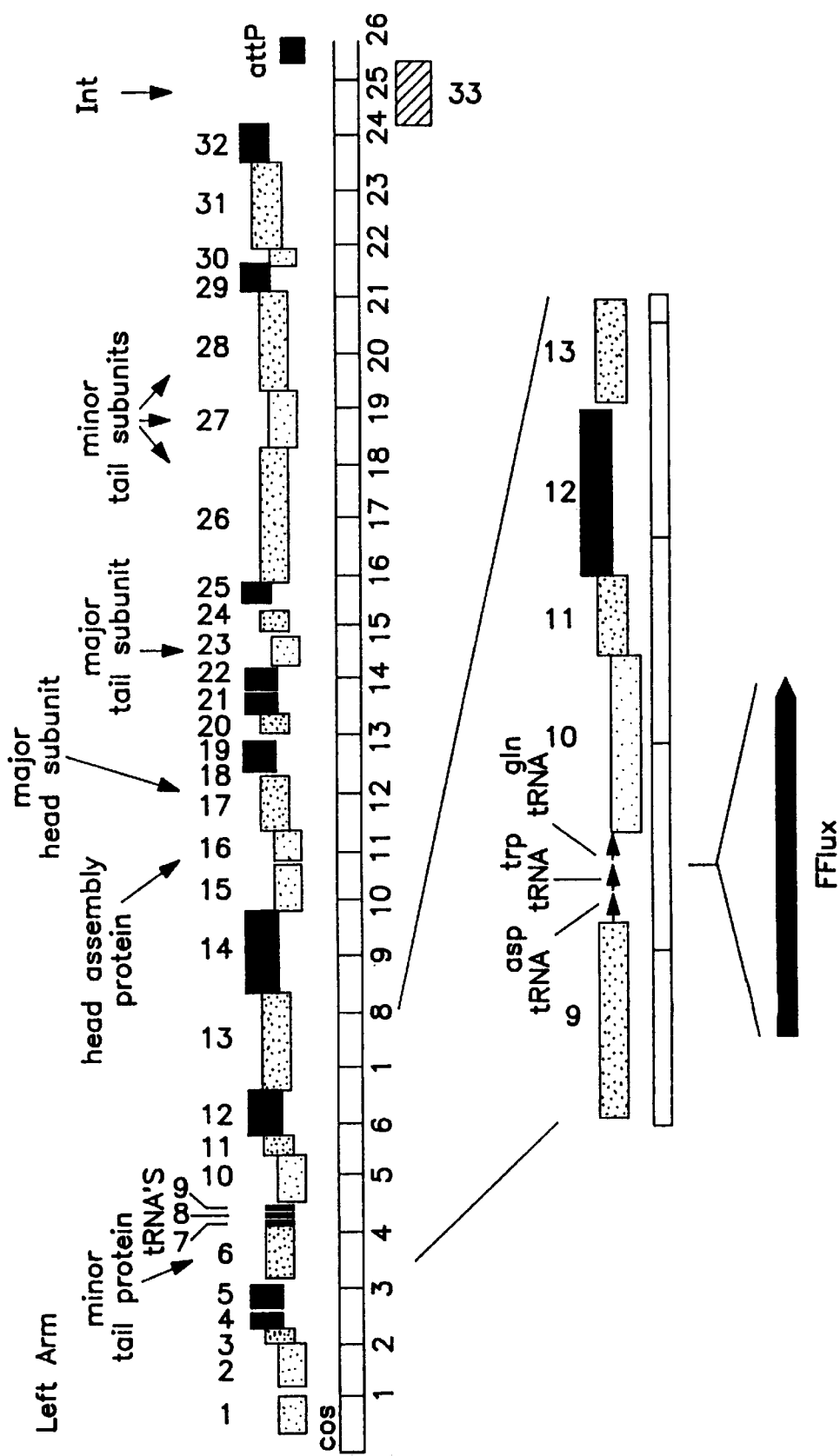
FIG. 19A represents a double crossover event between plasmid pGS24 and L5.

Having constructed a plasmid containing FFlux flanked by L5 DNA, FFlux was inserted onto the L5 genome by a double crossover event between plasmid pGS24 and L5. This was achieved by growth of an L5 lysate on *M. smegmatis* carrying plasmid pGS24 and searching among the progeny for FFlux-containing phage by hybridization. FIG. 19 shows the strategy for recombination between pGS24 and L5. Specifically, the upper part of the figure shows the left arm of L5 and the position of genes 1–33. The lower part shows the segment of L5 DNA present in pGS24 and the location of FFlux inserted between the tRNA-trp and tRNA-gln genes. It was hoped that by growth of L5 phage in cells containing plasmid pGS24 that progeny could be recovered in which the FFlux gene had been inserted into the L5 genome by homologous recombination within the common sequences to the left and right of FFlux in pGS24 and those in L5.

Plasmid pGS24 DNA was introduced into *M. smegmatis* mc²-155 by electroporation, and transformants recovered by selection with kanamycin. A lysate of phage L5 was prepared by infection of approximately 0.5 ml late-log phage *M. smegmatis* cells containing plasmid pGS24 with approximately $10^6$ L5ts11 particles and incubation on solid media at 37° C. [L5ts11 is a poorly characterized temperature-sensitive mutant of L5]. The phages were harvested and shown to have a titer of approximately $10^{10}$ plaque forming particles/ml (pfu/ml).

Approximately $10^6$–$10^7$ phage articles were added to *M. smegmatis* mc²-155 cells and plated onto large agar plates. After incubation, plaques were transferred to nitrocellulose filters and probed with radioactively labeled pYUB216 DNA. About 15 positive plaques were identified.

Several positive plaques were recovered from the agar plates purified through several rounds of plaque purification, checking with positive hybridization to the pYUB216 DNA probe at each stage. At the end of this procedure, two of the phages were chosen for further characterization. These phages were named phGS1 and phGS5.
Characterization of phGS1 and phGS5 DNA's Phage DNA's were prepared from high titer stocks of phGS1 and phGS5 using standard methods.

phGS1 and phGS5 DNA's were digested with several different restriction enzymes (including Bam HI, Nhe I, Bst E II, Asp718, Cla I, Bgl II) and the patterns observed compared with those obtained from wild-type L5, using agarose gel electrophoresis. Several differences were observed between phGS1 and phGS5 as compared to L5 DNA. Some of these changes were consistent with a double crossover recombination event inserting FFlux onto the L5 genome as anticipated. Other differences were consistent with deletion of some of the L5 DNA close to the right end of the genome.

Figure 20A:
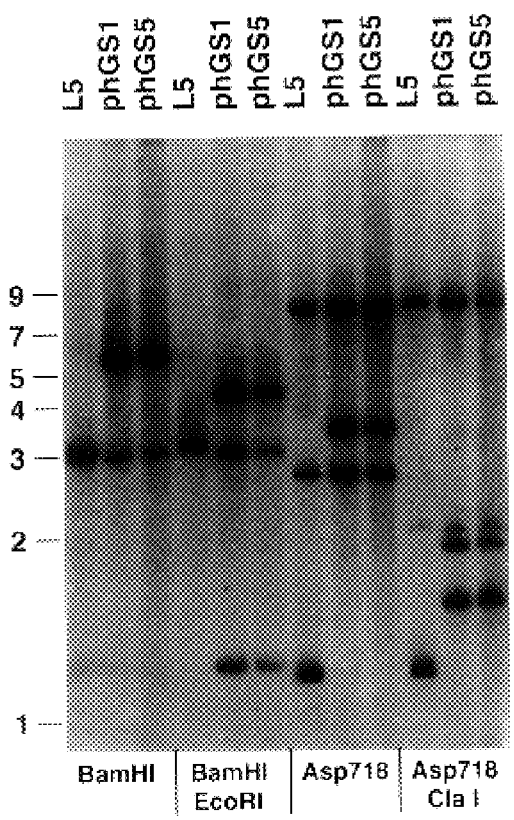
FIGS. 20A and 20B represent hybridized bands detected by autoradiography.
Figure 20B:
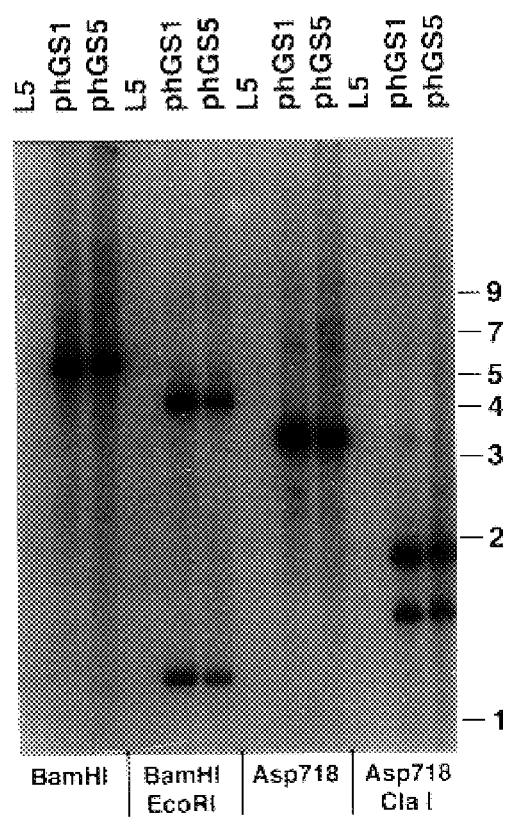

Confirmation of the structures of phGS1 and phGS5 was obtained by hybridization of Southern blots of the DNA's using a variety of DNA probes.

phGS1, phGS5 and L5 DNA's were digested with either Ban HI, Bam HI and EcoRI, Asp718 or Asp718 and ClaI. DNA fragments were separated by agarose gel electrophoresis and transferred to a nitrocellulose filter. This filter was probed with radiolabelled pGS12 DNA and the hybridizing bands detected by autoradiography. The results are shown in FIG. 20. FIG. 20 shows a Southern blot of the insertion of FFlux into L5. DNA purified from L5, phGS1 and phGS5 particles was cleaved with restriction enzymes as indicated and the fragments separated by agarose gel electrophoresis. The DNA fragments were transferred to a nitrocellulose filter and probed with radiolabelled pGS12 DNA (left panel). Following autoradiography, the filter was stripped and probed with radiolabelled pYUB216 DNA (right panel). These data conclusively demonstrate that FFlux is inserted into the L5 genome in a corresponding location to that in pGS24 as would be expected from a pair of homologous recombination events in the common flanking sequences. A map of the expected DNA fragments is shown in FIG. 21.

FIG. 21A maps show the expected restriction products from FFlux insertion-Bam HI. The location of the L5 probe (from pGS12) used for hybridization is shown (labeled 'probe'). This probe is expected to hybridize to two comigrating Bam HI fragments (3.010 bp and 3,104 bp) in wild-type L5 DNA (shown as 'labeled BAM HI fragments' in the top part of the figure). The lower part of the figure shows the anticipated structure of the FFlux insertion and the expected fragments resulting from digestion with either Bam HI or BAM HI+EcoRI that hybridize with the probe. These are 3,010 bp and 4,937 bp fragments from Bam HI digestion and 3,010 bp, 1,183 bp and 3,754 bp fragments from Bam HI and EcoRI digestion. The location of the FF lux probe derived from pYUB216 is indicated in the lower part of the figure. it is expected to hybridize to the 4,937 bp Bam HI fragment, and the 1,183 bp and 3,754 bp Bam HI/EcoRI fragments in the recombinants, but not to L5 at all. The data shown in FIG. 21 agree well with these predictions.

FIG. 21B maps show the expected restriction product& from FFlux insertion–Asp718/Cla I. The pGS12 probe is anticipated to hybridize to 2,690 bp, 1,148 bp and 8,078 bp fragments resulting from Asp718 digestion of L5 and 2,690 bp, 2,981 bp and 8,078 bp from the FFlux recombinants. This probe is also expected to hybridize to 645 bp, 1,148 bp and 8,078 bp L5 fragments from Asp718+Cla I digestion and 645 bp, 1,078 bp and 8,078 bp fragments from this digestion of the FFlux recombinants. Note that the 1,078 bp fragment migrates as a fragment of approximately 1.5 kb which reflects the difference between the DNA strider generated maps and empirically-determined maps. The FFlux probe in pYUB216 hybridizes to the 2,981 bp Asp718 fragments and the 1,903 bp and 1,078 bp fragments from Asp718–Cla I digestion's of the recombinant phage.

Digestion of phGS1 and phGS5 DNA with Bam HI indicated that neither contained the largest Bam HI fragment (7.711 bp). The coordinates of the Bam HI sites that yield this fragment in wild-type L5 are 43,933 and 51,644. phGS1 and phGS5 thus appear to have lost a segment of L5 DNA close to the right end of the genome. Since the adjacent Bam HI fragments appear to be intact, it seemed probable that both Bam HI sites were present in phGS1 and phGS5 and that segments within the 7.711 bp Bam HI fragment were deleted. It was also not clear whether phGS1 and phGS5 were identical in this respect.

Hybridization of a specific L5 DNA probe derived from the 7.711 bp Bam HI fragment to a Southern blot of digested DNA's showed that phGS1 and phGS5 contain deletions of different sizes. phGS1 contained a new hybridizing fragment of approximately 3.4 kb indicating that 4.3 kb of DNA internal to the 7.7 kb Bam HI fragment had been deleted. phGS5 contained a new hybridizing fragment of 5.3 kb indicating that 2.4 kb of DNA internal to the 7.7 kb Bam HI fragment had been deleted.

Figure 22:
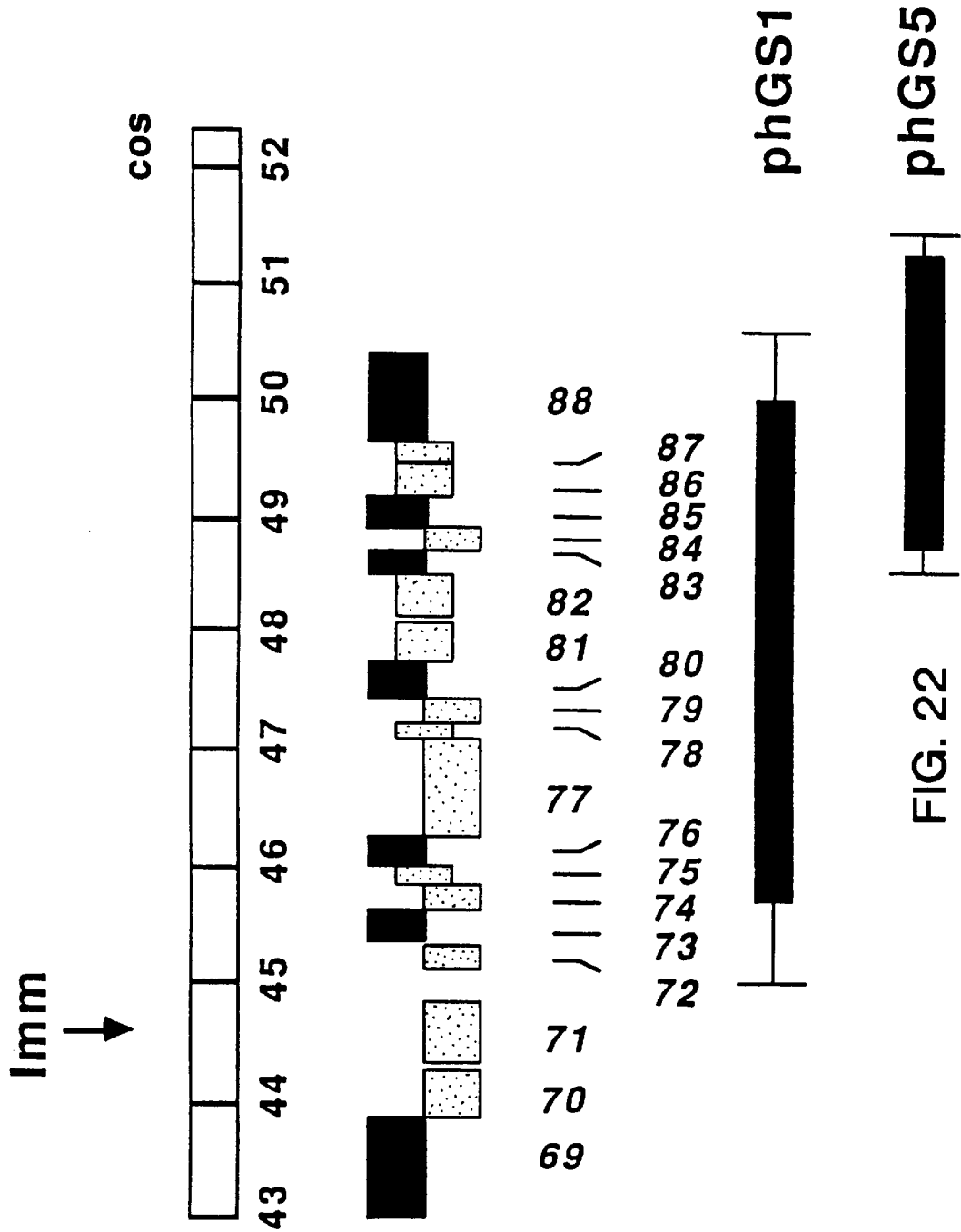
FIG. 22 represents restriction enzyme mapping and Southern blot hybridization for phGS1 and phGS5.

The exact end points of the deletions in phGS1 and phGS5 have not yet been determined. However, approximate end points were determined through a combination of restriction enzyme mapping and Southern blot hybridization as shown in FIG. 22. FIG. 22 map shows deleted regions in phGS1 and phGS5. phGS1 and phGS5 DNA's were found to contain deletions of L5 DNA in the right arm close to the right end of the genome. The location of these deletions was determined by a series of restriction enzyme digestions and Southern blot hybridizations and the approximate locations are shown here. The dark box represents the deleted portions and the limits of the positions are defined by the vertical lines. phGS1 contains a deletion of approximately 4.3 kb DNA and phGS5 contains a deletion of approximately 2.4 kb DNA.

For phGS1, the left end point appears to be to the right of the Bgl II site located at position 44,803 (wild-type L5 coordinates); the right end point is to the right of the BstE II site at 49,588 and to the left of the Bgl II site at 50,716. For phGS5, the left end point is to the right of the Sca I site at 47,559 and to the left of the Asp718 site at 48,750; the right end point is to the right of the Bgl II site at 50,716 and to the left of the Mse I site at 51,344.

Construction of other phGS1 and phGS5 Derivatives

In order to fully evaluate the behaviors of the L5::FFlux recombinants, several additional derivatives were isolated.

Isolation of phGS1$^{ts+}$ and phGS5$^{ts+}$:

It should be noted phGS1 and phGS5 are both derivatives of L5ts11. L5ts11 was chosen because some preliminary data indicated the temperature-sensitive mutation may lie within the region of DNA represented in pGS12. However, both phGS1 and phGS5 are still temperature-sensitive and fail to grow at 42° C. Temperature-resistant derivatives were isolated from phGS1 and phGS5 by plating approximately $10^6$ particles at 42° C. and recovering a derivative that was now competent to grow normally at 42° C. These were named phGS1$^{ts+}$ and phGS5$^{ts+}$, respectively. It is likely that these are simply derivatives of phGS1 and phGS5 that have resulted from the initial temperature-sensitive mutation in L5ts11. Phages phGS1$^{ts+}$ and phGS5$^{ts+}$ behave similarly to their direct parents in all respects except that they are competent to grow at high temperatures.

Isolation of phGS5$^{ts+}$cpm1, phGS5$^{ts+}$cpm2, phGS5$^{ts+}$cpm3, phGS5$^{ts+}$cpm4, and phGS5$^{ts+}$cpm5.

Several clear plaque mutants of phGS5$^{ts+}$ were isolated that are unable to form lysogens. These were isolated by plating various numbers of phage particles on M. smegmatis cells at 42° C. and looking for clear plaque versions. We have shown previously that these mutants arise at a frequency of $10^{-3}$–$10^{-4}$ (Donnelly-Wu et al., 1993). Five separate mutants were isolated and named phGS5$^{ts+}$cpm1, phGS5$^{ts+}$cpm2, phGS5$^{ts+}$cpm3, phGS5$^{ts+}$cpm4, and phGS5$^{ts+}$cpm5.

Isolation of phGS1 and phGS5 lysogens of M. smegmatis phGS1 and phGS5 lysogens of M. smegmatis mc$^2$-155 were generated using standard methods. The phage lysates were used to infect M. smegmatis mc$^2$-155. Cells were then recovered from the infected area and purified by plating for isolated colonies. One lysogenic isolate was prepared from each phage and shown to confer immunity to superinfection by L5, a known property of L5 lysogens (Donnelly-Wu et al., 1993). These were named M. smegmatis mc$^2$-155 (phGS1) and M. smegmatis mc$^2$-155(phGS5).

Luciferase activity of plasmids and lysogens

It was anticipated that plasmid pGS24 would have little or no luciferase activity in M. smegmatis mc$^2$-155. Likewise, it was not anticipated that M. smegmatis mc$^2$-155(phGS1) and M. smegmatis mc$^2$-155(phGS5) lysogens would have much luciferase activity. This view was arrived at via the assumption that transcriptional promoters for expression of the L5 genes 1–32 probably resided between genes 88 and 1. These promoters would thus have been removed from plasmid pGS24 and were expected to be inactive in the lysogenic state.

Figure 23:
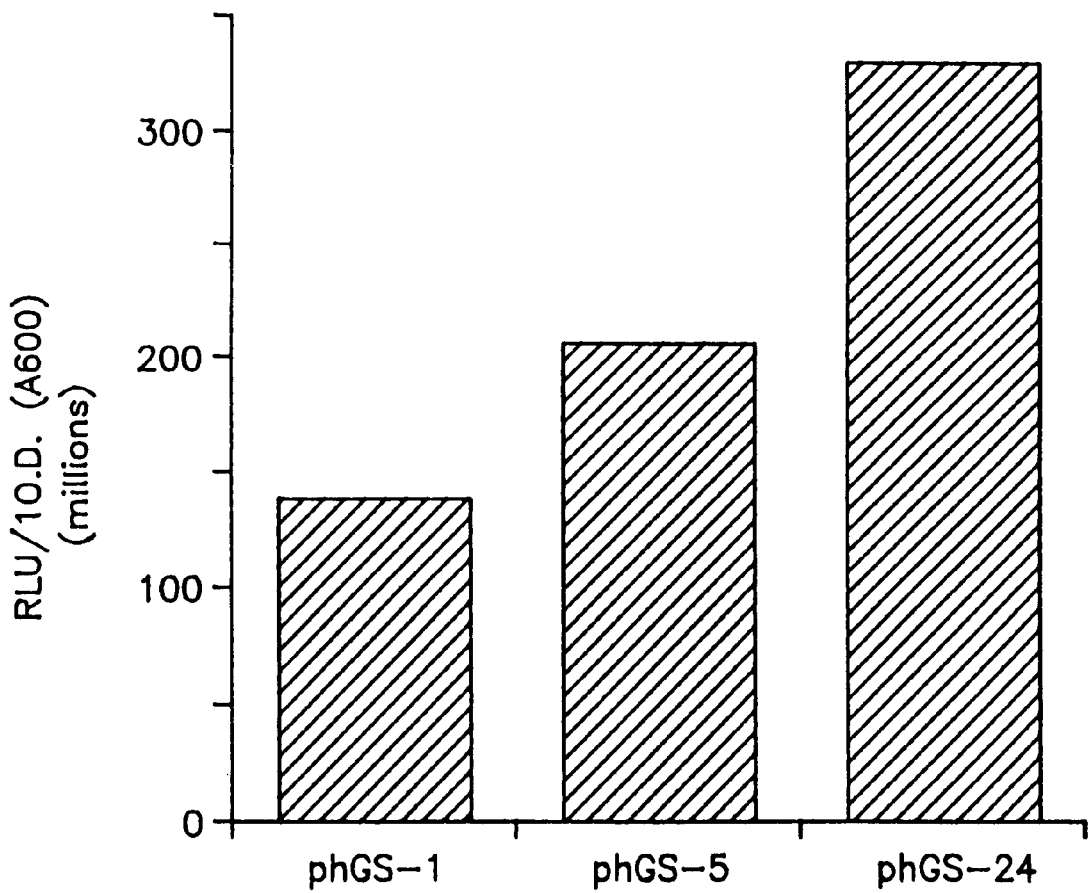
FIG. 23 represents determination of the luciferase activity of pGS24, phGS1 and phGS5.

Determination of the luciferase activity of pGS24 and the lysogens indicated that these assumptions were incorrect. FIG. 23 shows luciferase activity of pGS24 and phGS1 and phGS5 lysogens. Cultures of either M. smegmatis mc$^2$-155 lysogens of phGS1 or phGS5 or M. smegmatis mc$^2$-155 carrying pGS24 were grown to early log phase and the optical density (O.D.) determined at $A_{600}$. A portion (10–20 μl) was removed and FFlux activity determined in a Luminometer (Analytical Luminescence Monolight 2010) using luciferin as a substrate. The activities shown are normalized for 1.0 O.D. unit for 1 ml culture.

As shown in FIG. 23, lysogens of phGS1 and phGS5 and pGS24 all have considerable amounts of luciferase activity. There is a small difference between the activities of phGS1 and phGS5 which is probably not significant.

Luciferase activity following infection of M. smegmatis mc$^2$-155

Figure 24:
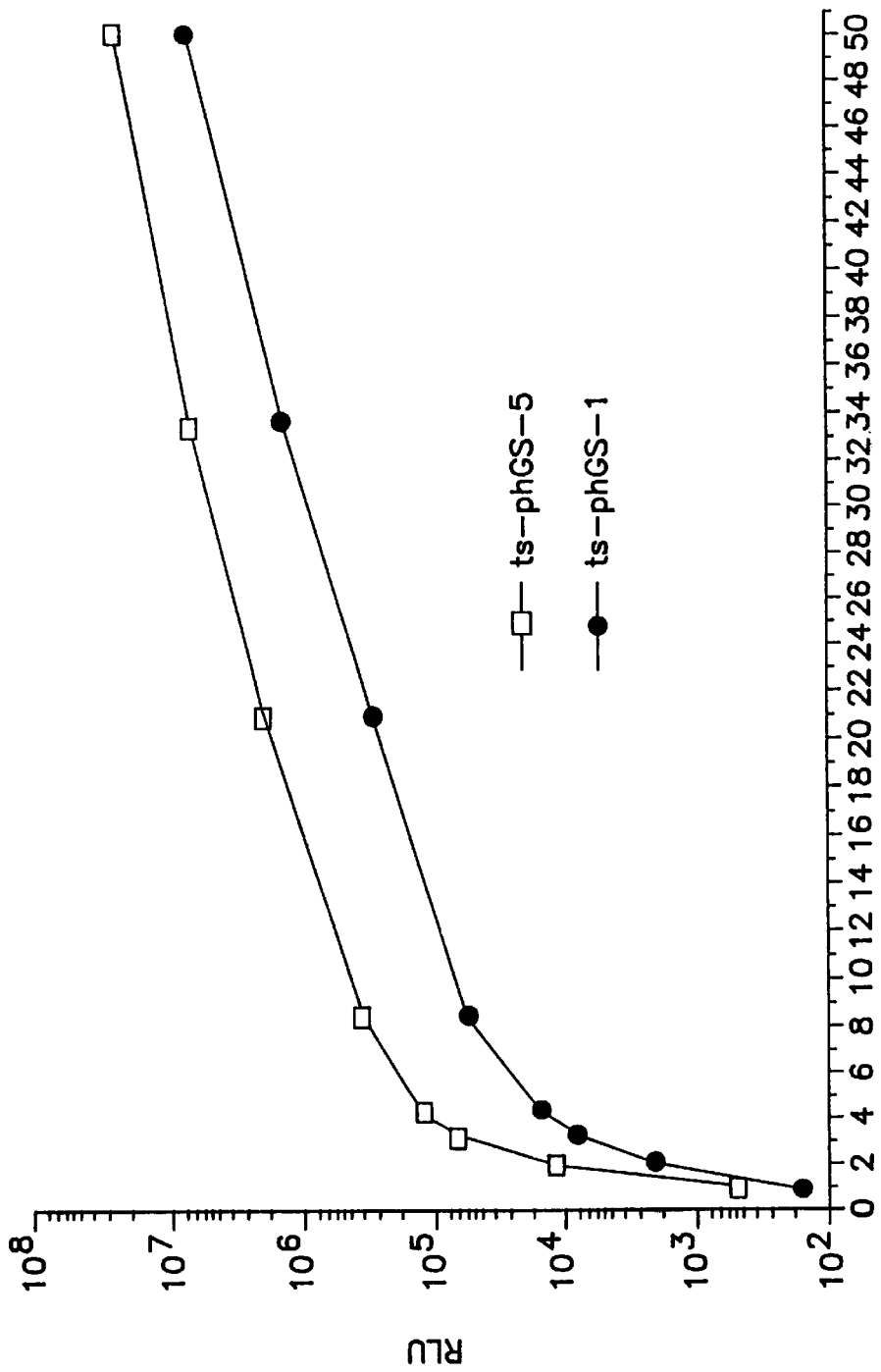
FIG. 24 represents luciferase activity as determined after liquid infection of *M. smegmatis* mc$^2$155 with phGS1 and phGS5.

Luciferase activity was determined following liquid infection of M. smegmatis mc$^2$-155 with phGS1 and phGS5. FIG. 24 shows luciferase activity following infection of M. smegmatis with phGS1 and phGS5. phGS1 or phGS5 (approximately $4\times10^7$ pfu) were added to an early log phase culture of M. smegmatis mc$^2$-155 (O.D. $A_{600}$=0.1) incubated at 30° C. and 50 μl samples removed for FFlux activity determination at various times. The absolute relative light units (RLU) obtained are shown at each time point. As shown in FIG. 24, activity increased sharply for four hours and then increased less rapidly for as long as the experiment was pursued, up to about 50 hours. phGS1 consistently produced less activity than phGS5 in this assay. These phages are extremely active in FFlux activity, and phGS5 produced almost $10^7$ relative light units (RLU) after 50 hours. The background in this assay (for example if phages are omitted) is routinely between 180 and 200 RLU's.

Efficient light production requires the formation of lysogens

Figure 25:
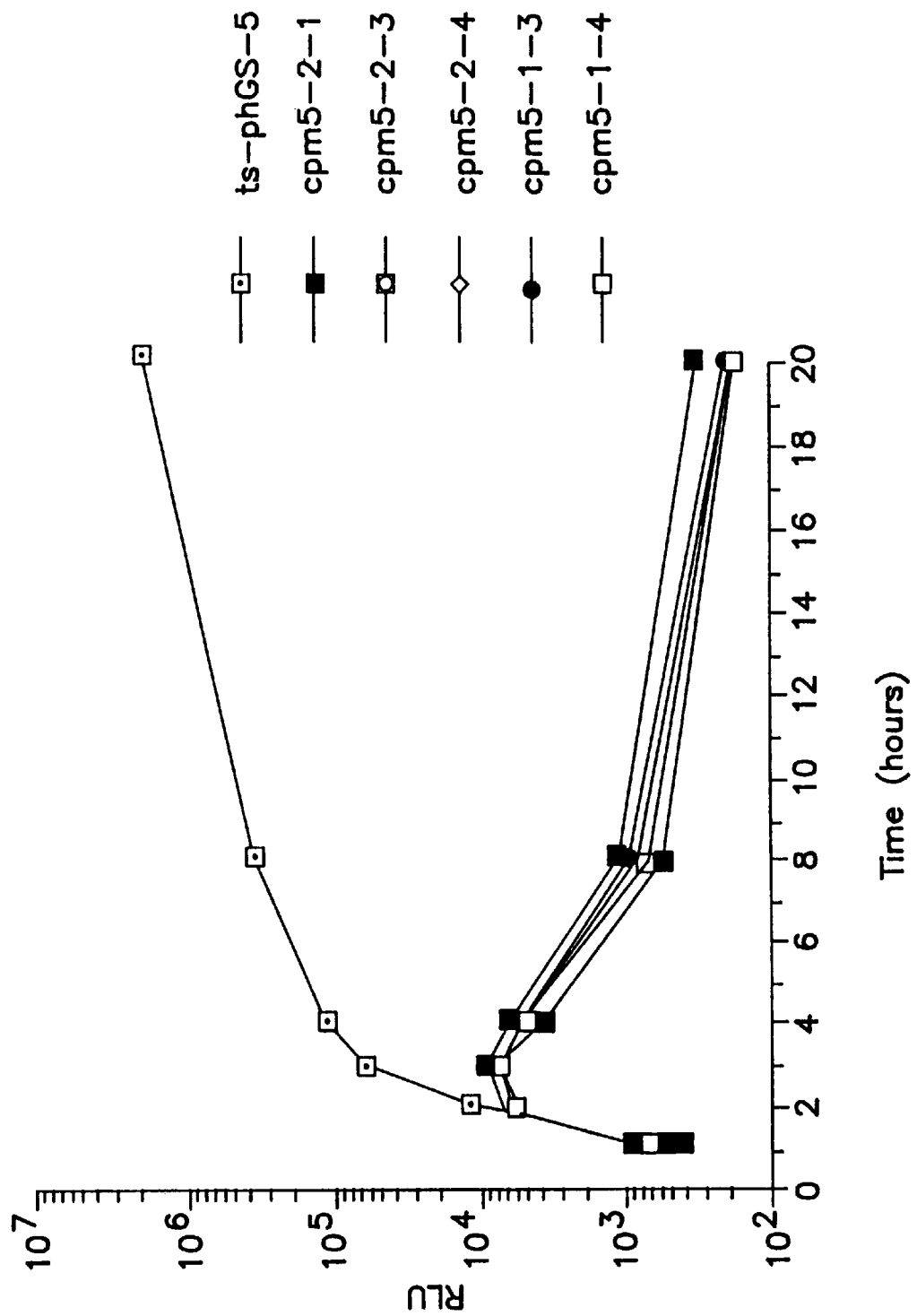
FIG. 25 represents a comparison of luciferase activity of phGS5 with clear plaque mutant derivatives that are not competent to form lysogens.

Since light production increases over a long period of time after phGS1 and phGS5 infection, it was reasoned that this could result from formation and growth of stable lysogens. It was shown above phGS1 and phGS5 strongly express FFlux in the lysogenic state. This hypothesis was tested by comparing the activity of phGS5 with clear plaque mutant derivatives that are not competent to form lysogens. The data are shown in FIG. 25. It was apparent that where the activity of phGS5 continued with time, the clear plaque mutant derivatives rose to a maximum activity after about three hours and then declined to a background level. The difference in activity of phGS5 and the clear plaque mutants was greater than $10^4$-fold at 20 hours after infection.

Comparison of L5::FFlux and TM4::FFlux phases

Figure 26:
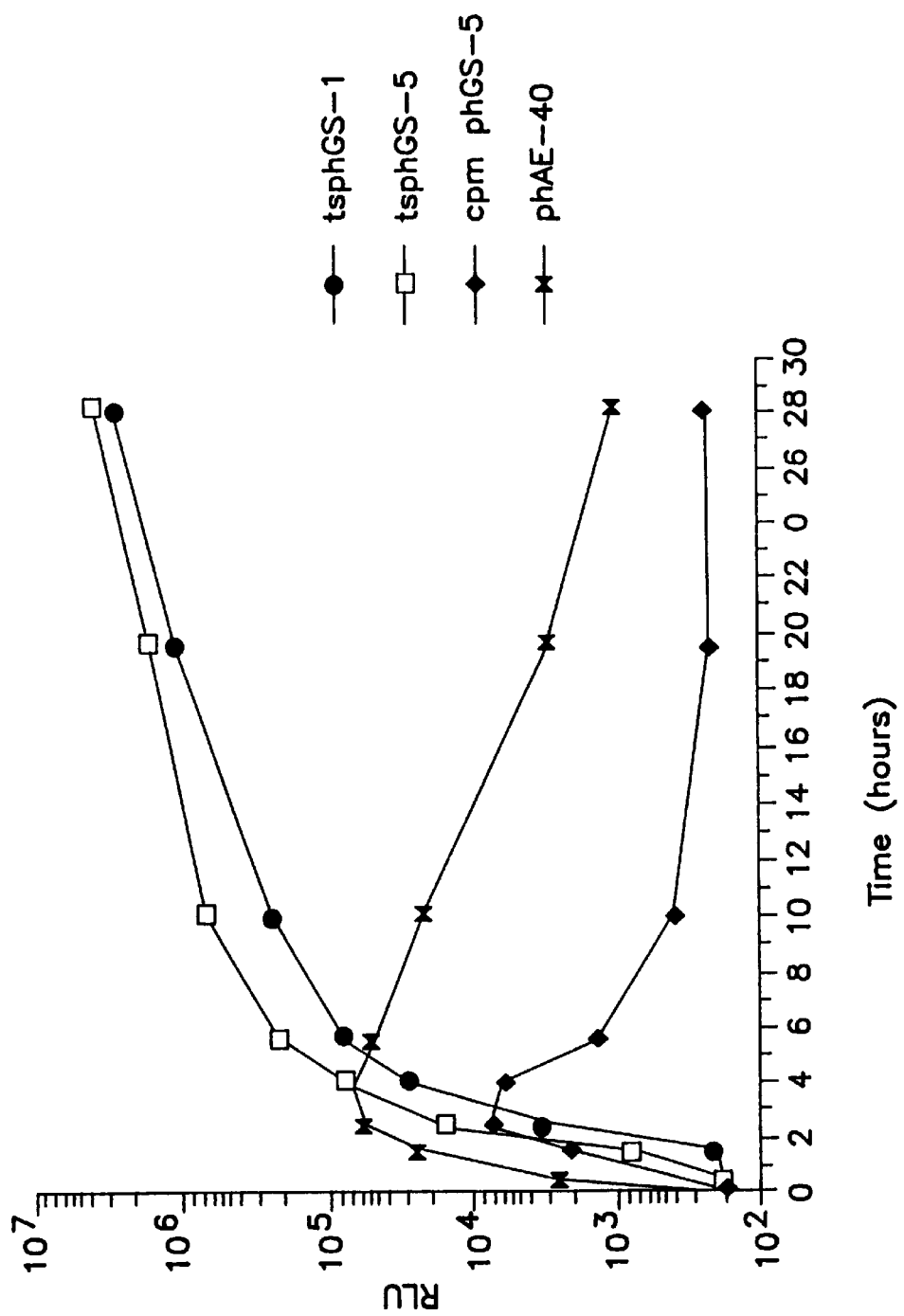
FIG. 26 represents the activity of phAE40 and the L5::FF lux phages following infection with *M. smegmatis* mc²155.

The activity of phages phAE40 and the L5::FFlux phages were compared following infection of M. smegmatis mc$^2$-155 (see FIG. 26). The activity of phAE40 had characteristics similar to that of the clear plaque mutants of phGS5 although the maximum activity was greater. However, at all points after 4 hours, the phGS5 and phGS1 phage had substantially greater activity.

Sensitivity of the phGS5 phage

It was apparent that phGS5 has the greatest potential of all of the luciferase reporter phages constructed to detect small numbers of mycobacterial cells. To evaluate its sensitivity, serial dilutions of a culture of M. Smegmatis mc$^2$-155 was prepared, infected with phGS5 and then FFlux activity 20 hours after infection was determined. Two different concentrations of phGS5 phage were used. A culture of M. smegmatis mc$^2$-155 (O.D. A$_{600}$=0.1) was diluted by serial 10-fold dilution. 100 μl portions were infected with either 4×10$^7$ pfu or 4×10$^5$ pfu phGS5 as indicated. After 20 hours incubation at 30° C., 50 μl samples were removed for measuring FFlux activity. Assuming that a culture of M. smegnatis mc$^2$-155 with an O.D. A$_{600}$=0.1 contains approximately 10$^8$ bacteria/ml, this experiment demonstrates that approximately 5,000 cells of M. smegmatis can be readily detected in this assay.

Figure 27:
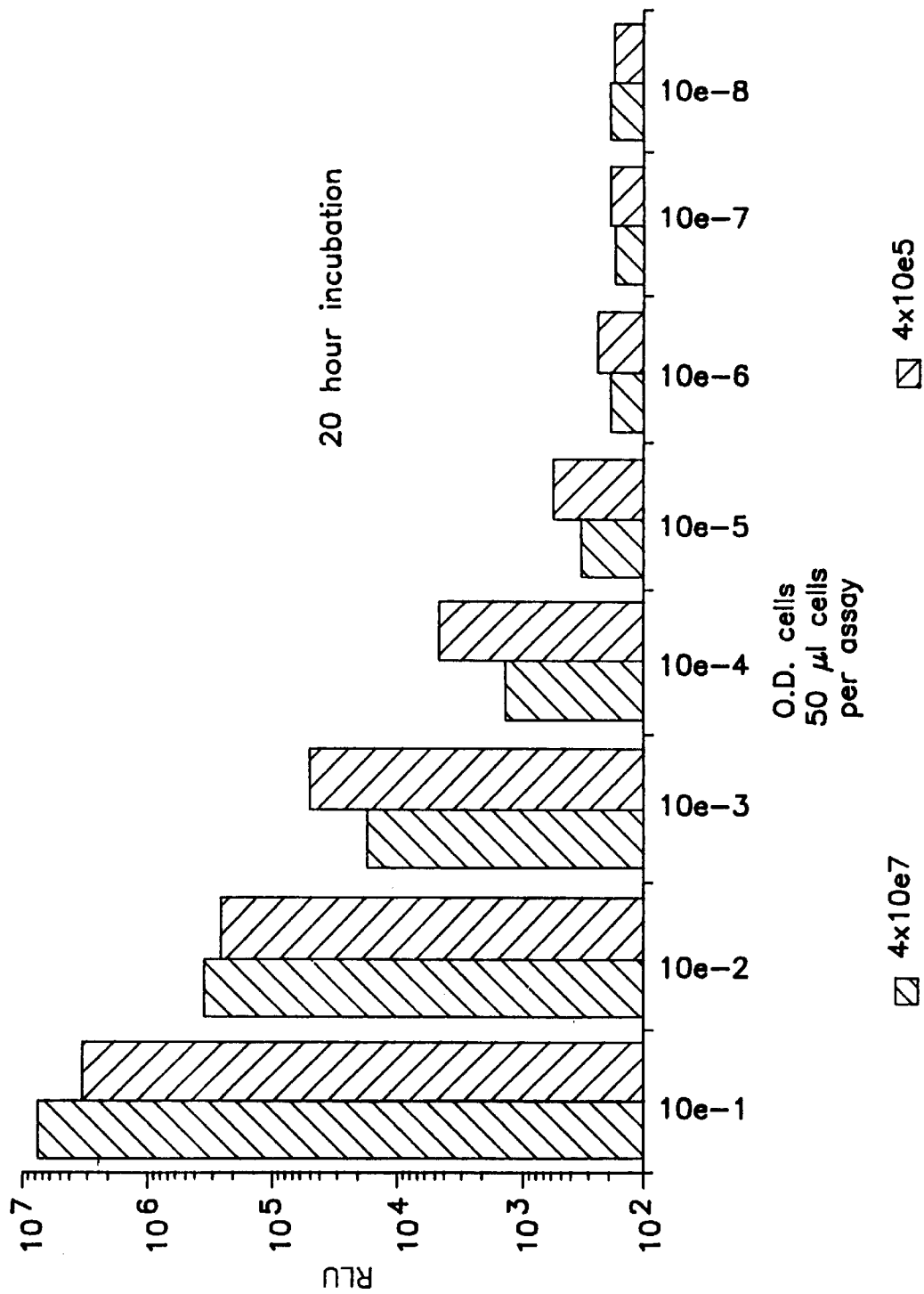
FIG. 27 represents the sensitivity of phage phGS5 after infecting *M. smegmatis* mc²155.

The results are shown in FIG. 27. These data demonstrate that a 50 μl culture with an O.D. ~0.0001 (equivalent to approximately 5,000 bacterial cells) infected with 4×10$^5$ pfu phGS5 produced a signal (4,000 RLU) more than 10-fold greater than in a culture containing no mycobacteria (180–200 RLU). A culture containing approximately 500 cells produced a signal (approximately 600 RLU) infected with a similar titer of phage gave a signal 2-fold greater than background. It was concluded that phGS5 offers exquisite sensitivity for the detection of small numbers of M. smegmatis cells.

Further Evaluation of Sensitivity of L5::FFlux Phages

Figure 28A:
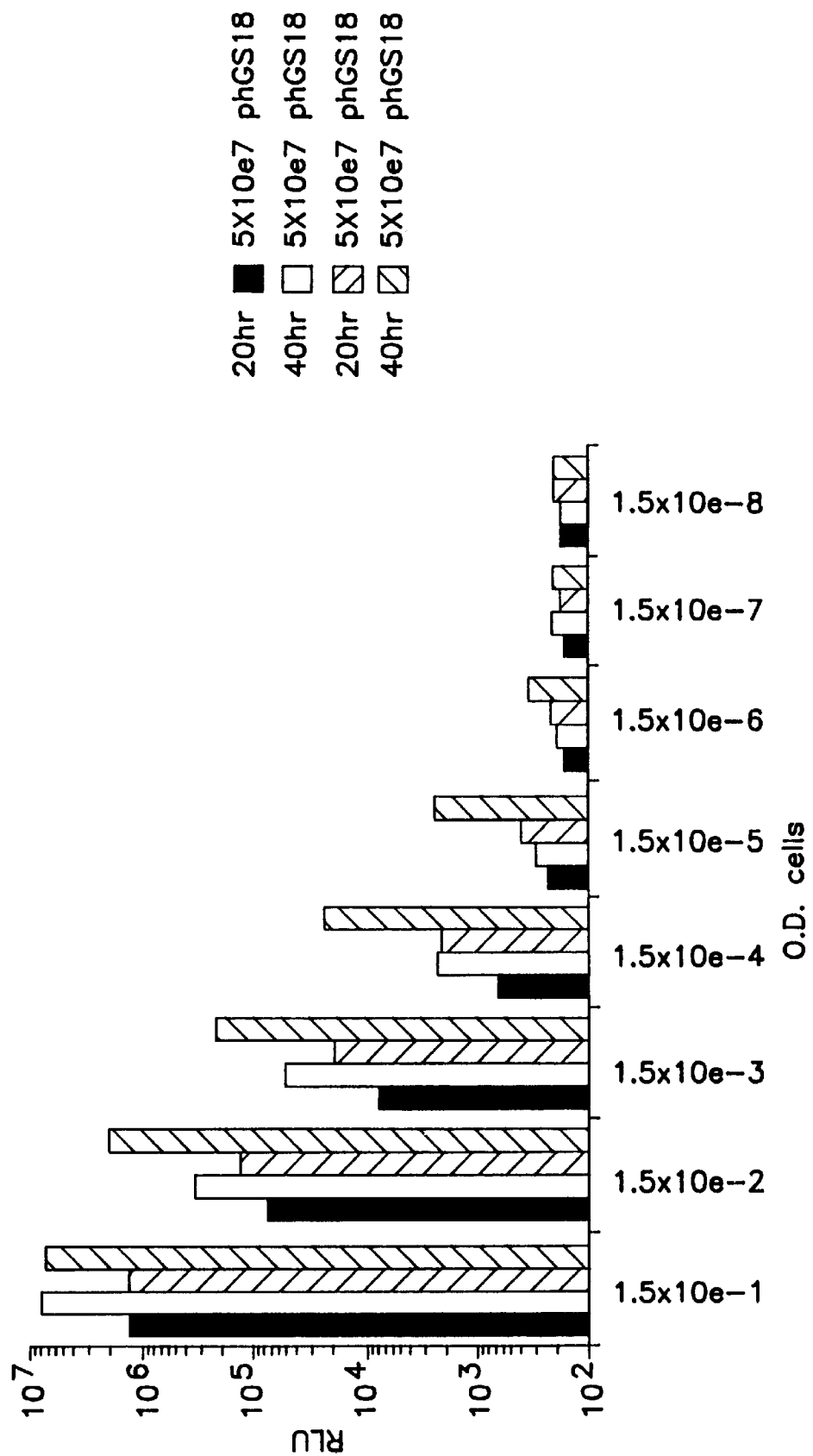
FIG. 28A represents the detection of luciferase activity after liquid infection of serial dilutions of *M. smegmatis* with phGS18.

An experiment similar to that described in FIG. 27 was performed to measure for light production (RLU) at both 20 hours and 40 hours after the addition of phage phGS18. Aliquots were plated onto agar for viable colony counts from several samples either before or after phage infection. Infections were done in duplicate and average numbers are shown in FIG. 28A.

10 μl aliquots were removed from samples either immediately prior to addition of phage (T=0), or 20 hours (T=20) or 40 hours (T=40) following addition of phage. Each row shows viable colony forming units present in a 50 μl sample for a given size of phage (either 5×10$^7$ or 5×10$^7$ pfu) and starting cell innoculum. FIG. 28B shows the light produced (RLU) for each sample and the calculated light per colony forming unit (RLA/Cell) at both 20 hours and 40 hours. These numbers correlate to FIG. 28A such that the sample shown as 1.5×10e–5 in FIG. 28A contained a starting innoculum of an estimated 69 colony forming units and when infected with 5×10$^5$ phage yielded a signal of 2,229 RLU after 40 hours at 30° C. This illustrates the exquisite sensitivity of these reporter phages and the use of lysogeny to amplify the signal.

Infection of an L5 Lysogen

Figure 29:
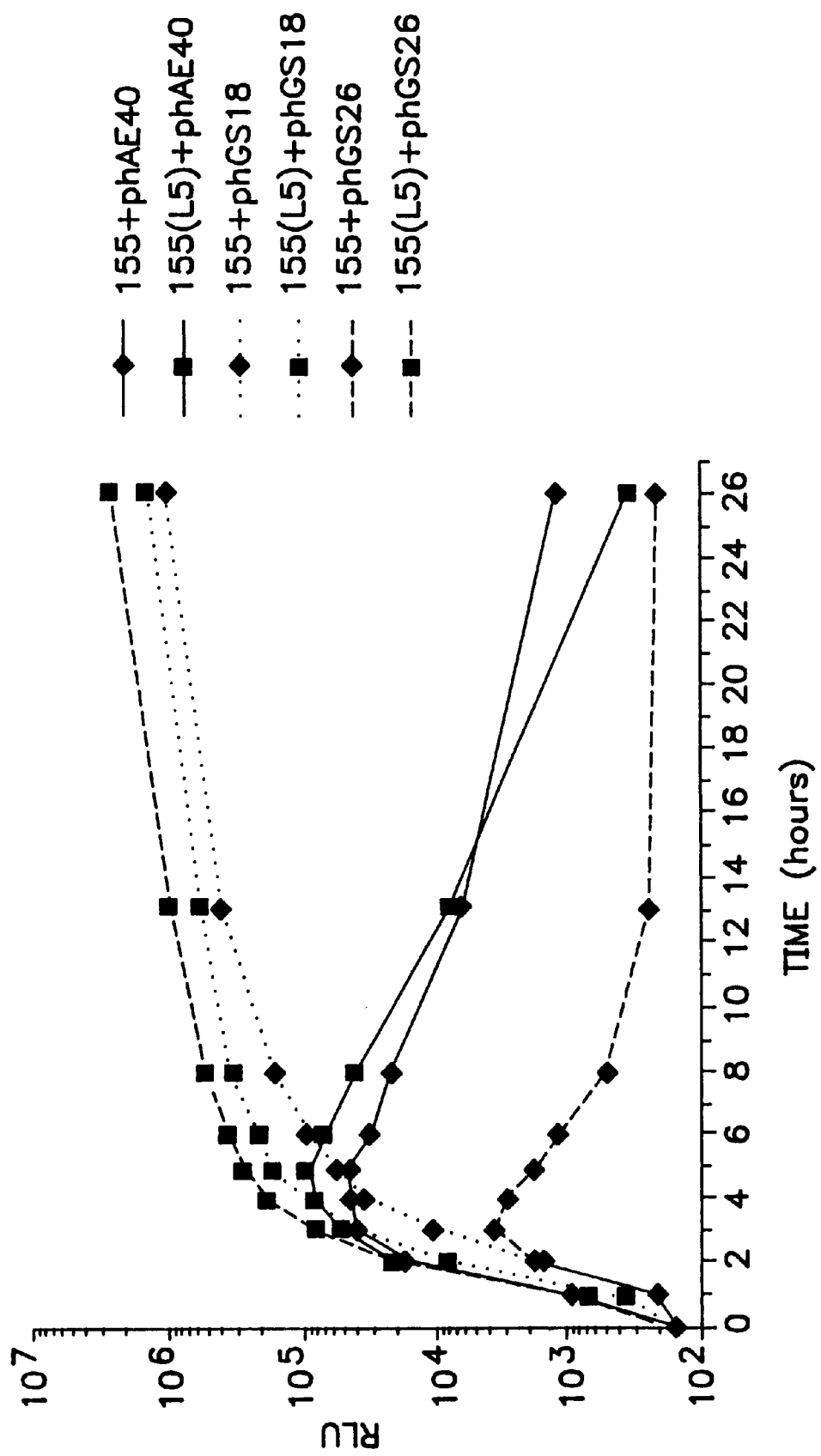
FIG. 29 represents the result of liquid infection of nonlysogen and lysogen strains of *M. smegmatis* with phAE40, phGS18 and phGS26.

To evaluate the influence of lysogeny of the host light production following infection of an M. smegmatis L5 lysogen [155(L5)] with a non-lysogen (155) was compared. FIG. 29 shows the data from a similar experiment using phAE40 which was expected to be unaffected by L5 lysogeny. Interestingly, it was observed that infection of an L5 lysogen [155(L5)] with phGS18 produced at least as much light (RLU) as from infection of a non-lysogen and is actually consistently 2-5 fold higher. Given this observation, it was predicted that the clear plaque mutant phGS26 would give extended light production after infection of an L5 lysogen, in contrast to the characteristic pattern observed in a non-lysogen (see also FIG. 25). FIG. 29 shows this to be exactly what was observed. In addition, FIG. 29 shows that L5 lysogeny has no effect on phAE40 infection. It was concluded that the potential problem of naturally occurring lysogens of M. tuberculosis does not present a significant one in this assay.

Each L5::FFlux phage constructed to date is listed in FIG. 30 along with any alternative or previous designation, whether or not it has been characterized further, a brief description and the date of isolation. Note that of the initial phage derivatives, only phGS1 and phGS5 have been characterized further with respect to the point of insertion of FF lux and approximate location of deletions in the right arm of the phage genome. The ts$^+$ derivatives and clear plaque mutant derivatives have not been fully characterized with respect to their specific differences from their phGS1 or phGS5 precursors.

Other Methods of Constructing L5 Reporter Mycobacteriophages

The use of the shuttle phasmid approach starting with L5 deletion derivatives, in which the size of the genome has been reduced, should be further explored in determining strategies for the construction of recombinant L5 mycobacteriophages. Initially, the largest gene 71 deletion available could be used, or deletions of the gene 72–88 region similar to those described for phGS1 and phGS5 as described in FIG. 22 could be used. Another approach would be to attempt to introduce genes by homologous recombination with plasmids. Still another approach would be to transpose lux genes onto L5 using either the mini-Mu in vitro transposition system or a mycobacterial transposon such as IS1096.

Recombining reporter genes from additional recombinant plasmids onto L5 using a double recombination event may be performed. This involves first constructing a recombinant plasmid that carries a reporter gene (lacZ may be more suitable) inserted into gene 71 such that both the upstream and downstream parts of gene 71 are present. Advantages of this approach are that lacZ can be easily detected in agar media, that gene 71 is not an essential gene, and that lacZ is efficiently expressed from a promoter immediately upstream of gene 71. An L5 mycobacteriophage lysate may be prepared by growth of the plasmid-containing strain and recombinant mycobacteriophage progeny identified by plating the lysate on wild-type M. smegmatis for individual plaques on agar containing the indicator X-gal. Alternatively, recombinant phage derivatives could be identified by hybridization.

This recombination approach may be expanded to introduce other gene or DNA segments of the L5 genome. For example, it should be possible to add luciferase genes from FFlux in an identical manner, provided that packaging limits are not exceeded. In addition, inclusion of polylinker containing restriction enzyme sites unique for L5 would open the way for construction of L5 recombinants in vitro. Similar genetic strategies may be used to systematically reduce the size of the L5 genome by deletion of non-essential sequences.

Transposition offers an alternative method for the construction of reporter mycobacteriophages. A transposition system which is available is the mini-Mu in vitro transposition system. This is a defined biochemical reaction in which a mini-Mu transposon carrying the desired gene is transposed onto the phage genome using purified MuA and MuB proteins. Similar transposition experiments have been tried with L5, but few L5 mini-Mu derivatives have been isolated. It is possible that this is due to the relatively large size of the transposon used. It is necessary to first construct a small Mu transposon which contains the reporter gene, a promoter and the two Mu in order for these experiments to be successful.

Development of L5 in vivo and in vitro Packaging Systems

λ cosmids and packaging systems provide the efficiency of mycobacteriophage infection with the ability to inject large segments of non-mycobacteriophage DNA. Analogous mycobacterial systems would overcome packaging constraints encountered with recombinant mycobacteriophage genomes and allow the introduction of multiple copies or types of reporter genes into mycobacteria, potentially enhancing the sensitivity of the assay. In addition, they would help overcome any problems with host synthesis inhibition.

The development of L5 cosmids and packaging systems is dependent on the finding that the L5 genome contains cohesive termini. The λ paradigm suggests that a relatively small region of DNA (approximately 500 bp) around the cos site (in the ligated form) is necessary to promote packaging. The first series of experiments with L5 would therefore be to identify the segment of the genome required for packaging by constructing a series of plasmids containing the L5 cos site and surrounding sequences. Cos activity may be determined by preparation of an L5 lysate on plasmid-containing *M. smegmatis* strains, followed by the identification of antibiotic-resistant transductants in the lysate, by transduction of *M. smegmatis*. This assay assumes that plasmid multimers of a total size of approximately 50 kb are present in the cell and will be packaged. Although the presence of such multimers has not been demonstrated directly, they are likely to be generated by the homologous recombination system of *M. smegmatis*. If this assay should fail, cosmid vectors which contain both L5 λ cos sites may be constructed. Insertion of 40–45 kb of DNA (as in the construction of cosmid libraries) followed by λ packaging in vitro and infection with *E. coli* will generate 50 kb sized molecules containing L5 cos site. These should be isolated from *E. coli* and introduced by electroporation into *M. smegmatis*. Assuming that one of these approaches is successful, it would then be possible to define a small segment of L5 DNA required for packaging.

The construction of in vivo cosmid packaging systems is a particularly attractive idea since it has proven very useful in *E. coli*. Thermoinducible lysogens of L5 may be suitable for in vivo packaging of L5 cosmids without further modification, since prophage excision may be a temperature-sensitive event. Efficient packaging of extrachromosomal cosmids present in the lysogen may be achieved by simple induction and growth at 42° C.

It is possible that some process other than excision is temperature-sensitive in lysogen induction. If so, it will be necessary to further debilitate the prophage in order to prevent DNA packaging of the prophage. There are a variety of ways to accomplish this. For example, the excise gene itself could be deleted (using a recombination strategy similar to that described above) such as to prevent excision. Another approach is to damage the cohesive termini (by exonucleolytic digestion) of an L5 thermoinducible derivative and construct a defective lysogen. A combination of approaches may be desirable, since even if prophage excision is a temperature-sensitive process, the destruction of cos might effectively reduce the background of spontaneous mycobacteriophage release.

Construction of in vitro packaging systems will follow similar lines. Extracts may be prepared from thermoinducible strains with non-packagable prophages and assessed for their ability to package exogenously added L5 cosmid or mycobacteriophage DNA. Optimization of conditions should follow both empirical biochemical approaches and the well-established λ systems. For example, it may be necessary to supplement the extracts with purified mycobacteriophage products such as the terminase or the tape-measure analogues (genes A/Nu and H of λ respectively), neither of which have yet been identified.

Construction of Novel Shuttle Phasmids From Any Mycobacteriophage

Although mycobacteriophages L5 and TM4 can be used in the development of diagnostic luciferase and β-galactosidase shuttle phasmids, there may be other mycobacteriophages, such as the mycobacteriophage DS6A which only infects BCG and M. tuberculosis strains, that might prove to have a more useful host range for clinical isolates. Diagnostic luciferase mycobacteriophages from these other mycobacteriophages may be developed by using the shuttle phasmid methodology described herein that has been proven successful for constructing mycobacteriophage vectors from both TM4 and phage L1.

Isolate Mycobacteriophage L5 and TM4 Mutants to Infect the Maximum Number of Clinical Isolates For the diagnostic luciferase mycobacteriophage system to have maximal use in the clinical laboratory, it will be essential that to develop a set of diagnostic mycobacteriophages that can efficiently infect any clinical isolate and possibly distinguish M. tuberculosis from *M. avium* and BCG. Both mycobacteriophages TM4 and L5 appear to have the ability to infect a large number of M. tuberculosis isolates. TM4 is very closely related to phage 33D, a mycobacteriophage that has been found not to infect every M. tuberculosis isolate used to define the mycobacteriophage typing schemes for M. tuberculosis isolates. However, this mycobacteriophage does not infect BCG. TM4 has been found to be almost identical by DNA hybridization and restriction analysis to 33D, and it shares the host-specificity with 33D in that it infects M. tuberculosis, but fails to infect BCG. Mycobacteriophage L5 appears to share the same receptor as mycobacteriophage D29 which receptor has been previously shown to infect a very large number of M. tuberculosis isolates. L5, unlike 33D or TM4, infects all three morphotypes of *M. avium* including a wide range of serovariants.

If L5 or TM4 are found not to infect certain M. tuberculosis isolates, it may be possible to isolate mutants of these mycobacteriophages which plaque on the particular isolate. The inability to plaque on a particular isolate could result from the lack of a mycobacteriophage receptor or be the result of lysogenization of the isolate with a homoimmune phage. Phage mutants with altered host range specificities or mutants which no longer bind a repressor (equivalent to virulent mutant of λ) have been isolated in other systems. Variants of TM4 which can efficiently infect BCG have been isolated at frequencies of $10^7$. Previous work has demonstrated that 33D, similarly to TM4, cannot adsorb to BCG cells. Host-range variants of TM4 which not only plaque BCG, but also still plaque M. tuberculosis have been isolated. Similar strategies for M. tuberculosis isolates which are uninfected by L5 or TM4 may be used.

Detecting the Presence of M. tuberculosis in Clinical Samples

The combined sensitivities of luciferase and mycobacteriophage infections should permit the detection of previously undetectable levels of M. tuberculosis cells in sputum, blood samples, or cerebral spinal fluid. A number of preliminary studies to optimize the detection of M. tuberculosis cells in a variety of body samples will be performed.

Detecting M. tuberculosis Grown In Primary Human Macrophages and Macrophage Cell Lines As a model system for optimizing detection of M. tuberculosis in infected monocytes and macrophages, primary human monocytes which have been purified by adherence for 1 hour or primary macrophages which have been cultured for 6 days in microwells will be infected with M. tuberculosis H37Ra at varying multiplicities. The number of cells initially infected will be determined microscopically, and then at various periods of time from 2 hours to 30 days, the cells will by lysed by non-ionic detergent NP40 which has no effect on viability of mycobacteria, concentrated by centrifugation, plated for viable organisms and infected with the luciferase plasmids. Quantitative studies at different moi's and with varying numbers of infected cells will indicate how few bacilli/cell and bacilli/specimen can be detected.

The inability of M. tuberculosis cells isolated from macrophages to be infected with diagnostic shuttle phasmids could result from either the absence of the expression of the mycobacteriophage-receptor or the masking of the receptor with a membrane from a phagosome of the macrophage. The level of expression of phage receptors may be regulated by the environment in which the host cell is grown. For example, the λ repressor of *E. coli* is induced by maltose and repressed by glucose. Studies to identify the receptors for mycobacteriophage L5 have been initiated. Similar studies for mycobacteriophage TM4 will also be performed. By identifying the genes encoding the receptor, it is possible to assay gene repression of the mycobacteriophage receptor of M. tuberculosis cells when grown in macrophages by hybridization for the mRNA synthesis. If the receptor is not expressed in macrophages, it may be necessary to use a mycobacteriophage which recognizes a receptor that is constitutively expressed.

If the receptor is masked by a membrane of the macrophage, the cells isolated from macrophages may be treated with a variety of different detergents to find a treatment that would allow infection of the M. tuberculosis cells with the mycobacteriophages. Again, it may be necessary to cultivate the detergent-treated macrophages in broth for a few generations to gain expression of the receptors. The assays to determine the infectability of macrophages from mycobacteria include not only the luciferase assay for the TM4::lux mycobacteriophages, but also infectious centers assays in which free mycobacteriophages are removed and mycobacteriophage-producing cells are scored by a mixed plating on a lawn of *M. smegmatis.* This assay would be useful since infectability can be scored even if there are insufficient M. tuberculosis cells to form a bacterial lawn. It is important to re-evaluate the host range specificities of all of the mycobacteriophages in this assay. Free mycobacteriophages can simply be removed through the use of specific anti-mycobacteriophage antibodies.

Detecting M. tuberculosis in Sputum Samples

Sputum from a patient infected with M. tuberculosis contains a mixture of mucopolysaccharide, free M. tuberculosis cells, macrophages containing M. tuberculosis cells and a variety of cellular debris. Sputum samples from patients thought to have pulmonary tuberculosis may be used for a study in which various numbers of M. tuberculosis cells are added to sputum samples found to have no or few organisms by acid-fast staining. A variety of methods can be used to treat sputum samples so as to liquify the mucous and decontaminate the specimen under conditions in which all bacteria other than mycobacteria are killed. Because of the specificity of the phasmids, decontamination may not be as important as preserving the mycobacteriophage receptors. Nonetheless, the sputum samples may be treated initially with 2% w/v NaOH for 30 minutes at 37° C. or with 0.5% N-acetyl cysteine+1% NaOH. Alternatively, the sample may be treated with a variety of hydrolytic enzymes, such as collagenase, to help dissolve the sputum sample. If mycobacteriophage receptors are carbohydrates possibly sensitive to these conditions, other conditions may be utilized or the cells will be cultured 3–16 hours to allow recovery of infectivity before mycobacteriophage infection.

Detecting Mycobacteria in Blood Samples

Tuberculosis has been known to have a bacteremia. If the sensitivity necessary to detect 100 to 200 M. tuberculosis cells in a ml of sample can be obtained, levels of bacteremia in tuberculosis patients which were not previously observable may be observed. White cells should be purified over Ficoil-hypaque and lysed with 2% NP40, 1% SDS or freeze-thawing in the presence of DNAse to liberate intracellular mycobacteria. The pellet should then be infected with the diagnostic luciferase mycobacteriophage, or if only few organisms are present they can be concentrated by filtration onto filters, and filter areas cut out and infected.

Assuring Specificity on a Variety of Clinical Isolates and Species; Assessment of False Positives and Negatives The luciferase assay may be optimized such that positive correlations of M. tuberculosis infections as indicated in the clinical lab may be obtained. The recombinant mycobacteriophages may be tested to ascertain the range of specificity that they have for other mycobacteria, and for the closely related genera Norcardia, Corynebacterium, and Actinomycetes strains. These strains may be obtained from the ATCC. A number of blinded tests including negative controls, M. tuberculosis-infected patients, samples from patients infected with *M. avium,* and samples infected with other non-mycobacterial pathogens may be performed to ascertain the range of specificity.

The ability to rapidly assess the susceptibilities of M. tuberculosis isolates to isoniazid, ethambutol, rifampicin, pyrazinamide and other antibiotics will have a major impact on the treatment of tuberculosis patients. After the isolation of M. tuberculosis cells from a sputum sample, which may take several weeks, the assessment of drug-susceptibilities may take an additional 2 to 9 weeks. Diagnostic reporter mycobacteriophages may allow for evaluations of drug-susceptibilities at the time a sputum sample is collected. Alternatively, this approach would shorten the time necessary to assess drug-susceptibilities of purified M. tuberculosis colonies grown up from clinical samples.

Luciferase Assays for M. tuberculosis Cells in the Presence of Drugs

The results of the experiments suggest that by using luciferase as an indicator for the metabolic ability of the cell, it may be possible to define conditions which will enable us to distinguish drug-resistant mycobacteria from drug-sensitive mycobacteria. To test this hypothesis, isolated mutants of M. tuberculosis H37Ra which are resistant to isoniazid, rifampicin, ethambutol, or pyrazinamide would be used to generate a set of cogenic mutants. These independent mutants and the parent strains would be transformed with pYUB180. Luciferase activity will be assessed in the presence and absence of drugs in order to determine the optimal conditions for distinguishing between drug-resistant and drug-sensitive cells. It is quite possible that the window of time to observe differences for different drugs could vary and require different incubation times for each drug.

The choice of the promoter for expressing luciferase may provide a needed parameter to more readily assess drug action. For example, in the case of *E. coli,* gyrase promoters are greatly stimulated in the presence of gyrase inhibitors.

Clinical isolates of M. tuberculosis may be transformed with PYUB180 and tested for luciferase activity in the presence and absence of drugs. The luciferase assays with mycobacteriophage infections with lux mycobacteriophages on in vitro-grown M. tuberculosis cells will first be optimized, and then extended to M. tuberculosis cells grown in macrophages or isolated from sputum samples.

Critical Assessment of Drug-Susceptibility Testing

As for the detection of M. tuberculosis from clinical samples, the luciferase assay may be optimized so that the drug-susceptibility patterns for any clinical isolate may be obtained. It may be possible to add diagnostic mycobacteriophages to a single clinical specimen, aliquot the mixture into various tubes and add antibiotic drugs. Thus every experiment would have an internal control and each drug-treated sample could be compared to an untreated control. The critical parameter to conclude drug-resistance or sensitivity lies in the comparison.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

What is claimed is:

1. A method for determining whether a mycobacterial strain is resistant to a drug comprising the steps of:

(a) incubating the mycobacterial strain in the presence of a drug and a temperate mycobacteriophage specific for the mycobacterial strain under conditions permitting the formation of mycobacterial lysogens capable of expressing a reporter molecule, wherein the mycobacteriophage contains in its genome DNA encoding the reporter molecule and a transcriptional promoter which controls transcription of the reporter molecule DNA; and (b) detecting whether the gene product of the reporter molecule is transcribed, said transcription indicating resistance of the mycobacterial strain to the drug.

2. The method of claim 1, wherein the reporter molecule is luciferase.

3. The method of claim 2, wherein the luciferase is firefly luciferase, *Vibrio fisceri* luciferase, or *Xenorhabdus luminescens* luciferase.

4. The method of claim 1, wherein the reporter molecule is β-galactosidase.

5. The method of claim 1, wherein the mycobacteria are *Mycobacterium smegmatis*.

6. The method of claim 1, wherein the mycobacteria are *Mycobacterium tuberculosis*.

7. The method of claim 1, wherein the mycobacteria are *Mycobacterium avium*.

8. The method of claim 1, wherein the mycobacteria are *Mycobacterium bovis*-BCG.

9. A method for determining whether a mycobacterial strain is resistant to a drug comprising the steps of:

(a) incubating the mycobacterial strain in the presence of a temperate mycobacteriophage specific for the mycobacterial strain under conditions permitting the formation of mycobacterial lysogens capable of expressing a reporter molecule, wherein the mycobacteriophage contains in its genome DNA encoding the reporter molecule and a transcriptional promoter which controls the transcription of the reporter molecule DNA;

(b) adding a drug to the mycobacterial lysogens; and (c) detecting whether the gene product of the reporter molecule is transcribed, said transcription indicating resistance of the mycobacterial strain to the drug.

10. The method of claim 9, wherein the reporter molecule is luciferase.

11. The method of claim 10, wherein the luciferase is firefly luciferase, *Vibrio fisceri* luciferase, or *Xenorhabdus luminescens* luciferase.

12. The method of claim 9, wherein the reporter molecule is β-galactosidase.

13. The method of claim 9, wherein the mycobacteria are *Mycobacterium smegmatis*.

14. The method of claim 9, wherein the mycobacteria are *Mycobacterium tuberculosis*.

15. The method of claim 9, wherein the mycobacteria are *Mycobacterium avium*.

16. The method of claim 9, wherein the mycobacteria are *Mycobacterium bovis*-BCG.

* * * * *